US006361501B1

(12) United States Patent
Amano et al.

(10) Patent No.: US 6,361,501 B1
(45) Date of Patent: Mar. 26, 2002

(54) PULSE WAVE DIAGNOSING DEVICE

(75) Inventors: Kazuhiko Amano; Kazuo Uebaba, both of Yokohama; Hitoshi Ishiyama, Toride, all of (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/284,932

(22) PCT Filed: Jun. 18, 1998

(86) PCT No.: PCT/JP98/02706

§ 371 Date: Jun. 21, 1999

§ 102(e) Date: Jun. 21, 1999

(87) PCT Pub. No.: WO99/09884

PCT Pub. Date: Mar. 4, 1999

(30) Foreign Application Priority Data

| Aug. 26, 1997 | (JP) | 9-230075 |
| Oct. 8, 1997 | (JP) | 9-275500 |
| Oct. 31, 1997 | (JP) | 9-301332 |

(51) Int. Cl.[7] ............................................. A61B 5/00
(52) U.S. Cl. ....................................... 600/500; 600/485
(58) Field of Search .............................. 600/485, 500, 600/503

(56) References Cited

U.S. PATENT DOCUMENTS

| 4,437,469 A | | 3/1984 | Djordjevich et al. | |
| 4,562,843 A | | 1/1986 | Djordjevich et al. | |
| 4,896,675 A | | 1/1990 | Ohsuga et al. | |
| 5,383,468 A | | 1/1995 | Nakayama et al. | |
| 5,638,823 A | * | 6/1997 | Akay et al. | 600/528 |
| 5,697,374 A | * | 12/1997 | Odagiri et al. | 600/500 |
| 5,913,826 A | * | 6/1999 | Blank | 600/500 |
| 5,957,866 A | * | 9/1999 | Shapiro et al. | 600/586 |
| 6,036,653 A | * | 3/2000 | Baba et al. | 600/500 |

FOREIGN PATENT DOCUMENTS

| EP | 0 630 608 | 12/1994 |
| JP | 56-161037 | 12/1981 |
| JP | 57-501665 | 9/1982 |
| JP | 62-22627 | 1/1987 |
| JP | 63-145631 | 6/1988 |
| JP | 2-1218 | 1/1990 |
| JP | 2-121007 | 10/1990 |
| JP | 4-51912 | 5/1992 |
| JP | 4-166130 | 6/1992 |
| JP | 4-136207 | 12/1992 |
| JP | 5-176913 | 7/1993 |

(List continued on next page.)

OTHER PUBLICATIONS

Application of Wavelet Transformation to Wave Pulse of Living Body (in Japanese), Preprint of 15th Scientific Lectures on Biomechanism, (Japan), (1994) pp. 121–124, particularly 2–3 and partial English language translation.

"ME Quick Reference Q & A Part 3 (in Japanese)", supervised by Yasuhisa Sakurai, Aug., 10, 1988 Nankodo pp. 105 and partial English language translation.

*Primary Examiner*—Robert L. Nasser, Jr.

(57) ABSTRACT

When pulse waveform MH is detected by pulse wave detection sensor unit 130, wavelet transformer 10 performs wavelet transformation on pulse waveform MH and generates analyzed pulse wave data MKD. This analyzed pulse wave data MKD consists of a time region in which one heartbeat is divided into eighths, and the frequency region of 0–4 Hz which has been divided into eighths. Frequency corrector 11 generates corrected pulse wave data MKD' by performing frequency correction on analyzed pulse wave data MKD. Pulse type data generator 12 compares corrected pulse wave data MKD' over each frequency-time region, and generates pulse type data ZD indicating the type of pulse. Display 13 displays the pulse type for pulse waveform MH based on pulse type data ZD.

18 Claims, 95 Drawing Sheets

FOREIGN PATENT DOCUMENTS

| | | |
|---|---|---|
| JP | 7-116137 | 5/1995 |
| JP | 7-136139 | 5/1995 |
| JP | 7-204167 | 8/1995 |
| JP | 8-229011 | 9/1996 |
| JP | 8-289876 | 11/1996 |
| JP | 9-113653 | 5/1997 |
| JP | 9-114955 | 5/1997 |
| JP | 9-135818 | 5/1997 |
| JP | 10-216293 | 8/1998 |
| WO | WO 94 15526 | 7/1994 |

* cited by examiner

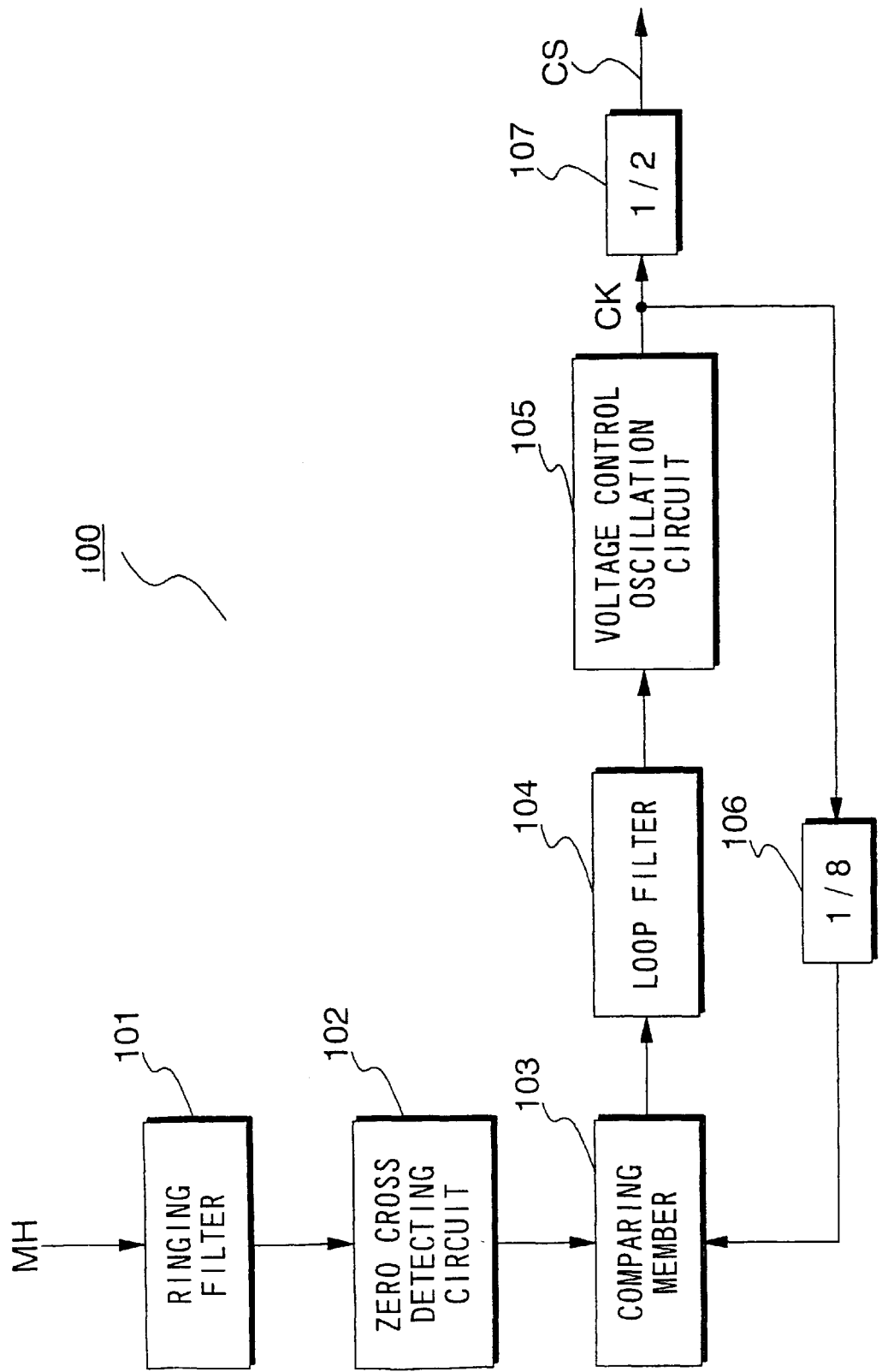

FIG. 7A  MH
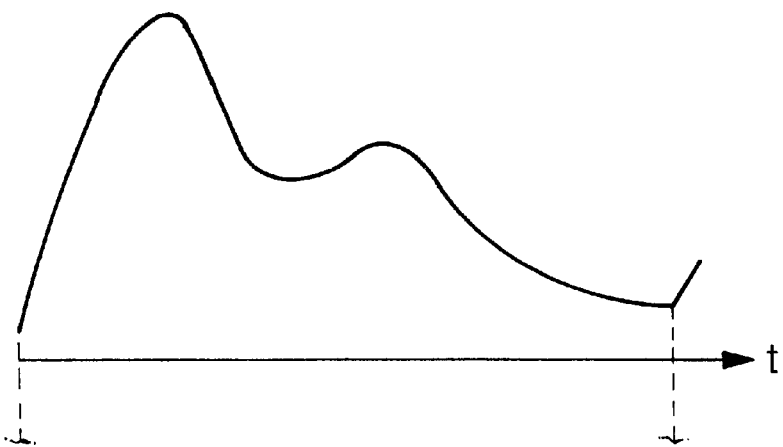
FIG. 7B  101 out
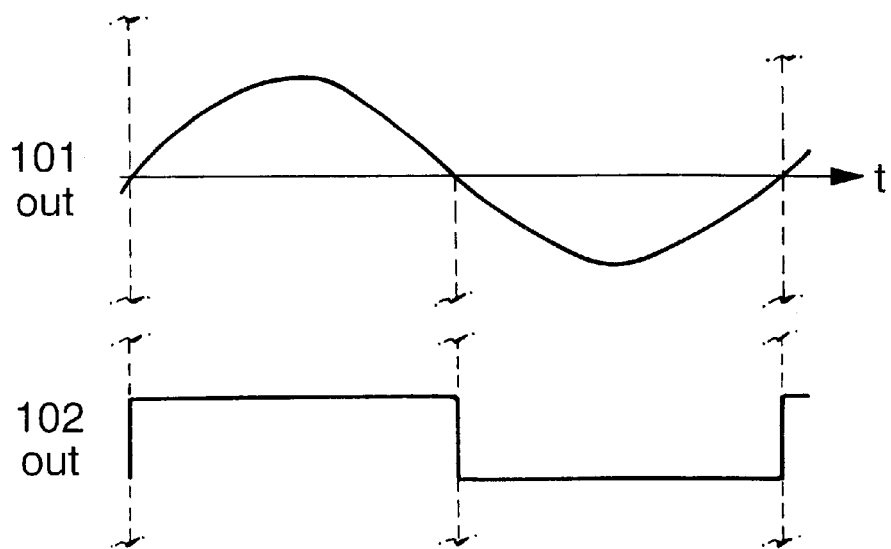
FIG. 7C  102 out
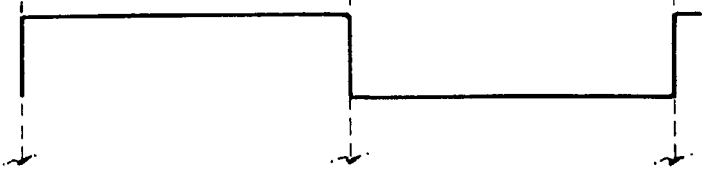
FIG. 7D  105 out CK
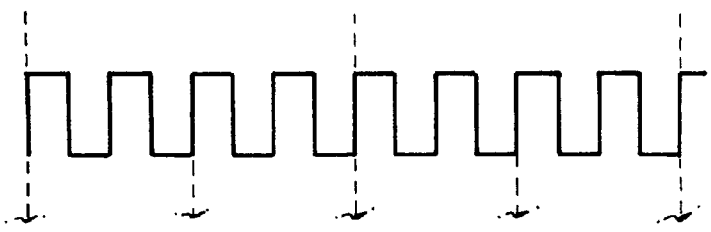
FIG. 7E  CS
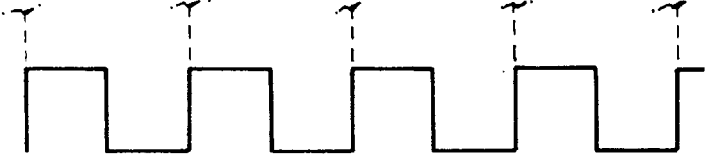

FIG. 17

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 1 |
| 2.0~1.5Hz | 2 | 3 | 1 | 1 | 1 | 0 | 0 | 1 |
| 1.5~1.0Hz | 4 | 5 | 5 | 5 | 5 | 6 | 5 | 4 |
| 1.0~0.5Hz | 4 | 7 | 8 | 8 | 6 | 8 | 8 | 8 |
| 0.5~0.0Hz | 6 | 7 | 7 | 10 | 10 | 9 | 9 | 9 |

FIG. 18

| | t1 | t2 | t3 | t4 | t5 | t6 | t7 | t8 |
|---|---|---|---|---|---|---|---|---|
| 4.0~3.5Hz | 0 | 0 | 0 | 0 | 0 | 0 | 0 | 0 |
| 3.5~3.0Hz | 0 | 0 | 0 | 0 | 0 | 0 | 0 | 0 |
| 3.0~2.5Hz | 0 | 0 | 0 | 0 | 0 | 0 | 0 | 0 |
| 2.5~2.0Hz | 0 | 0 | 0 | 0 | 0 | 0 | 0 | 0 |
| 2.0~1.5Hz | 0 | 0 | 0 | 0 | 0 | 1 | 0 | 0 |
| 1.5~1.0Hz | 0 | 1 | 1 | 0 | 0 | 2 | 1 | 0 |
| 1.0~0.5Hz | 4 | 5 | 7 | 7 | 5 | 6 | 6 | 7 |
| 0.5~0.0Hz | 5 | 6 | 6 | 6 | 7 | 6 | 6 | 6 |

FIG. 19

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 0 |
| 2.0~1.5Hz | 2 | 3 | 1 | 1 | 1 | 0 | 0 | 1 |
| 1.5~1.0Hz | 4 | 4 | 4 | 5 | 5 | 4 | 4 | 4 |
| 1.0~0.5Hz | 0 | 2 | 1 | 1 | 1 | 2 | 2 | 1 |
| 0.5~0.0Hz | 1 | 1 | 1 | 4 | 3 | 3 | 3 | 3 |

FIG. 23

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 1 |
| 2.0~1.5Hz | 2 | 3 | 1 | 1 | 1 | 0 | 0 | 1 |
| 1.5~1.0Hz | 4 | 5 | 5 | 5 | 5 | 6 | 5 | 4 |
| 1.0~0.5Hz | 0 | 0 | 0 | 0 | 0 | 0 | 0 | 0 |
| 0.5~0.0Hz | 0 | 0 | 0 | 0 | 0 | 0 | 0 | 0 |

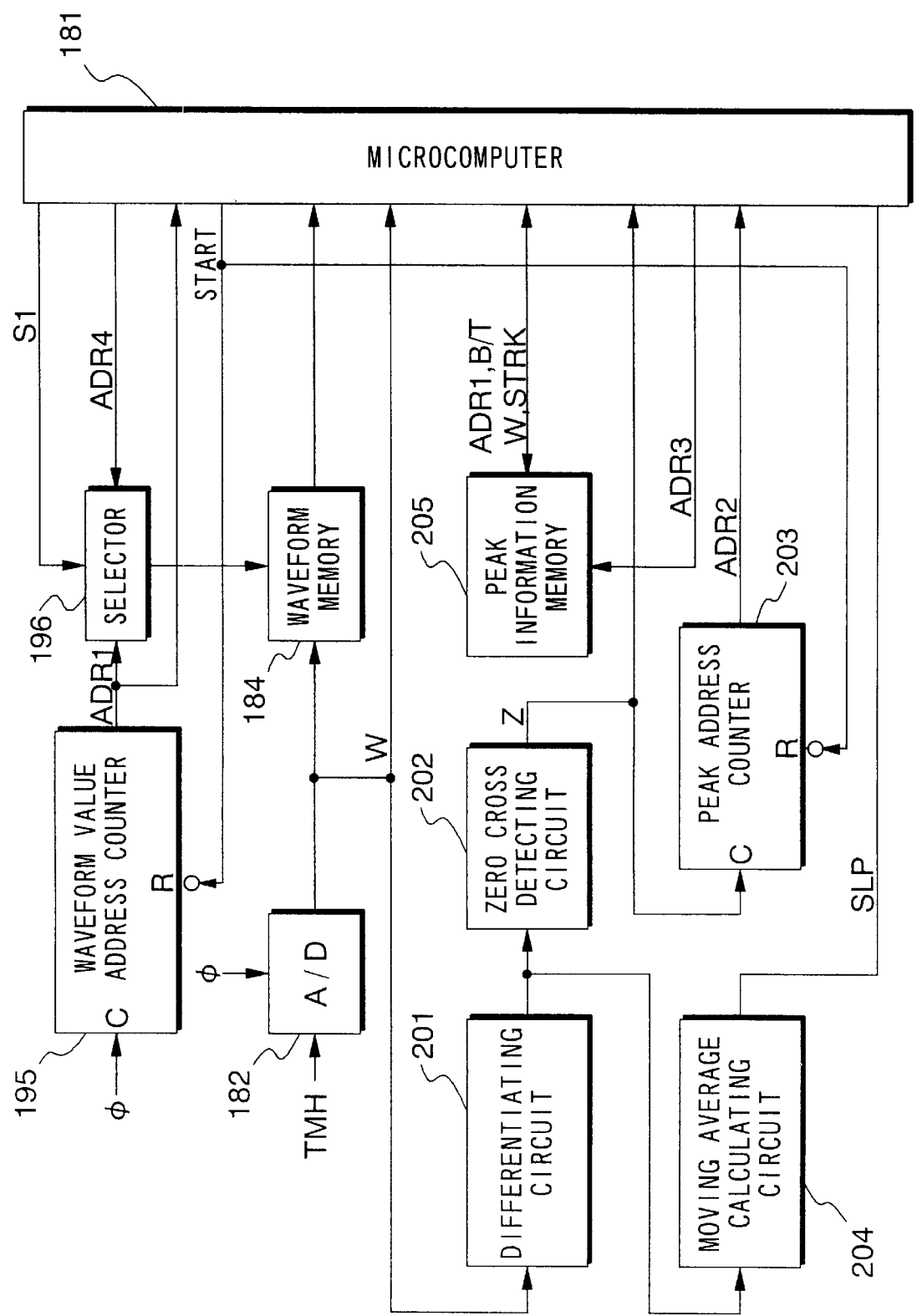

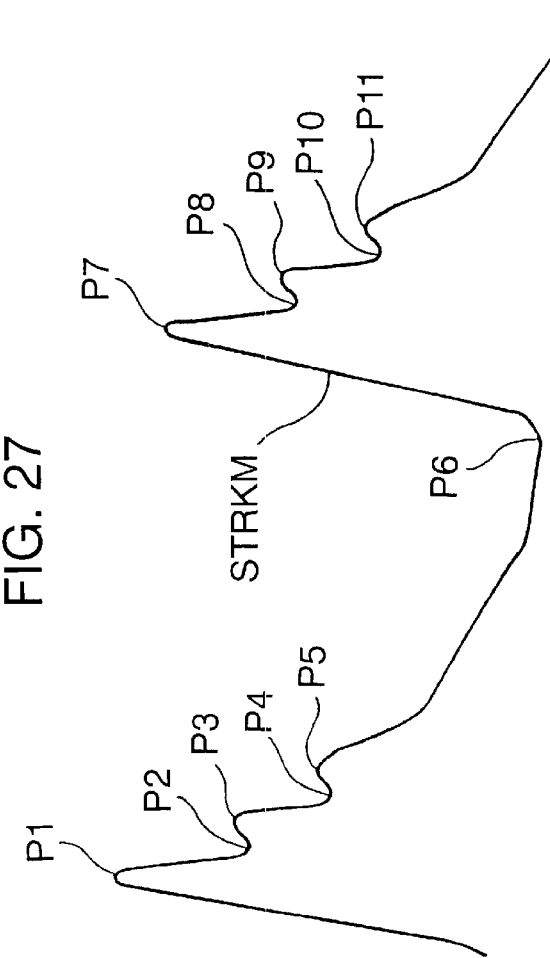

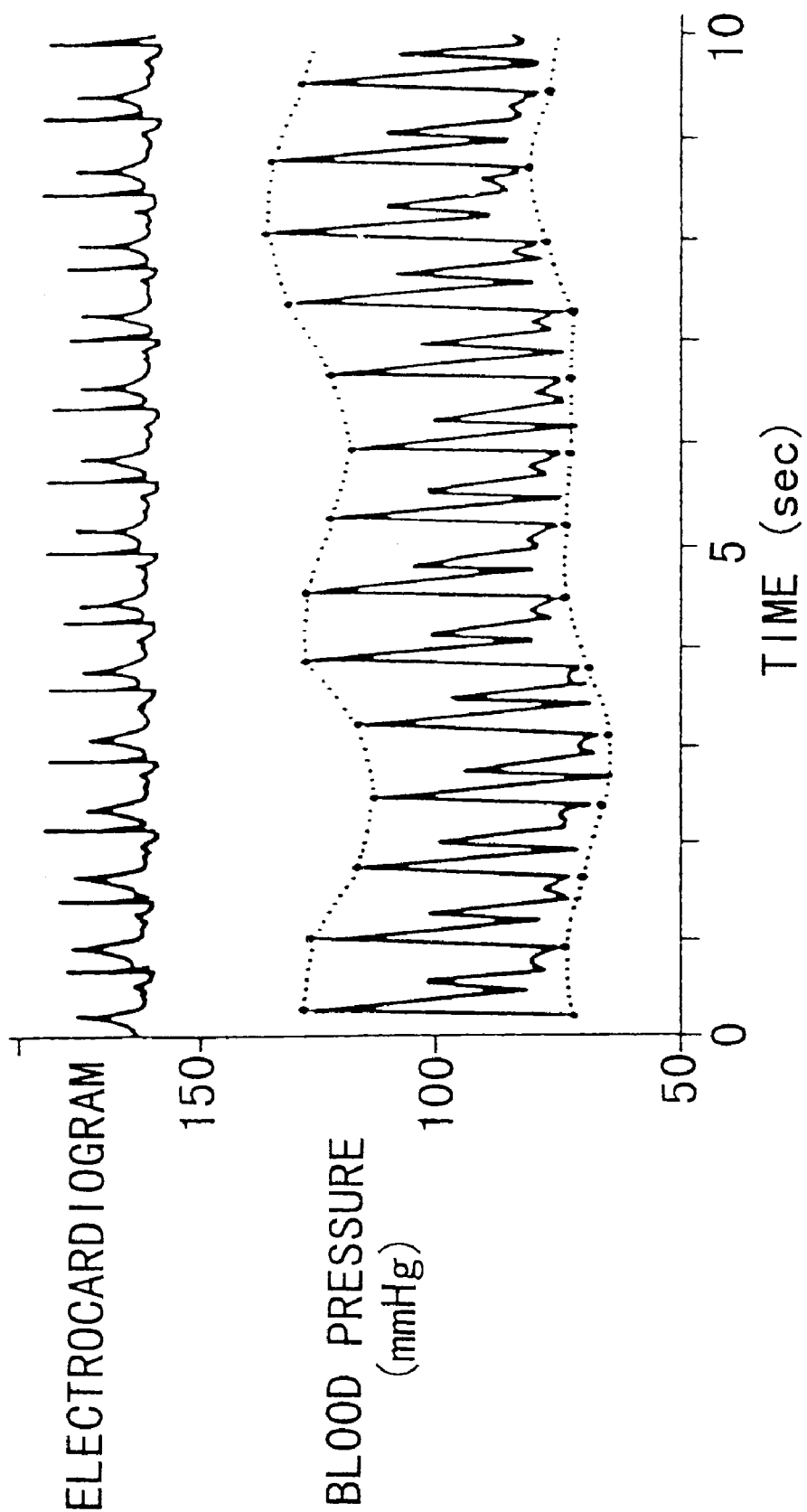

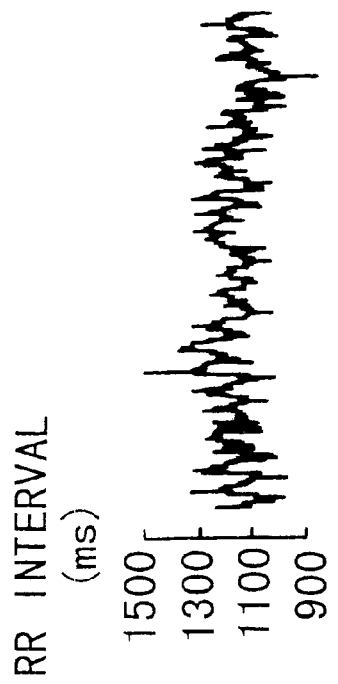
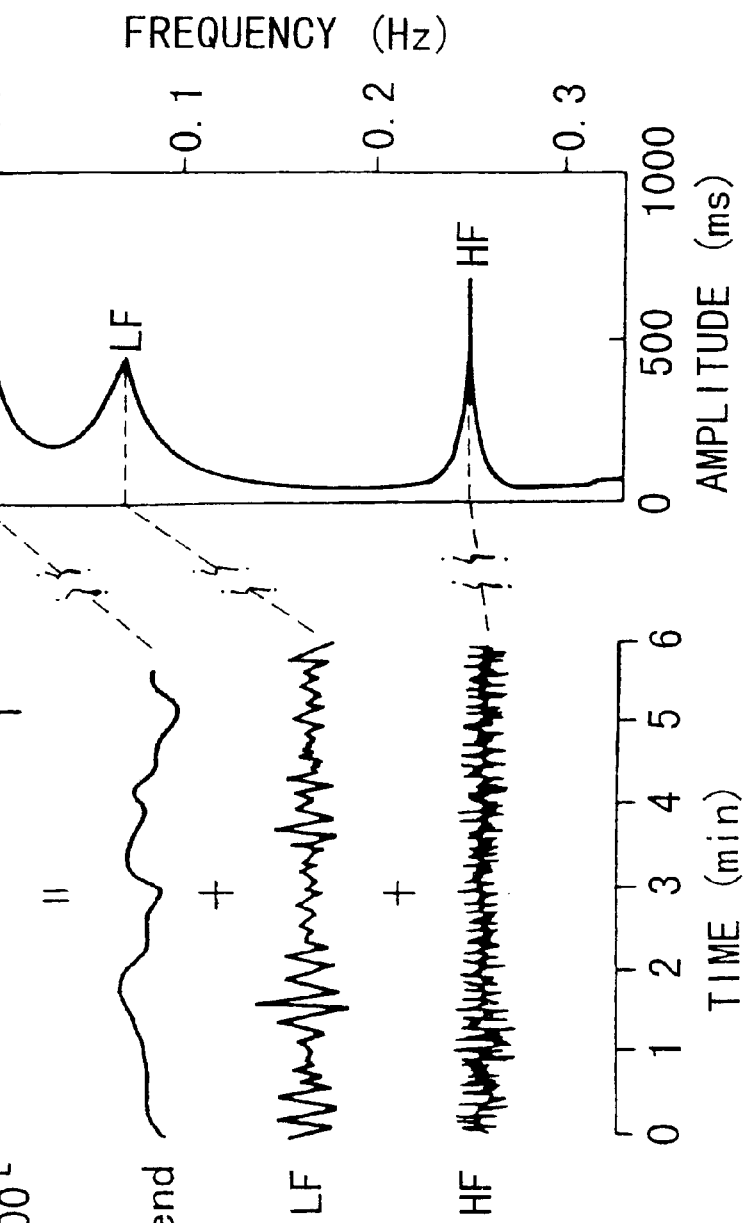
FIG. 41A
FIG. 41B

RUNNING PITCH, PULSE RATE
□ : RUNNING PITCH
■ : PULSE RATE

SUBJECTIVE EXERCISE INTENSITY

LACTIC ACID CONCENTRATION

FIG. 45

SUBJECTIVE EXERCISE INTENSITY

| POINTS | SUBJECTIVE SENSATION |
|--------|----------------------|
| 20     |                      |
| 19     | EXTREMELY DIFFICULT  |
| 18     |                      |
| 17     | RATHER DIFFICULT     |
| 16     |                      |
| 15     | DIFFICULT            |
| 14     |                      |
| 13     | SOMEWHAT DIFFICULT   |
| 12     |                      |
| 11     | EASY                 |
| 10     |                      |
| 9      | VERY EASY            |
| 8      |                      |
| 7      | EXTREMELY EASY       |
| 6      |                      |

FIG. 57

| RANGE FOR G (MINUS) | DISPLAY |
|---|---|
| G < -0.5 | |
| -0.5 ≦ G < -0.4 | |
| -0.4 ≦ G < -0.3 | |
| -0.3 ≦ G < -0.2 | |
| -0.2 ≦ G < -0.1 | |

| RANGE FOR G (APPROXIMATELY EQUAL) | DISPLAY |
|---|---|
| -0.1 ≦ G < 0.1 | |

| RANGE FOR G (PLUS) | DISPLAY |
|---|---|
| 0.5 ≦ G | |
| 0.4 ≦ G < 0.5 | |
| 0.3 ≦ G < 0.4 | |
| 0.2 ≦ G < 0.1 | |
| 0.1 ≦ G < 0.2 | |

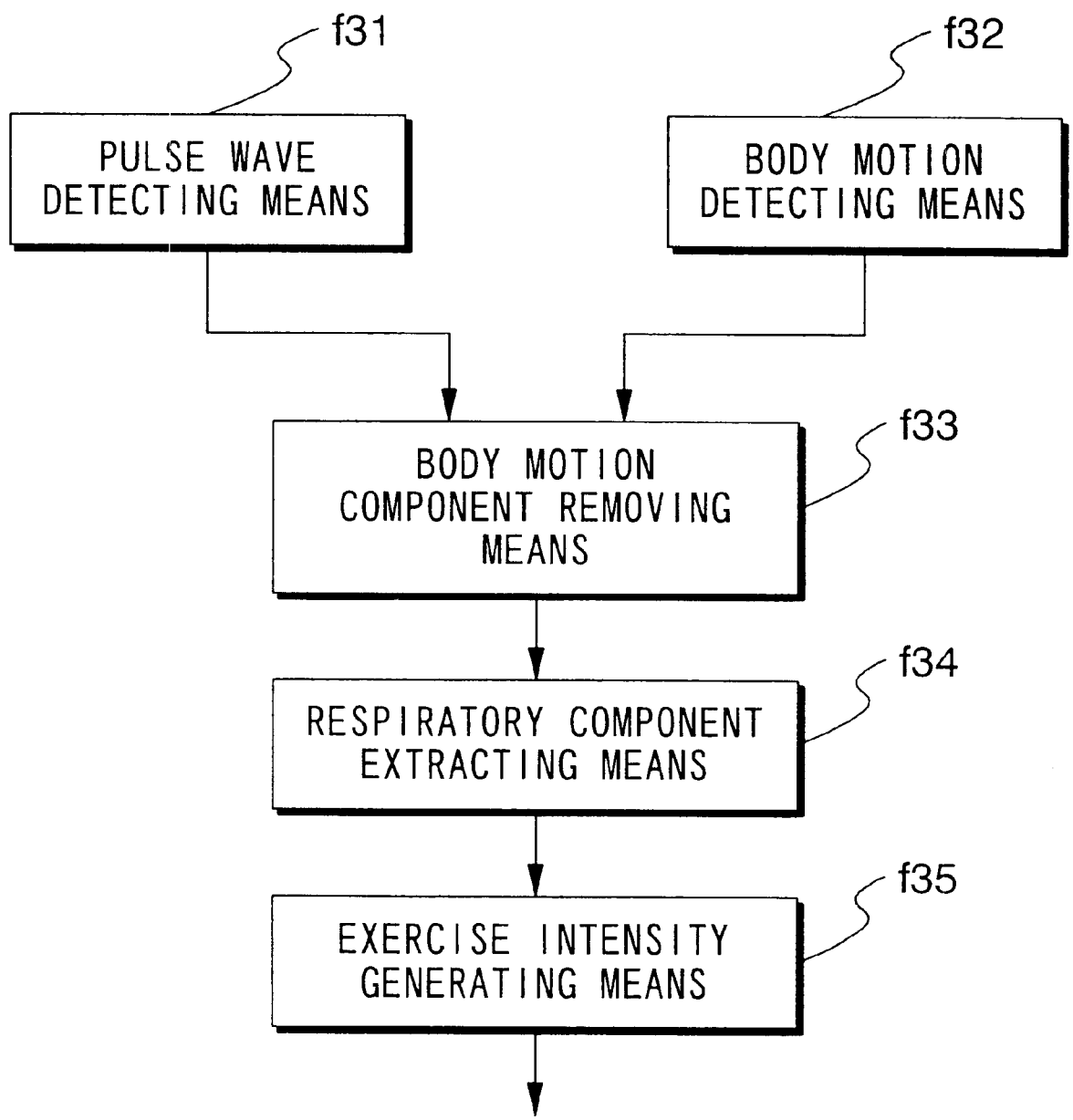

FIG. 68

MKD

| | t1 | t2 | t3 | t4 | t5 | t6 | t7 | t8 |
|---|---|---|---|---|---|---|---|---|
| 4.0~3.5Hz | 0 | 0 | 0 | 1 | 4 | 2 | 2 | 9 |
| 3.5~3.0Hz | 2 | 3 | 2 | 3 | 2 | 3 | 8 | 1 |
| 3.0~2.5Hz | 4 | 4 | 3 | 1 | 2 | 7 | 1 | 4 |
| 2.5~2.0Hz | 2 | 1 | 1 | 2 | 8 | 0 | 3 | 1 |
| 2.0~1.5Hz | 1 | 2 | 8 | 8 | 2 | 3 | 1 | 2 |
| 1.5~1.0Hz | 7 | 8 | 1 | 1 | 1 | 1 | 2 | 1 |
| 1.0~0.5Hz | 3 | 3 | 4 | 3 | 4 | 4 | 5 | 5 |
| 0.5~0.0Hz | 0 | 1 | 0 | 0 | 1 | 1 | 0 | 1 |

FIG. 69

| | t1 | t2 | t3 | t4 | t5 | t6 | t7 | t8 |
|---|---|---|---|---|---|---|---|---|
| 4.0~3.5Hz | 0 | 0 | 0 | 0 | 0 | 0 | 0 | 0 |
| 3.5~3.0Hz | 0 | 0 | 0 | 0 | 0 | 0 | 0 | 1 |
| 3.0~2.5Hz | 0 | 0 | 0 | 0 | 0 | 0 | 1 | 4 |
| 2.5~2.0Hz | 0 | 0 | 0 | 0 | 0 | 0 | 3 | 1 |
| 2.0~1.5Hz | 0 | 0 | 0 | 0 | 2 | 3 | 1 | 2 |
| 1.5~1.0Hz | 0 | 0 | 1 | 1 | 1 | 1 | 2 | 1 |
| 1.0~0.5Hz | 3 | 3 | 4 | 3 | 4 | 4 | 5 | 5 |
| 0.5~0.0Hz | 0 | 1 | 0 | 0 | 1 | 1 | 0 | 1 |

VKD

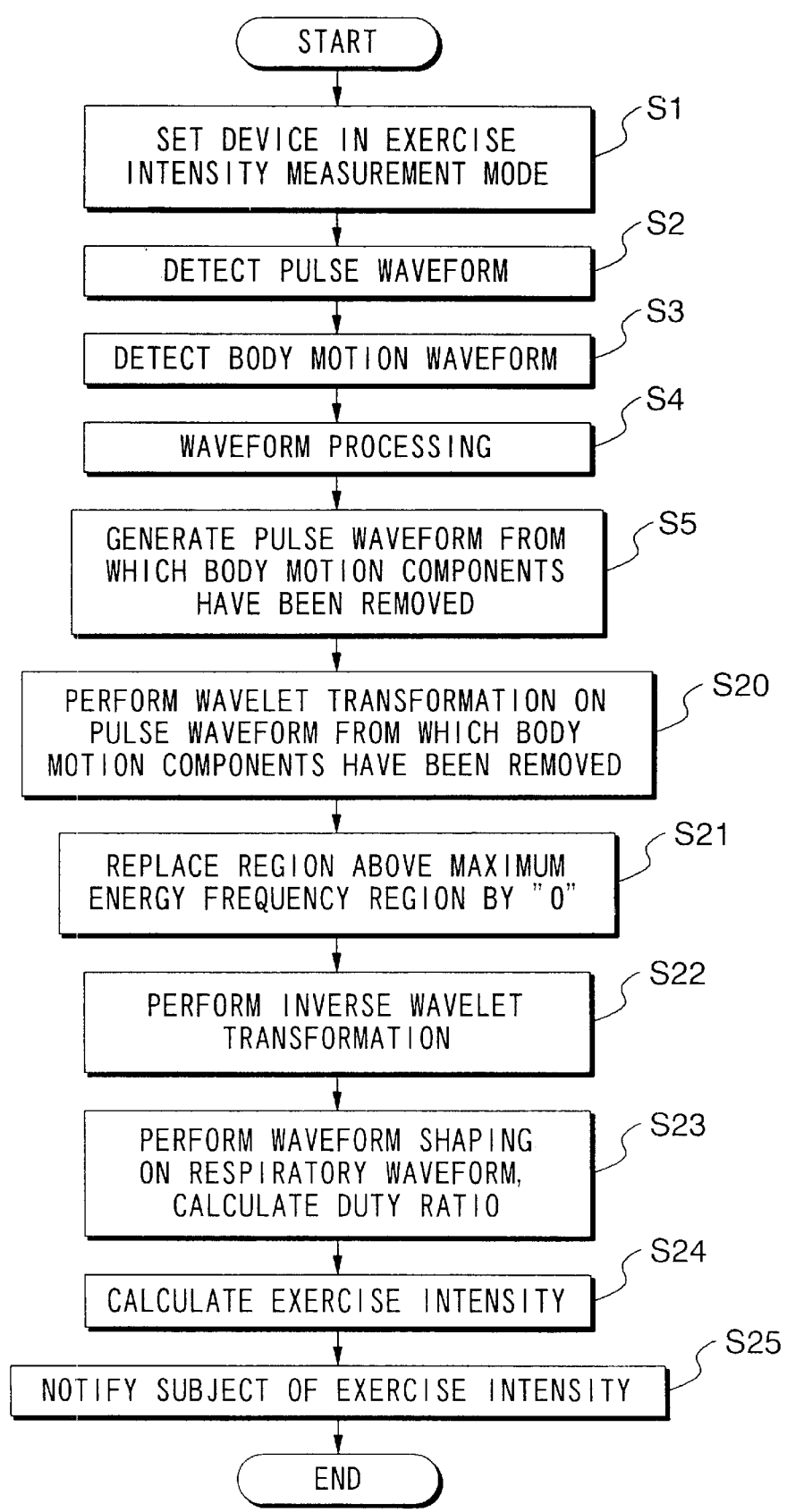

FIG. 85

MEASURED VALUES FOR HEART TRANSPLANT PATIENTS, HEALTHY PATIENTS

| SUBJECT | | PULSE RATE | STROKE VOLUME PER BEAT | NUMBER OF TEST SUBJECTS, N |
|---|---|---|---|---|
| HEART TRANSPLANT PATIENT | SITTING | 88 | 119 | 58 |
| | RECLINED | 87 | 127 | 58 |
| | STANDING UPRIGHT | 88 | 146 | 58 |
| HEALTHY SUBJECT | SITTING | 70 | 169 | 59 |
| | RECLINED | 64 | 155 | 45 |
| | STANDING UPRIGHT | 76 | 177 | 44 |

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 1 |
| 2.0~1.5Hz | 2 | 3 | 1 | 1 | 1 | 0 | 0 | 1 |
| 1.5~1.0Hz | 4 | 5 | 5 | 5 | 5 | 6 | 5 | 4 |
| 1.0~0.5Hz | 0 | 0 | 0 | 0 | 0 | 0 | 0 | 0 |
| 0.5~0.0Hz | 0 | 0 | 0 | 0 | 0 | 0 | 0 | 0 |

PULSE WAVE DIAGNOSING DEVICE

BACKGROUND OF THE INVENTION

1. Technical Field

The present invention relates to a method and device for extracting information related to the body's state from the pulse wave, and measuring or diagnosing the body's state based on this extracted information.

2. Background of the Invention

Blood pressure, heart rate and the like are typical measurements employed when diagnosing the condition of the circulatory system in the human body. Accordingly, systolic and diastolic blood pressure values and pulse rates measured in the body are of great importance as a type of information for understanding the state of the circulatory system and, in a greater sense, the state of the body. Since these indices are obtained by measuring the pulse over a fixed period of time, they serve as representative values for the period of measurement.

As research on pulse waves has progressed, it has become clear that a variety of physiological states which cannot be gleaned from blood pressure values and the pulse rate alone, can be obtained using a variety of methods to analyze a pulse waveform obtained in the human body. Diagnosis can then be made based on the thus-obtained physiological state. The term "pulse wave" as employed here indicates the wave of blood that is pumped out from the heart and propagates through the blood vessels. It is known that various medical information can be obtained by detecting and analyzing the pulse wave.

In Eastern medicine, for example, the physician performs a pulse diagnosis by applying pressure on the skin over the patient's radius artery with his fingers. A diagnosis of the patient's physiological state is then made based on the pulse sensed by the physician through his fingers. The Ping mai, Hua mai, and Xuan mai are representative forms which the pulse wave may assume.

However, since the pulse wave is used to diagnose the body's state based on very subtle touch sensations felt through the fingers of the examiner, it can be difficult to teach this technique. Accordingly, much practice over a period of months and years is required. Moreover, if body motion is present, then it can be particularly difficult to get an accurate pulse type due to fluctuations in blood flow.

When performing physical training, exercise of a certain intensity is carried out regularly. The intensity of this exercise is obtained from a subjective evaluation by the exerciser who qualifies the exercise as "difficult" or "easy".

However, an exercise intensity obtained based on a subjective evaluation is not a suitable index since it does not take into consideration the subject's physical strength.

When evaluating cardiac function, an index which focuses on the amount of blood ejected from the heart is employed. Stroke-volume-per-beat SV and cardiac output CO are examples of such indices.

Some degree of body motion accompanies exercise or daily activities, however. Accordingly, blood flow is acted upon by this body motion, causing a body motion component to be superimposed on the pulse waveform. As a result, it is not possible to continuously measure stroke-volume-per-beat SV and cardiac output CO while exercising or performing daily activities.

DISCLOSURE OF THE INVENTION

The present invention takes into consideration the aforementioned physiological states in providing the following devices.

1) A device and method for objectively specifying the pulse type based on the pulse waveform
2) A device and method for objectively detecting exercise intensity
3) A device and method for measuring stroke volume per beat and cardiac output.

The following devices and methods are available for objectively specifying the pulse type based on the pulse waveform.

The first aspect of the present invention relates to a pulse wave diagnosing device, characterized in that it comprises a pulse wave detecting means for detecting a pulse waveform at a detection site on the body; a wavelet transforming means for performing wavelet transformation on the pulse waveform detected by the pulse wave detecting means, and then generating analyzed pulse wave data in each frequency region; and a pulse type data generating means for performing calculations on the analyzed pulse wave data and then generating pulse type data indicating the type of pulse waveform.

The second aspect of the present invention relates to a pulse wave diagnosing device, characterized in that it comprises a pulse wave detecting means for detecting a pulse waveform at a detection site on the body; a first wavelet transforming means for performing wavelet transformation on the pulse waveform detected by the pulse wave detecting means, and then generating analyzed pulse wave data in each frequency region; a body motion detecting means for detecting body motion and outputting a body motion waveform; a second wavelet transforming means for performing wavelet transformation on the body motion waveform detected by the body motion detecting means, and generating analyzed body motion data in each frequency region; a mask means for subtracting analyzed body motion data from the analyzed pulse wave data, and generating corrected pulse wave data from which body motion components have been removed; and a pulse type data generating means for performing calculations on the corrected pulse wave data generated by the mask means, and generating pulse type data indicating the type of pulse waveform.

The third aspect of the present invention relates to a pulse wave diagnosing device, characterized in that it comprises a pulse wave detecting means for detecting a pulse waveform at a detection site on the body; a wavelet transforming means for performing wavelet transformation on the pulse waveform detected by the pulse wave detecting means, and then generating analyzed pulse wave data in each frequency region; a frequency correcting means for correcting analyzed pulse wave data by normalizing the power at each frequency based on each corresponding bandwidth in the frequency regions, and generating corrected pulse wave data; and a pulse type data generating means for performing calculations on the corrected pulse wave data, and then generating pulse type data indicating the type of pulse waveform.

The forth aspect of the present invention relates to a pulse wave diagnosing device, characterized in that it comprises a pulse wave detecting means for detecting a pulse waveform at a detection site on the body; a first wavelet transforming means for performing wavelet transformation on the pulse waveform detected by the pulse wave detecting means, and then generating analyzed pulse wave data in each frequency region; a first frequency correcting means for correcting analyzed pulse wave data based by normalizing the power at each frequency based on each corresponding bandwidth in the frequency regions, and generating corrected pulse wave data; a body motion detecting means for detecting motion of the body, and outputting a body motion waveform; a second wavelet transforming means for performing wavelet transformation on the body motion waveform detected by the body motion detecting means, and generating analyzed body motion data in each frequency region; a second frequency correcting means for correcting analyzed body motion data by normalizing the power at each frequency based on each corresponding bandwidth in the frequency regions, and generating corrected body motion data; a mask means for subtracting the corrected body motion data from the corrected pulse wave data, and generating corrected pulse wave data from which body motion components have been removed; and a pulse type data generating means for performing calculations on the corrected pulse wave data generated by the mask means, and generating pulse type data indicating the type of pulse waveform.

The fifth aspect of the present invention relates to a pulse wave diagnosing device, characterized in that it comprises a pulse wave detecting means for detecting a pulse waveform at a detection site on the body; a first wavelet transforming means for performing wavelet transformation on the pulse waveform detected by the pulse wave detecting means, and then generating analyzed pulse wave data in each frequency region; a body motion detecting means for detecting body motion and outputting a body motion waveform; a second wavelet transforming means for performing wavelet transformation on the body motion waveform detected by the body motion detecting means, and then generating analyzed body motion data in each frequency region; a mask means for subtracting the analyzed body motion data from the analyzed pulse wave data, and generating in each frequency region pulse wave data from which body motion components have been removed; a frequency correcting means for correcting pulse wave data by normalizing the power at each frequency based on each corresponding bandwidth in the frequency regions, and generating corrected pulse wave data; and a pulse type data generating means for performing calculations on the corrected pulse wave data generated by the mask means, and generating pulse type data indicating the type of pulse waveform.

The sixth aspect of the present invention relates to a pulse wave diagnosing device, characterized in that it comprises a pulse wave detecting means for detecting a pulse waveform at a detection site on the body; a wavelet transforming means for performing wavelet transformation on the pulse waveform detected by the pulse wave detecting means, and then generating analyzed pulse wave data in each frequency region; a body motion component removing means for removing the frequency component corresponding to body motion from the analyzed pulse wave data, and generating analyzed pulse wave data; a frequency correcting means for correcting the analyzed pulse wave data generated by the body motion component removing means in accordance with the corresponding frequency, and generating corrected pulse wave data; and a pulse type data generating means for performing calculations on the corrected pulse wave data, and generating pulse type data indicating the type of pulse waveform.

The seventh aspect of the present invention relates to a pulse wave diagnosing device, characterized in that the pulse type data generating means is provided with an inverse pulse wavelet transforming means for performing inverse wavelet transformation on the corrected pulse wave data, and generating pulse wave data from which body motion components have been removed; and a data generating means for generating pulse type data based peak information in the pulse wave data.

The eighth aspect of the present invention relates to a pulse wave diagnosing device, characterized in that it comprises a state detecting means for detecting the physiological exercise state based on the body motion waveform detected by the body motion detecting means; and a controlling means for controlling the first wavelet transforming means in accordance with the exercise state, so as to vary the frequency region subjected to frequency analysis.

The ninth aspect of the present invention relates to a pulse wave diagnosing device, characterized in that the controlling means is provided with a recording means for recording in advance the relationship between the physiological exercise state and the frequency region subjected to frequency analysis, and a reading out means for reading out the frequency region that is subjected to frequency analysis based on the physiological exercise state detected by the state detecting means; wherein the controlling means controls the frequency region that is subjected to frequency analysis based on the read out results.

The tenth aspect of the present invention relates to a pulse wave diagnosing device, characterized in that it comprises a pulse wave period detecting means for detecting the period of the pulse waveform, wherein the wavelet transforming means performs wavelet transformation in synchronization with the detected period.

The eleventh aspect of the present invention relates to a pulse wave diagnosing device characterized in that it comprises a pulse wave period detecting means for detecting the period of the pulse waveform, wherein the first and second wavelet transforming means perform wavelet transformation in synchronization with the detected period.

The twelfth aspect of the present invention is characterized in that it comprises a notifying means for notifying the subject of the pulse type data generated by the pulse type data generating means.

The thirteenth aspect of the present invention relates to a pulse wave diagnosing device, characterized in that the pulse wave detecting means consists of a pressure sensor for employing pressure to detect the arterial pulse in the body.

The fourteenth aspect of the present invention relates to a pulse wave diagnosing device, characterized in that the pulse wave detecting means detects as the pulse waveform a received light signal in which reflected light obtained when a detection site on the body is irradiated with light of wavelength 300~700 nm is received.

The fifteenth aspect of the present invention relates to a pulse wave diagnosing device, characterized in that the pulse wave detecting means detects as the pulse waveform a received light signal in which transmitted light obtained when a detection site on the body is irradiated with light of wavelength 600~1000 nm is received.

The sixteenth aspect of the present invention relates to a pulse type data generating method, characterized in that it comprises a first step in which a pulse waveform is detected at a detection site on the body; a second step in which wavelet transformation is performed on the detected a pulse waveform and analyzed pulse wave data is generated in each frequency region; and a third step in which calculations are performed on the analyzed pulse wave data and pulse type data indicating the type of pulse waveform is generated.

The seventeenth aspect of the present invention relates to a pulse type data generating method, characterized in that it comprises a first step in which a pulse waveform is detected at a detection site on the body; a second step in which wavelet transformation is performed on the pulse waveform detected in the first step, and analyzed pulse wave data is generated in each frequency region; a third step in which body motion is detected and a body motion waveform is generated; a forth step in which wavelet transformation is performed on the detected body motion waveform, and analyzed body motion data is generated in each frequency region; a fifth step in which the analyzed body motion data is subtracted from the analyzed pulse wave data, and corrected pulse wave data from which body motion components have been removed is generated; and a sixth step in which calculations are performed on the corrected pulse wave data and pulse type data indicating the type of pulse waveform is generated.

The eighteenth aspect of the present invention relates to a pulse type data generating method, characterized in that it comprises a first step in which a pulse waveform is detected at a detection site on the body; a second step in which wavelet transformation is performed on the pulse waveform detected in the first step, and analyzed pulse wave data is generated in each frequency region; a third step in which the analyzed pulse wave data is corrected by normalizing the power at each frequency based on each corresponding bandwidth in the frequency regions, and corrected pulse wave data is generated; and a fourth step in which calculations are performed on the corrected pulse wave data and pulse type data indicating the type of pulse waveform is generated.

The nineteenth aspect of the present invention relates to a pulse type data generating method, characterized in that it comprises a first step in which a pulse waveform is detected at a detection site on the body; a second step in which wavelet transformation is performed on the pulse waveform detected in the first step, and analyzed pulse wave data is generated in each frequency region; a third step in which analyzed pulse wave data is corrected by normalizing the power at each frequency based on each corresponding bandwidth in the frequency regions, and corrected pulse wave data is generated; a forth step in which body motion is detected and a body motion waveform is generated; a fifth step in which wavelet transformation is performed on the body motion waveform detected in the forth step, and analyzed body motion data is generated in each frequency region; a sixth step in which analyzed body motion data is corrected by normalizing the power at each frequency based on each corresponding bandwidth in the frequency regions, and corrected body motion data is generated; a seventh step in which the corrected body motion data is subtracted from the corrected pulse wave data, and corrected pulse wave data from which body motion components have been removed is generated; and an eighth step in which calculations are performed on the corrected pulse wave data and pulse type data indicating the type of pulse waveform is generated.

The twentieth aspect of the present invention relates to a pulse type data generating method, characterized in that it comprises a first step in which a pulse waveform is detected at a detection site on the body; a second step in which wavelet transformation is performed on the pulse waveform and analyzed pulse wave data is generated in each frequency region; a third step in which body motion is detected and a body motion waveform is generated; a fourth step in which wavelet transformation is performed on the body motion waveform detected in step 3 and analyzed body motion data is generated in each frequency region; a fifth step in which the analyzed body motion data is subtracted from the analyzed pulse wave data, and pulse wave data from which body motion components have been removed is generated in each frequency region; a sixth step in which pulse wave data is corrected by normalizing the power at each frequency based on each corresponding bandwidth in the frequency regions, and corrected pulse wave data is generated; and a seventh step in which calculations are performed on the corrected pulse wave data, and pulse type data indicating the type of pulse waveform is generated.

The twenty-first aspect of the present invention relates to a pulse type data generating method, characterized in that it comprises a first step in which a pulse waveform is detected at a detection site on the body; a second step in which wavelet transformation is performed on the pulse waveform and analyzed pulse wave data is generated in each frequency region; a third step in which the frequency components corresponding to body motion components are removed from the analyzed pulse wave data, and analyzed pulse wave data is generated; a fourth step in which analyzed pulse wave data is corrected in accordance with each corresponding frequency, and corrected pulse wave data is generated; and a fifth step in which calculations are performed on the corrected pulse wave data, and pulse type data indicating the type of pulse waveform is generated.

Next, the following devices and methods are available for objectively detecting exercise intensity.

The twenty-second aspect of the present invention relates to an exercise index measuring device, characterized in that it comprises a pulse rate detecting means for detecting the subject's pulse rate; a pitch detecting means for detecting the subject's exercise pitch; a determining means for determining the point at which the detected pulse rate and the detected exercise pitch are approximately the same; a first calculating means for obtaining the exercise intensity corresponding to the determined point; and a first notifying means for informing the subject of the obtained exercise intensity in the form of an exercise index.

The twenty-third aspect of the present invention relates to an exercise index measuring device, characterized in that the determining means determines that the detected pulse rate and the detected exercise pitch are the same if the difference between them is within the range of ±10%.

The twenty-fourth aspect of the present invention relates to an exercise index measuring device, characterized in that it comprises a first recording means for recording the exercise intensity obtained by the first calculating means in association with a time; and a second notifying means for notifying the subject of the details recorded in the first recording means along with changes over time.

The twenty-fifth aspect of the present invention relates to an exercise index measuring device, characterized in that it comprises a second calculating means for obtaining the exercise intensity from the detected exercise pitch or the detected pulse rate at that point in time; and a third notifying means for notifying the subject of the exercise intensity obtained by the second calculating means.

The twenty-sixth aspect of the present invention relates to an exercise index measuring device, characterized in that it comprises a pulse rate detecting means for detecting the subject's pulse rate; a pitch detecting means for detecting the subject's exercise pitch; a first comparing means for obtaining the difference between the pulse rate detected by the pulse rate detecting means and the pitch detected by the pitch detecting means, and comparing this difference with the pulse or the pitch; and a forth notifying means for notifying the subject of the results of the comparison obtained by the comparing means.

The twenty-seventh aspect of the present invention relates to an exercise index measuring device, characterized in that it comprises a pulse rate detecting means for detecting the subject's pulse rate; a pitch detecting means for detecting the subject's exercise pitch; a second comparing means for comparing the pulse rate detected by the pulse rate detecting means and the pitch detected by the pitch detecting means; and a fifth notifying means for providing the subject with an exercise index based on the results of the comparison by the comparing means which is in a direction that will eliminate the difference between the detected pitch and the detected pulse rate.

The twenty-eighth aspect of the present invention relates to an exercise index measuring device, characterized in that the exercise performed by the subject is running, and in that a second recording means for recording in advance the subject's stride is provided; wherein the pitch detecting means detects the subject's running pitch, the first or second calculating means obtains as the exercise intensity the result obtained by multiplying the running pitch detected by the pitch detecting means and the stride recorded in the second recording means.

The twenty-ninth aspect of the present invention relates to an exercise index measuring device, characterized in that it comprises a correcting means for correcting the stride recorded in the second recording means accompanying changes in the subject's running pitch or pulse rate.

The thirtieth aspect of the present invention relates to an exercise index measuring device, characterized in that it comprises a communicating means for sending and receiving information with an external piece of equipment.

The thirty-first aspect of the present invention relates to an exercise index measuring device, characterized in that it comprises a third recording means for recording at least one or more of data expressing stride corrected by the correcting means, pitch detected by the pitch detecting means, or pulse rate detected by the pulse rate detecting means; and a communicating means for transmitting the data recorded in the third recording means to an external piece of equipment.

The thirty-second aspect of the present invention relates to an exercise index measuring device, characterized in that the communicating means receives at least one or more data indicating the stride, the pitch or the pulse rate set by an external piece of equipment.

The thirty-third aspect of the present invention relates to an exercise index measuring method, characterized in that it comprises a second step in which the subject's exercise pitch is detected; a third step in which the point at which the detected pulse rate and the detected pitch are approximately the same is determined; a forth step in which the exercise intensity corresponding to the determined point is obtained; and a fifth step in which the subject is informed of the obtained exercise intensity as an exercise index.

The thirty-fourth aspect of the present invention relates to an exercise index measuring method, characterized in that it comprises a sixth step in which the exercise intensity is recorded in association with a time; and a seventh step in which the subject is informed of the recorded details along with changes over time.

The thirty-fifth aspect of the present invention relates to an exercise index measuring method, characterized in that a step in which the exercise intensity is determined from the detected exercise pitch and or the detected pulse rate at that point in time is provided in place of the third and fourth steps.

The thirty-sixth aspect of the present invention relates to an exercise index measuring method, characterized in that it comprises a first step in which the subject's pulse rate is detected; a second step in which the subject's exercise pitch is detected; a third step in which the difference between the detected pulse and the detected pitch is obtained, and this difference is compared with the pulse rate or the pitch; and a forth step in which the subject is notified of the results of the comparison.

The thirty-seventh aspect of the present invention relates to an exercise index measuring method, characterized in that it comprises a first step in which the subject's pulse rate is detected; a second step in which the subject's exercise pitch is detected; a third step in which the detected pitch and the detected pulse rate are compared; and a fourth step in which, based on the results of the comparison, the subject is informed of an exercise index in a direction which will eliminate the difference between the detected pitch and the detected pulse rate.

The thirty-eighth aspect of the present invention relates to an exercise intensity detecting device, characterized in that it comprises a pulse wave detecting means for detecting the pulse waveform at the detection site on the body; a body motion detecting means for detecting body motion waveforms which expresses the motion of the body; a body motion component removing means for generating the body motion components in the pulse waveform based on the body motion waveform, and removing the body motion components from the pulse waveform to generate a pulse waveform from which body motion components have been removed; a respiratory component extracting means for extracting the respiratory component based on the pulse waveform from which body motion components have been removed; and an exercise intensity generating means for calculating the exercise intensity based on the respiratory components extracted by the respiratory component extracting means.

The thirty-ninth aspect of the present invention relates to an exercise intensity detecting device, characterized in that the respiratory component extracting means is provided with a wavelet transformer for performing wavelet transformation on a pulse waveform from which body motion components have been removed, and generating analyzed pulse wave data from which body motion components have been removed; and a respiratory waveform generator for generating analyzed respiratory waveform data by removing the frequency components corresponding to the pulse wave components from the analyzed pulse wave data from which body motion components have been removed, and generating a respiratory waveform as the respiratory component by performing inverse wavelet transformation on the analyzed respiratory waveform data.

The fortieth aspect of the present invention relates to an exercise intensity detecting device, characterized in that the exercise intensity generating means calculates the exercise intensity based on the proportion of frequency components obtained by performing frequency analysis on the respiratory components extracted by the respiratory component extracting means.

The forty-first aspect of the present invention relates to an exercise intensity detecting device, characterized in that the exercise intensity generating means calculates the distortion factor from each frequency component obtained by performing frequency analysis on the respiratory components extracted by the respiratory component extracting means, and calculates the exercise intensity based on the distortion factor.

The forty-second aspect of the present invention relates to an exercise intensity detecting device, characterized in that the exercise intensity generating means calculates the ratio of the fundamental frequency component to the third harmonic component obtained by performing frequency analysis on the respiratory components extracted by the respiratory component extracting means, and calculates the exercise intensity based on this proportion.

The forty-third aspect of the present invention relates to an exercise intensity detecting device, characterized in that the respiratory component extracting means extracts the respiratory waveform as the respiratory component, and the exercise intensity generating means detects the duty ratio of the respiratory wavelength extracted by the respiratory component extracting means, and generates the exercise intensity based on the duty ratio.

The forty-fourth aspect of the present invention relates to an exercise intensity detecting device, characterized in that the body motion component removing means is provided with a first frequency analyzer for analyzing the frequency spectrum of the pulse waveform, a second frequency analyzer for analyzing the frequency spectrum of the body motion waveform, and a body motion component remover for removing a frequency which is identical to the frequency spectrum analyzed by the second frequency analyzer from the frequency spectrum analyzed by the first frequency analyzer and generating a spectrum from which body motion components have been removed; wherein the respiratory component extracting means extracts the frequency spectrum corresponding to the fundamental component of the respiratory component from among the spectrums from which body motion components have been removed, and the exercise intensity generating means calculates the exercise intensity based on the level of the frequency spectrum corresponding to the fundamental component of the respiratory component, and to the level of the frequency spectrum corresponding to the higher harmonic wave components thereof.

The forty-fifth aspect of the present invention relates to an exercise intensity detecting device, characterized in that the respiratory component extracting means specifies the band determined according to the pulse rate from among the spectrums from which body motion components have been removed, and extracts the frequency spectrum corresponding to the fundamental component of the respiratory component from the frequency spectrums in this band.

The forty-sixth aspect of the present invention relates to an exercise intensity detecting device, characterized in that the exercise intensity generating means calculates the distortion factor in the respiratory waveform based on the level of the spectrum corresponding to the fundamental component of the respiratory component and the level of the spectrum corresponding to the higher harmonic wave components thereof, and calculates the exercise intensity based on the distortion factor.

The forty-seventh aspect of the present invention relates to an exercise intensity detecting device, characterized in that the exercise intensity generating means obtains the ratio of the level of the spectrum corresponding to the fundamental component of the respiratory component to the level of the spectrum corresponding to the third order higher harmonic wave components, and calculates the exercise intensity based on this proportion.

The forty-eighth aspect of the present invention relates to an exercise intensity detecting device, characterized in that it comprises a pulse wave detecting means for detecting a pulse waveform at a detection site on the body; a respiratory component extracting means for extracting the respiratory component from the pulse waveform; and an exercise intensity generating means for calculating the exercise intensity based on the respiratory component extracted by the respiratory component extracting means.

The forty-ninth aspect of the present invention relates to an exercise intensity detecting device, characterized in that the respiratory component extracting means is provided with a frequency analyzer for performing frequency analysis on the pulse waveform, and generating analyzed pulse wave data; a pulse wave component remover for removing pulse wave components from the analyzed pulse wave data; a fundamental frequency table for storing relationships associated in advance between the fundamental frequencies of body motion and the fundamental frequencies of respiration; a frequency specifying member for referencing the fundamental frequency table, and then specifying the respiratory fundamental frequency and the body motion fundamental frequency from among the analyzed data; and an extractor for calculating each of the higher harmonic wave frequencies based on the respiratory fundamental frequencies specified by the frequency specifying member, and extracting the respiratory component.

The fiftieth aspect of the present invention relates to an exercise intensity detecting device, characterized in that the exercise intensity generating means calculates the distortion factor in the respiratory waveform based on the level of the spectrum corresponding to the fundamental component of the respiratory component and the level of the spectrum corresponding to the higher harmonic wave components thereof.

The fifty-first aspect of the present invention relates to an exercise intensity detecting device, characterized in that the exercise intensity generating means determines the ratio of the level of the spectrum corresponding to the fundamental component of the respiratory component, and the level of the spectrum corresponding to the third higher harmonic wave components, and calculates the exercise intensity based on this proportion.

The fifty-second aspect of the present invention relates to an exercise intensity detecting device, characterized in that it comprises a notifying means for informing the subject of the exercise intensity generated by the exercise intensity generating means.

The fifty-third aspect of the present invention relates to an exercise intensity detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which the body motion components are removed from the pulse waveform, and a pulse waveform from which body motion components have been removed is generated; a fifth step in which respiratory components are extracted based on the pulse waveform from which body motion components have been removed; and a sixth step in which the exercise intensity is calculated based on the extracted respiratory component.

The fifty-forth aspect of the present invention relates to an exercise intensity detecting method, characterized in that the fifth step is provided with a step in which wavelet transformation is performed on the pulse waveform from which body motion components have been removed, and analyzed pulse wave data from which body motion components have been removed is generated; and a step in which respiratory wave data is generated by removing frequency components corresponding to the pulse wave components from the analyzed pulse wave data from which body motion components have been removed, and a respiratory waveform is generated as the respiratory component by performing inverse wavelet transformation on the analyzed respiratory waveform data.

The fifty-fifth aspect of the present invention relates to an exercise intensity detecting method, characterized in that, in the sixth step, the exercise intensity is calculated based on the ratio of the frequency components obtained by performing frequency analysis on the extracted respiratory components.

The fifty-sixth aspect of the present invention relates to an exercise intensity detecting device, characterized in that, in the fifth step, a respiratory waveform is extracted as the respiratory component from the pulse waveform from which body motion components have been removed, and, in the sixth step, the duty ratio for the extracted respiratory waveform is detected, and the exercise intensity is generated based on the duty ratio.

The fifty-seventh aspect of the present invention relates to an exercise intensity detecting method, characterized in that it comprises a first step in which a pulse waveform is detected at a detection site on the body; a second step in which the frequency spectrum of the pulse waveform is analyzed; a third step in which the body motion waveforms expressing motion of the body are detected; a forth step in which the frequency spectrum of the body motion waveform is analyzed; a fifth step in which a frequency spectrum that is identical to the frequency spectrum of the analyzed body motion waveform is removed from the frequency spectrum of the analyzed pulse waveform, and a spectrum from which body motion components have been removed in generated; a sixth step in which the frequency spectrum corresponding to the fundamental component of the respiratory component is extracted from among the spectrums from which body motion components have been removed; and a seventh step in which the exercise intensity is calculated based on the level of the frequency spectrum corresponding to the fundamental component of the respiratory component and the level of the frequency spectrum corresponding to the higher harmonic wave components thereof.

The fifty-eighth aspect of the present invention relates to an exercise intensity detecting method, characterized in that it comprises a first step in which a pulse waveform is detected at a detection site on the body; a second step in which respiratory components are extracted from the pulse waveform; and a third step in which exercise intensity is calculated based on the extracted respiratory components.

The fifty-ninth aspect of the present invention relates to an exercise intensity detecting method, characterized in that the third step is provided with a step in which preassociated relationships between the fundamental frequency of body motion and the fundamental frequency of respiration are stored; a step in which frequency analysis is performed on the pulse waveform and analyzed pulse wave data is generated; a step in which the pulse wave components are removed from the analyzed pulse wave data; a step in which the fundamental frequency of body motion and the fundamental frequency of respiration are specified from among the analyzed data by referencing the contents of memory; and a step in which the higher harmonic wave frequencies are calculated based on the specified fundamental frequency of respiration, and the respiratory components are extracted.

Next, the following inventions relate to devices or methods for measuring stroke volume per beat or cardiac output.

The sixtieth aspect of the present invention relates to an exercise intensity detecting device, characterized in that it comprises a pulse wave detecting means for detecting a pulse waveform at a detection site on the body; a body motion detecting means for detecting body motion waveforms expressing motion of the body; a body motion component removing means for generating the body motion components in the pulse waveform based on the body motion waveform, removing the body motion components from the pulse waveform, and generating a pulse waveform from which body motion components have been removed; a heart rate detecting means for detecting the body's heart rate; an ejection duration detecting means for detecting the ejection duration of the heart based on the pulse waveform from which body motion components have been removed; and a cardiac output calculating means for calculating cardiac output based on the heart rate and the ejection duration of the heart.

The sixty-first aspect of the present invention relates to an exercise intensity detecting device, characterized in that it comprises a pulse wave detecting means for detecting a pulse waveform at a detection site on the body; a body motion detecting means for detecting body motion waveforms expressing motion of the body; a body motion component removing means for generating the body motion components in the pulse waveform based on the body motion waveform, removing the body motion components from the pulse waveform, and generating a pulse waveform from which body motion components have been removed; a heart rate detecting means for detecting the body's heart rate; an ejection duration detecting means for detecting the ejection duration of the heart based on the pulse waveform from which body motion components have been removed; and a cardiac output calculating means for calculating cardiac output based on the heart rate and the pulse waveform from which body motion components have been removed during the ejection duration of the heart.

The sixty-second aspect of the present invention relates to an exercise intensity detecting device, characterized in that it comprises a determining means for determining whether or not body motion is present based on the body motion waveform detected by the body motion detecting means; wherein the body motion component removing means suspends the operation to remove body motion components when the result of the determination by the determining means indicates that body motion is not present, and outputs the pulse waveform in place of a pulse waveform from which body motion components have been removed.

The sixty-third aspect of the present invention relates to an exercise intensity detecting device, characterized in that the heart rate detecting means obtains the heart rate based on the periodicity of an electrocardiogram of the heart or the periodicity of the pulse waveform from which body motion components have been removed.

The sixty-forth aspect of the present invention relates to an exercise intensity detecting device, characterized in that the heart rate detecting means performs frequency analysis on the electrocardiogram of the heart or the pulse waveform from which body motion components have been removed, and determines the heart rate based on the results of this analysis.

The sixty-fifth aspect of the present invention relates to an exercise intensity detecting device, characterized in that the ejection duration detecting means detects each peak in the pulse waveform from which body motion components have been removed, and detects the ejection duration by specifying the negative or minimum peaks which are the first or second peaks to appear after a maximum peak.

The sixty-sixth aspect of the present invention relates to an exercise intensity detecting device, characterized in that it comprises a pulse wave detecting means for detecting a pulse waveform at a detection site on the body; a body motion detecting means for detecting body motion waveforms expressing motion of the body; a body motion component removing means for generating the body motion components in the pulse waveform based on the body motion waveform, removing the body motion components from the pulse waveform, and generating a pulse waveform from which body motion components have been removed; a wavelet transforming means for performing wavelet transformation on the pulse waveform from which body motion components have been removed, and generating in each frequency region analyzed pulse wave data from which body motion components have been removed; a heart rate detecting means for detecting the heart rate based on analyzed pulse wave data from which body motion components have been removed; an ejection duration detecting means for detecting the ejection duration of the heart based on analyzed pulse wave data from which body motion components have been removed; and a cardiac output calculating means for calculating cardiac output based on the heart rate and the pulse waveform from which body motion components have been removed during the ejection duration of the heart.

The sixty-seventh aspect of the present invention relates to an exercise intensity detecting device, characterized in that it comprises a pulse wave detecting means for detecting a pulse waveform at a detection site on the body; a body motion detecting means for detecting body motion waveforms expressing motion of the body; a body motion component removing means for generating the body motion components in the pulse waveform based on the body motion waveform, removing the body motion components from the pulse waveform, and generating a pulse waveform from which body motion components have been removed; a body motion component removing means for performing wavelet transformation on the pulse waveform from which body motion components have been removed, and generating in each frequency region analyzed pulse wave data from which body motion components have been removed; a frequency correcting means for correcting analyzed pulse wave data from which body motion components have been removed by normalizing the power at each frequency based on each corresponding bandwidth in the frequency region, and generating corrected pulse wave data; a heart rate detecting means for detecting the heart rate based on the corrected pulse wave data; an ejection duration detecting means for detecting the ejection duration of the heart based on corrected pulse wave data; and a cardiac output calculating means for calculating cardiac output based on the heart rate and the pulse waveform from which body motion components have been removed during the ejection duration of the heart.

The sixty-eighth aspect of the present invention relates to an exercise intensity detecting device, characterized in that it comprises a pulse wave detecting means for detecting a pulse waveform at a detection site on the body; a first wavelet transforming means for performing wavelet transformation on the pulse waveform, and generating analyzed pulse wave data in each frequency region; a body motion detecting means for detecting body motion waveforms expressing motion of the body; a second wavelet transforming means for performing wavelet transformation on the body motion waveform, and generating analyzed body motion data in each frequency region; a body motion component removing means for subtracting the analyzed body motion data from the analyzed pulse wave data, and generating analyzed pulse wave data from which body motion components have been removed; a heart rate detecting means for detecting the heart rate based on analyzed pulse wave data from which body motion components have been removed; an ejection duration detecting means for detecting the ejection duration of the heart based on analyzed pulse wave data from which body motion components have been removed; and a cardiac output calculating means for calculating cardiac output based on the heart rate and the result obtained by adding the analyzed pulse wave data from which body motion components have been removed over each frequency region during the ejection duration of the heart.

The sixty-ninth aspect of the present invention relates to an exercise intensity detecting device, characterized in that it comprises a pulse wave detecting means for detecting a pulse waveform at a detection site on the body; a first wavelet transforming means for performing wavelet transformation on the pulse waveform, and generating analyzed pulse wave data in each frequency region; a first frequency correcting means for correcting analyzed pulse wave data by normalizing the power at each frequency based on each corresponding bandwidth in the frequency regions, and generating corrected analyzed pulse wave data; a body motion detecting means for detecting body motion waveforms expressing the motion of the body; a second wavelet transforming means for performing wavelet transformation on the body motion waveform, and generating analyzed body motion data in each frequency region; a second frequency correcting means for correcting analyzed body motion data by normalizing the power at each frequency based on each corresponding bandwidth in the frequency regions, and generating corrected analyzed body motion data; a body motion component removing means for subtracting the corrected analyzed body motion data from the corrected analyzed pulse wave data, and generating analyzed pulse wave data from which body motion components have been removed; a heart rate detecting means for detecting the heart rate based on analyzed pulse wave data from which body motion components have been removed; an ejection duration detecting means for detecting the ejection duration of the heart based on analyzed pulse wave data from which body motion components have been removed; and a cardiac output calculating means for calculating cardiac output based on the heart rate and the result obtained by adding the analyzed pulse wave data from which body motion components have been removed in each frequency region during the ejection duration of the heart.

The seventieth aspect of the present invention relates to an exercise intensity detecting device, characterized in that the first and second wavelet transforming means perform wavelet transformation in synchronization.

The seventy-first aspect of the present invention relates to an exercise intensity detecting device, characterized in that it comprises a pulse wave detecting means for detecting a pulse waveform at a detection site on the body; a wavelet transforming means for performing wavelet transformation on the pulse waveform detected by the pulse wave detecting means, and generating analyzed pulse wave data in each frequency region; a body motion component removing means for removing frequency components corresponding to body motion defined in advance from the analyzed pulse wave data, and generating analyzed pulse wave data from which body motion components have been removed; a heart rate detecting means for detecting the heart rate based on analyzed pulse wave data from which body motion components have been removed; an ejection duration detecting means for detecting the ejection duration of the heart based on analyzed pulse wave data from which body motion components have been removed; and a cardiac output calculating means for calculating cardiac output based on the heart rate and the result obtained by adding the analyzed pulse wave data from which body motion components have been removed in each frequency region during the ejection duration of the heart.

The seventy-second aspect of the present invention relates to an exercise intensity detecting device, characterized in that it comprises a pulse wave detecting means for detecting a pulse waveform at a detection site on the body; a wavelet transforming means for performing wavelet transformation on the pulse waveform detected by the pulse wave detecting means, and generating analyzed pulse wave data in each frequency region; a body motion component removing means for removing frequency components corresponding to body motion defined in advance from among the analyzed pulse wave data, and generating analyzed pulse wave data from which body motion components have been removed; a frequency correcting means for correcting analyzed pulse wave data from which body motion components have been removed by normalizing the power at each frequency based on each corresponding bandwidth in the frequency regions, and generating corrected analyzed pulse wave data; a heart rate detecting means for detecting the heart rate based on corrected analyzed pulse wave data; an ejection duration detecting means for detecting the ejection duration of the heart based on corrected analyzed pulse wave data; and a cardiac output calculating means for calculating cardiac output based on the heart rate and the result obtained by adding the analyzed pulse wave data from which body motion components have been removed in each frequency region during the ejection duration of the heart.

The seventy-third aspect of the present invention relates to an exercise intensity detecting device, characterized in that it comprises a pulse wave detecting means for detecting a pulse waveform at a detection site on the body; a wavelet transforming means for performing wavelet transformation on the pulse waveform detected by the pulse wave detecting means, and generating analyzed pulse wave data in each frequency region; a body motion component removing means for removing frequency components corresponding to body motion defined in advance from the analyzed pulse wave data, and generating analyzed pulse wave data from which body motion components have been removed; an inverse wavelet transforming means for performing inverse wavelet transformation on the analyzed pulse wave data from which body motion components have been removed, and generating a pulse waveform from which body motion components have been removed; a heart rate detecting means for detecting the heart rate based on the pulse waveform from which body motion components have been removed; an ejection duration detecting means for detecting the ejection duration of the heart based on the pulse waveform from which body motion components have been removed; and a cardiac output calculating means for calculating cardiac output based on the heart rate and the pulse waveform from which body motion components have been removed during the ejection duration of the heart.

The seventy-fourth aspect of the present invention relates to an exercise intensity detecting device, characterized in that the cardiac output calculating means calculates the area corresponding to the ejection duration of the heart under the pulse waveform from which body motion components have been removed, by integrating the pulse waveform from which body motion components have been removed during the ejection duration of the heart, and calculates the cardiac output based on this area.

The seventy-fifth aspect of the present invention relates to an exercise intensity detecting device, characterized in that the cardiac output calculating means calculates the area corresponding to the ejection duration of the heart under the pulse waveform from which body motion components have been removed, based on each peak value in the pulse waveform from which body motion components have been removed during the ejection duration of the heart, and calculates the cardiac output based on this area.

The seventy-sixth aspect of the present invention relates to an exercise intensity detecting device, characterized in that it comprises a pulse wave detecting means for detecting a pulse waveform at a detection site on the body; a heart rate detecting means for detecting the body's heart rate; an ejection duration detecting means for detecting the ejection duration of the heart based on the pulse waveform; a recording means for recording in advance the stroke volume per beat corresponding to the heart rate and the ejection duration of the heart; and a cardiac output calculating means for reading out the stroke volume per beat from the recording means based on the ejection duration of the heart detected by the ejection duration detecting means and the heart rate detected by the heart rate detecting means, and calculating the cardiac output by multiplying the stroke volume per beat and the heart rate.

The seventy-seventh aspect of the present invention relates to an exercise intensity detecting device, characterized in that it comprises a pulse wave detecting means for detecting a pulse waveform at a detection site on the body; a heart rate detecting means for detecting the heart rate; an ejection duration detecting means for detecting the ejection duration of the heart based on the pulse waveform; and a cardiac output calculating means for calculating the area under the pulse waveform corresponding to the ejection duration of the heart based on each peak value of the pulse waveform during the ejection duration of the heart, and calculating the cardiac output based on this area.

The seventy-eighth aspect of the present invention relates to an exercise intensity detecting device, characterized in that it comprises a recording means for recording as a correction coefficient the ratio between a reference cardiac output measured by a reference device and the cardiac output measured by the cardiac output calculating means; and a multiplying means for multiplying the correction coefficient read out from the recording means and the cardiac output calculated by the cardiac output calculating means, and outputting the multiplied result as the cardiac output.

The seventy-ninth aspect of the present invention relates to a cardiac function diagnosing device provided with a cardiac output detecting device, characterized in that it comprises a notifying means for notifying the subject of the cardiac output detected by the cardiac output detecting device.

The eightieth aspect of the present invention relates to a cardiac function diagnosing device provided with a cardiac output detecting device, characterized in that the cardiac function diagnosing device is provided with an evaluating means for comparing the cardiac output detected by the cardiac output detecting device and various threshold values, and generating an evaluation index; and a notifying means for notifying the subject of the evaluation index generated by the evaluating means.

The eighty-first aspect of the present invention is a cardiac function diagnosing device provided with a cardiac output detecting device, characterized in that the evaluating means is provided with a changing member for changing the threshold values in accordance with the heart rate detected by the heart rate detecting means.

The eighty-second aspect of the present invention is a cardiac function diagnosing device provided with a cardiac output detecting device, characterized in that the evaluating means is provided with an inputting member for inputting parameters for calculating the surface area of the subject's body; a calculator for calculating the body surface area based on the input parameters; and a changing member for changing each of the threshold values based on the calculated body surface area.

The eighty-third aspect of the present invention relates to a cardiac output detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which body motion components are removed from the pulse waveform and a pulse waveform from which body motion components have been removed is generated; a fifth step in which the heart rate is detected; a sixth step in which the ejection duration of the heart is detected based on the pulse waveform from which body motion components have been removed; and a seventh step in which cardiac output is calculated based on the ejection duration of the heart and the heart rate.

The eighty-fourth aspect of the present invention is a cardiac output detecting method, characterized in that it comprises a step in which cardiac output is calculated based on the heart rate and the pulse waveform from which body motion components have been removed during the ejection duration of the heart, in place of the seventh step.

The eighty-fifth aspect of the present invention is a cardiac output detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which body motion components are removed from the pulse waveform, and a pulse waveform from which body motion components have been removed is generated; a fifth step in which wavelet transformation is performed on the pulse waveform from which body motion components have been removed, and analyzed pulse wave data from which body motion components have been removed is generated in each frequency region; a sixth step in which the heart rate is detected based on analyzed pulse wave data from which body motion components have been removed; a seventh step in which the ejection duration of the heart is detected based on the analyzed pulse wave data from which body motion components have been removed; and an eighth step in which cardiac output is calculated based on the heart rate and the pulse waveform from which body motion components have been removed during the ejection duration of the heart.

The eighty-sixth aspect of the present invention is a cardiac output detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which body motion components are removed from the pulse waveform, and a pulse waveform from which body motion components have been removed is generated; a fifth step in which wavelet transformation is performed on the pulse waveform from which body motion components have been removed, and analyzed pulse wave data from which body motion components have been removed is generated in each frequency; a sixth step in which analyzed pulse wave data from which body motion components have been removed is corrected by normalizing the power at each frequency based on each corresponding bandwidth in the frequency regions, and corrected pulse wave data is generated; a seventh step in which the heart rate is detected based on corrected pulse wave data; an eighth step in which the ejection duration of the heart is detected based on the corrected pulse wave data; and an eighth step in which cardiac output is calculated based on the heart rate and the pulse waveform from which body motion components have been removed during the ejection duration of the heart.

The eighty-seventh aspect of the present invention relates to a cardiac output detecting method, characterized in that it comprises a first step in which a pulse waveform is detected at a detection site on the body; a second step in which wavelet transformation is performed on the pulse waveform, and analyzed pulse wave data is generated in each frequency region; a third step in which body motion waveforms expressing motion of the body are detected; a fourth step in which wavelet transformation is performed on the body motion waveform, and analyzed body motion data is generated in each frequency region; a fifth step in which analyzed body motion data is subtracted from analyzed pulse wave data, and analyzed pulse wave data from which body motion components have been removed is generated; a sixth step in which the heart rate is detected based on the analyzed pulse wave data from which body motion components have been removed; a seventh step in which the ejection duration of the heart is detected based on the analyzed pulse wave data from which body motion components have been removed; and an eighth step in which cardiac output is calculated based on heart rate and the result obtained by adding the analyzed pulse wave data from which body motion components have been removed in each frequency region during the ejection duration of the heart.

The eighty-eighth aspect of the present invention relates to a cardiac output detecting method, characterized in that it comprises a first step in which a pulse waveform is detected at a detection site on the body; a second step in which wavelet transformation is performed on the pulse waveform, and analyzed pulse wave data is generated in each frequency region; a third step in which analyzed pulse wave data is corrected by normalizing the power at each frequency based on each corresponding bandwidth in the frequency regions, and corrected analyzed pulse wave data is generated; a fourth step in which body motion waveforms expressing motion of the body are detected; a fifth step in which wavelet transformation is performed on the body motion waveform, and analyzed body motion data is generated in each frequency region; a sixth step in which analyzed body motion data is corrected by normalizing the power at each frequency based on each corresponding bandwidth in the frequency regions, and corrected analyzed body motion data is generated; a seventh step in which corrected analyzed body motion data is subtracted from corrected analyzed pulse wave data, and analyzed pulse wave data from which body motion components have been removed is generated; an eighth step in which the heart rate is detected based on the analyzed pulse wave data from which body motion components have been removed; a ninth step in which the ejection duration of the heart is detected based on the analyzed pulse wave data from which body motion components have been removed; and a tenth step in which cardiac output is calculated based on the heart rate and the result obtained by adding the analyzed pulse wave data from which body motion components have been removed in each frequency region during the ejection duration of the heart.

The eighty-ninth aspect of the present invention is a cardiac output detecting method, characterized in that it comprises a first step in which a pulse waveform is detected at a detection site on the body; a second step in which wavelet transformation is performed on the pulse waveform, and analyzed pulse wave data in each frequency region is generated; a third step in which frequency components corresponding to body motion defined in advance are removed from the analyzed pulse wave data, and analyzed pulse wave data from which body motion components have been removed is generated; a fourth step in which the heart rate is detected based on analyzed pulse wave data from which body motion components have been removed; a fifth step in which the ejection duration of the heart is detected based on the analyzed pulse wave data from which body motion components have been removed; and a sixth step in which cardiac output is calculated based on the heart rate and the result obtained by adding the analyzed pulse wave data from which body motion components have been removed in each frequency region during the ejection duration of the heart.

The ninetieth aspect of the present invention is a cardiac output detecting method, characterized in that it comprises a first step in which a pulse waveform is detected at a detection site on the body; a second step in which wavelet transformation is performed on the pulse waveform, and analyzed pulse wave data in each frequency region is generated; a third step in which frequency components corresponding to body motion defined in advance are removed from the analyzed pulse wave data, and analyzed pulse wave data from which body motion components have been removed is generated; a fourth step in which analyzed pulse wave data from which body motion components have been removed is corrected by normalizing the power at each frequency based on each corresponding bandwidth in the frequency regions, and corrected analyzed pulse wave data is generated; a fifth step in which the heart rate is detected based on the corrected analyzed pulse wave data; a sixth step in which the ejection duration of the heart is detected based on the corrected analyzed pulse wave data; and a seventh step in which the cardiac output is calculated based on the heart rate and the result obtained by adding the analyzed pulse wave data from which body motion components have been removed in each frequency region during the ejection duration of the heart.

The ninety-first aspect of the present invention is a cardiac output detecting method, characterized in that it comprises a first step in which a pulse waveform is detected at a detection site on the body; a second step in which wavelet transformation is performed on the pulse waveform to generate analyzed pulse wave data in each frequency region; a third step in which frequency components corresponding to body motion defined in advance are removed from the analyzed pulse wave data, and analyzed pulse wave data from which body motion components have been removed is generated; a fourth step in which inverse wavelet transformation is performed on the analyzed pulse wave data from which body motion components have been removed, and a pulse waveform from which body motion components have been removed is generated; a fifth step in which the heart rate is detected based on the pulse waveform from which body motion components have been removed; a sixth step in which the ejection duration of the heart is detected based on the pulse waveform from which body motion components have been removed; and a seventh step in which the cardiac output is calculated based on heart rate and the pulse waveform from which body motion components have been removed during the ejection duration of the heart.

The ninety-second aspect of the present invention is a cardiac output detecting method, characterized in that it comprises a first step in which a pulse waveform is detected at a detection site on the body; a second step in which the heart rate is detected; a third step in which the ejection duration of the heart is detected based on the pulse waveform; a fourth step in which a stroke volume per beat associated with the ejection duration of the heart and heart rate is recorded in advance; a fifth step in which the stroke volume per beat recorded in the fourth step is read out from the memory contents based on the detected ejection duration and the detected heart rate; and a sixth step in which the cardiac output is calculated by multiplying the stroke volume per beat and the heart rate.

The ninety-third aspect of the present invention is a cardiac output detecting method, characterized in that it comprises a first step in which a pulse waveform is detected at a detection site on the body; a second step in which the heart rate is detected; a third step in which the ejection duration of the heart is detected based on the pulse waveform; a fourth step in which the area under the pulse waveform which corresponds to the ejection duration of the heart is calculated based on each of the peak values of the pulse waveform during the ejection duration of the heart; and a fifth step in which cardiac output is calculated based on the results of calculations in the fourth step.

The ninety-fourth aspect of the present invention is a cardiac function measuring method for measuring cardiac function based on the cardiac output detected by the cardiac output detecting method, characterized in that it comprises a step in which the cardiac output is compared with each of the threshold values and an evaluation index is generated, and a step in which the subject is informed of the evaluation index.

The ninety-fifth aspect of the present invention relates to a stroke-volume-per-beat detecting device, characterized in that it comprises a pulse wave detecting means for detecting a pulse waveform at a detection site on the body; a body motion detecting means for detecting body motion waveforms expressing the motion of the body; a body motion component removing means for generating the body motion components in the pulse waveform based on the body motion waveform, removing the body motion components from the pulse waveform, and generating a pulse waveform from which body motion components have been removed; an ejection duration detecting means for detecting the ejection duration of the heart based on the pulse waveform from which body motion components have been removed; a heart beat interval calculating means for calculating the heart beat interval based on the pulse waveform from which body motion components have been removed; and a stroke-volume-per-beat calculating means for calculating the stroke volume per beat based on the ejection duration of the heart and the heart beat interval.

The ninety-sixth aspect of the present invention relates to a stroke-volume-per-beat detecting device, characterized in that it comprises a pulse wave detecting means for detecting a pulse waveform at a detection site on the body; a body motion detecting means for detecting body motion waveforms expressing the motion of the body; a body motion component removing means for generating the body motion components in the pulse waveform based on the body motion waveform, removing the body motion components from the pulse waveform, and generating a pulse waveform from which body motion components have been removed; an ejection duration detecting means for detecting the ejection duration of the heart based on the pulse waveform from which body motion components have been removed; and a stroke-volume-per-beat calculating means for calculating the stroke volume per beat based on the pulse waveform from which body motion components have been removed during the ejection duration of the heart.

The ninety-seventh aspect of the present invention relates to a stroke-volume-per-beat detecting device, characterized in that it comprises a determining means for determining whether or not body motion is present based on the body motion waveform detected by the body motion detecting means; wherein the body motion component removing means suspends the operation to remove body motion components when the results of the determination by the determining means indicate that body motion is not present, and outputs the pulse waveform in place of a pulse waveform from which body motion components have been removed.

The ninety-eighth aspect of the present invention relates to a stroke-volume-per-beat detecting device, characterized in that the ejection duration detecting means detects each peak in the pulse waveform from which body motion components have been removed, and detects the ejection duration by specifying the negative or minimum peaks which are the first or second peaks to appear after a maximum peak.

The ninety-ninth aspect of the present invention relates to a stroke-volume-per-beat detecting device, characterized in that it comprises a pulse wave detecting means for detecting a pulse waveform at a detection site on the body; a body motion detecting means for detecting body motion waveforms expressing the motion of the body; a body motion component removing means for generating the body motion components in the pulse waveform based on the body motion waveform, removing the body motion components from the pulse waveform, and generating a pulse waveform from which body motion components have been removed; a wavelet transforming means for performing wavelet transformation on the pulse waveform from which body motion components have been removed, and generating in each frequency region analyzed pulse wave data from which body motion components have been removed; an ejection duration detecting means for detecting the ejection duration of the heart based on the analyzed pulse wave data from which body motion components have been removed; and a stroke-volume-per-beat calculating means for calculating the stroke volume per beat based on the pulse waveform from which body motion components have been removed during the ejection duration of the heart.

The one hundredth aspect of the present invention relates to a stroke-volume-per-beat detecting means, characterized in that it comprises a pulse wave detecting means for detecting a pulse waveform at a detection site on the body; a body motion detecting means for detecting body motion waveforms expressing the motion of the body; a body motion component removing means for generating the body motion components in the pulse waveform based on the body motion waveform, removing the body motion components from the pulse waveform, and generating a pulse waveform from which body motion components have been removed; a body motion component removing means for performing wavelet transformation on the pulse waveform from which body motion components have been removed, and generating in each frequency region analyzed pulse wave data from which body motion components have been removed; a frequency correcting means for correcting analyzed pulse wave data from which body motion components have been removed by normalizing the power at each frequency based on each corresponding bandwidth in the frequency regions, and generating corrected pulse wave data; an ejection duration detecting means for detecting the ejection duration of the heart based on corrected pulse wave data; and a stroke-volume-per-beat calculating means for calculating the stroke volume per beat based on the pulse waveform from which body motion components have been removed during the ejection duration of the heart.

The one hundred-first aspect of the present invention relates to a stroke-volume-per-beat detecting device, characterized in that it comprises a pulse wave detecting means for detecting a pulse waveform at a detection site on the body; a first wavelet transforming means for performing wavelet transformation on the pulse waveform, and generating analyzed pulse wave data in each frequency region; a body motion detecting means for detecting body motion waveforms expressing the motion of the body; a second wavelet transforming means for performing wavelet transformation on the body motion waveform, and generating analyzed body motion data in each frequency region; a body motion component removing means for subtracting analyzed body motion data from the analyzed pulse wave data, and generating analyzed pulse wave data from which body motion components have been removed; an ejection duration detecting means for detecting the ejection duration of the heart based on analyzed pulse wave data from which body motion components have been removed; and a stroke-volume-per-beat calculating means for calculating the stroke volume per beat based on the result obtained by adding the analyzed pulse wave data from which body motion components have been removed in each frequency region during the ejection duration of the heart.

The one hundred-second aspect of the present invention relates to a stroke-volume-per-beat detecting device, characterized in that it comprises a pulse wave detecting means for detecting a pulse waveform at a detection site on the body; a first wavelet transforming means for performing wavelet transformation on the pulse waveform, and generating analyzed pulse wave data in each frequency region; a first frequency correcting means for correcting analyzed pulse wave data by normalizing the power at each frequency based on each corresponding bandwidth in the frequency regions, and generating corrected analyzed pulse wave data; a body motion detecting means for detecting body motion waveforms expressing the motion of the body; a second wavelet transforming means for performing wavelet transformation on the body motion waveform, and generating analyzed body motion data in each frequency region; a second frequency correcting means for correcting analyzed body motion data by normalizing the power at each frequency based on each corresponding bandwidth in the frequency regions, and generating corrected analyzed body motion data; a body motion component removing means for subtracting the corrected analyzed body motion data from the corrected analyzed pulse wave data, and generating analyzed pulse wave data from which body motion components have been removed; an ejection duration detecting means for detecting the ejection duration of the heart based on analyzed pulse wave data from which body motion components have been removed; and a stroke-volume-per-beat calculating means for calculating the stroke volume per beat based on the result obtained by adding the analyzed pulse wave data from which body motion components have been removed in each frequency region during the ejection duration of the heart.

The one hundred-third aspect of the present invention relates to a stroke-volume-per-beat detecting device, characterized in that the first and second wavelet transforming means perform wavelet transformation in synchronization.

The one hundred-forth aspect of the present invention relates to a stroke-volume-per-beat detecting device, characterized in that it comprises a pulse wave detecting means for detecting a pulse waveform at a detection site on the body; a wavelet transforming means for performing wavelet transformation on the pulse waveform detected by the pulse wave detecting means, and generating analyzed pulse wave data in each frequency region; a body motion component removing means for removing frequency components corresponding to body motion defined in advance from the analyzed pulse wave data, and generating analyzed pulse wave data from which body motion components have been removed; an ejection duration detecting means for detecting the ejection duration of the heart based on the analyzed pulse wave data from which body motion components have been removed; and a stroke-volume-per-beat calculating means for calculating stroke volume per beat based on the result obtained by adding the analyzed pulse wave data from which body motion components have been removed in each frequency regions during the ejection duration of the heart.

The one hundred-fifth aspect of the present invention relates to a stroke-volume-per-beat detecting means, characterized in that it comprises a pulse wave detecting means for detecting a pulse waveform at a detection site on the body; a wavelet transforming means for performing wavelet transformation on the pulse waveform detected by the pulse wave detecting means, and generating analyzed pulse wave data in each frequency region; a body motion component removing means for removing frequency components corresponding to body motion defined in advance from the analyzed pulse wave data, and generating analyzed pulse wave data from which body motion components have been removed; a frequency correcting means for correcting analyzed pulse wave data from which body motion components have been removed by normalizing the power at each frequency based on each corresponding bandwidth in the frequency regions, and generating corrected analyzed pulse wave data; an ejection duration detecting means for detecting the ejection duration of the heart based on corrected analyzed pulse wave data; and a stroke-volume-per-beat calculating means for calculating stroke volume per beat based on the result obtained by adding the corrected analyzed pulse wave data in each frequency region during the ejection duration of the heart.

The one hundred-sixth aspect of the present invention relates to a stroke-volume-per-beat detecting device, characterized in that it comprises a pulse wave detecting means for detecting a pulse waveform at a detection site on the body; a wavelet transforming means for performing wavelet transformation on the pulse waveform detected by the pulse wave detecting means, and generating analyzed pulse wave data in each frequency region; a body motion component removing means for removing the frequency component corresponding to body motion defined in advance from the analyzed pulse wave data, and generating analyzed pulse wave data from which body motion components have been removed; an inverse wavelet transforming means for performing inverse wavelet transformation on the analyzed pulse wave data from which body motion components have been removed, and generating a pulse waveform from which body motion components have been removed; an ejection duration detecting means for detecting the ejection duration of the heart based on the pulse waveform from which body motion components have been removed; and a stroke-volume-per-beat calculating means for calculating the stroke volume per beat based on the pulse waveform from which body motion components have been removed during the ejection duration of the heart.

The one hundred-seventh aspect of the present invention relates to a stroke-volume-per-beat detecting device, characterized in that the stroke-volume-per-beat calculating means calculates the area corresponding to the ejection duration of the heart under the pulse waveform from which body motion components have been removed, by integrating the pulse waveform from which body motion components have been removed during the ejection duration of the heart, and calculates the stroke volume per beat based on this area.

The one hundred-eighth aspect of the present invention relates to a stroke-volume-per-beat detecting device, characterized in that the stroke-volume-per-beat calculating means calculates the area corresponding to the ejection duration of the heart under the pulse waveform from which body motion components have been removed, based on each peak value in the pulse waveform from which body motion components have been removed during the ejection duration of the heart, and calculates the stroke volume per beat based on this area.

The one hundred-ninth aspect of the present invention relates to a stroke-volume-per-beat detecting device, characterized in that it comprises a pulse wave detecting means for detecting a pulse waveform at a detection site on the body; a heart rate detecting means for detecting the body's heart rate; an ejection duration detecting means for detecting the ejection duration of the heart based on the pulse waveform; a recording means for recording in advance a stroke volume per beat associated with the body's heart rate and the ejection duration of the heart; and a stroke-volume-per-beat calculating means for calculating the stroke volume per beat by reading out the stroke volume per beat from the recording means based on the ejection duration of the heart detected by the ejection duration detecting means and the heart rate detected by the heart rate detecting means.

The one hundred-tenth aspect of the present invention is characterized in that it comprises a pulse wave detecting means for detecting a pulse waveform at a detection site on the body; a heart rate detecting means for detecting the heart rate; an ejection duration detecting means for detecting the ejection duration of the heart based on the pulse waveform; and a stroke-volume-per-beat calculating means for calculating the area under the pulse waveform corresponding to the ejection duration of the heart, based on each of the peak values of the pulse waveform during the ejection duration of the heart, and calculating the stroke volume per beat based on this area.

The one hundred-eleventh aspect of the present invention relates to a stroke-volume-per-beat detecting device, characterized in that it comprises a correction coefficient calculating means for calculating the ratio between a reference stroke volume per beat measured by a reference device and the stroke volume per beat measured by the stroke-volume-per-beat calculating means, as a correction coefficient; a recording means for recording the correction coefficient is association with the heart rate; and a multiplying means for reading out the correction coefficient in accordance with the heart rate from the recording means, multiplying the read out correction coefficient with the stroke volume per beat calculated by the stroke-volume-per-beat calculating means, and outputting the multiplied result as the stroke volume per beat.

The one hundred-twelfth aspect of the present invention is a cardiac function diagnosing device provided with a stroke-volume-per-beat detecting device, characterized in that it comprises a notifying means for notifying the subject of the stroke volume detected by the stroke-volume-per-beat detecting device.

The one hundred-thirteenth aspect of the present invention is a cardiac function diagnosing device equipped with a stroke-volume-per-beat detecting device, characterized in that it comprises an evaluating means for comparing the stroke volume per beat detected by the stroke-volume-per-beat detecting device with various threshold values, and generating an evaluation index; and a notifying means for notifying the subject of the evaluation index generated by the evaluating means.

The one hundred-fourteenth aspect of the present invention is a cardiac function diagnosing device provided with a stroke-volume-per-beat detecting device, characterized in that it comprises a rate-of-change calculating member for calculating the rate of change in the stroke volume per beat; an evaluating means for comparing the rate of change in the stroke volume per beat with various threshold values, and generating an evaluation index; and a notifying means for notifying the subject of the evaluation index generated by the evaluating means.

The one hundred-fifteenth aspect of the present invention is a cardiac function diagnosing device provided with a stroke-volume-per-beat detecting device, characterized in that the evaluating means is provided with a changing member for changing the threshold values in accordance with the heart rate.

The one hundred-sixteenth aspect of the present invention is a cardiac function evaluating device provided with a stroke-volume-per-beat detecting device, characterized in that the evaluating means is provided with an inputting member for inputting parameters for calculating the surface area of the subject's body; a calculator for calculating the body surface area based on the input parameters; and a changing member for changing each of the threshold values based on the calculated body surface area.

The one hundred-seventeenth aspect of the present invention relates to a stroke-volume-per-beat detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which the body motion components are removed from the pulse waveform, and a pulse waveform from which body motion components have been removed is generated; a fifth step in which the ejection duration of the heart is detected based on the pulse waveform from which body motion components have been removed; a sixth step in which the pulse interval is calculated based on the pulse waveform from which body motion components have been removed; and a seventh step in which the stroke volume per beat is calculated based on the pulse interval and the ejection duration of the heart.

The one hundred-eighteenth aspect of the present invention relates to a stroke-volume-per-beat detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which the body motion components are removed from the pulse waveform, and a pulse waveform from which body motion components have been removed is generated; a fifth step in which the ejection duration of the heart is detected based on the pulse waveform from which body motion components have been removed; and a sixth step in which the stroke volume per beat is calculated based on the pulse waveform from which body motion components have been removed during the ejection duration of the heart.

The one hundred-nineteenth aspect of the present invention relates to a stroke-volume-per-beat detecting method, characterized in that it comprises a first step in which a pulse waveform is detected at a detection site on the body; a second step in which body motion waveforms expressing motion of the body are detected; a third step in which the body motion components in the pulse waveform are generated based on the body motion waveform; a forth step in which the body motion components are removed from the pulse waveform, and a pulse waveform from which body motion components have been removed is generated; a fifth step in which wavelet transformation is performed on the pulse waveform from which body motion components have been removed, and analyzed pulse wave data from which body motion components have been removed is generated in each frequency region; a sixth step in which the ejection duration of the heart is detected based on the analyzed pulse wave data from which body motion components have been removed; and a seventh step in which the stroke volume per beat is calculated based on the pulse waveform from which body motion components have been removed during the ejection duration of the heart.

The one hundred-twentieth aspect of the present invention relates to a stroke-volume-per-beat detecting method, characterized in that it comprises a first step in which a pulse waveform is detected at a detection site on the body; a second step in which body motion waveforms expressing body motion are detected; a third step in which the body motion components in the pulse waveform are generated based on the body motion waveform; a fourth step in which the body motion components are removed from the pulse waveform, and a pulse waveform from which body motion components have been removed is generated; a fifth step in which wavelet transformation is performed on the pulse waveform from which body motion components have been removed, and analyzed pulse wave data from which body motion components have been removed is generated at each frequency region; a sixth step in which analyzed pulse wave data from which body motion components have been removed is corrected by normalizing the power at each frequency based on each corresponding bandwidth in the frequency regions, and corrected pulse wave data is generated; a seventh step in which the ejection duration of the heart is detected based on the corrected analyzed pulse wave data; and an eighth step in which the stroke volume per beat is calculated based on the pulse waveform from which body motion components have been removed during the ejection duration of the heart.

The one hundred twenty-first aspect of the present invention relates to a stroke-volume-per-beat detecting method, characterized in that it comprises a first step in which a pulse waveform is detected at a detection site on the body; a second step in which wavelet transformation is performed on the pulse waveform, and the analyzed pulse wave data for each frequency region is generated; a third step in which body motion waveforms expressing body motion are detected; a fourth step in which wavelet transformation is performed on the body motion waveform, and analyzed body motion data in each frequency region is generated; a fifth step in which the analyzed body motion data is subtracted from the analyzed pulse wave data, and analyzed pulse wave data from which body motion components have been removed is generated; a sixth step in which the ejection duration of the heart is detected based on analyzed pulse wave data from which body motion components have been removed; and a seventh step in which the stroke volume per beat is calculated based on the result obtained by adding the analyzed pulse wave data from which body motion components have been removed in each frequency region during the ejection duration of the heart.

The hundred twenty-second aspect of the present invention relates to a stroke-volume-per-beat detecting method, characterized in that it comprises a first step in which a pulse waveform is detected at a detection site on the body; a second step in which wavelet transformation is performed on the pulse waveform to generate analyzed pulse wave data in each frequency region; a third step in which analyzed pulse wave data is corrected by normalizing the power at each frequency based on each corresponding bandwidth in the frequency regions, and corrected analyzed pulse wave data is generated; a fourth step in which body motion waveforms expressing body motion are detected; a fifth step in which wavelet transformation is performed on the body motion waveform, and analyzed body motion data in each frequency region is generated; a sixth step in which analyzed body motion data is corrected by normalizing the power at each frequency based on each corresponding bandwidth in the frequency regions, and corrected analyzed body motion data is generated; a seventh step in which the corrected analyzed body motion data is subtracted from the corrected analyzed pulse wave data, and analyzed pulse wave data from which body motion components have been removed is generated; an eighth step in which the ejection duration of the heart is detected based on analyzed pulse wave data from which body motion components have been removed; and a ninth step in which the stroke volume per beat is calculated based on the result obtained by adding the analyzed pulse wave data from which body motion components have been removed in each frequency region during the ejection duration of the heart.

The one hundred twenty-third aspect of the present invention relates to a stroke-volume-per-beat detecting method, characterized in that it comprises a first step in which a pulse waveform is detected at a detection site on the body; a second step in which wavelet transformation is performed on the pulse waveform, and analyzed pulse wave data is generated in each frequency region; a third step in which frequency components corresponding to body motion defined in advance are removed from the analyzed pulse wave data, and analyzed pulse wave data from which body motion components have been removed is generated; a fourth step in which the ejection duration of the heart is detected based on the analyzed pulse waveform from which body motion components have been removed; and a fifth step in which stroke volume per beat is calculated based on the result obtained by adding the analyzed pulse wave data from which body motion components have been removed in each frequency region during the ejection duration of the heart.

The one hundred twenty-forth aspect of the present invention relates to a stroke-volume-per-beat detecting method, characterized in that it comprises a first step in which a pulse waveform is detected at a detection site on the body; a second step in which wavelet transformation is performed on the pulse waveform and analyzed pulse wave data is generated in each frequency region; a third step in which frequency components corresponding to body motion defined in advance are removed from the analyzed pulse wave data, and analyzed pulse wave data from which body motion components have been removed is generated; a forth step in which analyzed pulse wave data from which body motion components have been removed is corrected by normalizing the power at each frequency based on each corresponding bandwidth in the frequency regions, and corrected analyzed pulse wave data is generated; a fifth step in which the ejection duration is detected based on corrected analyzed pulse wave data; and a sixth step in which stroke volume per beat is calculated based on the result obtained by adding corrected analyzed pulse wave data in each frequency region during the ejection duration of the heart.

The one hundred twenty-fifth aspect of the present invention relates to a stroke-volume-per-beat detecting method, characterized in that it comprises a first step in which a pulse waveform is detected at a detection site on the body; a second step in which wavelet transformation is performed on the pulse waveform and analyzed pulse wave data is generated in each frequency region; a third step in which frequency components corresponding to body motion defined in advance are removed from the analyzed pulse wave data, and analyzed pulse wave data from which body motion components have been removed is generated; a forth step in which inverse wavelet transformation is performed on analyzed pulse wave data from which body motion components have been removed, and a pulse waveform from which body motion components have been removed is generated; a fifth step in which the ejection duration of the heart is detected based on the pulse waveform from which body motion components have been removed; and a sixth step in which stroke volume per beat is calculated based on the pulse waveform from which body motion components have been removed during the ejection duration of the heart.

The one hundred twenty-sixth aspect of the present invention relates to a stroke-volume-per-beat detecting method, characterized in that it comprises a first step in which a pulse waveform is detected at a detection site on the body; a second step in which the heart rate is detected; a third step in which the ejection duration of the heart is detected based on the pulse waveform; a fourth step in which a stroke volume per beat associated with the ejection duration of the heart and the body's heart rate is stored in advance; and a fifth step in which stroke volume per beat is calculated by reading out the stroke volume per beat recorded in the fourth step from the memory, based on the detected ejection duration and the detected heart rate.

The one hundred twenty-seventh aspect of the present invention relates to a stroke-volume-per-beat detecting method, characterized in that it comprises a first step in which a pulse waveform is detected at a detection site on the body; a second step in which the heart rate is detected; a third step in which the ejection duration of the heart is detected based on the pulse waveform; and a fourth step in which the area under the pulse waveform which corresponds to the ejection duration of the heart is calculated based on each of the peak values of the pulse waveform during the ejection duration of the heart, and the stroke volume per beat is calculated based on this area.

The one hundred twenty-eighth aspect of the present invention is a cardiac function measuring method for measuring cardiac function based on the stroke volume per beat detected by the stroke-volume-per-beat method, characterized in that it comprises a step in which an evaluation index is generated by comparing the stroke volume per beat with various threshold values, and a step in which the subject is notified of the evaluation index.

The one hundred twenty-ninth aspect of the present invention is a cardiac function measuring method for measuring cardiac function based on the stroke volume per beat detected according to the stroke-volume-per-beat method, characterized in that it comprises a step in which the rate of change in the stroke volume per beat is calculated; a step in which an evaluation index is generated by comparing the rate of change in the stroke volume per beat with various threshold values; and a step in which the subject is notified of the evaluation index.

BRIEF DESCRIPTION OF THE FIGURES

FIG. 6 is a block diagram of waveform shaping member 100 according to the same embodiment in Chapter 1.

FIGS. 7A–7E are timing charts for explaining the operation of wavelet transformer 10 according to the same embodiment in Chapter 1.

FIG. 17 is a diagram showing corrected pulse wave data MKD' in time period Tc in the second embodiment in Chapter 1.

FIG. 18 is a diagram showing corrected body motion data TKD' in time period Tc in the second embodiment in Chapter 1.

FIG. 19 is a diagram showing corrected pulse wave data MKD" from which body motion components have been removed in the second embodiment in Chapter 1.

FIG. 23 is a diagram showing one example of pulse wave data TBD from which body motion components have been removed according to the fourth embodiment in Chapter 1.

FIG. 26 is a block diagram showing the structure of pulse type determining member 22 according to the fifth embodiment in Chapter 1.

FIG. 27 is a diagram showing one example of the pulse waveform according to the fifth embodiment in Chapter 1.

FIG. 28 is a diagram showing the details of peak information according to the fifth embodiment in Chapter 1.

FIG. 40 is a diagram showing the relationship between the electrocardiogram and blood pressure in a modification in Chapter 1.

FIG. 41A is a diagram showing the changing waveform of the RR interval in the measured pulse, and the waveform of the changing components when the changing waveform is divided into the three frequency components described above. FIG. 41B shows the result of spectral analysis on the changing waveform in the RR interval shown in FIG. 41A.

FIG. 45 is a diagram for explaining the subjective point assignment for exercise intensity.

FIG. 57 is a diagram showing an example of the display on the display shown in the same exercise index measuring device in Chapter 2.

FIG. 61 is a function block diagram for the exercise intensity detecting device according to the second embodiment in Chapter 3.

FIG. 68 is a diagram showing one example of analyzed pulse wave data MKD from which body motion components have been removed according to the second embodiment in Chapter 3.

FIG. 69 is a diagram showing the maximum energy region for the analyzed pulse wave data MKD from which body motion components have been removed shown in FIG. 68.

FIG. 74 is a flow chart showing the operation of the exercise intensity detecting device according to the second embodiment in Chapter 3.

FIG. 85 is a diagram showing the change in stroke volume per beat accompanying posture changes in heart transplant patients and healthy individuals in Chapter 4.

PREFERRED EMBODIMENTS OF THE PRESENT INVENTION

Figure 1:
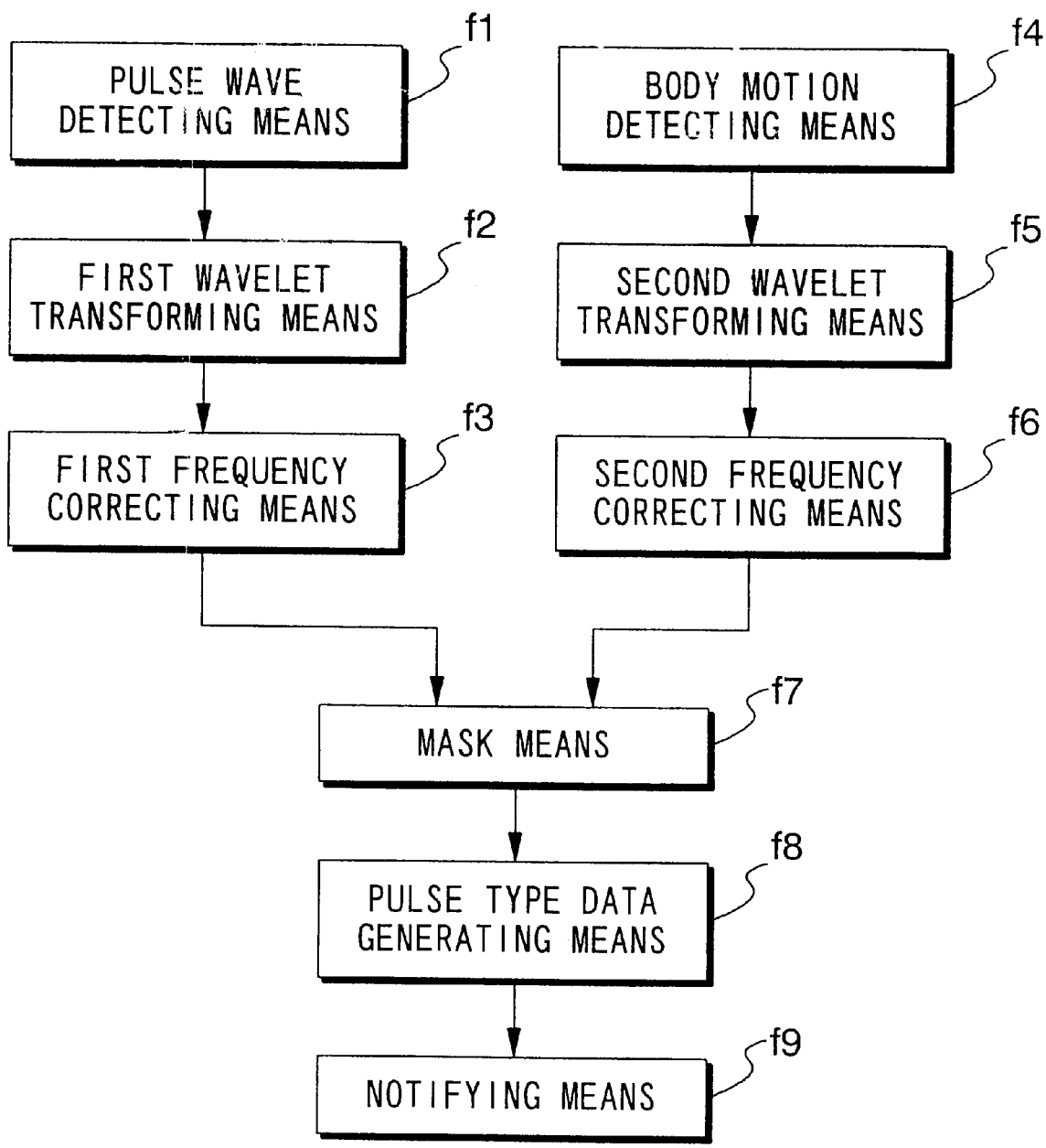
FIG. 1 is a function block diagram showing the functional structure of the pulse wave diagnosing device discussed in Chapter 1.

Preferred embodiments of the present invention will now be explained below with reference to the accompanying figures. The following explanation will be separated into chapters in order to better facilitate the exercise of the present invention by one skilled in the art.

In Chapter 1, a pulse wave diagnosing device employed to specify the individual's pulse type will be explained. It is necessary in this case to categorize the pulse waveform as Ping mai, Hua mai, or Xuan mai. The characteristics of the pulse waveform are suitably extracted using a wavelet transformer or the like. A device convenient for mobility which enables the subject to know the pulse type during normal daily activities will be disclosed. In addition, the techniques employed for eliminating the effects of motion will also be discussed.

Next, in Chapter 2, an exercise index measuring device which measures the exercise intensity for the training required to improve overall body endurance, and provides this exercise intensity to the subject in the form of an exercise index will be explained. Note that "exercise intensity" as employed here comprehensively takes into consideration the subject's physical and psychological strength during exercise.

In Chapter 3, an exercise intensity detecting device for calculating the exercise intensity based on the respiratory components extracted from the pulse waveform will be explained.

In Chapter 4, a device for detecting the stroke volume per beat and cardiac output based on the pulse waveform, and a device for diagnosing cardiac function will be explained.

1. Chapter 1
1-1: Summary

In Chinese medicine, the physician performs a pulse diagnosis by applying pressure on the skin over the patient's radius artery with his fingers. A diagnosis of the patient's physiological state is then made based on the pulse sensed through the physician's fingers. Representative pulse waves include Ping mai, Hua mai, and Xuan mai. The Ping mai is characteristic of a healthy subject, and is relaxed, having a constant rhythm without disruption. The Hua mai, on the other hand, is caused by an abnormality in the flow of blood in which the movement of the pulse becomes extremely smooth due to a mammary tumor, liver or kidney ailment, respiratory ailment, stomach or intestinal ailment, inflammation, or some other illness. On the other hand, the Xuan mai is caused by tension or aging of the walls of the blood vessels, and is seen in diseases such as liver and gall ailments, skin ailments, high blood pressure, and pain ailments. It is believed that the elasticity of the walls of the blood vessels decreases, so that the effect of the pulse movement of the pumped blood is not readily expressed, causing this phenomenon. The waveform of a Xuan mai rises violently, but does not fall off immediately, remaining at a high pressure state for a fixed period of time. In terms of the sensation registered by the fingers, a Hua mai feels like a straight tense and long pulse.

Since the physiological state of the patient is diagnosed based on subtle sensations registered by the fingers, it is difficult to convey the technique of pulse diagnosis between practitioners, so that typically practice on the order of months and years is required. In addition, because blood flow changes when the body is in motion, it is difficult to specify an accurate pulse wave if the subject is moving.

With this in mind, Chapter 1 addresses a pulse wave diagnosing device capable of objectively specifying the pulse type even when body motion is present.

1-2: Functional Structure of Embodiments

The function of a pulse wave diagnosing device according to one embodiment of the present invention will be explained with reference to the figures. FIG. 1 is a function block diagram of the pulse wave diagnosing device according to this embodiment. In the figure, f1 is a pulse wave detecting means, for detecting the pulse waveform. The pulse waveform is, for example, detected by applying pressure on the skin over the radius artery. f2 is a first wavelet transforming means for performing wavelet transformation on the pulse waveform detected by pulse wave detecting means f1, and generating analyzed pulse wave data in each frequency region. f3 is a first frequency correcting means for correcting the analyzed pulse wave data so that the power density at each frequency based on each corresponding bandwidth in the frequency regions becomes constant, and generating corrected pulse wave data. As a result, it is possible to compare wavelets detected in different frequency time regions.

Next, f4 is a body motion detecting means for detecting body motion and outputting a body motion waveform. As a result, it is possible to detect when the subject is moving. f5 is a second wavelet transforming means for performing wavelet transformation on the body motion waveform detected by body motion detecting means f4, and generating analyzed body motion data in each frequency region. f6 is a second frequency correcting means for correcting analyzed body motion data based on each corresponding frequency so that the power density at each frequency becomes constant, and then generating corrected body motion data. Since frequency correction is performed on the corrected body motion data calculated in this way, it can be compared with corrected pulse wave data.

f7 is a mask means for subtracting the corrected body motion data from the corrected pulse wave data, and generating corrected pulse wave data from which body motion components have been removed. f8 is a pulse type data generating means for generating pulse type data indicating the pulse type by analyzing in each frequency region the corrected pulse wave data generated by mask means f7. The types of pulse waves include Xuan mai, Ping mai and Hua mai, for example.

Note that it is not necessary to detect body motion in the case where detecting an irregular pulse for sleeping or sedate subjects. Therefore, body motion detecting means f4, second wavelet transforming means f5, second frequency correcting means f6, and mask means f7 may be eliminated, since there is no need to detect body motion. In addition, it is acceptable to simplify the structure by providing a frequency correcting means after mask means f7, in place of first frequency correcting means f3 and the second frequency correcting means. It is also acceptable to omit all of the frequency correcting means.

f9 is a notifying means for informing the subject of the pulse type based on the pulse type data generated by pulse type data generating means f8. As a result, the subject or a third party such as a physician is able to view the pulse type.

1-3: Embodiment 1

1-3-1: Structure of Embodiment 1

The structure of a pulse wave diagnosing device according to a first embodiment of the present invention will now be explained with reference to the figures.

1-3-1-1: External Structure of Embodiment 1

Figure 2:
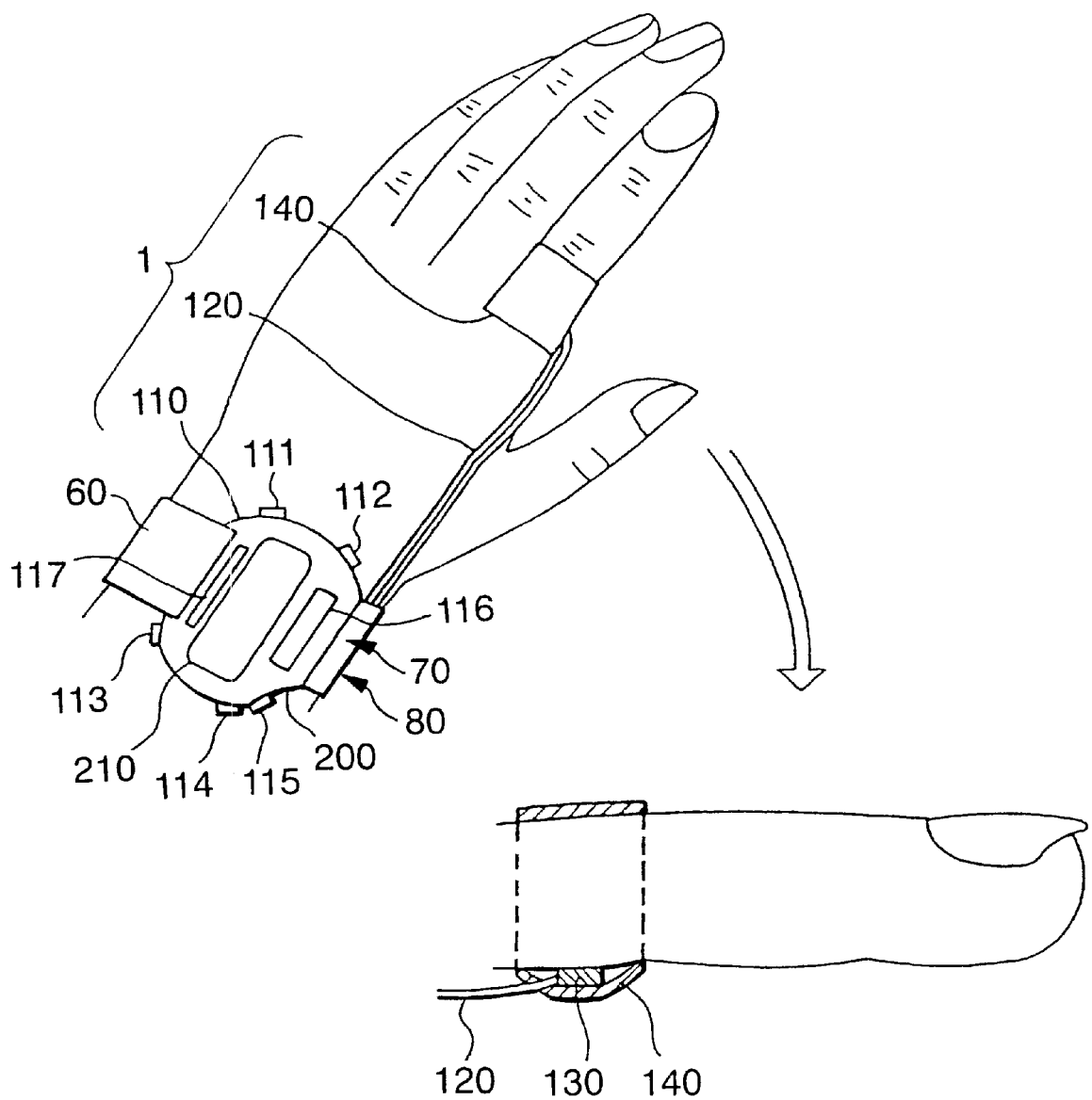
FIG. 2 is an orthogonal view showing the outer structure of the pulse wave diagnosing device according to the first embodiment in Chapter 1.

FIG. 2 is an orthogonal view showing the external structure of the pulse wave diagnosing device according to the first embodiment in Chapter 1.

The pulse wave diagnosing device 1 of this example shown in FIG. 2 is approximately formed of device main body 11 having a wristwatch structure, cable 120 connected to device main body 110, and pulse wave detection sensor unit 130 which is provided to one end of cable 120. A connector piece 80 is provided to an end of cable 120. Connector piece 80 is attached in a freely releasing manner to connector 70 which is formed at the 6 o'clock position on device main body 110. A wrist band 60 is provided to device main body 110 for wrapping around the wrist of the subject from the 12 o'clock position, and fixing in place at the 6 o'clock position. Device main body 110 is designed to be freely detachable from the arm of the subject by means of wrist band 60. Pulse wave detection sensor unit 130 attaches to the base of the index finger and is blocked from light by a band 140 for fixing the sensor in place. When pulse wave detection sensor unit 130 is attached in this way to the base of the finger, cable 120 can be made shorter, making it less likely to be a hindrance to the subject while running, for example. When the temperature distribution is measured from the palm to the fingertip at a cool ambient temperature, it is clear that the temperature at the fingertip falls noticeably while the temperature at the base of the finger does not fall. Accordingly, if pulse wave detection sensor unit 130 is attached to the base of the finger, accurate measurements may still be obtained even on a cold day when the subject is running outdoors.

Device main body 110 is provided with a resin watch case 200 (main body case). A liquid crystal display 210 having an EL back light is provided to the surface of watch case 200 for displaying the current time and date, as well as the length of time spent running, the running pitch and pulse wave information such as the pulse rate. LCD device 210 may be comprised of segmental or dot display regions. When dot display regions are employed, then the various information may be graphically displayed.

A control member comprising a microcomputer or the like is formed inside watch case 200 for executing a various commands or performing data processing to determine changes in the pulse rate or pulse type based on pulse waveform MH measured by pulse wave detection sensor unit 130, and displaying this information on LCD 210. A watch circuit is formed in the control member and is designed to display clock time, lap time, split time or the like on LCD 210. Button switches 111~115 are provided to the outer periphery and surface of watch case 200 to enable such external manipulations as setting the time or changing the display mode.

Figure 3:
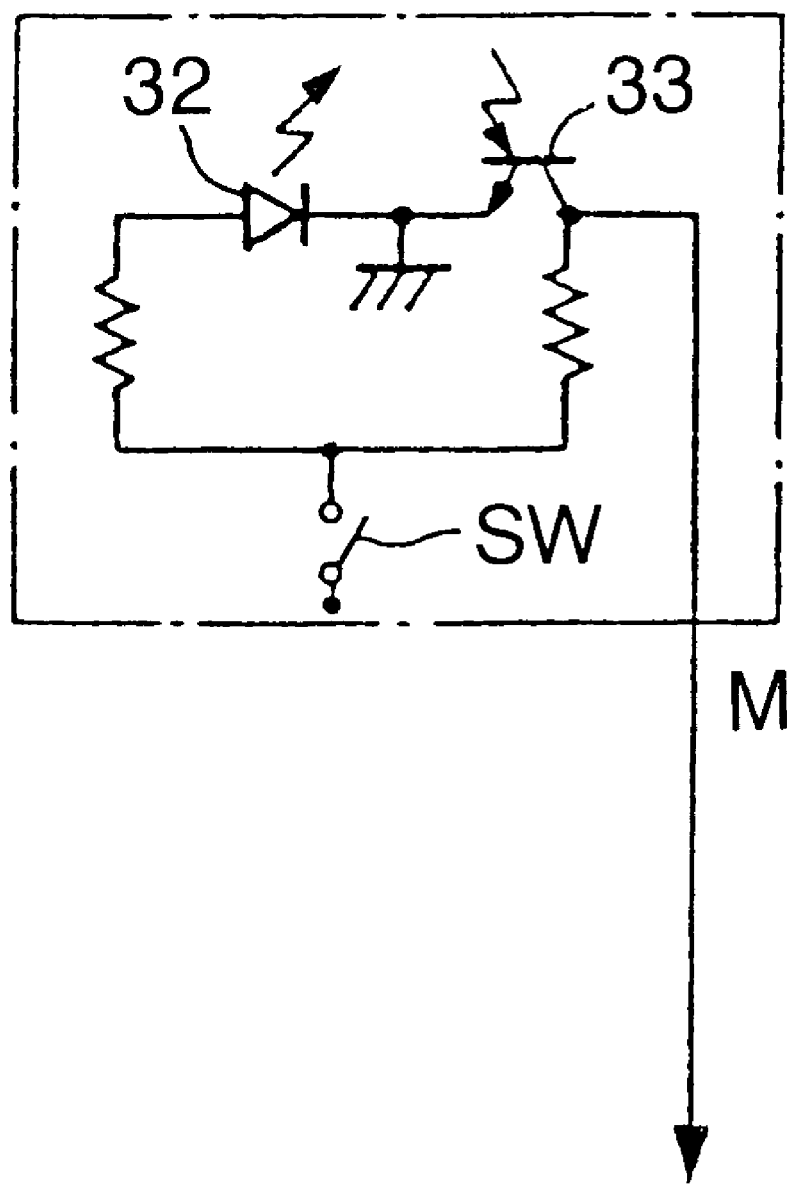
FIG. 3 is a circuit diagram of pulse wave detection sensor unit 130 in the same embodiment in Chapter 1.

Pulse wave detection sensor unit 130 is formed of LED 32, photo transistor 33 and the like shown in FIG. 3. When switch SW is ON and voltage from an electric source is impressed, light is emitted from LED 32, reflected by blood vessels and tissues, received by photo transistor 33, and pulse wave signal M is detected.

The wavelength of the light emitted by the LED is selected to be in the vicinity of the absorption wavelength peak for hemoglobin in the blood. As a result, the level of received light will vary in response to the amount of blood flow. Thus, the pulse waveform can be detected by detecting the level of received light.

A InGaN-type (indium-gallium-nitrogen) blue LED is suitably employed for the LED 32. The emitted light spectrum of a blue LED has a peak at 450 nm, for example, with the emitted light wavelength region being in the range of 350 to 600 nm. In this case, a GaAsP-type (gallium-arsenic-phosphorous) photo transistor may be used for photo transistor 33 corresponding to the LED having the light emitting characteristics described above. The received light wavelength region of photo transistor 33 has, for example, a main sensitive region in the range of 300 to 600 nm, with a sensitive region also present below 300 nm. When a blue LED and photo transistor 33 such as described above are combined, the pulse wave is detected in the overlapping wavelength region of 300 to 600 nm. This offers the following advantages.

It tends to be difficult for outside light having a wavelength region of 700 nm or less to pass through the tissues of the finger. For this reason, even if the portion of the finger not covered by the sensor fixing band is irradiated with outside light, the light does not reach photo transistor 33 through the finger tissue. Rather, only light in wavelength regions which do not influence the detection reaches photo transistor 33. On the other hand, light in the low wavelength region from 300 nm is almost entirely absorbed at the skin surface. Thus, even if the received light wavelength region is set to 700 nm or less, the actual received light wavelength region is 300 to 700 nm. Accordingly, it is possible to control the impact of outside light, without having to significantly cover the finger.

Moreover, the absorption coefficient of blood hemoglobin with respect to light having a wavelength of 300 to 700 nm is large, and is several to 100-fold greater than the absorption coefficient with respect to light having a wavelength of 880 nm. Accordingly, as in this example, when light in the wavelength region (300 to 700 nm) having large absorption characteristics matching the absorption characteristics of hemoglobin is employed as the light which is detected, the detected values therefor vary with good sensitively in response to changes in blood volume. Thus, it is possible to increase the S/N ratio of the pulse wave signal which is based on the change in blood volume.

1-3-1-2: Electrical Structure of Embodiment 1

Figure 4:
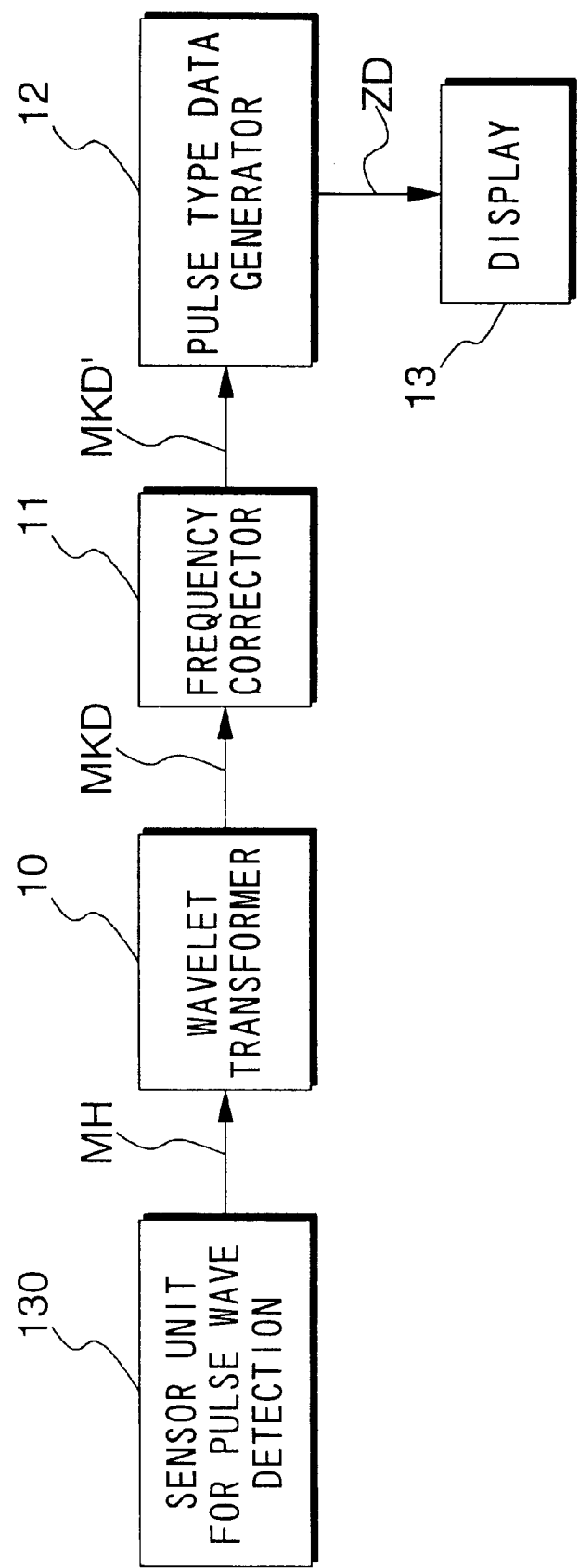
FIG. 4 is a block diagram showing the electrical structure of a pulse wave diagnosing device according to the same embodiment in Chapter 1.

Next, the electrical structure of the pulse wave diagnosing device will be explained with reference to FIG. 4. FIG. 4 is a block diagram showing the electrical structure of the pulse wave diagnosing device.

Pulse wave diagnosing device 1 is formed of the following parts. The numeral 10 is a wavelet transformer for performing conventional wavelet transformation on pulse waveform MH output from pulse wave detection sensor unit 130, and generating analyzed pulse wave data MKD.

In general, the wavelet is the unit for excising the signal parts in a time-frequency analysis for capturing the signal on both the time and frequency basis. Wavelet transformation expresses the size of the parts of the signal excised in these units. As the base function for defining wavelet transformation, a function $\psi(x)$ which has been localized with respect to both time and frequency is introduced as the mother wavelet. Here, wavelet transformation employing the mother wavelet $\psi(x)$ of a function f(x) is defined as follows.

$$(W\varphi f)(b, a) = \int_{-\infty}^{\infty} \frac{1}{\sqrt{a}} \varphi\left[\frac{x-b}{a}\right] f(x) dx \qquad \text{EQUATION 1}$$

In equation 1, b is the parameter employed when translating mother wavelet $\psi(x)$, while a is the parameter used when scaling. Accordingly, wavelet $\psi((x-b)/a)$ in equation 1 is the wavelet obtained when translating mother wavelet $\psi(x)$ by b only, and scaling it by a only. Since the width of the mother wavelet $\psi(x)$ is extended in correspondence to the scale parameter a, 1/a corresponds to the frequency. The detailed structure of wavelet transformer 10 will be explained below.

Frequency corrector 11 carries out frequency correction on analyzed pulse wave data MKD. When comparing data from different frequency regions, it is necessary to correct for the effect of the term $[1/a^{1/2}]$ corresponding to frequency in the preceding equation 1. Frequency corrector 11 is provided for this purpose. Namely, frequency corrector 11 generates corrected pulse wave data MKD' by multiplying wavelet data WD by a coefficient $a^{1/2}$. As a result, it is possible to carry out correction based on each of the corresponding frequencies, so that the power density per frequency becomes constant.

Next, pulse type data generator 12 specifies Ping mai, Xuan mai, or Hua mai pulse types based on corrected pulse wave data MKD', and generates pulse type data ZD expressing this. Display 13 is composed of a ROM, control circuit, LCD display and the like. Pulse type data ZD is supplied to display 13. The control circuit detects this, reads out characters stored in ROM, and displays these on the liquid crystal display. Letters spelling out "Ping mai", "Xuan mai" or "Hua mai", or specific symbols or icons, may be used. As a result, the subject or physician is informed of the health state.

1-3-1-3: Wavelet Transformer

Figure 5:
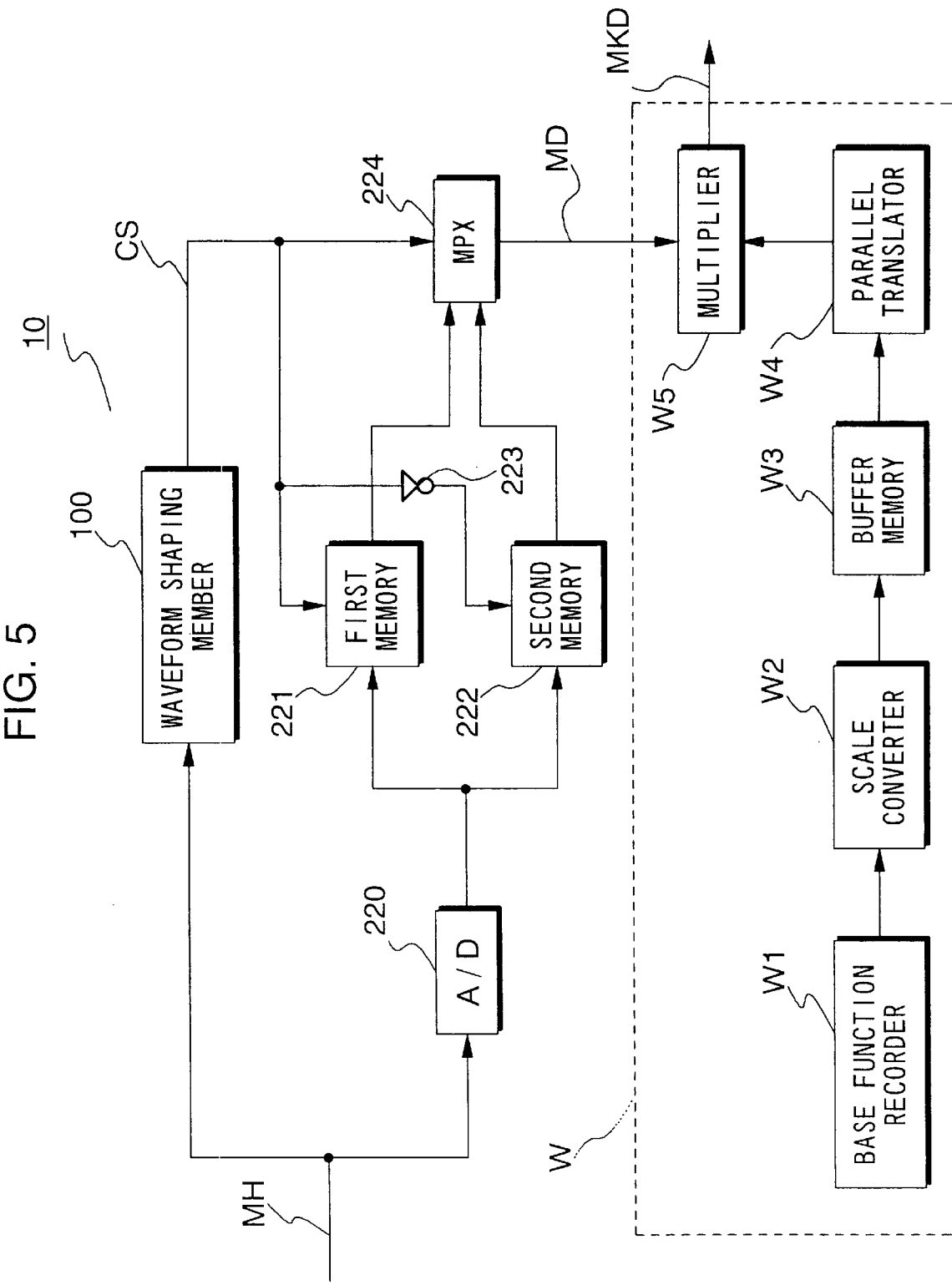
FIG. 5 is a block diagram of wavelet transformer 10 according to the same embodiment in Chapter 1.

The structure of wavelet transformer 10 will be explained in detail using the figures. FIG. 5 is a block diagram of wavelet transformer 10 according to the first embodiment.

Pulse waveform MH is supplied to waveform shaping member 100 and A/D converter 220. Waveform shaping member 100 generates a control signal CS and clock CK in synchronization with a pulse waveform MH. A block diagram of waveform shaping member 100 is shown in FIG. 6. In this figure, ringing filter 101 is a filter with a high Q value having a central frequency of 2.2 Hz and a pass band of 0.8 to 3.5 Hz. The fundamental component of the pulse waveform is typically in the range of 0.8 to 3.5 Hz. Thus, when pulse waveform MH passes through ringing filter 101, that fundamental component is extracted. For example, when pulse waveform MH shown in FIG. 7A passes through ringing filter 101, then the sinusoidal wave shown in FIG. 7B is obtained.

Zero cross detecting circuit 102 is composed of a comparator, or the like. Zero cross detecting circuit 102 compares the output signal and ground level of ringing filter 101, and generates a rectangular wave. This rectangular wave is synchronized with heart beat. For example, if the output signal of ringing filter 101 is as shown in FIG. 7B, then the output signal of zero cross detecting circuit 102 becomes as shown in FIG. 7C.

A phase lock loop is formed of comparing member 103, loop filter 104, voltage control oscillating circuit 105 and dividing circuit 106. When the signal output from zero cross detecting circuit 102 is supplied to one of the inputs of comparing member 103, and the other signal output from dividing circuit 106 is supplied to the other input of comparing member 103, comparing member 103 outputs an error difference signal in proportion to the phase difference between the two signals. When an error difference signal is supplied to voltage control oscillating circuit 105 via loop filter 104, voltage control oscillating circuit 105 outputs clock CK. Clock CK is divided into ⅛ fractions by dividing circuit 106, and fed back to the other input of comparing member 103. The frequency of clock CK in this case is compared to the frequency of the output signal of zero cross detecting circuit 102 as shown in FIG. 7D, to become an 8-fold frequency. Thereafter, clock CK is divided into halves by dividing circuit 107, and output as control signal CS shown in FIG. 7E.

A pulse waveform MH shown in FIG. 5 is converted to a digital signal by A/D converter 220, and then stored in first memory 221 and second memory 222. Control signal CS is directly supplied to the write enable terminal of first memory 221, and control signal CS which has been inverted by inverter 223 is supplied to the write enable terminal of second memory 222. First and second memories 221,222 alternately store pulse waveforms MH in clock frequency unit.

The numeral 224 indicates a multiplexor which selects pulse wave data MD alternately read out from first and second memories 221, 222 and outputs this data to base function developer W. Pulse wave data MD is read out from second memory 222 during the write period of first memory 221, and written to second memory 222 during the read out of first memory 221.

Base function developer W is designed to carry out the calculations for the preceding equation (1) above. Base function developer W is supplied with clock CK, and carries out calculations according to the clock period. Base function developer W is composed of a base function recorder W1 which records the mother wavelet $\psi(x)$; a scale converter W2 which converts scale parameter a; buffer memory W3; parallel translator W4 which carries out translation; and multiplier W5. Note that various types of wavelets may be suitably employed for mother wavelet $\psi(x)$ which is stored in base function recorder W1, including Gabor wavelet, Mexican hat wavelet, Harr wavelet, Meyer wavelet, Shannon wavelet and the like.

When a mother wavelet $\psi(x)$ is read out from base function recorder W1, conversion of scale parameter a is carried out by scale converter W2. Scale parameter a corresponds to period, thus, the bigger a is, the more the mother wavelet $\psi(x)$ extends above the time axis. In this case, the quantity of data for mother wavelet $\psi(x)$ recorded in base function recorder W1 is fixed, so that when a gets larger, the amount of data per unit time decreases. Scale converter W2 carries out interpolation to compensate for this, and generates a function $\psi(x/a)$ by performing weeding out processing when a gets smaller. This data is stored once in buffer memory W3.

Next, parallel translator W4 reads out function $\psi(x/a)$ from buffer memory W3 at a timing in response to translation parameter b, carrying out the parallel transition of function $\psi(x/a)$, to generate a function $\psi(x-b/a)$.

Next, multiplier W4 multiplies variable $1/a^{1/2}$, function $\psi(x-b/a)$ and pulse wave data MD, and carries out wavelet transformation in heartbeat units. In this way, analyzed pulse wave data MKD is generated. In this example, analyzed pulse wave data MDK is segregated into the frequency regions 0 Hz~0.5 Hz, 0.5 Hz~1.0 Hz, 1.0 Hz~1.5 Hz, 1.5 Hz~2.0 Hz, 2.0 Hz~2.5 Hz, 2.5 Hz~3.0 Hz, 3.0 Hz~3.5 Hz, and 3.5 Hz~4.0 Hz, and output. Base function developer W performs calculations on the clock period as described above, and. the clock frequency is set to be eight fold greater than the base frequency of pulse waveform MH. Thus, analyzed pulse wave data MKD generated at each beat becomes data M11~M88 shown in FIG. 8.

1-3-1-4: Pulse Type Data Generator

Figures 9, 10:
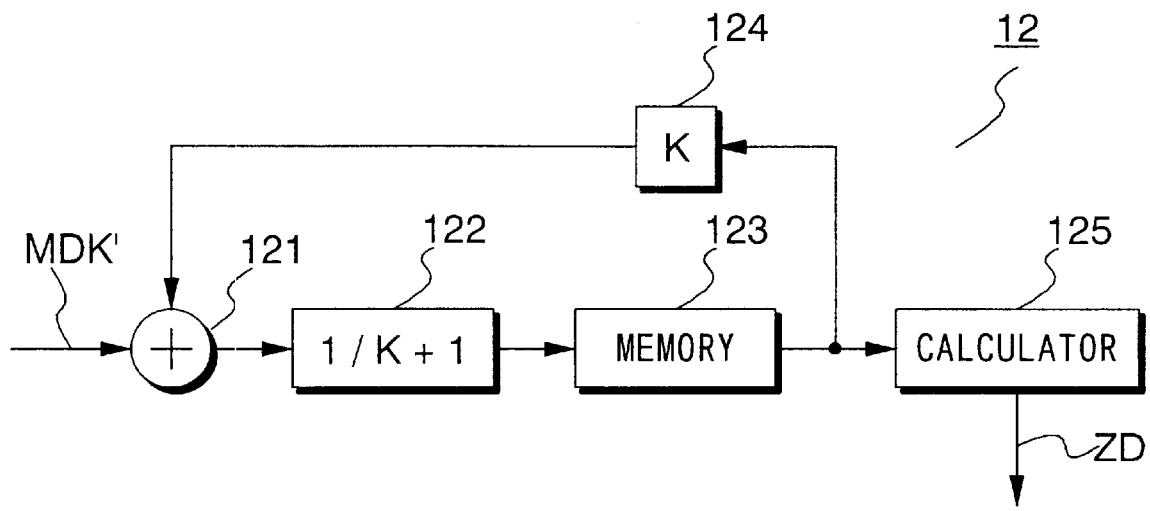
FIG. 9 is a block diagram of pulse type data generator 12 according to the same embodiment in Chapter 1.
FIG. 10 is a diagram showing the average value of corrected pulse wave data MKD' stored in memory 124 according to the same embodiment in Chapter 1.

Next, pulse type generator 12 will be explained. FIG. 9 is a block diagram of pulse type data generator 12 according to the present embodiment.

In the figure, adder 121, coefficient circuits 122 and 124, and memory 123 are circuits for calculating the average value of corrected pulse wave data MKD' in each frequency region. The coefficient of coefficient circuit 122 is 1/K+1, while the coefficient of coefficient circuit 124 is K. Adder 121 adds the corrected pulse wave data MKD' and the output from coefficient circuit 124. The data output from adder 121 is stored in memory 123 via coefficient circuit 122. Memory 123 outputs the input data which has been delayed by just 8 clock periods.

Here, if the period of the heart beat is t, the current clock time is T, and the data stored in memory 123 is Ma, then data Ma(T) at clock time T may be obtained by the following equation.

$$Ma(T)=\{Ma(T-t)*K+MKD'(T)\}/(K+1)$$

Ma(T-t) in this equation is data obtained at an interval of time t ago, i.e., Ma(T-t) shows the data from the previous heart beat. Accordingly, data Ma(T) is the weighted average of past data and the current data. Since this processing is repeated at every interval of time t, the result is that the average value of corrected pulse wave data MKD' is stored in memory 123. Since corrected pulse wave data MKD' is generated in each frequency region, the average value is calculated in each frequency region. For this reason, the average values Ma11~Ma88 of corrected pulse wave data MDK' is stored in memory 123 in units of 0.5 Hz, as shown in FIG. 10. In this sense, then, memory 123 functions as an average value table.

Next, calculator 125 generates pulse type data ZD based on average value Ma11~Ma88 stored in memory 123. The relationship between the average value and the representative waveforms, Xuan mai, Ping mai and Hua mai, will be explained here. Note that in the example explained below, the fundamental frequency of pulse waveform MH is 1.3 Hz.

Figure 8:
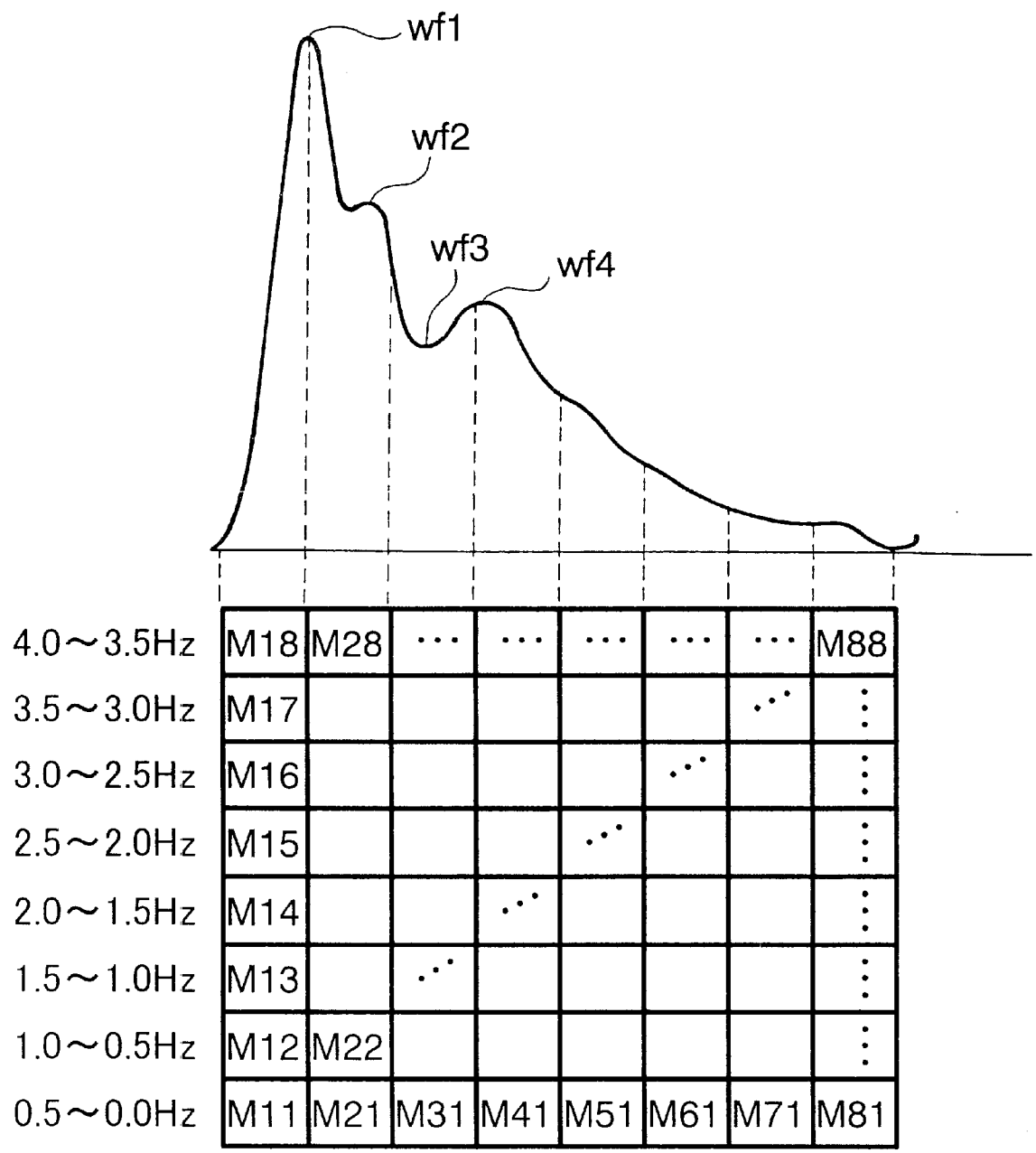
FIG. 8 is a diagram showing the analyzed pulse wave data MKD generated at each heart beat in the same embodiment in Chapter 1.

In general, as shown in FIG. 8, pulse waveform MH is formed of main wave wf1 caused by the initial rise, tidal wave wf2 which follows wf1, dicrotic notch wf3, and overlap wave wf4. Main wave wf1 corresponds to the acute ejection period in the left ventricle. Tidal wave wf2 is formed according to the correlation between the elastic expansion of the aorta and the reflected wave at the periphery. Dicrotic notch wf3 expresses the pressure of the aorta during diastole of the left ventricle, and corresponds to diastolic pressure. The overlap wave wf4 is the wave due to reverse flow of retrograde blood flow accompanying closing of the aortic valve.

Figure 11:
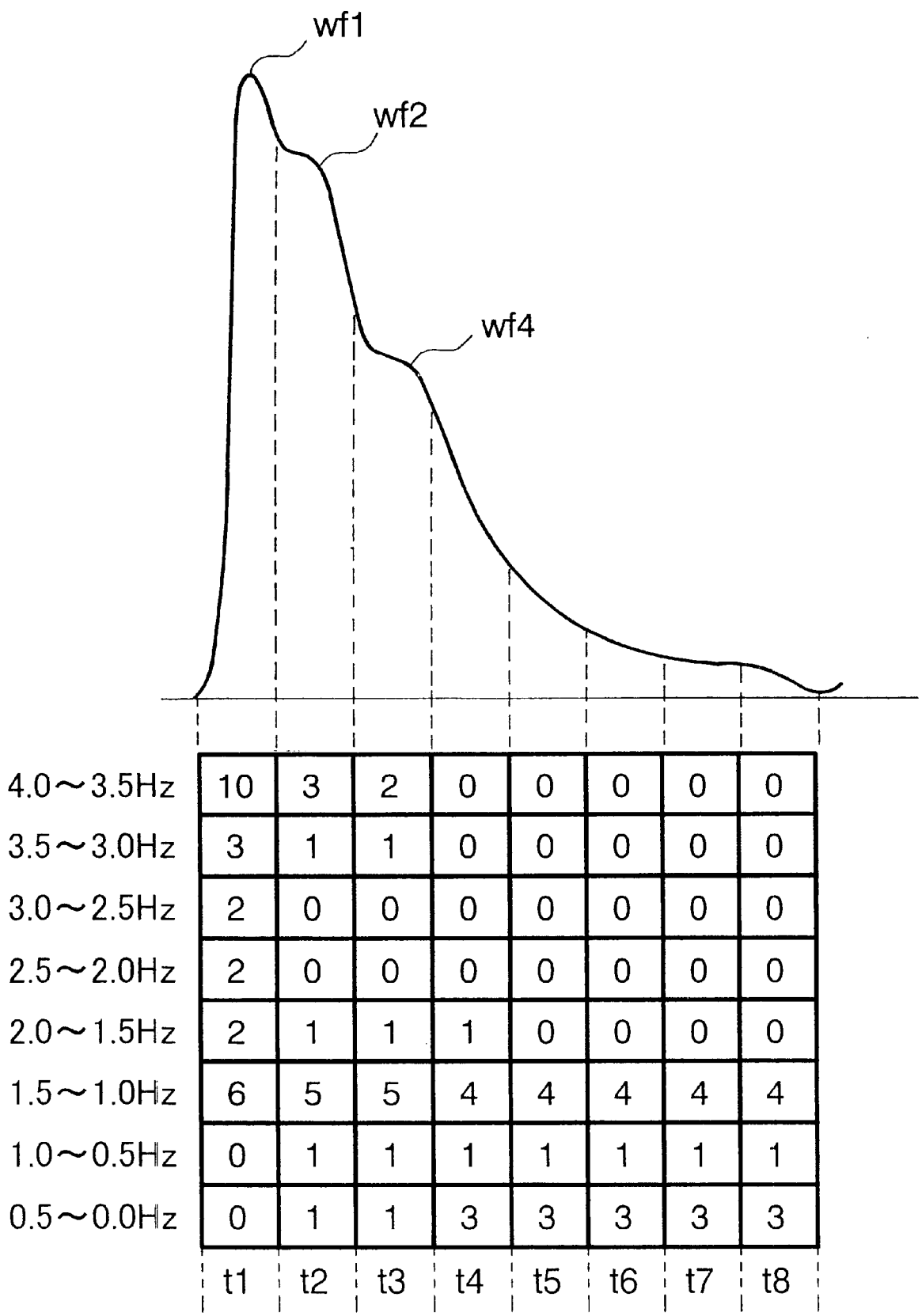
FIG. 11 is a diagram showing the relationship between the average value and a waveform representative of a Xuan mai in the same embodiment in Chapter 1.

FIG. 11 shows the relationship between average values Ma11~Ma88 and a representative example of a Xuan mai. A Xuan mai is characterized in that tidal wave wf2 is fused with primary wave wf1, and in that dicrotic notch wf3 does not appear. In other words, waveform characteristics appear in time periods t2 and t3. When tidal wave wf2 and dicrotic notch wf3 appear clearly, the second and third harmonic components become larger with respect to the fundamental component of pulse waveform MH. Thus, in the case of a Xuan mai, frequency components above 2 Hz tend to become relatively smaller in time periods t2 and t3. In the case of both time periods t2 and t3 in this example, the total S1 of frequency components above 2 Hz is [7]. Note that S1 is defined by the following equation.

$$S1=Ma23+Ma24+Ma25+Ma26+Ma27+Ma28+Ma33+Ma34+Ma35+Ma36+Ma37+Ma38$$

Figure 12:
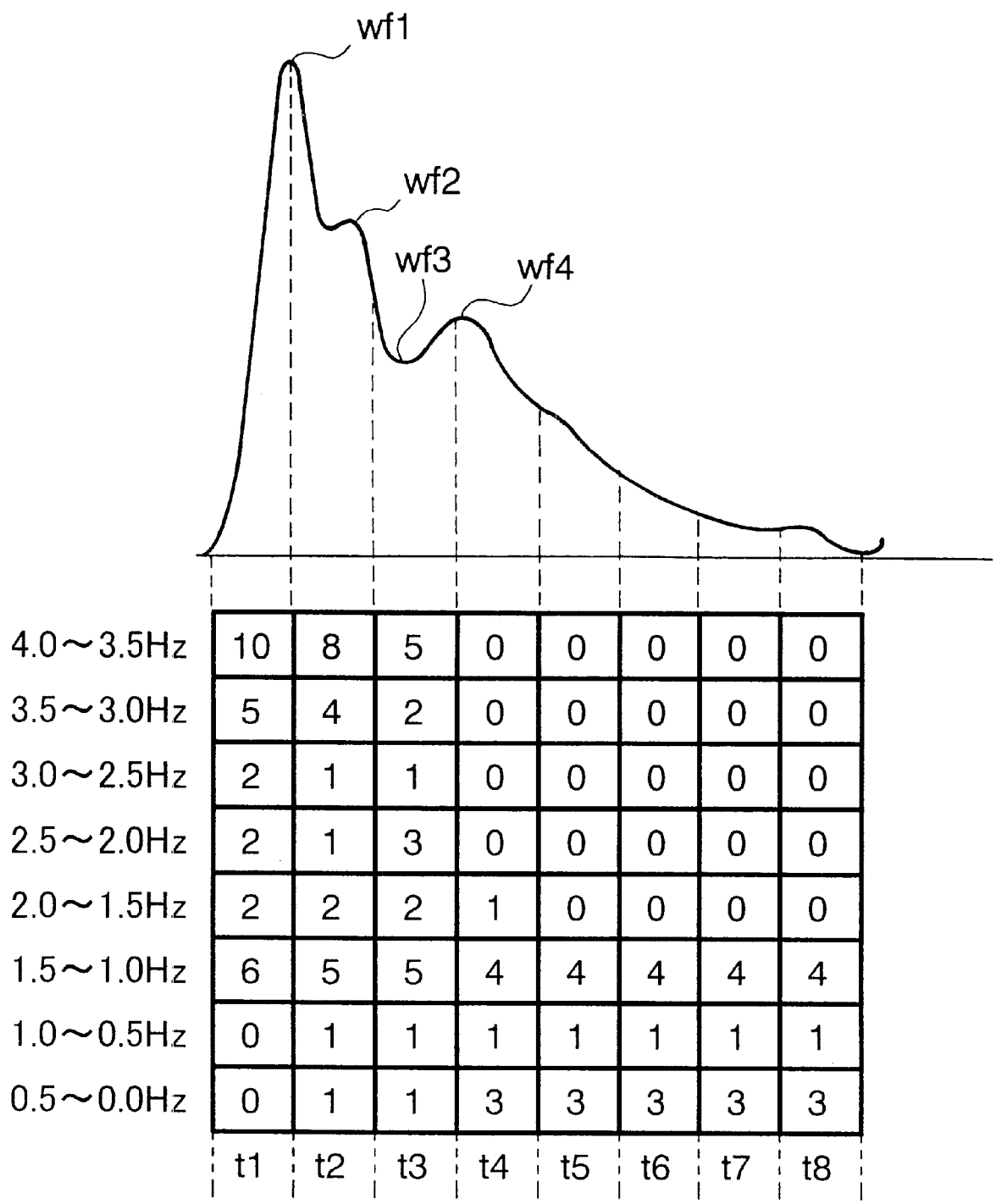
FIG. 12 is a diagram showing the relationship between the average value and a waveform representative of a Ping mai in the same embodiment in Chapter 1.

FIG. 12 shows the relationship between the average values and a representative waveform for a Ping mai. A Ping mai is characterized in being formed of a three peak wave consisting of main wave wf1, tidal wave wf2, and overlap wave wf4. In other words, the characteristics of the waveform appear in time periods t2 and t3. Since tidal wave wf2, dicrotic notch wf3 and wf4 appear clearly, the second and third higher harmonic components of pulse waveform MH become larger. Thus, in the case of a Ping mai, frequency components above 2 Hz tend to become relatively larger in time periods t2 and t3. In particular, when time periods t2 and t3 are compared, a peak for tidal wave wf2 is present in time period t2. Accordingly, it may be said that many high frequency components are present. In the case of both time periods t2 and t3 in this example, the total S1 of frequency components above 2 Hz is [25]. The total S2 for 4.0~3.0 Hz frequency components for time period t2 is [12], while the total S3 for 4.0~3.0 Hz frequency components for time period t3 is [7]. Note that S2 and S3 are defined by the following equations.

$$S2=Ma27+Ma28$$

$$S3=Ma37+Ma38$$

Figure 13:
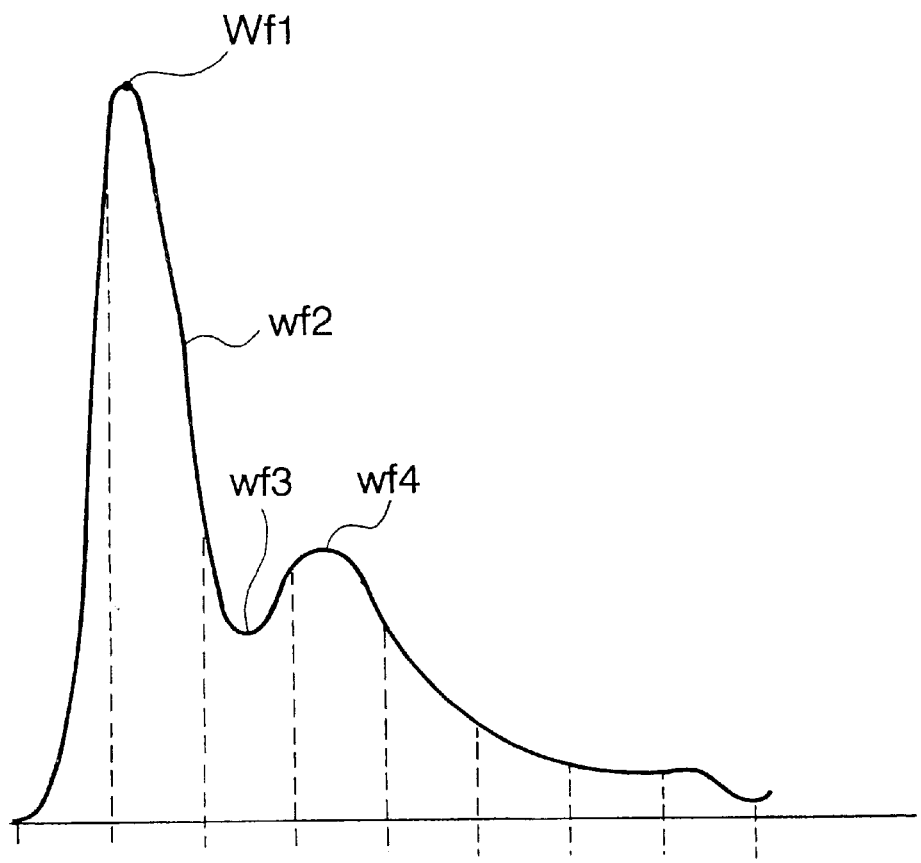
FIG. 13 is a diagram showing the relationship between the average value and a waveform representative of a Hua mai in the same embodiment in Chapter 1.

FIG. 13 shows the relationship between the average values and a representative example of a Hua mai. A Hua mai is characterized in being formed of a two peak wave in which main wave wf1 and tidal wave wf2 are almost entirely superimposed. In other words, the characteristics of the waveform appear in time periods t2 and t3. Since tidal wave wf2 is almost not visible, while dicrotic notch wf3 appears clearly, the second and third harmonic components of pulse waveform MH become larger. Thus, in the case of a Hua mai, frequency components above 2 Hz tend to become relatively larger in time periods t2 and t3. In particular, when time periods t2 and t3 are compared, a peak for tidal wave wf2 is not present in time period t2. In contrast, a dicrotic notch wf3 is present in time period t3, so that it may be said that more high frequency components are present in time period t3. In the case of both time periods t2 and t3 in this example, the total S1 of frequency components above 2 Hz is [24]. The total S2 for 4.0~3.0 Hz frequency components for time period t2 is [6], while the total S3 for 4.0~3.0 Hz frequency components for time period t3 is [10].

Figure 14:
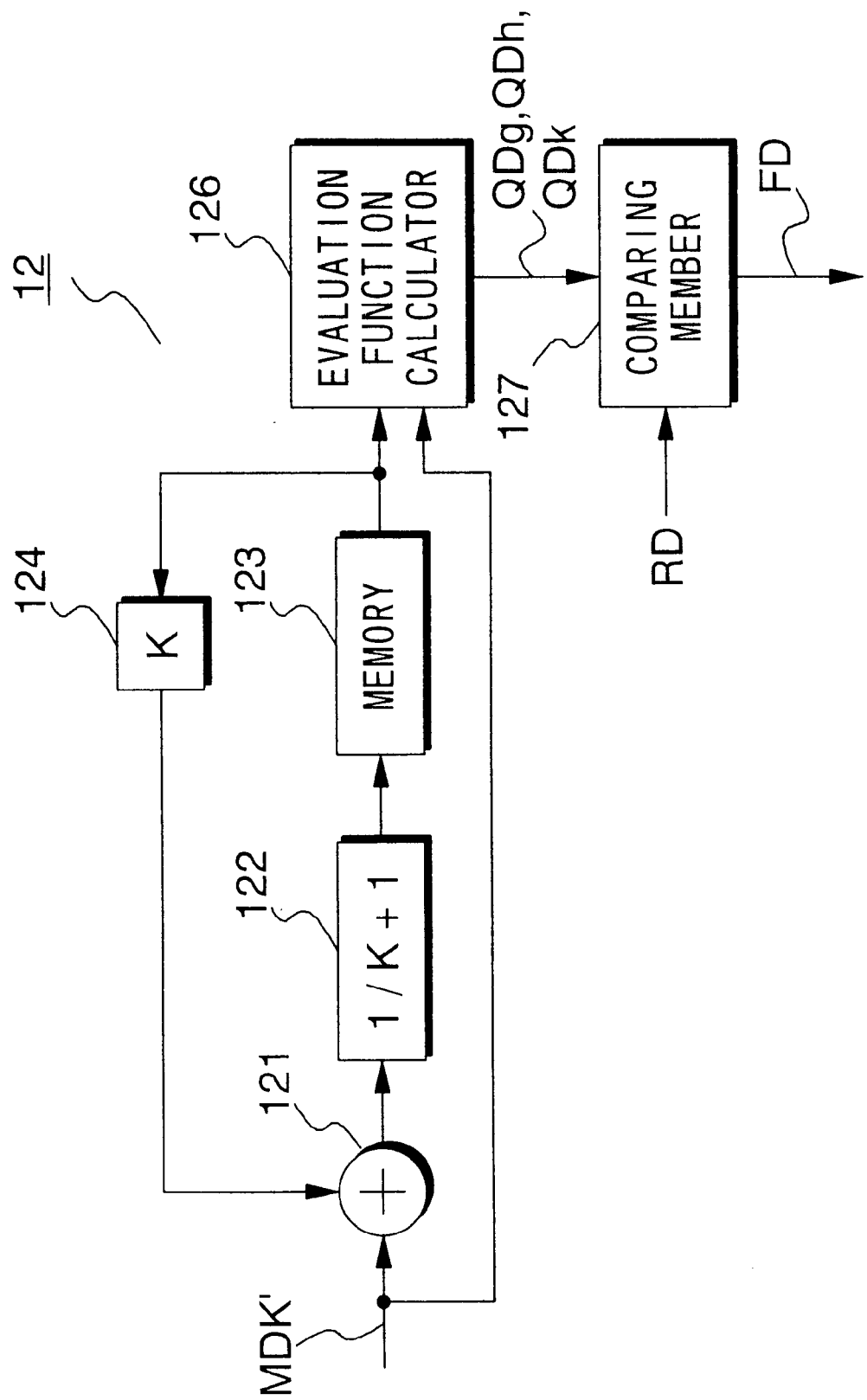
FIG. 14 is a block diagram showing another structural example for pulse type data generator 12 according to the same embodiment in Chapter 1.

As explained above, characteristic parts are present in each pulse type. This embodiment focuses on these points in order to determine the pulse type based on the following determination standards.
1) Determination of Xuan Mai
A determination is made that a Xuan mai is present when the total S1 for frequency components above 2.0 Hz in time periods t2 and t3 is [S1<15]. In this case, calculating means 125 generates data Dg indicating pulse type data ZD is a Xuan mai.
2) Determination of Ping Mai
A determination is made that a Ping mai is present when the total S1 of frequency components above 2.0 Hz in time periods t2 and t3 is [S1≧15], and the total S2 of frequency components in the range of 4.0~3.0 Hz in time period t2 and the total S3 of frequency components in the range of 4.0~3.0 Hz in time period t3 is [S2≧S3]. In this case, calculating means 125 generates data Dh indicating that pulse type data ZD is a Xuan mai.
3) Determination of Hua Mai
When the total S1 of frequency components above 2.0 Hz is [S1≧15} for time periods t2 and t3, and the total S2 for frequency components in the range of 4.0~3.0 Hz for time period t2 and the total S3 for frequency components in the range of 4.0~3.0 Hz for time period t3 is [S2<S3], then a determination is made that a Hua mai is present. In this case, calculating means 125 generates data Dk indicating that pulse type data ZD is a Hua mai.
1-3-1-5: Other Examples of the Pulse Type Data Generator
FIG. 14 is a block diagram showing an example of another structure for the pulse type data generator. Memory 123 functions as an average value table. Evaluation function calculator 126 generates evaluation data QDg, QDh, and QDk based on the average values stored in memory 123. Evaluation function calculator 126 is provided with a memory in which the results obtained from performing wavelet transformation on representative pulse waveforms corresponding to Xuan mai, Ping mai and Hua mai respectively are stored in advance in the same form as in the average value table. Note that the data corresponding to the pulse waveform which is representative of Xuan mai, Ping mai and Hua mai are indicated by Mg11~Mg88, Mh11~Mh88 and Mk11~Mk88, respectively.

Evaluation data QDg is data showing the degree to which the measured pulse waveform MH matches the pulse waveform of a representative Xuan mai, and is generated by calculations using the following equation.

$$QDg = \Sigma Pij \cdot |Mgij - Maij|/Mgij : i=1\sim8, j=1\sim8$$

Evaluation data QDh is data showing the degree to which the measured pulse waveform MH matches the pulse waveform of a representative Ping mai, and is generated by the following equation.

$$QDh = \Sigma Pij \cdot |Mhij - Maij|/Mhij : i=1\sim8, j=1\sim8$$

Evaluation data QDk is data showing the degree to which the measured pulse waveform MH matches the pulse waveform of a representative Xuan mai, and is generated by calculations using the following equation.

$$QDk = \Sigma Pij \cdot |Mkij - Maij|/Mkij : i=1\sim8, j=1\sim8$$

Pij is a coefficient which is set to [0] in time-frequency regions in which there are no characteristics and set to [1] for the characteristic portions only. The coefficient is set this way because the pulse type can be discerned based on the characteristic portions of the waveform which have a large amount of energy. In contrast, if the pulse type was determined based on low level portions of the waveform, then an accurate determination could not be carried out due to the poor SN ratio.

Comparing member 127 compares the size of evaluation data QDg, QDh, and QDk, specifies the pulse type corresponding to the evaluation data expressing the smallest value as the pulse type of the measured pulse waveform MH, and generates pulse type data ZD.

In this embodiment as described, wavelet transformation is performed in synchronization with pulse waveform MH, one pulse waveform is divided into a plurality of frequency time regions, the portions which characteristically express the pulse type are extracted from the divided frequency-time regions, and the pulse type is specified based on these extracted portions. As a result, it becomes possible to accurately determine the pulse type.
1-4: Embodiment 2
The pulse wave diagnosing device according to the first embodiment presumed that the subject was at rest. Since the heartbeat becomes stronger in proportion to body motion, the pulse waveform is effected by body motion and will vary if the subject is walking, picking up an object, etc. Thus, it is difficult to accurately detect the pulse type with the pulse wave diagnosing device according to the first embodiment when body motion is present. Accordingly, this second embodiment takes into consideration this point. Namely, the second embodiment provides a pulse wave diagnosing device which cancels the body motion component from the pulse waveform, so that an accurate pulse type can be detected even when body motion is present.

1-4-1: Structure of Embodiment 2

The external structure of the second embodiment is equivalent to that of the first embodiment shown in FIG. 2. However, the pulse wave diagnosing device according to the second embodiment is provided with an acceleration sensor 21 inside the main body 110 of the device.

Figure 15:
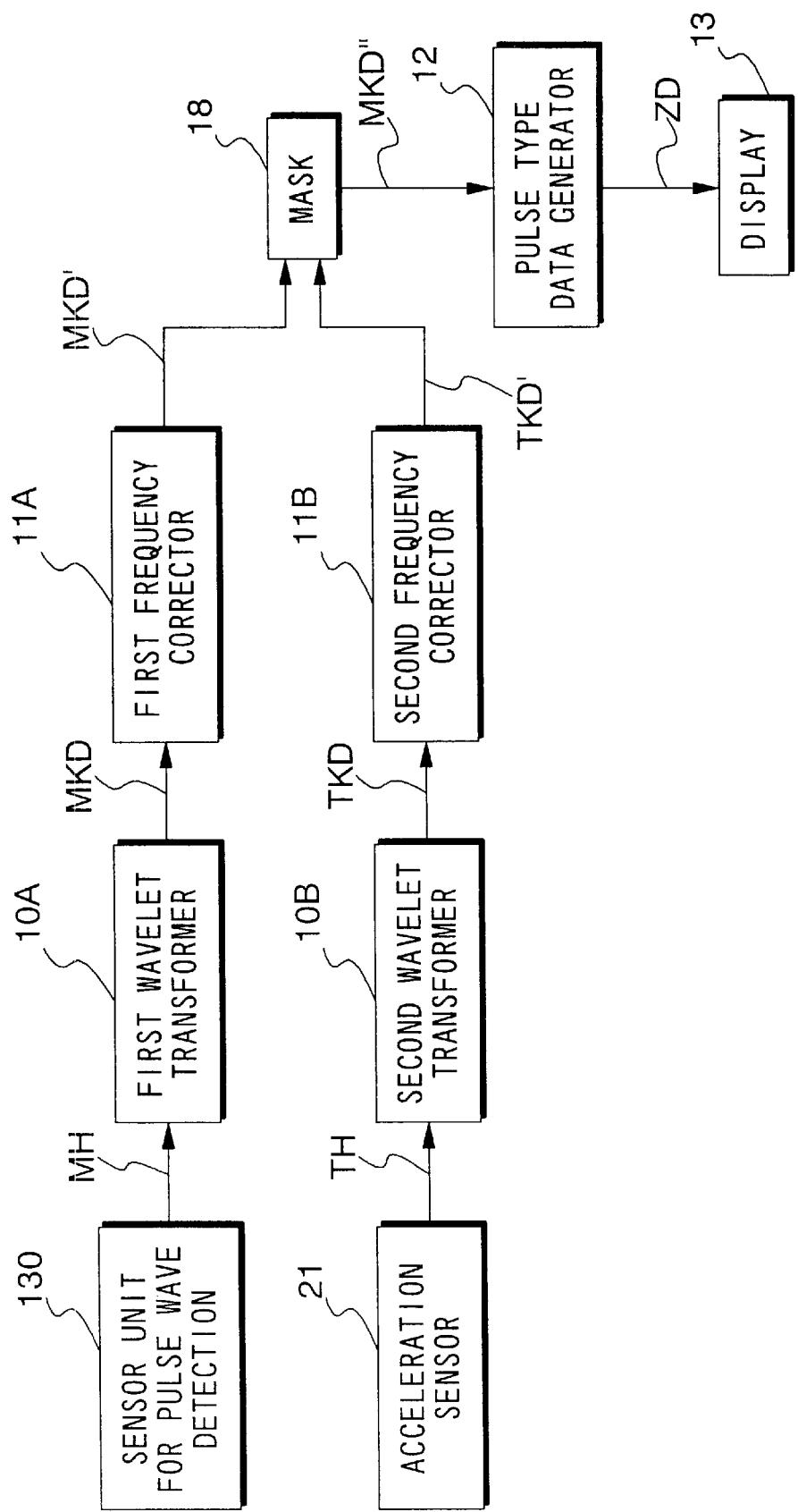
FIG. 15 is a block diagram of the pulse wave diagnosing device according to the second embodiment in Chapter 1.

The electrical structure of the pulse wave diagnosing device according to the second embodiment will now be explained. FIG. 15 is a block diagram of the pulse wave diagnosing device according to the second embodiment. In this figure, first wavelet transformer 10A and first frequency corrector 11A have the same structures as the first embodiment's wavelet transformer 10 and frequency corrector 11 respectively, and are designed to output corrected pulse wave data MKD' from first frequency corrector 11A.

Body motion waveform TH is detected by acceleration sensor 21, and then supplied to second wavelet transformer 10B. Wavelet transformation is performed on body motion waveform TH, to generate analyzed body motion data TKD. Second wavelet transformer 10B is formed in the same manner as wavelet transformer 10 in the first embodiment. Accordingly, analyzed body motion data TKD is formed from the various frequency components which result when the 0~4 Hz frequency region is divided every 0.5 Hz. Second frequency corrector 11B is formed in the same manner as frequency corrector 11 in the first embodiment, and performs frequency correction on analyzed body motion data TKD to generate corrected body motion data TKD'.

Next, mask 18 subtracts corrected body motion data TKD' from corrected pulse wave data MKD', to generate corrected pulse wave data MKD" from which body motion components have been removed. Pulse type data generator 12 generates pulse type data ZD based on corrected pulse wave data MKD" in the same way as in the first embodiment. Display 13 displays the pulse type based on pulse type data ZD.

1-4-2: Operation of Embodiment 2

Next, the operation of the second embodiment will be explained with reference to the figures.

Figure 16A:
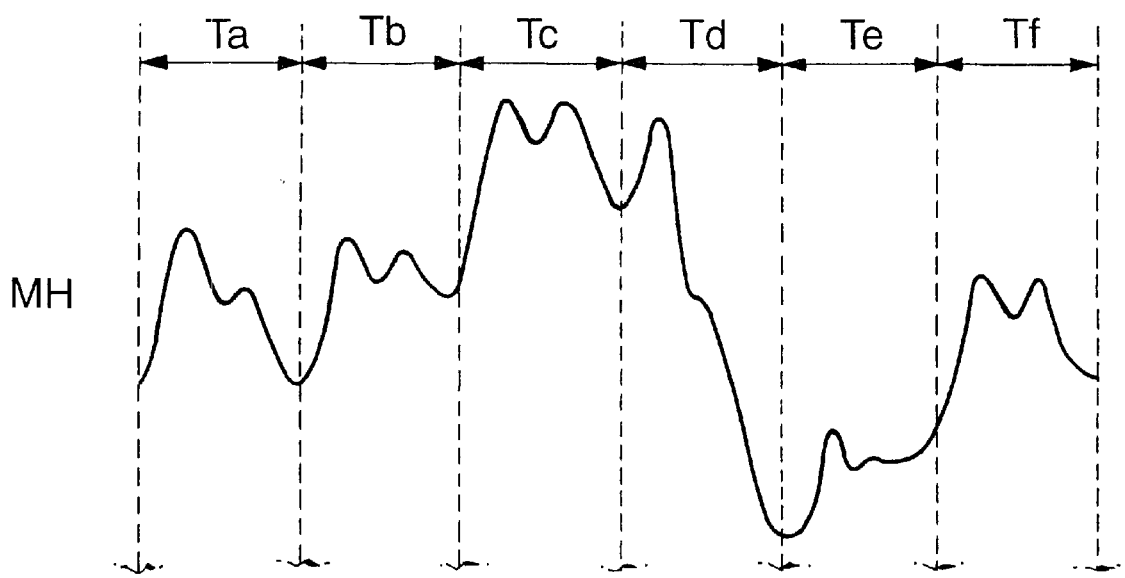
FIGS. 16A–16C are timing charts for explaining the operation of the pulse wave diagnosing device according to the second embodiment in Chapter 1.
Figure 16B:
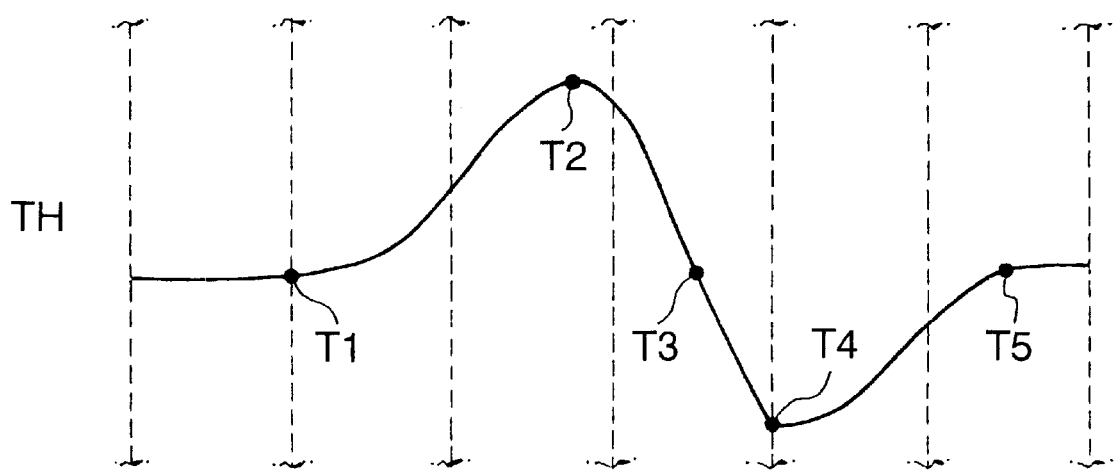

This example assumes the case in which the subject lifts a cup with his hand, and then returns it to its original position during the pulse type detection. In this case, pulse waveform MH shown in FIG. 16A is detected by a pulse wave detection sensor unit 130. The body motion waveform TH shown in FIG. 16B is detected simultaneously.

Figure 16C:
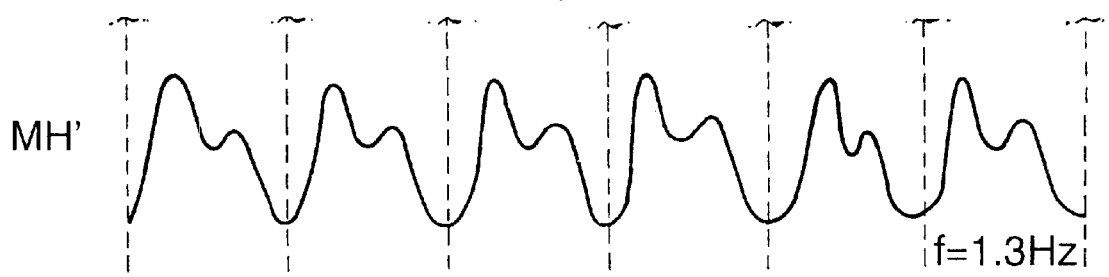

Body motion waveform TH begins to increase from time T1, and reaches a positive peak at time T2. Thereafter, body motion waveform TH gradually falls, passing through level 0 at time T2, reaching a negative peak at time T3, and returning to level 0 at time T4. Since body motion waveform TH is detected by acceleration sensor 21, time T3 corresponds to the clock time at which the cup is maximally lifted by the subject, time T1 corresponds to the clock time at which the subject starts to lift the cup, and time T4 corresponds to the clock time at which the lifting operation is terminated. Accordingly, the time period from time T1 to T4 is the time period during which body motion is present. Note that FIG. 16C shows pulse waveform MH' assuming the absence of body motion. In this example, the fundamental frequency of pulse waveform MH is 1.3 Hz.

The operation of the pulse wave diagnosing device according to the second embodiment during time period Tc shown in FIG. 16 will now be explained with reference to FIGS. 17~19.FIG. 17 shows corrected pulse wave data MKD' in the interval Tc and FIG. 18 shows corrected body motion data TKD' in the interval Tc. It may be understood from these FIGS. that frequency components of a relatively large level are present in the 0.0 Hz~0.1 Hz frequency regions in body motion waveform TH.

When corrected pulse wave data MKD' and corrected body motion data TKD' are supplied to mask 18, mask 18 subtracts corrected body motion data TKD' from corrected pulse wave data MKD', to generate the corrected pulse wave data MKD" from which body motion components have been removed shown in FIG. 19. As a result, even if body motion is present, its effect is canceled, making it possible to obtain a corrected pulse wave data MKD" which is the same as the corrected pulse wave data MKD' obtained from the pulse wave of a subject at rest.

Pulse type data generator 12 determines the pulse type based on corrected pulse wave data MKD". In this example, the total S1 of frequency components above 2.0 Hz in intervals t2 and t3 is 28, so that $[S1 \geq 15]$. The total S2 of frequency components in the 4.0~3.0 Hz range in interval t2 is 9. And total S3 of frequency components in the 4.0~3.0 Hz range in interval t3 is 13. Accordingly, $[S2<S3]$. Therefore, based on the determination standards cited above, a determination is made that a Hua mai is present. Pulse type data generator 12 generates data Dk indicating that pulse type data ZD is a Hua mai.

In the second embodiment, wavelet transformation is performed on body motion waveform TH, and body motion components are canceled based on the result obtained. According, by means of the second embodiment, it is possible to accurately detect the pulse type even during daily activities or when exercising.

1.5: Embodiment 3

In the second embodiment, frequency correction was performed on the wavelets in the pulse waveform and the body motion waveform, and the pulse waveform wavelet was masked by the body motion waveform. However, two types of frequency correctors are required in this case, so that the structure becomes complicated. This point was taken into consideration in the conception of the third embodiment.

The external structure of the third embodiment is the same as that of the first embodiment shown in FIG. 2. However, the pulse wave diagnosing device according to the third embodiment is provided with an acceleration sensor 21 inside the main body 110 of the device, as in the case of the second embodiment.

Figure 20:
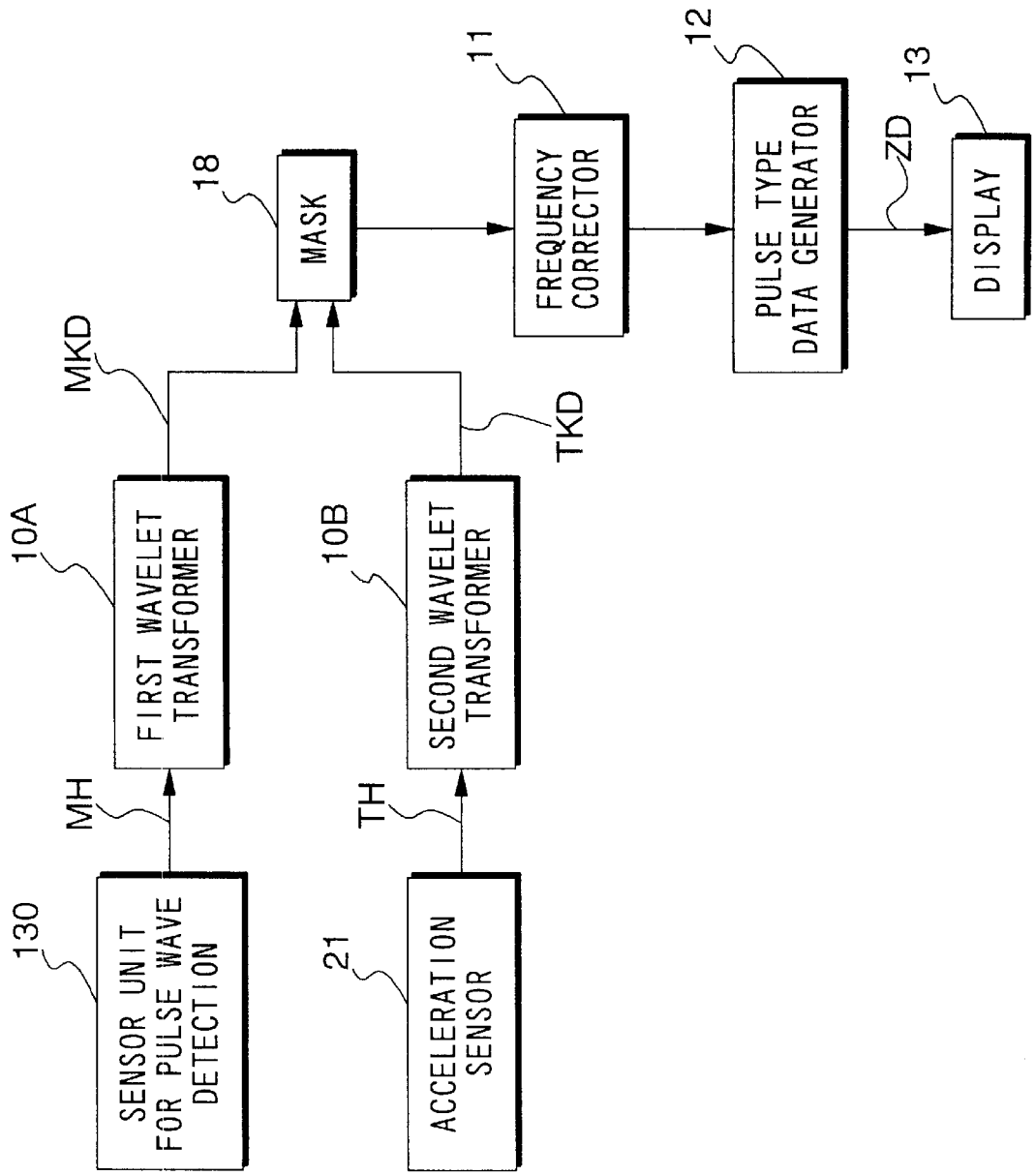
FIG. 20 is a block diagram showing the pulse wave diagnosing device according to the third embodiment in Chapter 1.

The electrical structure of the pulse wave diagnosing device according to the second embodiment will be explained. FIG. 20 is a block diagram of the pulse wave diagnosing device according to the third embodiment. The first and second wavelet transformers 10A, 10B and frequency corrector 11 in this figure have the same structures as wavelet transformer 10 and frequency corrector 11 in the first embodiment.

Prior to correcting the frequency, mask 18 subtracts analyzed body motion data TKD from analyzed pulse wave data MKD in order to cancel the body motion components, thereby generating pulse wave data from which body motion components have been removed. Subsequently, frequency corrector 11 corrects the pulse wave data from which body motion components have been removed by performing frequency correction so that the power density at each frequency becomes constant, thereby generating corrected pulse wave data MKD". As a result, it becomes possible to compare levels between different frequency components. Next, when pulse type data generator 12 generates pulse type data ZD based on corrected pulse wave data MKD", and displays this pulse type data ZD on display 13.

Since frequency corrector 11 is provided after mask 18 in the third embodiment, the structure of the pulse wave diagnosing device is simple, and it is possible to specify the pulse type even in the presence of body motion.

1-6: Embodiment 4

In the second and third embodiments, body motion waveform TH was detected by acceleration sensor 21, and wavelet transformation was performed on the body motion waveform TH. The pulse type was then specified by comparing the result of wavelet transformation on pulse waveform MH and the result of wavelet transformation on body motion waveform TH, and canceling the body motion component included in the frequency components of pulse waveform MH. However, since acceleration sensor 21 and second wavelet transformer 10B are required, the structure becomes complicated. The fourth embodiment takes this point into consideration, providing a pulse wave diagnosing device that not only has a simple structure, but by means of which it is possible to specify an accurate pulse type even when body motion is present.

1-6-1: Structure of Embodiment 4

Figure 21:
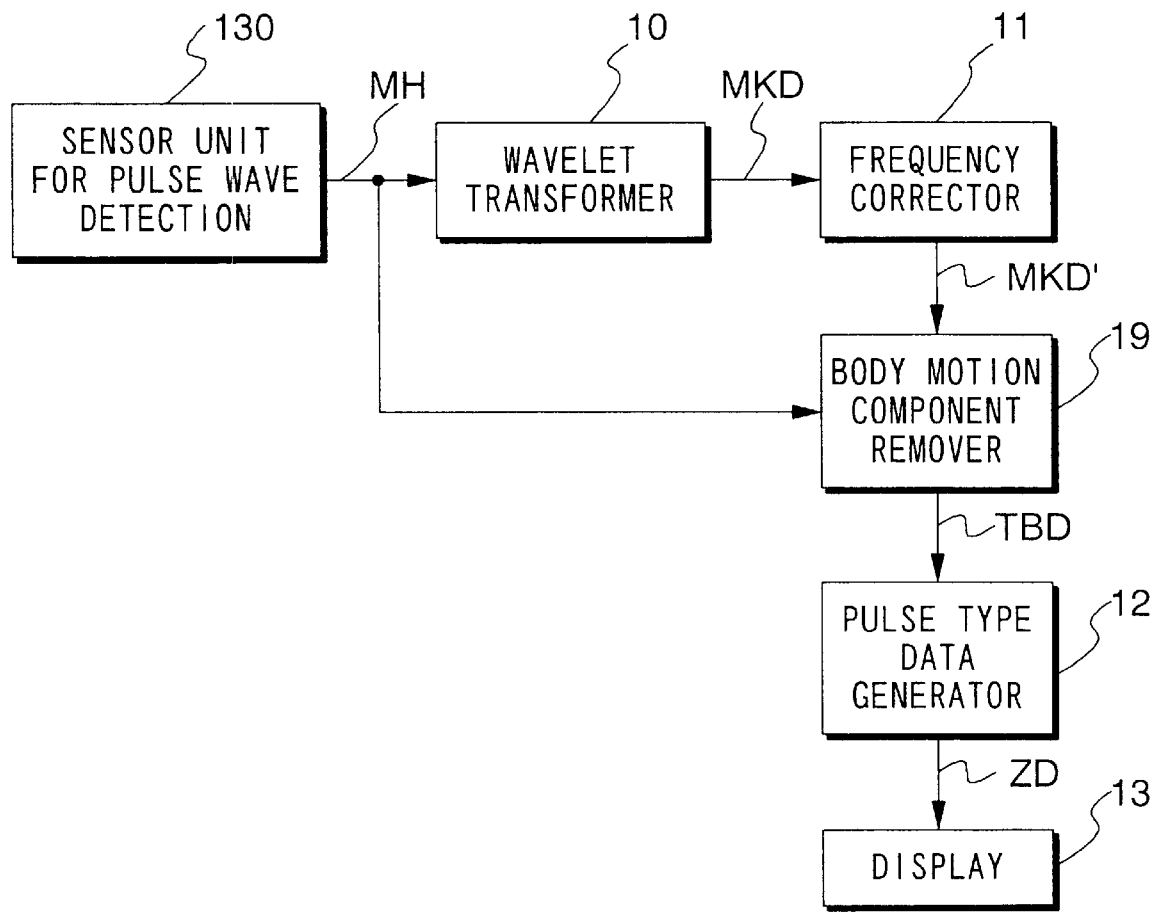
FIG. 21 is a block diagram of the pulse wave diagnosing device according to the fourth embodiment in Chapter 1.

The external structure of the pulse wave diagnosing device according to the fourth embodiment is equivalent to the external structure of the first embodiment shown in FIG. 2, and an explanation thereof will therefore be omitted here. An explanation will be made of the electrical structure, however. FIG. 21 is a block diagram of a pulse wave diagnosing device according to the fourth embodiment. With the exception of the provision of a body motion component remover 19 between frequency corrector 11 and pulse type data generator 12, FIG. 21 is equivalent to FIG. 4 explained in connection with the first embodiment. Accordingly, only points of difference will be explained below.

Body motion component remover 19 eliminates and removes the body motion component from corrected pulse wave data MKD', and generates pulse wave data TBD from which body motion components have been removed. Body motion component remover 19 takes advantage of the following properties of body motion.

Namely, body motion is generated as a result of the vertical movement of the arms or the swinging motion of the arms during running. During the course of daily activities, however, there is almost no instantaneous movement of the body. For this reason, the frequency component of the body motion waveform TH does not become so high during daily activities, but is typically in the range of 0 Hz~1 Hz. In this case, the fundamental frequency of pulse waveform MH is frequently in the range of 1 Hz~2 Hz. Accordingly, during daily activities, the frequency components of body motion waveform TH are in a frequency region which is lower than the fundamental frequency of pulse waveform MH.

In contrast, an effect is exerted by the swinging motion of the arms and the like which accompanies sports such as jogging, so that the frequency component of the body motion waveform TH becomes somewhat higher. However, the pulse rate also increases in accordance with the amount of exercise, so that the fundamental frequency of pulse waveform MH is becoming higher at the same time. Accordingly, even in the case where the subject is performing a sport, the frequency components of body motion waveform TH are typically in a frequency range which is lower than the fundamental frequency of pulse waveform MH.

Figure 22:
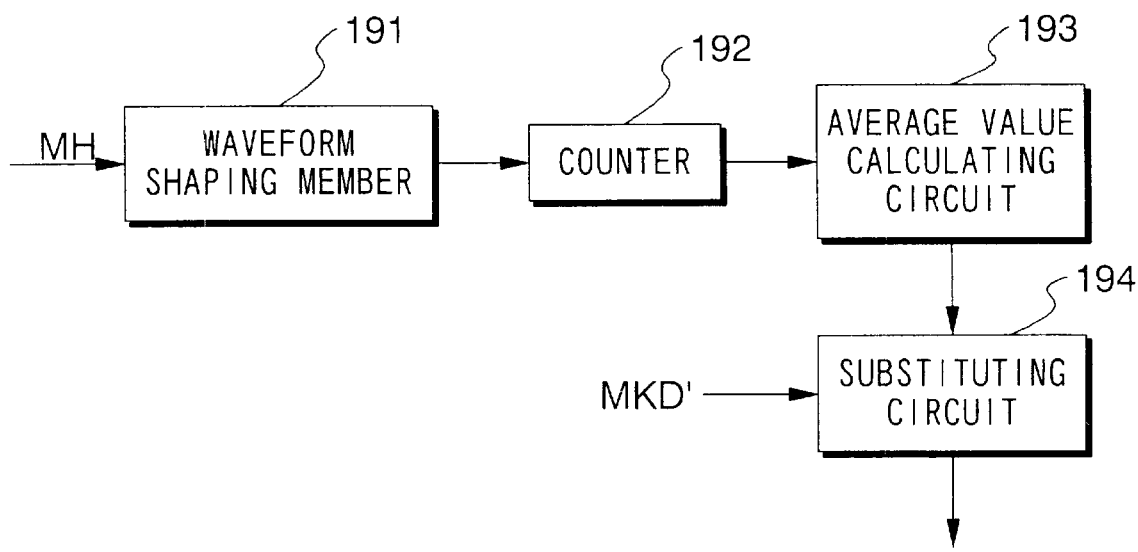
FIG. 22 is a block diagram showing the details of body motion component remover 19 according to the fourth embodiment in Chapter 1.

Body motion component remover 19 takes advantage of this point to remove body motion components, being designed to ignore frequency regions which are lower than the fundamental component of pulse waveform MH. In this case, if body motion components are present in a frequency region which is higher than the fundamental component of pulse waveform MH, then the accuracy of pulse type detection falls. However, since there is a higher probability that body motion components will be in a frequency region which is lower than the fundamental component of pulse waveform MH, it is possible to carry out highly accurate pulse type detection. FIG. 22 is a detailed block diagram of body motion component remover 19. Waveform shaping member 191 performs waveform shaping on pulse waveform MH, and generates a reset pulse synchronized with pulse waveform MH. More specifically, waveform shaping member 191 is composed of ringing filter 101, zero cross detecting circuit 102, and the like shown in FIG. 6. Counter 192 counts the clock pulses, which are not shown in the figures, and is designed so that the counter value is reset by the reset pulse. Average value calculating circuit 193 calculates the average of the counter value of counter 192, and may be composed of adder 121, coefficient circuits 122 and 123, memory 123 and the like shown in FIG. 8. In this case, the average value calculated by average value calculating circuit 193 corresponds to the average period of pulse waveform MH. Accordingly, the fundamental frequency of pulse waveform MH can be detected by referring to the average value.

Based on the aforementioned average value, substituting circuit 194 specifies the frequency region which includes the fundamental frequency of pulse waveform MH. For example, when the average value is 0.71 sec, then the fundamental frequency becomes 1.4 Hz. Thus, the frequency region specified is 1 Hz~1.5 Hz. Thereafter, for frequency regions which are less than the specified frequency region, substituting circuit 194 substitutes the corrected pulse wave data MKD' with [0], to generate pulse wave data TBD from which body motion components have been removed. As a result, components of frequency regions lower than the fundamental frequency of pulse waveform MH are ignored in the pulse type determination. In this case, pulse wave components are replaced by [0], along with the body motion components. However, since the characteristic portions of pulse waveform MH are present in frequency regions which are higher than the fundamental frequency, this substitution by [0] as described above has almost no impact on the determination of the pulse type.

Based on the thus-generated pulse wave data TBD from which body motion components have been removed, pulse type data generator 12 shown in FIG. 21 determines the pulse type and generates pulse type data ZD. When pulse type data ZD is supplied to display 13, display 13 displays a phrase such as "Ping mai", "Xuan mai" or "Hua mai", or specific symbols or icons.

1-6-2: Operation of Embodiment 4

The operation of the fourth embodiment will now be explained with reference to the figures.

In this example, if pulse waveform MH (fundamental frequency 1.3 Hz) shown in FIG. 16A is detected by a pulse wave detection sensor unit 130, then corrected pulse wave data MKD' in time period Tc becomes as shown in FIG. 17.

The frequency region specified by substituting circuit 194 is the 1.0 Hz~1.5 Hz frequency region in this case. Thus, the frequency region subject to substitution becomes Ma12~Ma82 corresponding to 0.5 Hz~1.0 Hz and Ma11~Ma81 corresponding to 0 Hz~0.5 Hz. Accordingly, data M12~Ma82 and Ma11~Ma81 of corrected pulse wave data MKD' are substituted by [0], generating pulse wave data TBD from which body motion components have been removed, shown in FIG. 23.

Pulse type data generator 12 determines the pulse type based on this pulse wave data TBD from which body motion components have been removed. In this example, the total S1 of frequency components above 2.0 Hz in time periods t2 and t3 is 28, so that [S1≧15]. The total S2 of frequency components in the range of 4.0~3.0 Hz for time period t2 is 9. And total S3 of frequency components in the range of 4.0~3.0 Hz in time period t3 is 13. Accordingly, [S2<S3]. Therefore, based on the determination standards cited above, a determination is made that a Hua mai is present. Pulse type data generator 12 generates data Dk indicating that pulse type data ZD is a Hua mai.

In the fourth embodiment, the body motion components are removed by taking advantage of the property of body motion it that body motion components are likely to be present in a frequency region which is lower than the fundamental frequency component of pulse waveform MH. Thus, it is. possible to omit such structures as acceleration sensor 21 and second wavelet transformer 10B, which were required in the second and third embodiments. Moreover, accurate detection of the pulse type is possible even when body motion is present.

1-7: Embodiment 5

In the second through fourth embodiments, body motion components were removed from the results obtained after performing wavelet transformation on pulse waveform MH, and the pulse type was specified based on the energy level of this time-frequency domain. By the way, in wavelet processing, it is known to be possible to reproduce the signals on the time axis by performing inverse wavelet transformation on the result obtained from wavelet transformation. The fifth embodiment focuses on this point in order to specify the pulse type on the time axis by performing inverse wavelet transformation on the wavelet—transformed-result from which body motion components have been removed.

1-7-1: Structure of Embodiment 5

The external structure of the pulse wave diagnosing device according to the fifth embodiment is equivalent to the external structure of the first embodiment shown in FIG. 2, so that an explanation thereof will be omitted here. An explanation will be made of the electrical structure, however. Note that this example explains the case in which inverse wavelet transformation is employed in the fourth embodiment. However, it is also acceptable to employ inverse wavelet transformation in the second or third embodiments to specify the pulse type along the time axis.

Figure 24:
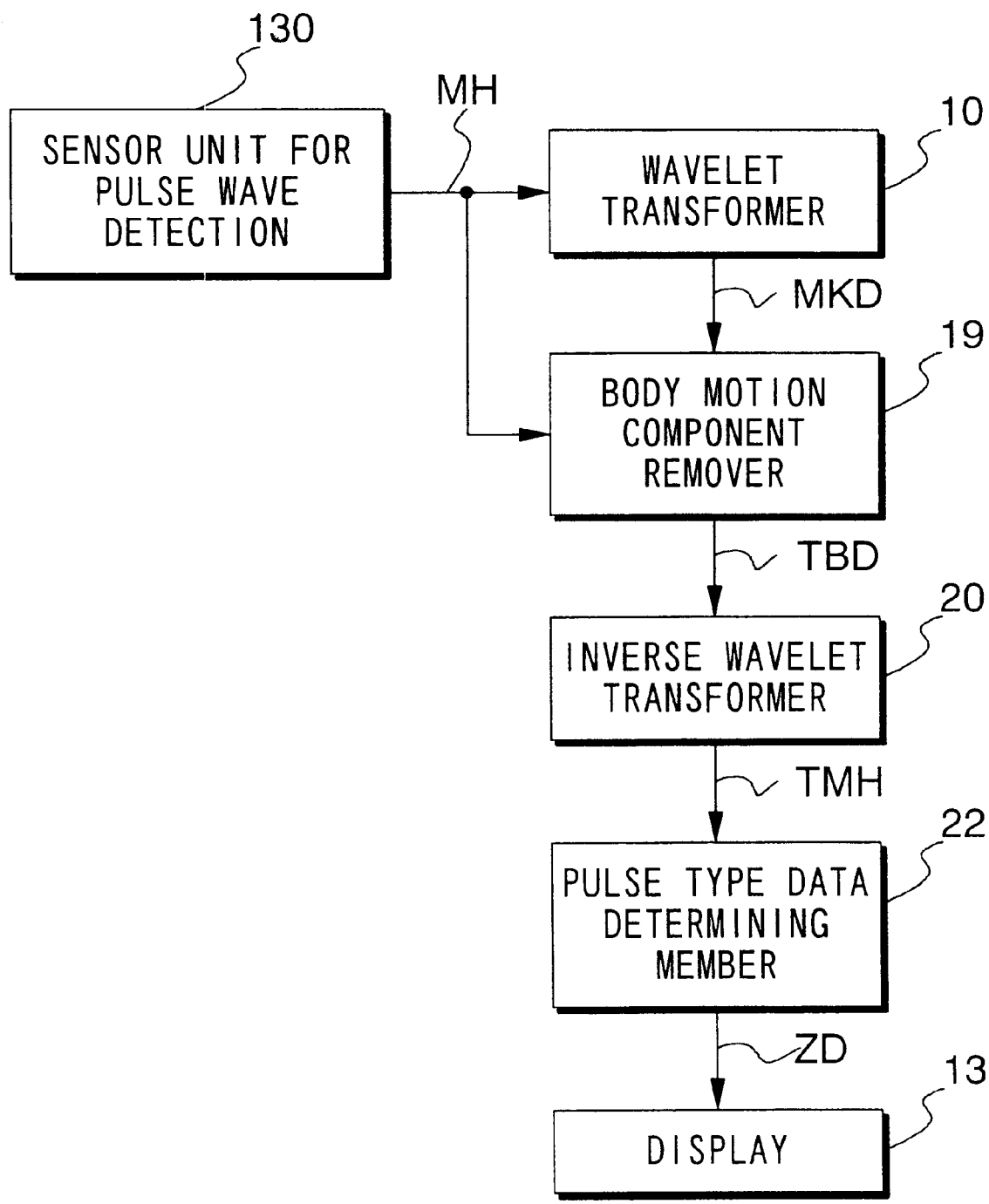
FIG. 24 is a block diagram of a pulse wave diagnosing device according to the fifth embodiment in Chapter 1.

FIG. 24 is a block diagram of a pulse wave diagnosing device according to the fifth embodiment. The pulse wave diagnosing device according to the fifth embodiment differs from that of the forth embodiment shown in FIG. 21 in that frequency corrector 11 is not employed, pulse type determining member 22 is provided in place of pulse type data generator 12, and inverse wavelet transformer 20 is provided in between body motion component remover 19 and pulse type determining member 22. These points of difference will be explained below.

The reason that frequency corrector 11 is not provided is because it is not necessary to compare the results of wavelet transformation in each time-frequency region since the pulse type is specified from the signal waveform along the time axis in this example. In addition, another reason why frequency corrector 11 is not provided is because the inverse wavelet transformer reproduces the signal waveform on the time axis by processing the result obtained by wavelet transformation. Accordingly, the signal waveform would not be correctly reproduced if frequency correction were performed.

Next, inverse wavelet transformer 20 has a complementary relationship with wavelet transformer 10, and calculates equation 2 below.

$$f(x) = \frac{1}{C\varphi} \int \int_{R^2} (W\varphi f)(a, b) \frac{1}{\sqrt{a}} \varphi\left[\frac{x-b}{a}\right] \frac{da\, db}{a^2} \quad \text{EQUATION 2}$$

Pulse waveform TMH from which body motion components have been removed is obtained based on pulse wave data TBD from which body motion components have been removed. For example, when pulse waveform MH shown in FIG. 16A is detected by sensor unit 130 for detecting the pulse wave, analyzed pulse wave data MKD becomes as shown in FIG. 17 in time period Tc. Next, when the body motion component is removed by body motion component remover 19, pulse wave data TBD from which body motion components have been removed shown in FIG. 23 is obtained. When inverse wavelet transformation is performed by inverse wavelet transformer 20, then pulse waveform MH' shown in FIG. 16C is generated as pulse waveform TMH from which body motion components have been removed.

Figure 25:
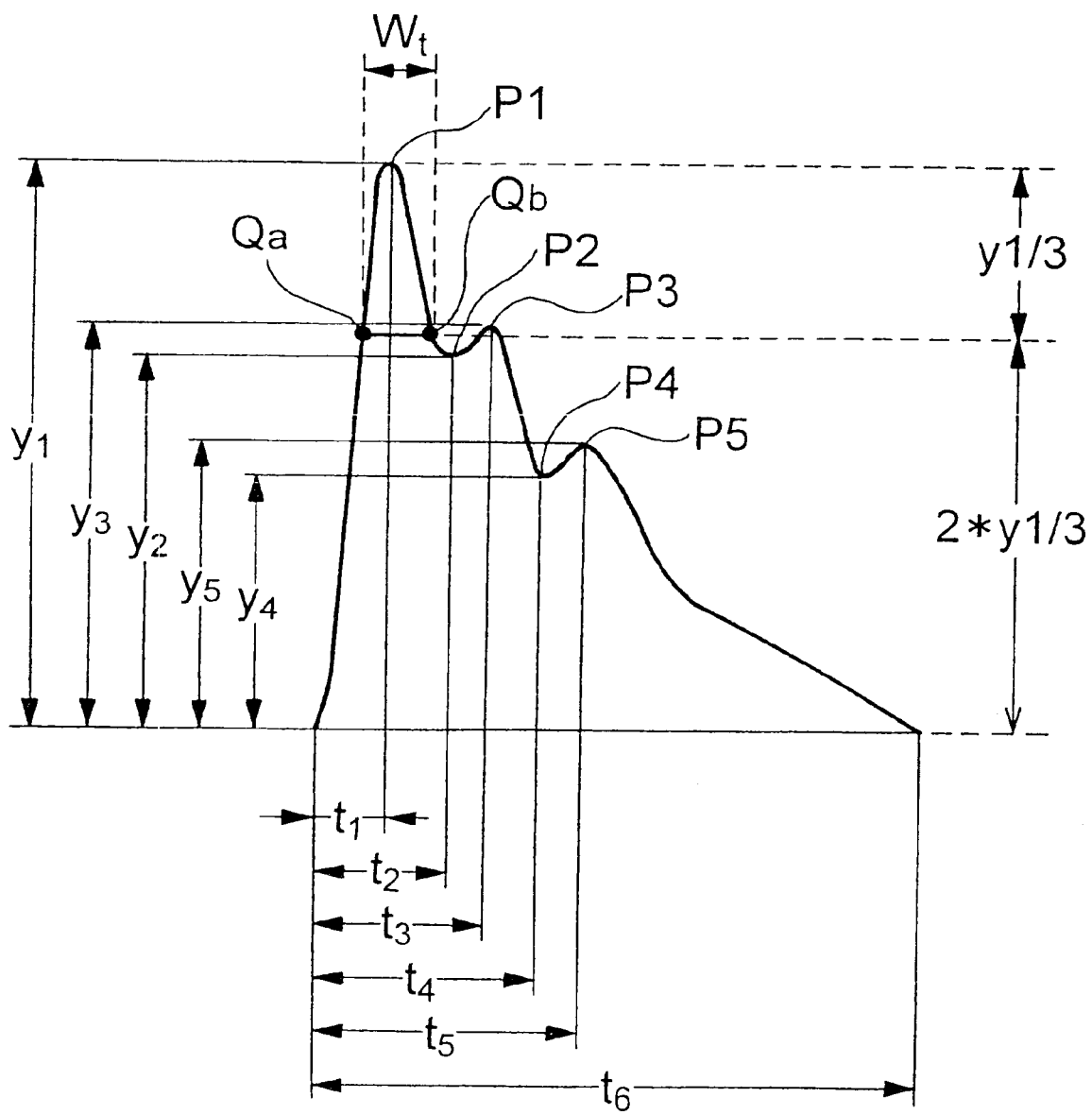
FIG. 25 is a diagram showing one example of pulse wave data TMH from which body motion components have been removed for one beat according to the fifth embodiment in Chapter 1.

Next, in order to specify the pulse type, pulse type determining member 22 first extracts waveform parameters specifying the shape of pulse waveform TMH from which body motion components have been removed. Assuming the pulse waveform TMH from which body motion components have been removed during one beat has the shape as shown in FIG. 25, then the waveform parameter is defined as below. Note that blood pressure is plotted along the vertical axis and time is plotted along the horizontal axis in FIG. 21.

1) Time $t_6$ from when the pulse wave corresponding to one beat (hereinafter the time at which the pulse wave rises will be referred to as the "pulse wave start time") until the pulse wave corresponding to the next beat starts to rise 2) Blood pressure values $y_1$~$y_5$ at maximum point P1, minimum point P2, maximum point P3, minimum point P4, and maximum point P5 appearing sequentially in the pulse wave 3) Elapsed time $t_1$~$t_5$ after the pulse wave start time until each of points P1~P5 appear In order to calculate the waveform parameters, pulse type determining member 22 extracts the so-called peak information, i.e., information relating to each of the maximum and minimum points. The content of peak information is related to the operation and structure of the pulse type determining member. Accordingly, peak information will be explained in detail when explaining the structure of the circuit.

FIG. 26 is a block diagram showing the structure of pulse type determining member 22. Numeral 181 in the figure indicates a microcomputer for controlling each of the structural parts. 184 is a waveform memory composed of RAM. Waveform value W of pulse waveform TMH from which body motion components have been removed is taken up via A/D converter 182, and sequentially stored. 195 is a waveform value address counter which starts counting sampling clock φ during the time period in which microcomputer 181 is outputting a START directive to collect the pulse waves. Waveform value address counter 195 outputs the counter result as the waveform value address ADR1 at which waveform value W is to be written. This waveform value address ADR1 is monitored by microcomputer 181.

The numeral 196 indicates a selector. When microcomputer 181 is not outputting a select signal S1, selector 196 selects the waveform value address ADR1 output by waveform value address counter 195, and supplies the selected waveform value address ADR1 to the address input terminal of waveform memory 184. In contrast, when a select signal S1 is being output by microcomputer 181, selector 196 selects the readout address ADR4 which is output by microcomputer 181, and supplies the selected readout address ADR4 to the address input terminal of waveform memory 184.

The numeral 201 in the figure is a differentiating circuit which calculates the time derivative of the waveform values W which are sequentially output from low-pass filter 183.

202 is a zero cross detecting circuit which outputs zero cross detection pulse Z when the time derivative of the waveform value W is 0 due to the presence of maximum or minimum values. More specifically, zero cross detecting circuit 202 is provided to detect peaks P1, P2, . . . in the waveform of the pulse wave disclosed in FIG. 27. Zero cross detection pulse Z is output when waveform values W corresponding to these peaks are input.

203 is a peak address counter. Peak address counter 203 counts zero cross detection pulse Z while microcomputer 181 is outputting a START directive to begin collecting the pulse waves. Peak address counter 203 then outputs the counted result as peak address ADR2.

204 is a moving average calculating circuit which calculates the average value of the time derivative of a fixed number of past waveform values W output from differentiating circuit 201 through the present point in time. The calculated result is output as slope information SLP indicating the slope of the pulse wave up through the current point in time.

205 indicates peak information memory provided to store the peak information which will be explained next. Peak information will be explained in greater detail below. Namely, the details of the content of peak information shown in FIG. 28 are listed as follows.

(1) Waveform Value Address ADR1

The waveform value address ADR1 is the write address output from waveform value address counter 195 when the waveform value W output from low-pass filter 183 is a maximum or minimum value. In other words, this is the write address in waveform memory 184 for waveform value W corresponding to a maximum or minimum value.

(2) Peak Type B/T

The peak type is information indicating whether the waveform value W which is written in waveform value address ADR1 is a maximum value T (Top) or a minimum value B (Bottom).

(3) Waveform Value W

This is the waveform value corresponding to a maximum or minimum value.

(4) Stroke Information STRK

The stroke information STRK is the amount of change in the waveform value from the immediately preceding peak value to the peak value of interest.

(5) Slope Information SLP

This is the average value of the time derivative of a fixed number of past waveform values up through the peak value of interest.

Next, the operation of pulse type determining member 22 under the control of microcomputer 181 will be explained.
(a) Collection of Waveforms and Corresponding Peak Information When microcomputer 181 outputs a START directive to collect waveforms, waveform value address counter 195 and peak address counter 203 are released from resetting.

As a result, the sampling clock φ counter is started by waveform value address counter 195. The counter value is supplied to waveform memory 184 via selector 196 as waveform value address ADR1. The pulse wave signals detected from the human body are input to A/D converter 182, and sequentially converted to digital signals in accordance with the sampling clock. These converted digital signals are then sequentially output via low-pass filter 183 as waveform values W. The waveform values W output in this way are sequentially supplied to waveform memory 184, and written in the memory area specified by waveform value address ADR1 at that point in time. As a result of the preceding operations, a continuous waveform value W corresponding to the pulse waveform is stored in waveform memory 184. This continuous waveform value W is shown in FIG. 27.

In parallel with the preceding operation, detection of peak information and writing to peak information memory 205 are carried out as explained below.

First, the time derivative of the waveform values W of pulse waveform TMH from which body motion components have been removed is calculated at differentiating circuit 201, and then input to zero cross detecting circuit 202 and moving average calculating circuit 204. Moving average calculating circuit 204 calculates the average value (i.e., moving average value) of a specified past number of time derivatives each time the time derivative of a waveform value W is supplied, and outputs the calculated result as slope information SLP. A positive value will be output for slope information SLP when waveform value W is rising or has reached a maximum value. Conversely, a negative value will be output for slope information SLP when waveform value W is falling or has reached a minimum value.

When waveform value W corresponding to maximum point P1 shown in FIG. 27, for example, is output from low-pass filter 183, 0 is output from differentiating circuit 201 as the time derivative, and zero cross detection pulse Z is output from zero cross detecting circuit 202.

As a result, microcomputer 181 uptakes the waveform address ADR1, which is the counter value of waveform value address counter 195; waveform value W; peak address ADR2, which is the counter value of the peak address counter (here, ADR2=0); and slope information SLP, at that point in time. Further, when zero cross detection pulse Z is output, the counter value ADR2 of peak address counter 203 becomes 1.

Microcomputer 181 creates peak type B/T based on the sign of the uptaken slope information SLP. In this case, when the waveform value W of maximum value P1 is output, then positive slope information is output at that point in time. As a result, microcomputer 181 sets the value of peak information B/T to one corresponding to a maximum value. Microcomputer 181 indicates peak address ADR2 uptaken from peak address counter 203 (here ADR2=0) without modification as write address ADR3, and writes waveform value W, its waveform address ADR1, peak type B/T, and slope information SLP as the first time peak information in peak information memory 205. When writing first time peak information, stroke information STRK is not created or written since there is no immediately preceding peak information.

When waveform value W corresponding to minimum point P2 shown in FIG. 27, for example, is subsequently output from low-pass filter 183, zero cross detection pulse Z is output in the same way as above, and write address ADR1, waveform value W, peak address ADR2 (=1), and slope information SLP (<0) are taken up by microcomputer 181.

Next, in the same way as above, microcomputer 181 determines the peak type B/T (B, in this case) based on slope information SLP. Next, the address which is 1 less than peak address ADR2 is read out by microcomputer 181, and supplied to peak. information memory 205 as address ADR3. The waveform value W which was written first is then read. Next, microcomputer 181 calculates the difference between waveform value W taken up at the current time from the low-pass filter 183 and the waveform value W read out from peak information memory 205 that was first taken up, thereby obtaining stroke information STRK. The thus obtained peak type B/T and stroke information STRK are written in the memory area corresponding to peak address ADR3=1 in peak information memory 205 as second time peak information together with other information such as waveform value address ADR1, waveform value W and slope information SLP. The same operation is then carried out when peaks P3, P4, . . . , are detected.

Once a specific period of time has elapsed, microcomputer 181 stops outputting the waveform collection directive START, and the collection of waveform value W and peak information terminates.

(b) Pulse Waveform Partitioning Processing

Microcomputer 181 carries out processing to specify from among the various information stored in peak information memory 205 the information corresponding to the waveform of a single beat at which waveform parameter collection is carried out.

First, slope information SLP and stroke information STRK corresponding to each of the peaks P1, P2, . . . are sequentially read out from peak information memory 205. Next, stroke information corresponding to positive slopes is selected from each stroke information STRK (i.e., the corresponding slope information SLP which is positive). A specified number of the largest values are then selected from among this stroke information. Next, stroke information corresponding to medium values is selected from among the selected stroke information, and the stroke information for the rising portion (for example, the rising portion indicated by symbol STRKM in FIG. 27) of the pulse wave of one beat at which waveform parameter extraction is to be carried out is obtained. Next, the peak address immediately preceding the peak address of this slope information (i.e., the peak address at point P6, the initiation of the pulse wave of one beat at which waveform parameter extraction is to be performed) is obtained.

(c) Extraction of Waveform Parameters

Microcomputer 181 calculates each waveform parameter by referencing each peak information corresponding to the pulse wave of one beat recorded in peak information memory 205. This processing may be obtained as follows.

(1) Blood Pressure Values $y_1$~$y_5$

The waveform values corresponding to peaks P7~P11 are designated as $y_1$~$y_5$ respectively (2) Time $t_1$ The waveform address corresponding to peak P6 is subtracted from the waveform address corresponding to peak P7. $t_1$ is calculated by multiplying the period of the sampling clock with this result.

(3) Time $t_2$~$t_6$

As in the case of $t_1$ above, $t_2$~$t_6$ are calculated based on the difference in the waveform addresses between each of the corresponding peaks.

Further, each of the waveform parameters obtained in this way are stored in the buffer memory inside microcomputer 181.

(d) Pulse Type Determination Based on Waveform Parameters

Figure 29:
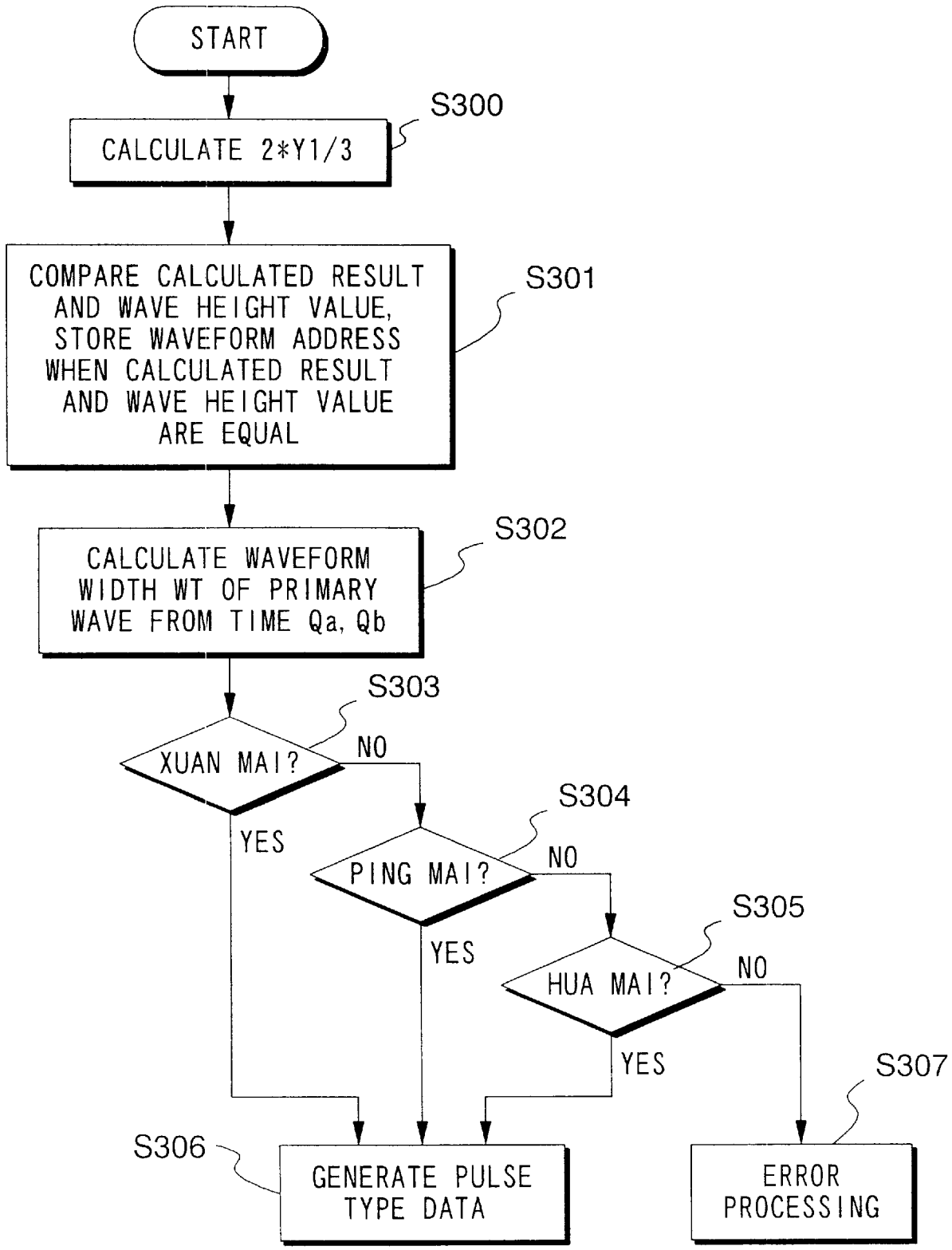
FIG. 29 is a flow chart for explaining the operation of the fifth embodiment in Chapter 1.

Next, processing to determine the pulse type based on the waveform parameter will be explained with reference to the flow chart shown in FIG. 29.

d-1: Operation for Calculating Waveform Width Wt of Main Wave

Peak information as described above consists of time periods $t_1$~$t_5$, blood pressure $y_1$~$y_4$, and period $t_6$ of the waveform for waveform peaks P1~P5 shown in FIG. 25. In general, the pulse waveform is formed of a main wave (corresponding to peak P1) caused by the initial rise, a tidal wave (corresponding to peak P3) which follows the main wave, a dicrotic notch (from P3 to P4), and an overlap wave (corresponding to peak P5). The main wave corresponds to the acute ejection period in the left ventricle. The tidal wave is formed according to the correlation between the elastic expansion of the aorta and the reflected wave at the periphery. The dicrotic notch expresses the pressure of the aorta during diastole of the left ventricle, and corresponds to diastolic pressure. The overlap wave is the wave due to return flow accompanying closing of the aortic valve.

Microcomputer 181 determines the type of pulse wave based on peak information as described below. Before this, however, Wt shown in FIG. 25 is calculated. Wt is the waveform width at a position which is ⅓the height y1 of the main wave. In FIG. 21, microcomputer 181 calculates 2*y1/3 (step S300), and sequentially compares the results of this calculation with the wave height value read out from waveform memory 184. The waveform address at the point where both coincide is stored in a buffer memory inside microcomputer 181 (step S301). As a result, the time intervals for points Qa,Qb are determined, and the waveform width Wt of the main wave is calculated by calculating the difference between the two (step S302).

d-2: Operation to Determine Type of Pulse

Next, microcomputer 181 determines the type of pulse as follows.

(1) Since the tidal wave is fused to the main wave as shown in FIG. 11, Xuan mai is characterized in that 1) the main wave widens and 2) the height of the tidal wave is relatively high compared to the height of the main wave. Thus, microcomputer 181 calculates the following relational equations (55)~(59), and determines that a Xuan mai is present when these relationships are met (step S303).

$$0.20 < Wt/t < 0.28 \tag{55}$$

$$y3/y1 \geq 0.7 \tag{56}$$

$$y4/y1 > 0.5 \tag{57}$$

$$(y5-y4)/y1 < 0.03 \tag{58}$$

$$t1 < 0.12 \tag{59}$$

(2) A Ping mai is formed of a three-peak wave consisting of a main wave, tidal wave, and overlap wave, as shown in FIG. 12. Thus, microcomputer 181 calculates the following relationships (60)~(64), and determines that a Ping mai is present when these relationships are met (step S304).

$$Y3/y1 < 0.7 \tag{60}$$

$$y3/y1 > y4/y1 \tag{61}$$

$$0.3 \leq y4/y1 < 0.5 \tag{62}$$

$$(y5-y4)/y1 > 0.05 \tag{63}$$

$$0.12 < Wt/t < 0.2 \tag{64}$$

(3) Hua mai is two-peaked waves in which the main wave and the tidal wave a r e almost entirely superimposed, as shown in FIG. 13. Thus, microcomputer 181 calculates the following relational equations (65)~(68), and determines that a Hua mai is present when these relationships are satisfied (step S305).

$$0.2 < y3/y1 < 0.4 \quad (65)$$

$$0.2 < y4/y1 < 0.4 \quad (66)$$

$$(y5-y4)/y1 > 0.1 \quad (67)$$

$$Wt/t < 0.20 \quad (68)$$

When the type of pulse type is specified in this way, pulse type determining member 22 generates pulse type data ZD showing the pulse type (step S306). Note that error processing is performed when the wave does not correspond to Xuan mai, Ping mai or Hua mai (step S306).

In the fifth embodiment, wavelet transformation is performed on pulse waveform MH, the body motion components are removed by exploiting the properties of body motion, and pulse waveform TMH from which body motion components have been removed is reformed. As a result, body motion components functioning as noise components can be removed. Thus, even when body motion is present, it is possible to accurately detect the pulse type using the signal waveform.

1-8: Modifications for Chapter 1

The present invention is not limited to the above described embodiments. Rather, a variety of modifications are possible as follows.

1-8-1: Omission of Frequency Correcting Means

In the embodiments in Chapter 1, the frequency correcting means was employed for comparing energy in different frequency regions. However, it is also acceptable to focus on a given frequency region, and specify the pulse type based on the energy level thereof.

For example, when the frequency correcting means is omitted in the first embodiment, then an arrangement is acceptable in which the wavelet transforming means performs wavelet transformation on pulse waveform MH detected by pulse wave detection sensor unit 130, generates analyzed pulse wave data MKD for each frequency region, performs calculations on the analyzed pulse wave data MKD, and generates pulse type data ZD indicating the type of pulse waveform.

In the case where the frequency correcting means is omitted from the second and third embodiments, when pulse waveform MH is detected by pulse wave detection sensor unit 130, first wavelet transformer 10A performs wavelet transformation on pulse waveform MH, and generates analyzed pulse wave data MKD for each frequency region. When body motion waveform TH is detected by acceleration sensor 21, second wavelet transformer 10B performs wavelet transformation on body motion waveform TH, and generates analyzed body motion data TKD for each frequency region. Mask 18 subtracts analyzed body motion data TKD from analyzed pulse wave data MKD, and generates corrected pulse wave data MKD" from which body motion components have been removed. Pulse type data generator 12 then performs calculations on corrected pulse wave data MKD", and generates pulse type data ZD indicating the type of pulse waveform MH.

1-8-2: Other Examples of Removal of Body Motion Components

In the fifth embodiment, pulse waveform TMH from which body motion components have been removed was generated by performing inverse wavelet transformation on the output from body motion component remover 19. However, since this invention evaluates the pulse type along the time axis by reconstructing a wavelet in which body motion components have been removed, the present invention is not limited thereto. Rather, provided that inverse wavelet transformation is performed based on the wavelet from which body motion components have been removed, any arrangement is acceptable. For example, it is also acceptable that, when pulse waveform MH is detected by pulse wave detection sensor unit 130, first wavelet transformer 10A performs wavelet transformation on pulse waveform MH to generate analyzed pulse wave data for each frequency region. When body motion waveform TH is detected by acceleration sensor 21, second wavelet transformer 10B performs wavelet transformation on body motion waveform TH, to generate analyzed body motion data TKD in each frequency region. Subsequently, mask 19 subtracts analyzed body motion data TKD from analyzed pulse wave data MKD, to generate corrected pulse wave data MKD" from which body motion components have been removed. Inverse wavelet transformation is then performed on this corrected pulse wave data MDK".

1-8-3: Filter Bank Employed in Wavelet Transformation

Figure 30:
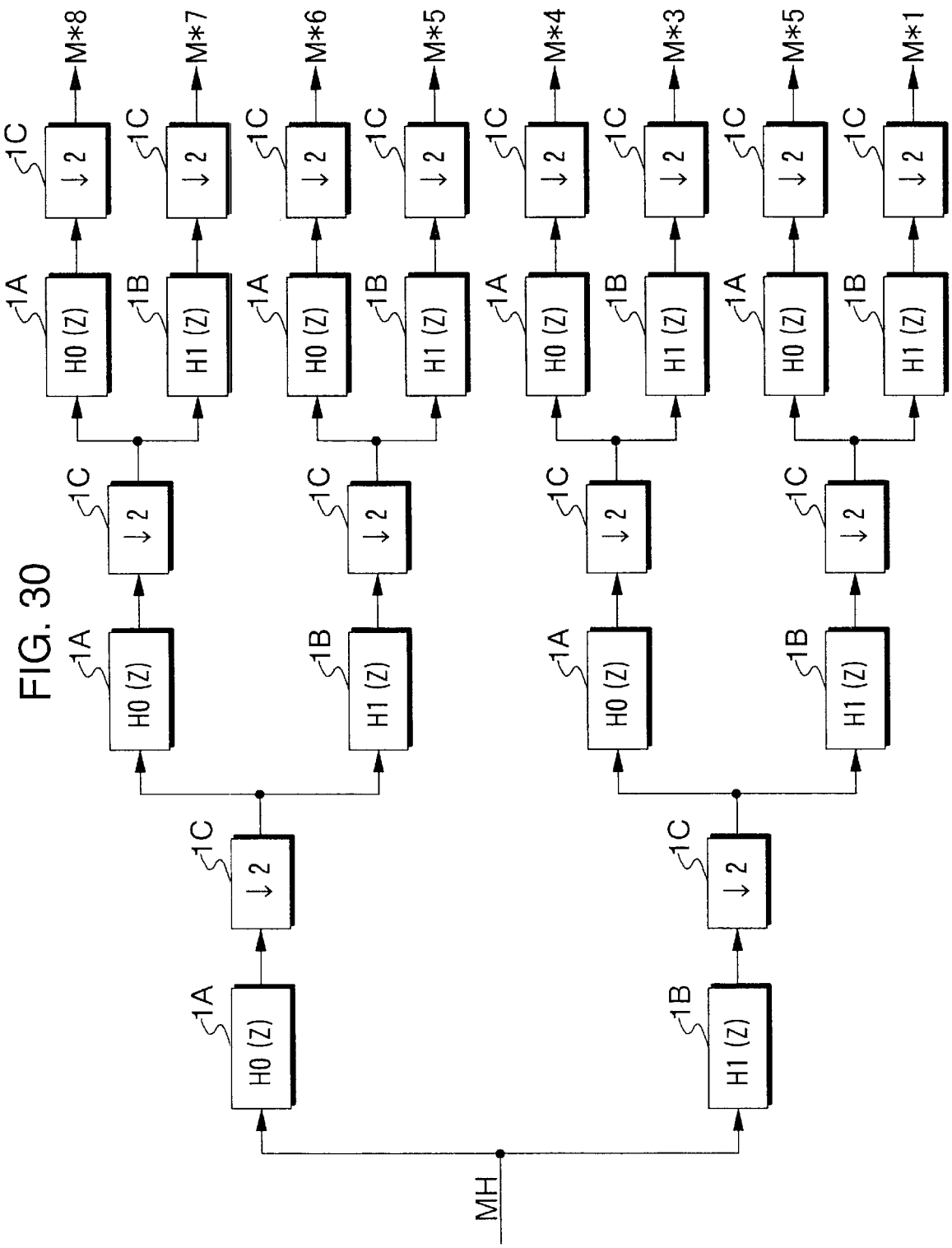
FIG. 30 is a block diagram showing an example of the case in which the wavelet transformer is formed of a filter bank in a modification in Chapter 1.

In the preceding embodiments, wavelet transformers 10, 10A, and 10B were provided with a base function developer W which performed wavelet transformation. However, the present invention is not limited thereto. Rather, it is also acceptable to realize wavelet transformation using a filter bank. An example of the structure of a filter bank is shown in FIG. 30. In this figure, the filter bank is composed of three stages, with the fundamental units being high-pass filter 1A and decimation filter 1C, and low-pass filter 1B and decimation filter 1C. High-pass filter 1A and low-pass filter 1B are designed to partition a given frequency region, and output a high-pass frequency component and a low-pass frequency component, respectively. This example assumes a range of 0 Hz~4 Hz for the frequency region of pulse wave data MD, so that the transmission region of the first high-pass filter 1A is set to 2 Hz~4 Hz, while the transmission region of the first low-pass filter 1B is set to 0 Hz~2 Hz. Decimation filter 1C weeds out data in each sample.

The thus generated data is supplied to the next stage, and partitioning of the frequency region and data weed out are repeated, with data M1~M8 ultimately obtained in which the 0 Hz~4 Hz frequency region is partitioned into 8 parts.

The high-pass filter 1A and low-pass filter 1B may be composed of a transversal filter which includes a delay element (D flip-flop) inside. The human pulse rate is in the range of 40~200 beats. The fundamental frequency of pulse waveform MH fluctuates moment by moment in response to physiological state. If it is possible to vary the region to be partitioned in synchronization with the fundamental frequency, then it is possible to obtain dynamic information which tracks the physiological state. Therefore, a clock supplied to the transversal filter may be timed to pulse waveform MH, thereby varying the region to be partitioned appropriately.

Of analyzed pulse wave data MKD, the frequency components of the fundamental wave, second harmonic wave and third harmonic wave are the representative frequency components which express the characteristics of pulse waveform MH. Accordingly, a portion of the output data M1~M8 of the filter bank may be used to carry out pulse type determination. In this case, if the filter bank is designed so as to be synchronous with pulse waveform MH, then it is possible to omit a portion of the high-pass filter 1A, low-pass filter 1B and decimation filter 1C, thereby simplifying the structure.

1-8-4: Filter Bank Employed in Inverse Wavelet Transformation

Figure 31:
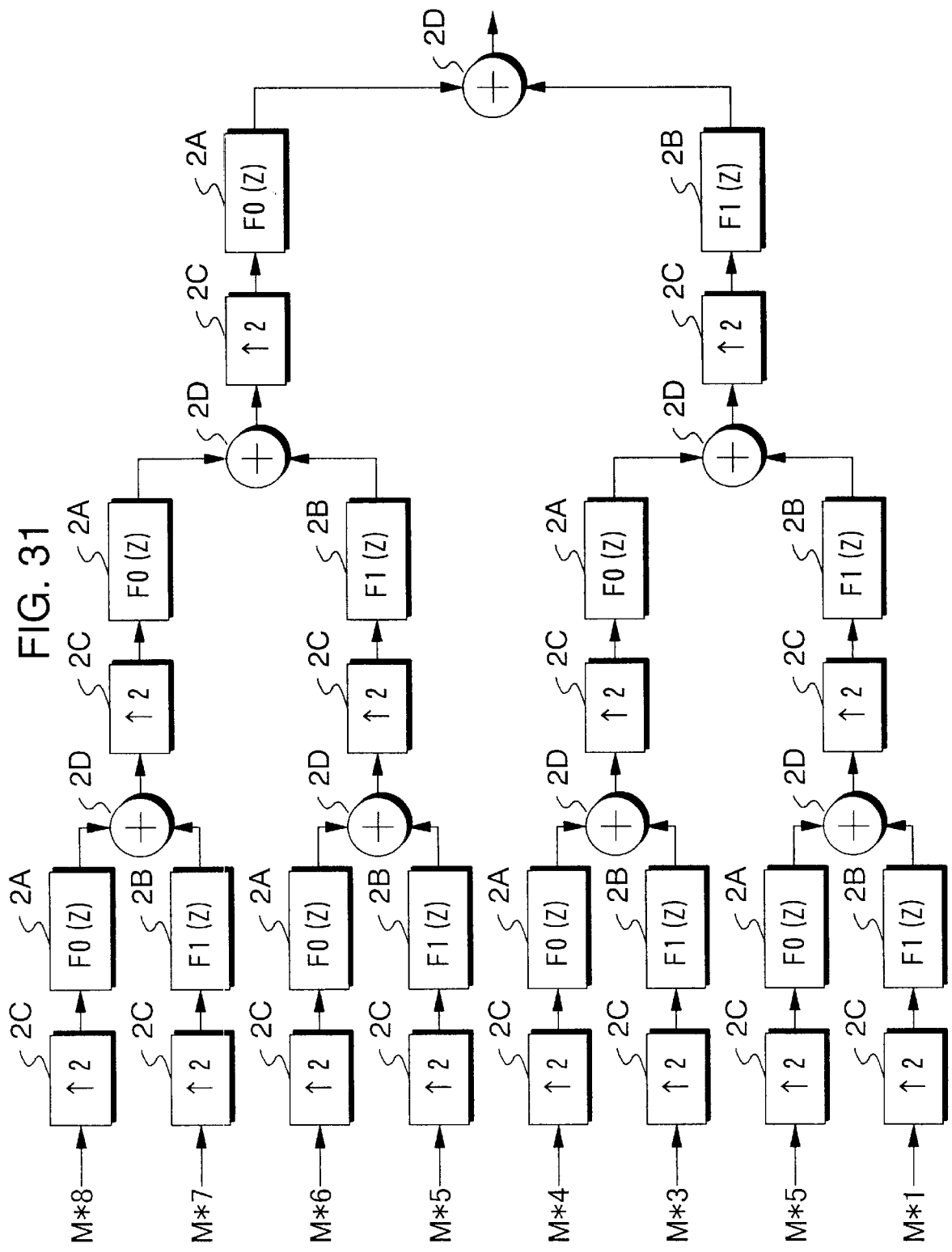
FIG. 31 is a block diagram showing an example of the case where the inverse wavelet transformer is formed of a filter bank in a modification in Chapter 1.

When wavelet transformer 10 is formed of the filter bank shown in FIG. 30 in the fifth embodiment, then inverse wavelet transformer 20 may be formed of the filter bank shown in FIG. 31. In this figure, the filter bank is formed of three stages with the fundamentals unit being high-pass filter 2A and interpolating filter 2C, and low-pass filter 1B and interpolating filter 2C, and adder 2D. High-pass filter 2A and low-pass filter 2B are designed to partition a given frequency region, and output a high-pass frequency component and a low-pass frequency component, respectively. Interpolating filter 2C interpolates one sample out of every two.

In order to reproduce the waveform, it is necessary to use an exact reconstruction filter bank for the filter banks shown in FIGS. 30 and 31. In this case, the characteristics of high-pass filters 1A,2A and low-pass filters 1B,2B must have the following relationships.

$$H0(-Z)F0(Z)+H1(-Z)F1(Z)=0$$

$$H0(Z)F0(Z)+H1(-Z)F1(Z)=2Z^{-L}$$

High-pass filter 2A and low-pass filter 2B may be formed of a transversal filter which includes a delay element (D flip-flop) inside. Note that the filter bank employed in wavelet transformer 10 is synchronized with the fundamental frequency of pulse waveform MH, and varies the regions that are partitioned. Thus, when the supplied clock is synchronized with pulse waveform MH, this clock may be supplied to high-pass filter 2A and low-pass filter 2B.

1-8-5: Automatic Adjustment of the Frequency Region Subjected to Frequency Analysis The body motion waveform TH was detected using an acceleration sensor 21 in the second and third embodiments. When body motion is detected, the fundamental frequency of pulse waveform MH is higher because the subject is in a state of motion. This pulse waveform MH undergoes frequency analysis at first wavelet transformer 10A. However, if the frequency region which is subjected to frequency analysis is fixed, then it may be difficult to fully analyze the characteristic portions of pulse waveform MH. For example, when an individual in which the fundamental frequency of pulse waveform MH at rest is 1 Hz goes running, the fundamental frequency of pulse waveform MH changes to 2 Hz (corresponding to a pulse rate of 120). By carrying out wavelet transformation within the region 0~4 Hz explained above in the second embodiment, it is possible to carry out frequency analysis through the third higher harmonic wave of pulse waveform MH. However, since the third harmonic wave reaches 6 Hz during running, it becomes impossible to carry out frequency analysis.

Therefore, the exercise quantity may be obtained based on the body motion waveform TH, with the first and second wavelet transformers 10A,10B being controlled so that the frequency region in which wavelet transformation is carried out shifts to a higher region as the amount of exercise increases.

When forming the first and second wavelet transformers 10A,10B from filter banks as described above, control of the clock frequency may be carried out in response to the amount of exercise. In other words, it is acceptable to carry out conventional feed back control so that the clock frequency becomes higher as the amount of exercise increases.

During running, the pitch of body motion waveform TH indicates the pitch of the return cycle of the runner's arms, and has a constant relationship with the pitch of the stride of the feet. Typically, two steps are taken with each swing of the arms. Further, the exercise quantity can be shown as the product of running speed and length of step. In general, as running speed is increased, the pitch tends to increase while the length of step tends to decrease. Accordingly, there is a constant relationship between the body motion waveform TH and exercise quantity. For example, FIG. 32 shows both the relationship between pulse rate and running speed when running on the ground, and the relationship between running pitch and running speed. As shown in this figure, it is clear that the pulse rate and running pitch of the test subject increase as the running speed increases. Namely, when the running pitch increases, the exercise quantity and the pulse rate increase accompanying this. Accordingly, the relationship between exercise quantity and the pitch of the body motion waveform TH may be measured in advance, and stored in a table, with the exercise quantity calculated by referring to this table.

1-8-6: Other Examples of Notifying Means

In the preceding embodiments, display 13 was explained as an example of a notifying means. In addition, however, the following arrangements described below may also be cited as means for providing notification between the device and the individual. These means may be appropriately categorized on the basis of the five senses. These means may of course be used alone, or in combination with one another. As explained below, if a means is employed which relies on a sense other than sight, then it is possible for even a visually-impaired individual to understand the details of the notification. Similarly, if a means is employed which relies on a sense other than hearing, then notification can be carried out to a hearing-impaired individual. As a result, it is possible to compose a device which is superior for use by a physically-disabled subject.

In the case of a notifying means which relies on the sense of hearing, arrangements are available for informing the subject of the results of pulse type analysis and diagnosis, or for warning the subject. In addition to buzzers, other examples include a piezoelement or a speaker. As a specialized example, a means may also be considered in which the person to be informed is provided with a portable pager, and notification is carried out by paging from a device. When carrying out notification to a subject using this kind of equipment, it is frequently desired to communicate some sort of information along with the notice. In this case, information such as volume levels may be changed in response to the details of the information to be communicated. For example, the pitch, volume, tone, sound, or type of music (program, etc.) may be changed.

Next, a means relying on sight may be employed when the objective is to inform the subject of various measured results or messages from the device, or to provide a warning. The following equipment may be considered as such types of means. For example, a display device, CRTs (cathode ray tube display device), LCDs (liquid crystal display), printers, X-Y plotters, and lamps are available. A lens projector is also available as one type of specialized display device. Further, the following variations may also be considered when providing notification. For example, separate analog or digital displays in the case of notification involving numerical values, display using graph, addition of contrast to a display color, bar graph display where providing notification of a numerical value as is or applying a grade to a numerical value, circular graph, or a face chart are available. In the case of a face chart, an elderly person's face may be used to indicate a Xuan mai, a healthy young person's face may be used to indicate a Ping mai, and an unhealthy young person's face may be used to indicate a Hua mai, for example.

A means relying on the sense of touch may also be considered for providing a warning. Examples thereof include the following: electrical stimulation in which a form memory alloy projecting outward from the rear surface of a portable device such a wrist watch is provided, with electricity passed through this form memory alloy; and mechanical stimulation in which a retractable projection (such as a needle-shaped object which is not very pointed) may be formed to the rear of a portable device such as a wrist watch, and stimulation may be administered via this projection.

A notifying means relying on the sense of smell is also acceptable. Namely, an emitting mechanism for emitting a fragrance is provided to the device, a correspondence is formed between the notification details and the scent, and the device emits a fragrance in response to the notification contents. A micropump or the like is optimally employed for the mechanism for emitting fragrance or the like.

1-8-7: Modifications for Pulse Wave Detector

In the preceding embodiments, pulse wave detection sensor unit 130 was cited as one example of pulse wave detecting means f1. However, the present invention is not limited thereto. Rather, any arrangement is possible provided that it is capable of detecting the pulse wave.

1-8-7-1: Detection Method 1-8-7-1-1: Transmitted Light Method

Pulse wave detection sensor unit 130 employed reflected light, however, it is also acceptable for it to use transmitted light. It tends to be difficult for light in the 700 nm wavelength region or lower to pass through the finger tissue. For this reason, when transmitted light is employed, light having a wavelength of 600 to 1000 nm is irradiated from the light emitting element, with the irradiated light being transmitted in the order of tissue→blood vessels→tissue. The change in the amount of light transmitted is then detected. Since the transmission light is subject to absorption by the hemoglobin in the blood, it is possible to detect the pulse waveform by detecting the change in the quantity of the transmitted light.

A InGaAs-type (iridium-gallium-arsenic) or GaAs-type (gallium-arsenic) laser emitting diode may be suitably employed for the light emitting element. Since outside light of wavelength 600 to 1000 nm passes readily through the tissues, the S/N of the pulse wave signal will deteriorate if outside light incidences on the light receiving element. Therefore, laser light which has been polarized from the light emitting element may be radiated, with the transmitted light received at the light receiving element via a polar light filter. As a result, there is no impact from outside light, so that the pulse wave signal can be detected at a good S/N ratio.

Figure 32A:
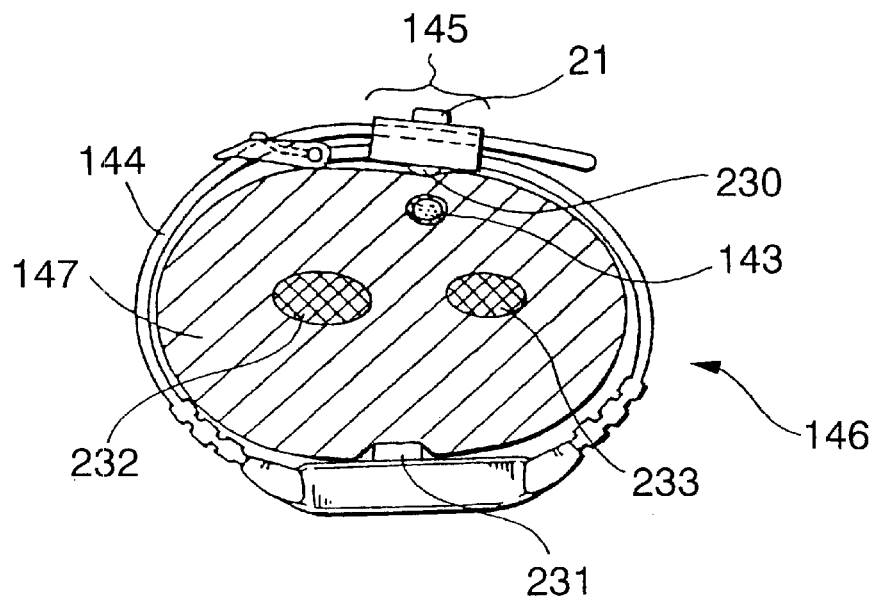
FIGS. 32A–32C are diagrams showing an example of a transmitted light-type pulse wave sensor according to a modification in Chapter 1.

In this case, as shown in FIG. 32A, a light emitting member 230 is provided to belt-shaped fastener 145, and a light emitting member 231 is provided to the side of the main body of the wrist watch. Light emitted from emitting member 200 passes through blood vessel 143, and then travels between the radius 232 and the ulna 233 to reach the light receiving element 231. Since it is necessary that the radiating light pass through the tissue in the case where employing transmitted light, a wavelength of 600 to 1000 nm is desirable in view of absorption by the tissues.

Figure 32B:
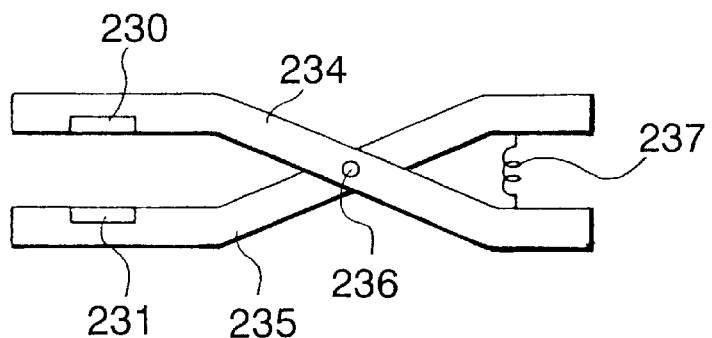
Figure 32C:
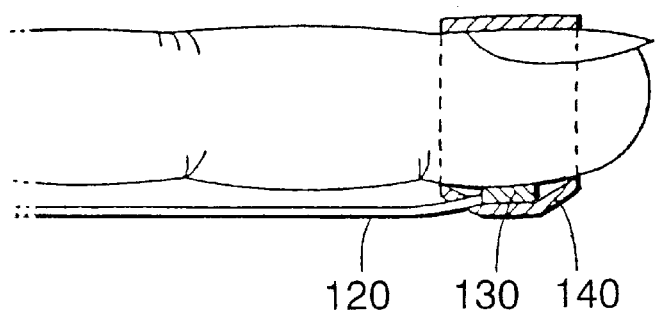

FIG. 32B shows an example in which the detection site is at the earlobe. Gripping member 234 and gripping member 235 are biased by means of a spring 237, and are designed to rotate around axis 236. Light emitting element 230 and light receiving element 231 are provided to gripping member 234 and gripping member 235. When employing this pulse wave detector, the pulse is detected by gripping the earlobe between gripping members 234 and 235. Note that when employing reflected light, it is also acceptable to detect pulse waveform MH at the fingertip as shown in FIG. 32C.

1-8-7-1-2: Pressure Sensor Method

Figure 33A:
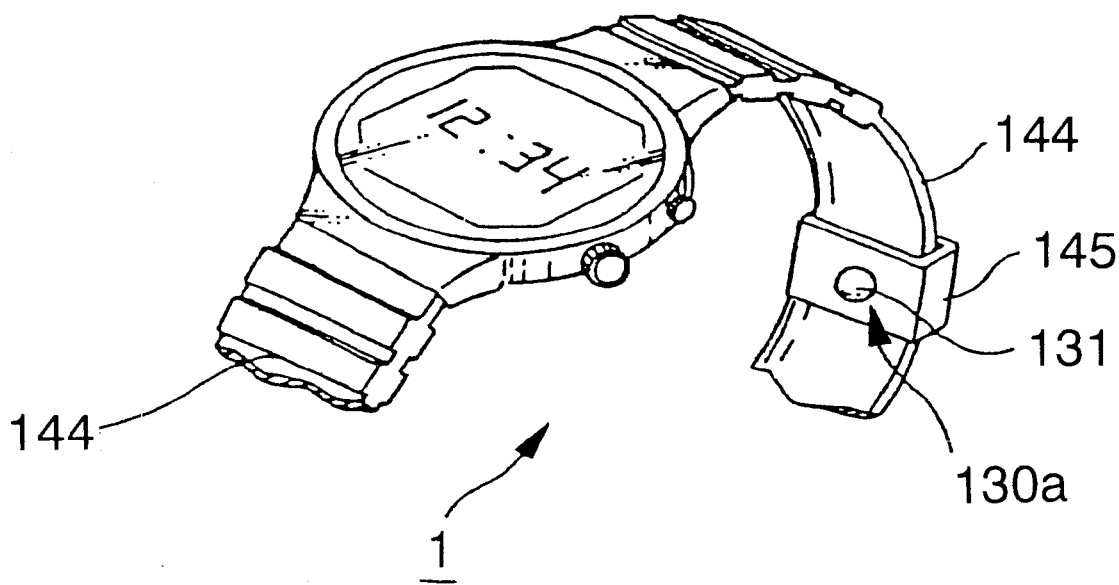
FIG. 33A and FIG. 33B are an orthogonal views showing the outer structure of a pulse wave diagnosing device employing a pressure sensor in a modification in Chapter 1.

Next, an example in which pulse waveform MH is detected using a pressure sensor will be explained. FIG. 33A is an orthogonal view showing the external structure of a pulse wave diagnosing device employing the pressure sensor shown in FIG. 33A. As shown in the figure, pulse wave diagnosing device 1 is provided with a pair of bands 144,144. An elastic rubber piece 131 of pressure sensor 130a projects outward from the fastening side of a belt-shaped fastener 145 which is provided to one of bands 144,144. Although not shown in detail in the figure, band 144 provided with belt-shaped fastener 145 is designed so that the FPC (flexible printed circuit) substrate which is to supply the detection signal from pressure sensor 130 is coated with a soft plastic.

Figure 33B:
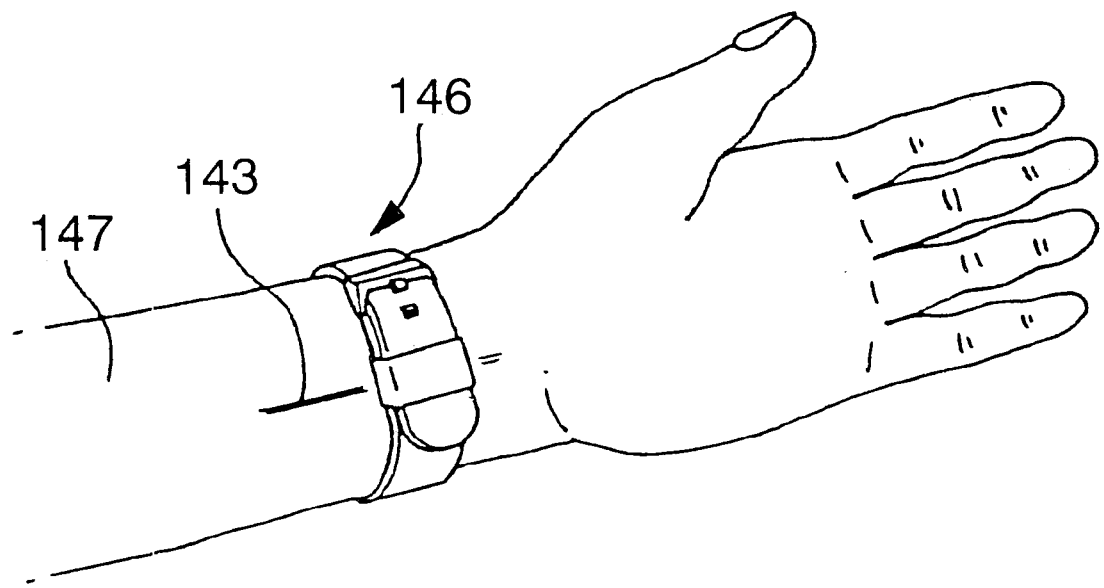

As shown in FIG. 33B, when in use, wrist watch 146 incorporating this pulse wave detector is wrapped around the left wrist 147 of a test subject so that the elastic rubber 131 provided to belt-shaped fastener 145 is positioned in the vicinity of radius artery 143, enabling constant detection of the pulse wave. Further, the operation to wrap this device around the arm of the subject is equivalent to that when using an ordinary wrist watch. When elastic rubber 131 is pressed against the vicinity of the subject's radius artery 143, changes in arterial blood flow (i.e., the pulse wave), are propagated to pressure sensor 130a via elastic rubber 131, and detected as the blood pressure.

1-8-7-2: Arrangement for use 1-8-7-2-1: Eyeglasses

An explanation will now be made of the case where a photoelectric pulse wave sensor is incorporated in a pair of eyeglasses. Further, this embodiment employs a structure in which a display device is also incorporated as a notifying means for informing the subject. Accordingly, the function of this display device will be explained together with the function of the pulse wave detector.

Figure 34:
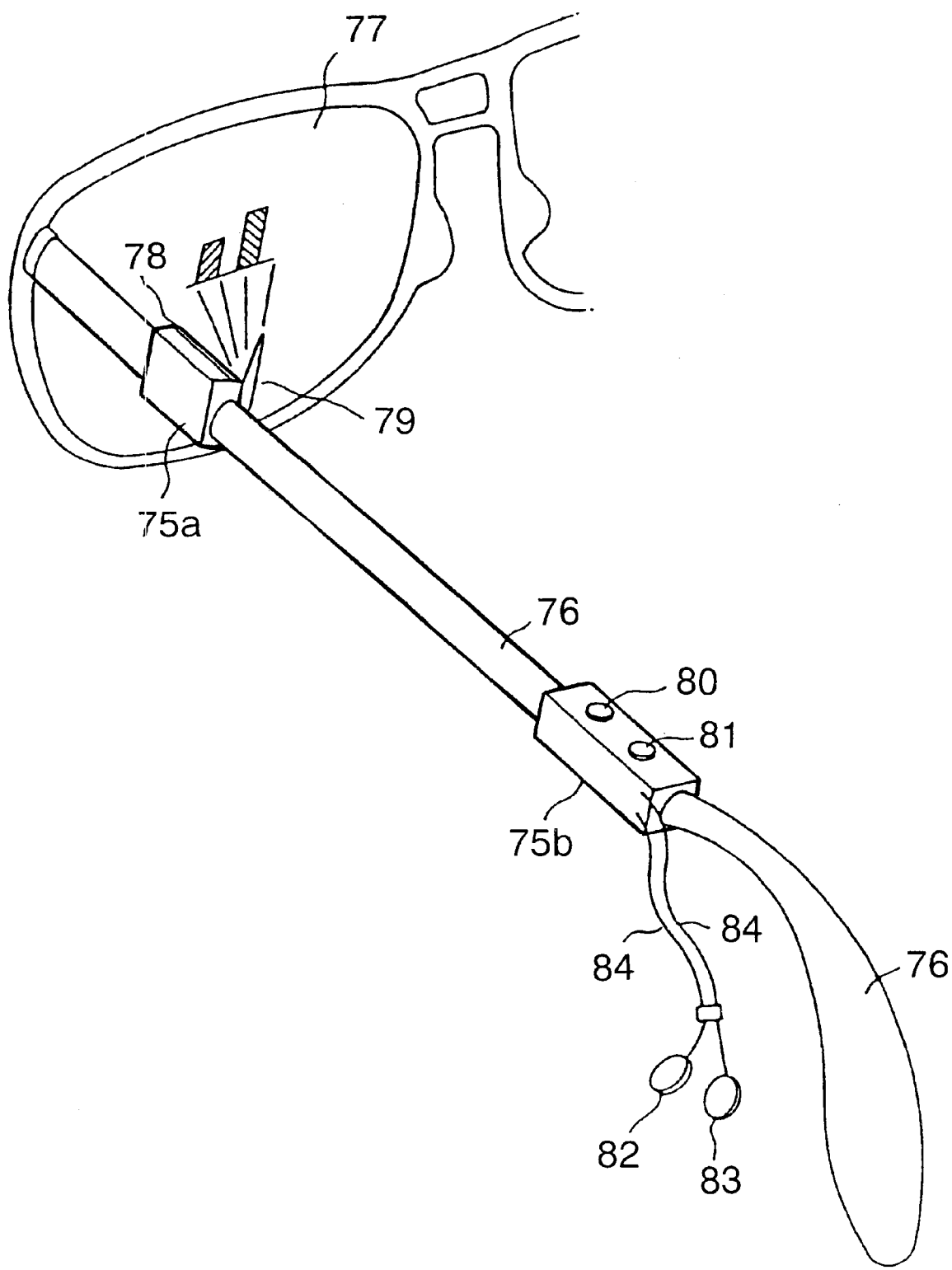
FIG. 34 is a diagram showing an example in which a photoelectric pulse wave sensor is employed in a pair of eyeglasses in a modification in Chapter 1.

FIG. 34 is an orthogonal view showing an arrangement in which a device connected to a pulse wave detector is attached to a pair of eyeglasses. As shown in this figure, the main body of the device is divided into main body 75a and main body 75b which are attached respectively to the stems 76 of the eyeglasses. These main bodies are electrically attached via a lead wire embedded inside stems 76.

Main body 75a houses a display control circuit. A liquid crystal panel 78 is provided across the entire lateral surface of the lens side of lens 77 of main body 75a. A mirror 79 is fixed at a specific angle at one edge of this lateral surface. A drive circuit for liquid crystal panel 78 which includes a light source (not shown) and a circuit for creating display data are incorporated in main body 75a. The light emitted from this light source passes via liquid crystal panel 78, and is reflected at mirror 79 to incident on lens 77 of the eyeglasses. Further, the main portion of the device is incorporated in main body 75b, with a variety of buttons provided on the top surface thereof. The functions of these buttons 80,81 differ in each device. LED 32 and photo transistor 33 (see FIG. 3) which form the photoelectric pulse wave sensor are housed in pads 82,83, with pads 82,83 fixed to the ear lobes of the subject. These pads 82,83 are electrically connected by lead wires 84,84 which are pulled out from main body 75b.

1-8-7-2-2: Necklace

Figure 35:
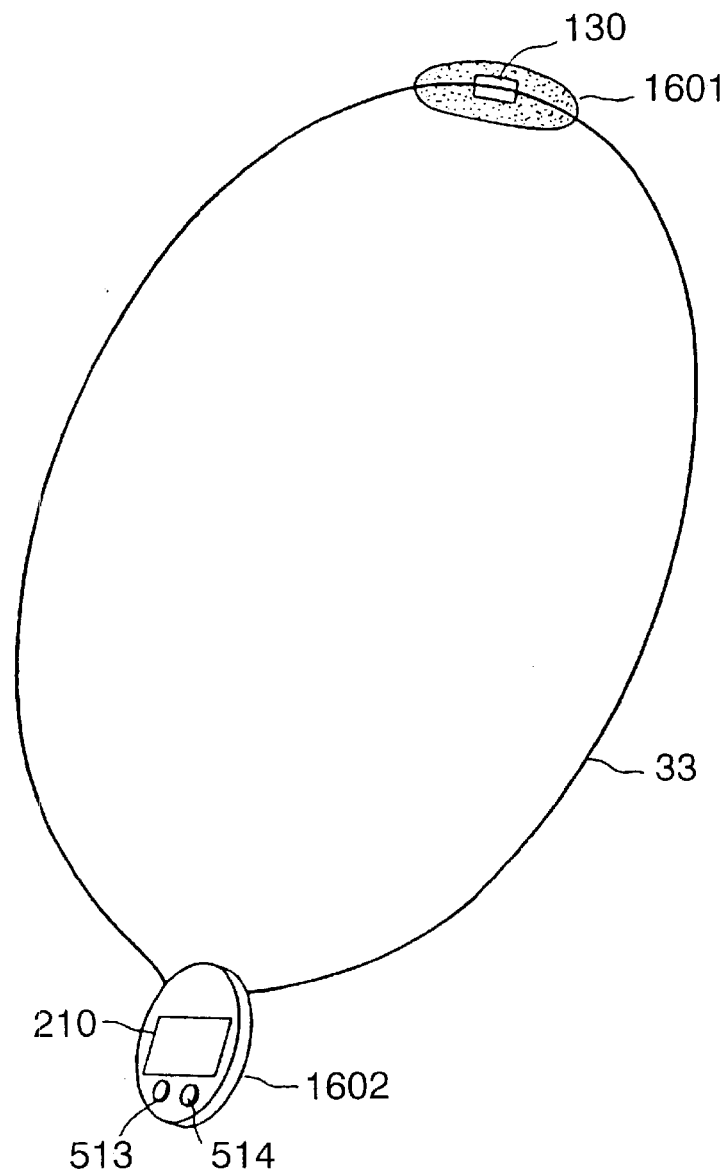
FIG. 35 is a diagram showing an example in which a photoelectric pulse wave sensor is employed in a necklace in a modification in Chapter 1.

The case where a photoelectric pulse wave sensor is modified into a necklace will now be explained. For example, the entire device may be formed into the necklace shown in FIG. 35.

In this figure, 1601 is a sensor pad, and is comprised, for example, of a shock absorbing material such as a sponge. Pulse wave detection sensor unit 130 is attached in the middle of sensor pad 1601 so as to come in contact with the skin surface. As a result, when this necklace is worn around the neck, pulse wave detection sensor unit 130 comes in contact with the skin at the back of the neck, enabling measurement of the pulse wave. The main portion of the device is incorporated inside case 1602 which is hollow and resembles a brooch. Button switches for performing various settings for the LED, photodiode, etc. for communications are provided as needed to the rear surface of case 1602 (not shown). Pulse wave detector 101 and case 1602 are attached respectively to a chain 1603, and are electrically connected via a lead wire (not shown) embedded inside chain 1603.

1-8-7-2-3: Card

Figure 36:
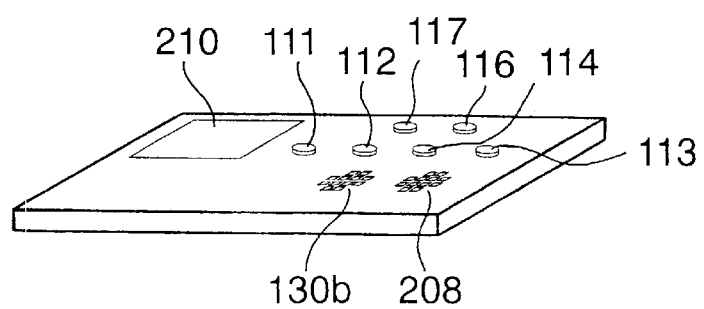
FIG. 36 is a diagram showing an example in which a piezoelectric mike sensor is employed in a card in a modification in Chapter 1.

The card arrangement shown in FIG. 36 will now be considered as another embodiment. This device in the form of a card is designed to be held in the left breast pocket of a shirt worn by the test subject. The pulse wave detector is formed of a piezomike 130b provided to the card surface, and is provided so as to face the skin surface of the test subject and detect the pulse rate by detecting the test subject's pulse. Numeral 208 indicates a notifying member for informing the subject by means of an alarm or a voiced sound. In the case of a pulse wave detector formed using a mike in this way, however, the emitted sound will be detected when notifying member 208 generates an alarm or voiced sound. Accordingly, it is necessary to provide processing so that the CPU provided inside the device does not perform pulse rate detection using piezomike 130b when the alarm is sounded.

1-8-7-2-4: Pedometer

Figure 37A:
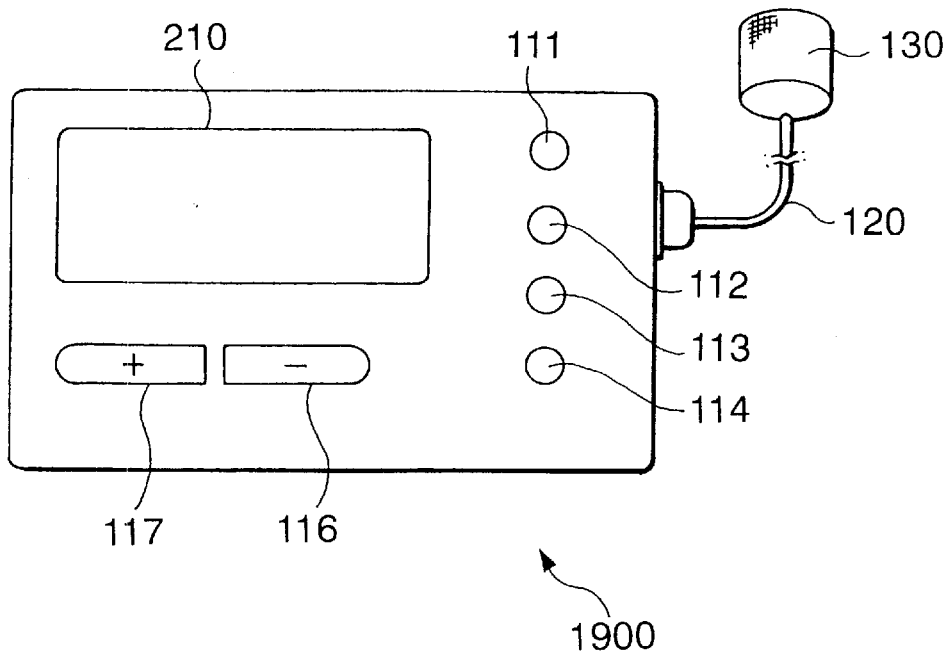
FIG. 37A and FIG. 37B are diagrams showing an example in which a photoelectric pulse wave sensor is employed in a pedometer in a modification in Chapter 1.
Figure 37B:
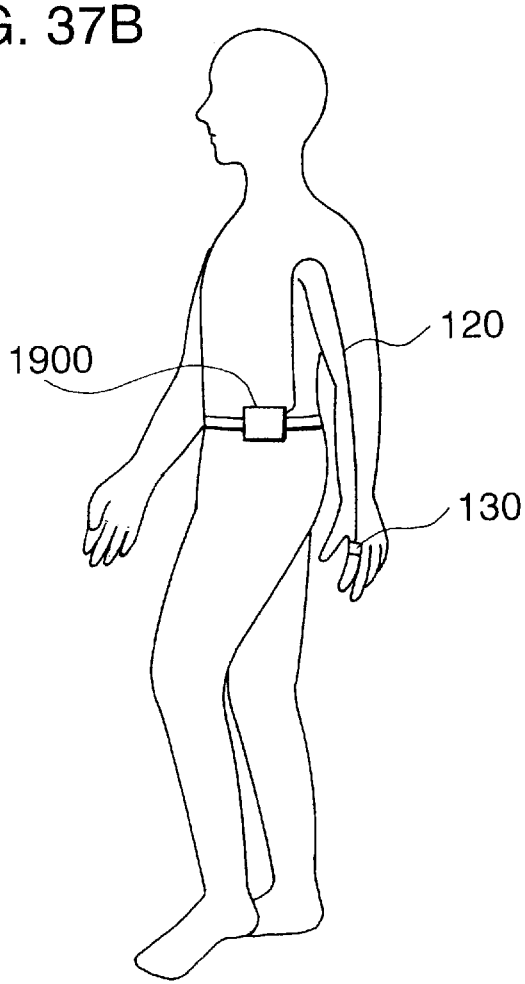

A pedometer as shown in FIG. 37A may be considered as another embodiment. Device main body 1900 of this pedometer is attached to a waist belt on the test subject, as shown in FIG. 37B. Pulse wave detection sensor unit 130 in this embodiment is attached between base and second joint of the index finger on the test subject's left hand, similar to the wrist watch arrangement shown in FIG. 2. It is desirable to sew cable 120 for joining device main body 1900 and pulse wave detection sensor unit 130 into the collar so as not to hinder the test subject during exercise.

1-8-8: Modification of First Wavelet Transformer 10A

Figure 38:
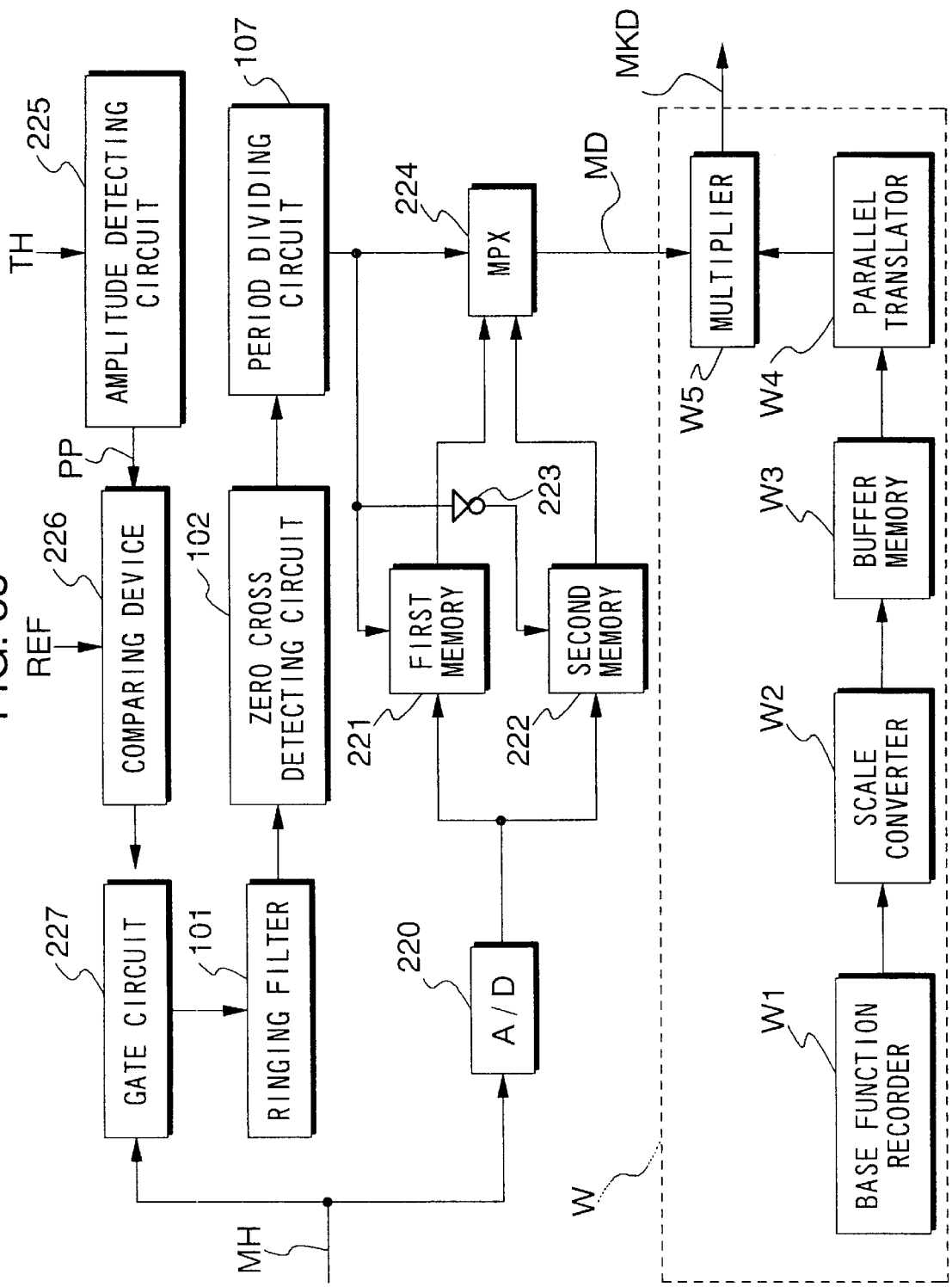
FIG. 38 is a block diagram showing the structure of first wavelet transformer 10A according to a modification in Chapter 1.

First wavelet transformer 10A in the second embodiment may be formed as shown in FIG. 38.

In FIG. 38, amplitude value PP is detected when body motion waveform TH is supplied to amplitude detecting circuit 225. This amplitude value PP is compared with reference value REF by comparing member 226. Comparing member 226 generates a low-level control signal when amplitude value PP exceeds reference value REF, and a high-level control signal when amplitude value PP is below reference value REF. This control signal indicates the presence or absence of body motion. Namely, body motion is present when the control signal is at a low level, but is absent when the control signal is at a high level. Here, reference value REF is determined in advance by experiments to enable discrimination between the presence and absence of body motion. Gate circuit 227 applies a gate to pulse waveform MH based on the control signal. Specifically, pulse waveform MH may be supplied to the ringing filter when the control signal is at a high level, but not supplied to the ringing filter when the control signal is at a low level. As a result, it is possible to mask pulse waveform MH during the time interval when body motion is present.

The Q value of the ringing filter 101 in this case is set to be high, so that even if the supply of pulse waveform MH is stopped for a fixed period of time, it is possible to continue outputting a sinusoidal wave which is continuous with the waveform output prior to the cessation of supply of pulse waveform MH. Accordingly, even if body motion is present, it is possible to calculate the period of pulse waveform MH, and carry out wavelet transformation based on the result of this calculation.

1-8-9: Use of Result of Wavelet Transformation to Obtain Various Physiological Information In the preceding embodiments, the pulse type was determined by performing wavelet transformation on pulse waveform MH, however, it is also acceptable to use the results of wavelet transformation in order to obtain various physiological information.

1-8-9-1: Determining Degree of Relaxation

It is acceptable to detect the degree of relaxation by analyzing the pulse waveform or the electrocardiogram, for example.

Figure 39:
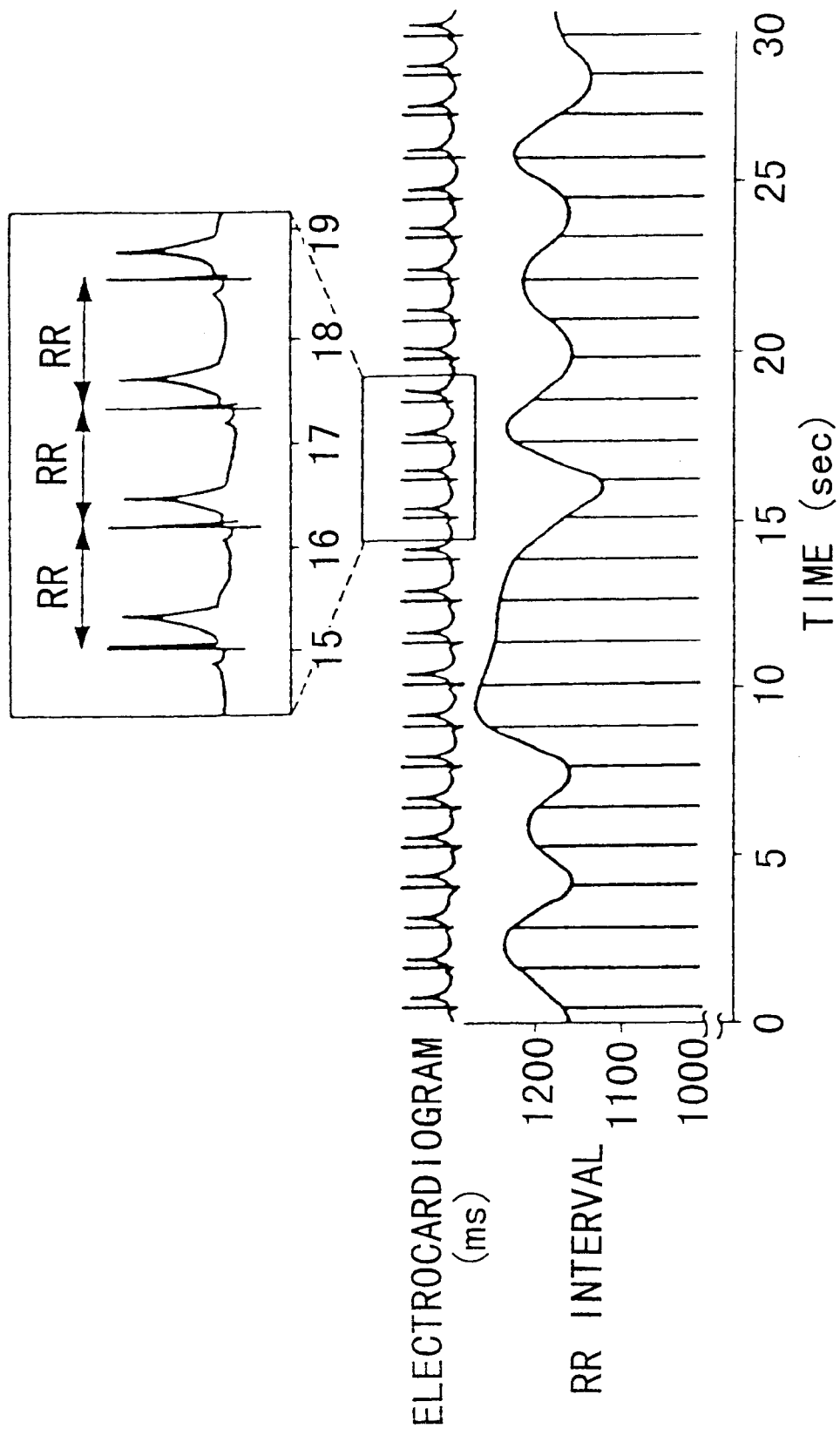
FIG. 39 shows the heart beat and the RR interval obtained from the waveform of these heart beats in an electrocardiogram in a modification in Chapter 1.

In an electrocardiogram, the interval between the R wave of one heart beat and the R wave of the next heart beat is referred to as the RR interval. This RR interval is a numerical value which serves as an indicator of the functioning of the autonomic nervous system in the human body. FIG. 39 shows heartbeat and the RR interval obtained from the waveform of this heartbeat in an electrocardiogram. As may be understood from this figure, an analysis of the measured results in an electrocardiogram reveals that the RR interval varies over time.

On the other hand, variation in blood pressure measured at the radius artery or the like, is defined as the variation in blood pressure at each beat from contraction to relaxation of the heart, and corresponds to variation in the RR interval in an electrocardiogram. FIG. 40 shows the relationship between the electrocardiogram and blood pressure. As may be understood from this figure, the blood pressure during each contraction and relaxation in a heart beat can be measured as the maximum value of arterial pressure, and the minimum value immediately preceding this maximum value in each RR interval.

By carrying out spectral analysis of variations in heart beat or blood pressure, it may be understood that the variations are composed of waves having a plurality of frequencies. These may be classified into the following three types of variation components.

1. HF (high frequency) component which is the variation coinciding with respiration
2. LF (low frequency) component which varies with a periodicity of around 10 seconds
3. Trend which varies with a frequency which is lower than the measurement limits In order to obtain these components, the RR interval between neighboring pulse waves is obtained for each measured pulse wave, and the discrete value of the obtained RR interval is interpolated using a suitable method (for example, 3rd order spline interpolation) (see FIG. 39). An FFT operation is carried out on the curved lined after interpolation, followed by spectral analysis. As a result, it is possible to pick out the variation component as a peak on the frequency axis. FIG. 41A shows the waveform of variation in the RR interval of a measured pulse wave and the waveform of each of the components of variation in the case where the waveform of variation is segregated into the three frequency components noted above. FIG. 41B shows the results of spectral analysis on the waveform of variation in the RR interval shown in FIG. 41A.

As may be understood from this figure, peaks are apparent at two frequencies near 0.07 Hz and 0.25 Hz when the subject is at rest for example. The former frequency value is the LF component, while the latter is the HF component. The trend component cannot be read in the figure because it is below the limit for measurement.

The LF component is related to the activity of the sympathetic nervous system. The larger this component, the greater the increase in tension (or state of arousal). On the other hand, the HF component is related to the activity of the parasympathetic nervous system. The larger the amplitude of this component, the more relaxed the state (or the degree of sedation).

The amplitude values for the LF and HF components will vary according to the individual. Accordingly, with this in mind, the ratio LF/HF, which is the ratio of the amplitudes of the LF and HF components, is useful to estimate the subject's degree of tension. When the value of LF/HF is large, than the degree of tension is high, while when LF/HF is small, the degree of tension is low indicating the subject is relaxed.

RR50 is defined by the number at which the absolute value of the pulse wave interval corresponding to the RR interval for two consecutive heart beats varies by 50 milliseconds or more, when measurements of pulse wave are carried out over a prespecified period of time. The larger the value of RR50, the more sedate the subject is, while the smaller the value of RR50, the more aroused the subject is.

Accordingly, it is also acceptable to calculate LF and HR by performing wavelet transformation on the electrocardiogram and pulse waveform, and then calculating the degree of relaxation based on this result. Since the electrocardiogram and pulse waveform rise sharply on each beat, when wavelet transformation is performed on the electrocardiogram or pulse waveform, the high-pass frequency component becomes larger in the rising portion. Therefore, the degree of relaxation may be detected by determining the RR interval from the change in the high-pass frequency components, and calculating the RR50 based on this RR interval.

1-8-9-2: Doze Prevention

In recent years, numerous accidents have occurred due to drivers dozing off while operating an automobile. A variety of devices have been proposed to prevent this from occurring. One example which may be considered is a device attached to the steering wheel. In this device, conductors are attached to the left and right sides of the steering wheel, and measurements of the driver's resistance are made by having both of the driver's hands in constant contact with the conductor. If the driver dozes off and his hand falls from the steering wheel, the resistance value between the conductors changes. As a result, it is perceived that the driver has dozed off, and a warning sound is issued to the driver. In this way, it becomes possible to prevent an accident from occurring due to dozing off by the driver.

Other devices may employ changes in heart beats obtained from measurements in the electrocardiogram of the driver, or changes in the driver's respiration.

However, in the method described above in which conductors are attached to the steering wheel, it is not possible to accurately monitor for a doze state when the driver is driving with just one hand, or is wearing gloves. Additionally, in the methods employing changes in heart beat or respiration, the devices used are large, and thus not convenient for the driver to carry about with him.

However, the doze state may also be detected by analyzing the alertness level of the human body from the results obtained from wavelet transformation of the pulse waveform.

A doze prevention device employing wavelet transformation is principled on the correlation relationship which exists between the information included in the pulse wave and the level of alertness in the human body in order to detect the subject's doze state. In this case, a number of measured quantities obtained from the pulse wave are employed as indices to determine the level of alertness in the human body. LF, HF, [LF/HF] and RR50 will be employed as specific examples below. From the above correlation relationship, the physiological state becomes more sedate as the doze state becomes deeper. RR50, for example, is believed to gradually become larger as the doze state progresses. Accordingly, it is possible to detect a doze state by detecting the change in these indices.

2. Chapter 2

2-1: Summary

In general, if an individual (test subject) who is performing exercise is able to know the exercise intensity at a given point in time, then it becomes possible to exercise in accordance with an exercise plan, or to apply this knowledge to pacing during various competitions.

There are a variety of methods for expressing exercise intensity. They can be broadly divided into three types: an absolute method using numerical values showing the work rate, exercise pitch, etc.; a relative method using pulse rate, etc.; and a method combining these.

Even when exercise intensity is not calculated, some sort of subjective evaluation (i.e., "difficult", "easy") is performed when exercising. Thus, a variety of training is typically performed by the subject determining the exercise intensity at a point in time based on his own subjective evaluation. For example, by continuing exercise at an intensity which is not difficult, so that the subject still perceives a psychological surplus, it is possible to improve the maximum oxygen uptake quantity (see Sindo, M., Exercise Values for Promoting Health, Hoken-No-Kagaku, Vol. 32, No. 3, 1990.).

Thus, exercise at a given intensity is regularly carried out during various forms of training, with the current exercise intensity determined from a subjective evaluation as described above.

However, exercise intensity determined based on a subjective evaluation does not take into consideration physical strength. Accordingly, it cannot be deemed an appropriate evaluator.

With the exception of the relative method, exercise intensity expressed by the above methods quantitatively expresses the physical intensity of the exercise performed by the subject at a given point in time, and does not take into consideration the subject's physical or psychological strength. At the same time, relatively expressed exercise intensity takes into consideration the subject's physical strength, but not his psychological strength.

Accordingly, even if exercise is performed using an exercise intensity determined in this way as the exercise index, since the subject's physical and psychological strengths are not directly related, such problems may occur as the subject over-extending himself at too strong an exercise intensity, or exercising too mildly so that no training effect is achieved.

Accordingly, Chapter 2 provides an exercise index measuring device that measures the exercise intensity required during training to improve endurance which comprehensively takes into consideration the subject's physical and psychological strength during exercise, and then informs the subject of this exercise intensity.

Second, an exercise index measuring device which informs the subject of a quantified exercise index for the exercise intensity which has been determined after comprehensively taking into consideration the subject's physical and psychological strength is provided.

Third, an exercise index measuring device is provided which enables the subject to easily reach the training intensity required for improving overall endurance at an exercise intensity which comprehensively considers the subject's physical and psychological strength during exercise.

2-2: Theory Outline

Before explaining the embodiments in Chapter 2, the principles which form the theoretical outline thereof will be explained.

First, the present inventors had test subjects vary their running speed in a step like manner for the purpose of obtaining various data useful as indices of ergonomic exercise intensity. The results of these experiments will be explained with reference to FIG. 44.

Figure 44A:
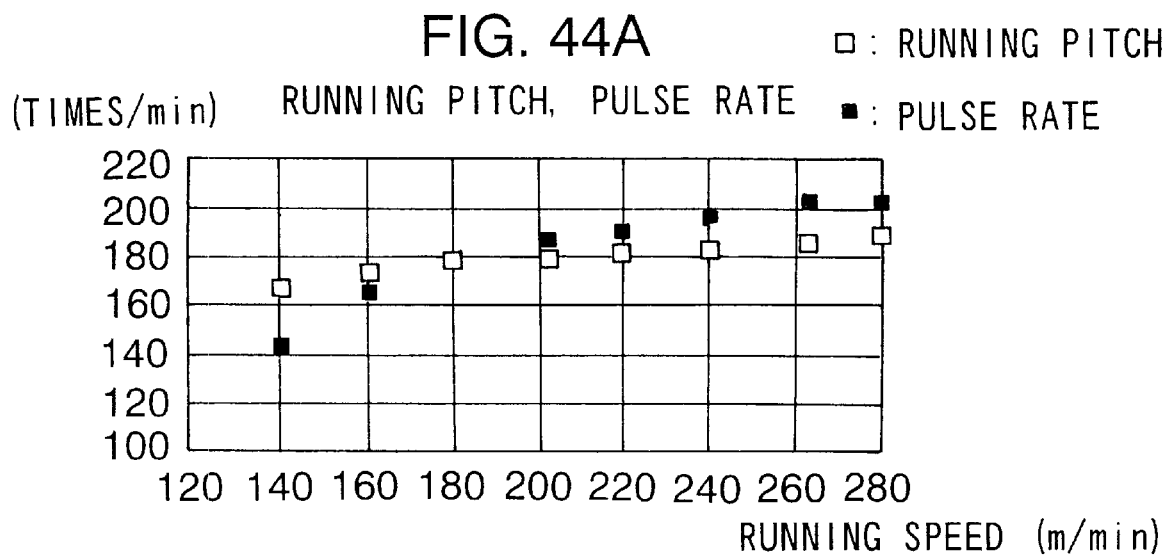
FIGS. 44A–44C are diagrams showing the experimental results on which the exercise index measuring device in Chapter 2 is premised.

FIG. 44A shows the relationship between pulse rate and running speed when running on the ground, and the relationship between running speed and running pitch. As clear from the figure, the subject's pulse rate and running pitch increase with running speed.

Figure 44B:
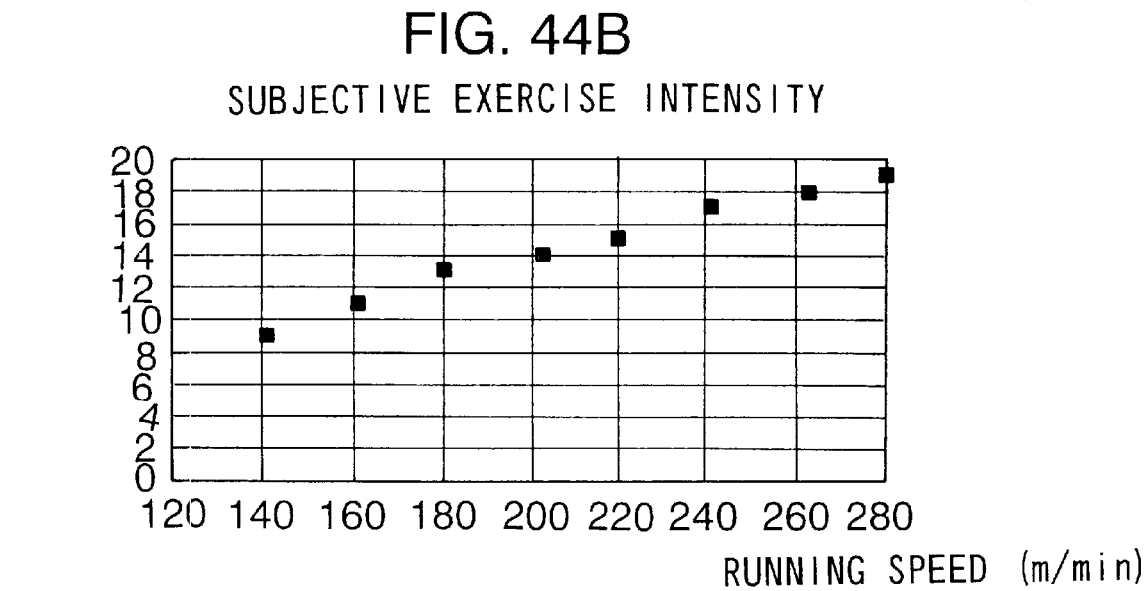

FIG. 44B shows the relationship between running speed on ground and exercise intensity as subjectively judged by the subject. The subjective exercise intensity is obtained from the subject assigning a point value based on his subjective assessment of his sensation while running at that speed. As shown in FIG. 45, the subjective exercise intensity may be set so high that the subject registers the exercise intensity as "difficult". As shown in FIG. 44B, as the running speed increases, the point number expressing the subjective exercise intensity increases and the difficulty perceived by the subject becomes greater.

Figure 44C:
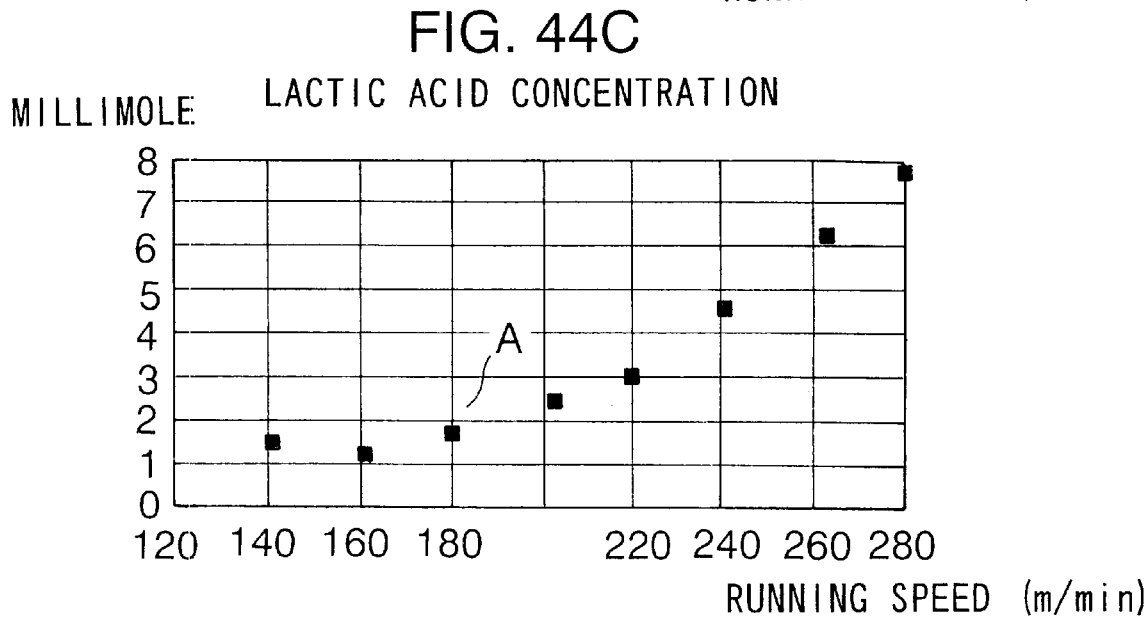

FIG. 44C is a diagram showing the relationship between running speed on the ground and the concentration of lactic acid in blood which is obtained by a method of sampling from the earlobe. As shown in the figure, the concentration of lactic acid in the subject's blood begins to increase sharply around point A.

It is well known that lactic acid is a metabolite of fatigue. Thus, as its concentration rises, it becomes impossible for the subject to continue exercising at a constant intensity. Stating this from another perspective, if just maintenance exercise is to be performed, then this exercise may be carried out at an intensity which is in a range where the lactic acid concentration is low. However, when exercising at an intensity where the lactic acid concentration remains at a low level, if the subject perceives the exercise intensity as "easy", then no training benefits can be expected.

Accordingly, when performing maintenance exercise in order to increase overall body endurance, it is preferable that the subject exercise at an intensity which is in a range at which the blood lactic acid concentration remains low but the subject perceives the exercise intensity to be "somewhat difficult". An exercise intensity of this type corresponds to point A in the figure.

In actuality, the exercise intensity corresponding to point A at which the blood lactic acid concentration starts to increase is known to be about $50\%VO_{2max}$ when expressed as a relative intensity using the maximal oxygen uptake quantity. This value is known to be appropriate as the exercise intensity for training designed to improve overall endurance.

Thus, the exercise intensity corresponding to point A takes into consideration the subject's physical and psychological states during exercise, and thus can be considered the exercise intensity which should serve as the index when performing training to improve endurance.

However, in order to obtain A directly, it is necessary to continuously measure the subject's blood lactic acid concentration during exercise. This is extremely difficult as a practical problem.

Accordingly, the present inventors focused on the mutual synchronization of the subject's pulse and pitch around point A where the lactic acid concentration rises. As described in the conventional technology, the exercise intensity can be expressed by employing the subject's pulse and running pitch during exercise.

Accordingly, by determining the point at which the pulse and pitch correspond, and then obtaining the exercise intensity at that point, it is possible to indirectly determine the exercise intensity at point A. By informing the subject of this exercise intensity, an index appropriate for performing training to increase overall body endurance can be provided.

Moreover, by informing the subject of the extent to which his exercise intensity deviates from the point at which the pulse and pitch coincide, it becomes possible to provide an exercise index which has been quantified after taking into consideration the subject's physical and psychological strength.

In addition, if the subject is provided with an exercise index which is in a direction which will eliminate the difference between the pulse and the pitch, it becomes an easy matter for him to reach the exercise intensity required for improving overall body endurance.

2-3: Embodiment 1

The exercise index measuring device according to the first embodiment will now be explained. First, the exercise index measuring device in this embodiment informs the subject of the exercise intensity at which his running pitch and pulse are approximately equal, this exercise intensity serving as the target exercise index. Second, the exercise index measuring device provides the subject with an index showing the degree of difference between his actual exercise intensity and the exercise intensity expressed by the aforementioned exercise index. Third, the exercise index measuring device provides the subject with an exercise index in the direction which will eliminate the difference between the subject's pulse and pitch.

2-3-1: Functional Structure

Figure 42:
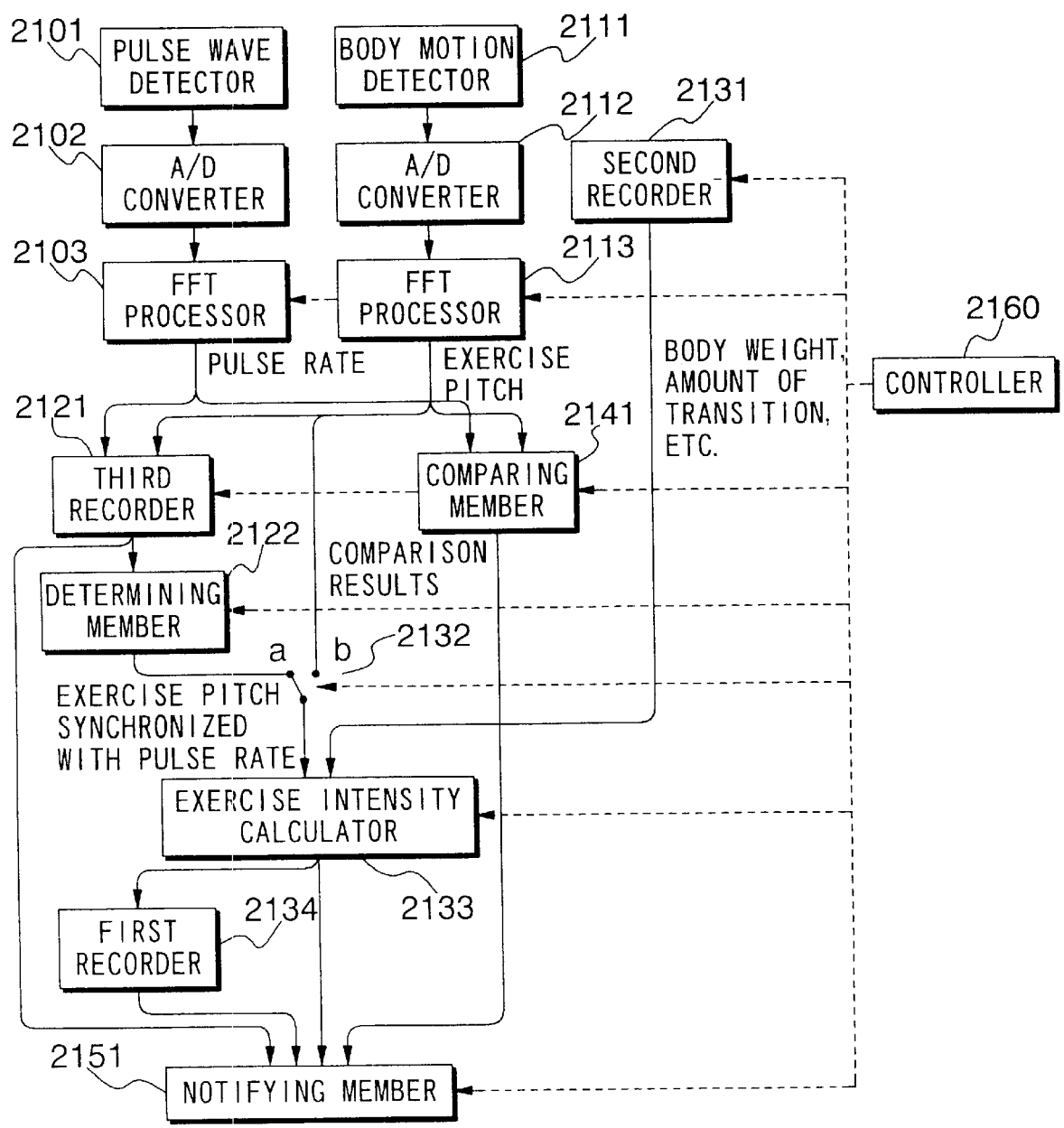
FIG. 42 is a block diagram showing the functional structure of the exercise index measuring device according to the first embodiment in Chapter 2.

First, the functional structure of an exercise index device according to this embodiment will be explained. FIG. 42 is a block diagram showing this functional structure.

In this figure, pulse wave detector 2101 is a sensor for detecting the subject's pulse waveform. The pulse waveform signal from pulse wave detector 2101 is converted to a digital signal by A/D converter 2102 and subjected to FFT (Fast Fourier Transform) by FFT processor 103. The pulse rate is obtained based on the result of this processing. The essential requirement is the heart rate, i.e., the pulsation of the heart per unit time. Since the heart rate equals the pulse rate, however, the obtained pulse rate is determined directly as the heart rate. Accordingly, it is also acceptable to design pulse wave detector 2101 to directly detect the heartbeat.

Body motion detector 2111 is a sensor for detecting body motion when the test subject is exercising. It may be formed of an acceleration sensor, for example. The body motion signal from this body motion detector 2111 is converted to a digital signal by A/D converter 2112, and is subjected to FFT processing by FFT processor 113 in the same manner as the pulse waveform. The exercise pitch is obtained from the results of this processing. In other words, "exercise" as used in this embodiment refers to rhythmic repetitive motion performed with a constant periodicity. The number of times which this motion is performed during a given unit of time is determined. For example, in the case of running, the number of steps (running pitch) per unit time is determined, while in the case of swimming, the number of strokes per unit time is determined.

Third recording member 2121 records as a pair the obtained pulse and exercise pitch, along with time elapsed, exercise intensity, and the like. Determining member 122 determines the point at which the pulse and exercise pitch coincide based on the details recorded in third recording member 2121, and outputs the exercise pitch corresponding to this point as the target value.

Note that determining member 2122 in FIG. 42 is designed to determine the point at which pulse and exercise pitch coincide from the details recorded in third recording member 2121. However, the present invention is not limited thereto, but rather a design is also acceptable in which the pulse and pitch are constantly compared and the point at which they coincide is detected. In addition, determining member 2122 is designed to output the exercise pitch corresponding to the point at which the pulse and exercise pitch coincide, however, a design is also acceptable in which the pulse is output, or in which both pulse and exercise pitch are output.

Second recording member 2131 records the subject's weight and the like, as well as the amount of shift each time during the repetitive exercise. For example, second recording member 2131 records the stride when the exercise performed is running, and records distance during one stroke when the exercise is swimming.

Switch 2132 selects one of either the exercise pitch (input terminal a) designated as the target value by determining member 2122, or the exercise pitch (input terminal b) at the current point in time determined by FFT processor 2113. This selection is directed by controller 2160.

Exercise intensity calculator 2133 calculates the exercise intensity from the exercise pitch, the amount of shift each time during the repetitive exercise, and the subject's body weight. Accordingly, if input terminal a is selected at switch 2132, then the targeted exercise intensity is determined. On the other hand, if input terminal b is selected, then the exercise intensity when the subject is actually exercising is obtained. Here, the exercise performed by the subject is assumed to be running, so that running speed may be determined by multiplying the subject's running pitch and stride. Exercise intensity may then be determined as the product of the running speed and the test subject's body weight.

Note that there is also a method for expressing exercise intensity using the pulse rate. A design is also acceptable in which exercise intensity calculator 2133 calculates the exercise intensity by inputting the pulse rate obtained by FFT processor 2103, rather than the running pitch. Assuming the exercise is running, then running speed, which is the product of running pitch and stride, the product of running speed and pulse rate, the product of pitch and pulse rate, or the product of stride and pulse rate, may be employed as the exercise intensity, and exercise intensity calculator 2133 may be designed to calculate these values.

When input terminal a is selected, first recording member 2134 records the exercise intensity obtained by exercise intensity calculator 2133, i.e., the targeted exercise intensity, along with data showing the month and day.

When executing the fourth function described below, comparing member 2141 determines the difference between the pulse rate determined by FFT 2103 and the exercise pitch obtained from FFT processor 2113, and determines the extent to which this difference comprises the pulse rate or pitch. Comparing member 2141 then performs grading based on this extent.

When executing the fifth function explained below, comparing member 2141 compares the pulse rate determined by FFT 2103 and exercise pitch obtained from FFT processor 2113, and determines the exercise index for eliminating this difference.

When the difference between the pulse rate and the exercise pitch is zero, i.e., when the two values coincide, this indicates that the subject is currently exercising at the targeted exercise intensity, which is a level which the subject can maintain. Accordingly, the extent obtained by comparing member 2141 in the fourth function indicates the degree of difference between the current exercise intensity and the targeted exercise intensity. The exercise index obtained in the fifth function serves as an index for approaching the targeted exercise intensity.

Notifying member 2151 primarily performs the following notification based on the details recorded in first recording member 2134, third recording member 2121, the calculated results from exercise intensity calculator 2133, and the results of the comparison by comparing member 2141. In other words, notifying member 2151 is provided with a first function for displaying the obtained pulse rate-exercise pitch pair in association with elapsed time; second function for informing and displaying the targeted exercise intensity; a third function for displaying the intensity of the exercise being currently performed by the subject; a fourth function for informing and displaying the degree of difference between the current exercise intensity with respect to the targeted exercise intensity; a fifth function for informing the subject of the index for approaching the targeted exercise intensity with respect to the current exercise intensity; and a sixth function for displaying how the exercise intensity obtained by the second function is progressing with the elapse of time in terms of days and months.

Controller 2160 controls the operations in all parts.

2-3-2: Electrical Structure

Figure 43:
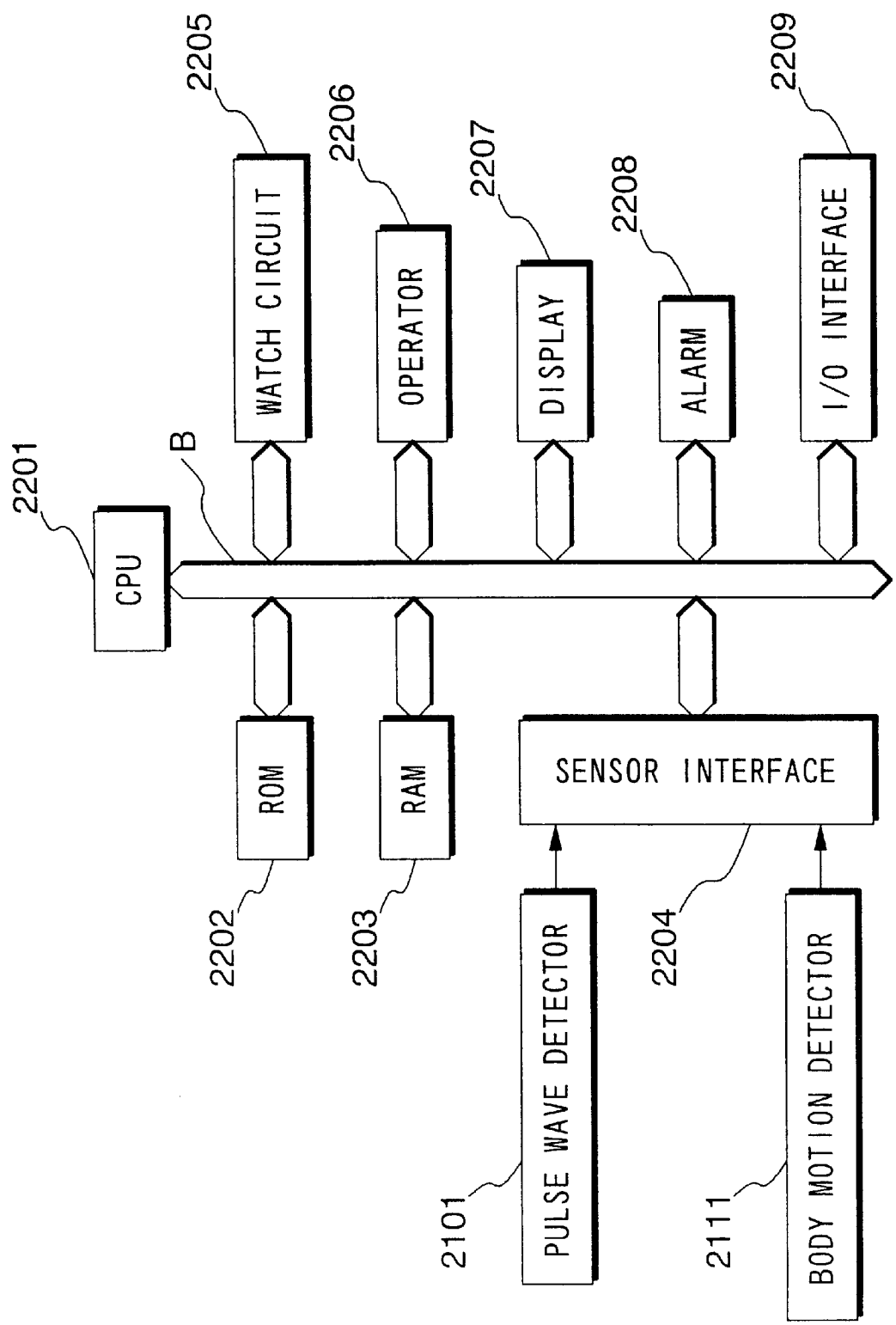
FIG. 43 is a block diagram showing the electrical structure of the same device in Chapter 2.

Next, the electrical structure for realizing the functional structure shown in FIG. 42 will be explained. FIG. 43 is a block diagram showing this structure.

In this figure, CPU 2201 carries out control of all parts via bus B, execution of various processing, and calculations based on basic programs stored in ROM 2202. CPU 2201 corresponds to FFT processor 2103, 2113, determining member 2122, exercise intensity calculator 2133, comparing member 2141 and controller 2160.

RAM 2203 stores the obtained pulse rate-exercise pitch pairs in association with the elapse of time since exercise began. RAM 2203 also temporarily stores various data employed in control by CPU 2201, such as the test subject's body weight or stride. RAM 2203 corresponds to first recording member 2134, second recording member 2131 and third recording member 2121.

Sensor interface 2204 carries out sampling of each analog output signal from pulse wave detector 2101 and body motion detector 2111 at respective set time periods, and then converts the analog signal to a digital signal and outputs it. Sensor interface 2204 corresponds to A/D converters 2102, 2112 in FIG. 42.

In addition to the normal functions of a watch, watch circuit 2205 is provided with a function for sending an interrupt signal to CPU 2201 at specific time intervals determined in advance.

Operator 2206 is provided so that the test subject can input various values such as body weight and stride, and select and set various functional modes. It consists of various button switches which will be described later.

Display 2210 displays various information under the control of CPU 2201, and is composed, for example, of an LCD (liquid crystal display). Alarm 208 generates an alarm under the control of CPU 2201, and informs the subject of various state changes. Display 2210 and alarm 2208 correspond to notifying member 2151 in FIG. 42.

I/O interface 2209 is provided with an LED and photo transistor, explained below, and sends and receives information with an external device.

2-3-3: External Structure

A variety of arrangements are possible for the external structure of the exercise index measuring device according to this embodiment, however, an arrangement is preferred which will not distract the subject while exercising. Accordingly, the external structure of the exercise index measuring device is the same as that of the pulse wave diagnosing device explained in the first chapter (see FIG. 2). In this case, the first through sixth functions are executed as one function in the wrist watch shown in FIG. 2. Note that the pulse wave detector 2101 described above is formed as the pulse wave detector sensor unit 130 shown in FIG. 2.

Button switches 116,117 are disposed below and above display 210 on the surface of device main body 110. Button switch 117 is employed for turning forward the setting value by one when correcting the stride, body weight, time or date values. Button switch 116 is for turning back the setting values by one when correcting stride, body weight, time or date values.

Figure 46:
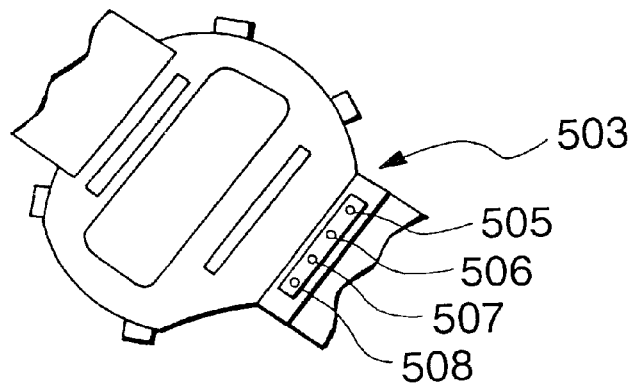
FIG. 46 is a diagram showing the external structure of the same exercise index measuring device in Chapter 2.

FIG. 46 is a figure showing the external structure in which a connector piece 80 has been removed from connector 70. As shown in this figure, connection terminals 505,506 for connecting to cable 120, LED 507 and photo transistor 508 are provided inside connector 70, for carrying out optical communications with an external device. In other words, LED 507 and photo transistor 508 are formed as one part of the I/O interface shown in FIG. 2.

Note that parts not appearing externally, such as CPU 2201, body motion detector 2111, sensor interface 2204, alarm 2208 and the like, are housed in device main body 110.

2-3-4: External Device

Figure 47:
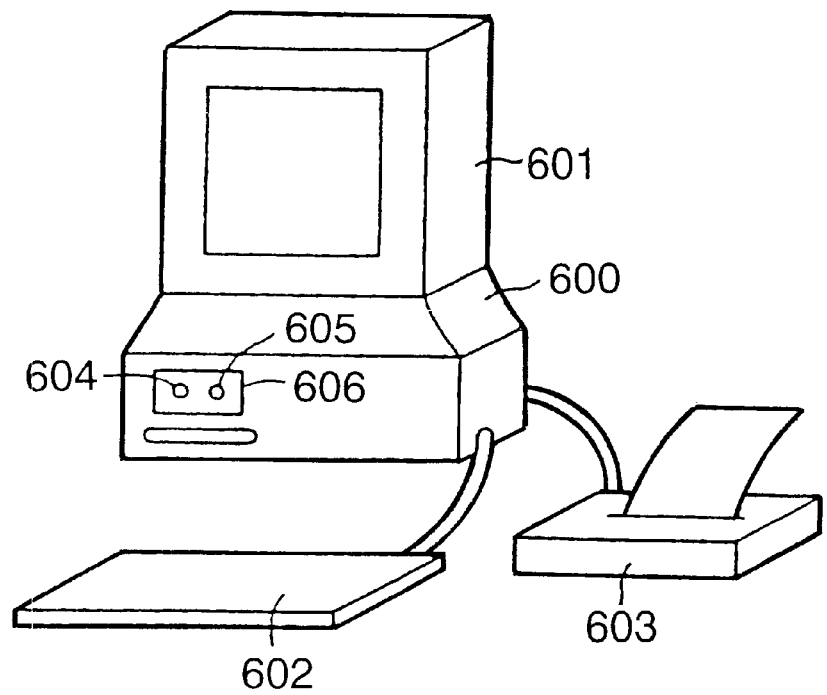
FIG. 47 is a diagram showing the structure of an external device for sending and receiving various information to and from the same exercise index measuring device in Chapter 2.

Next, the external device for carrying out sending and receiving of information with the main device will be explained in overview with reference to FIG. 47. As shown in this figure, the external device may be formed of a device main body 600, display 601, key board 602, printer 603, and the like. With the exception of the following points, it is formed in the same manner as an ordinary personal computer.

Namely, device main body 600 houses an optical interface consisting of a transmission controller and a reception controller, which are not shown in the figures, for sending and receiving data by means of optical signals. The transmission controller is provided with LED 604 for sending optical signals, and the reception controller is provided with a photo transistor 605 for receiving optical signals. Devices having the same or nearly the same characteristics as LED 503 and photo transistor 504 in device main body 110 of the exercise index measuring device are employed in LED 604 and photo transistor 605. A near infrared type device (having a central wavelength of 940 nm, for example), is preferred in this case. When a near infrared type device is used, a visible light cutting filter for blocking visible light is provided to the front surface of device main body 600, forming a communications window 606 for optical communications.

Device main body 110 of the exercise index measuring device and the external device are designed to carry out sending and receiving of information by optical communications. The details of this transmission and reception of information will be explained in connection with the operations.

2-3-5: Operations

Next, the operation of the exercise index measuring device according to this embodiment will be explained.

As explained above, since device main body 110 has a variety of functions, its operations will be explained in connection with each of these functions. For the purpose of convenience, an explanation will be made for the case where the exercise performed by the subject is running, however, the present invention is not limited thereto.

2-3-5-1: First Function

The operation when executing the first function (i.e., the function for displaying the obtained pulse rate and running pitch corresponding to time elapsed) will be explained.

Figure 48:
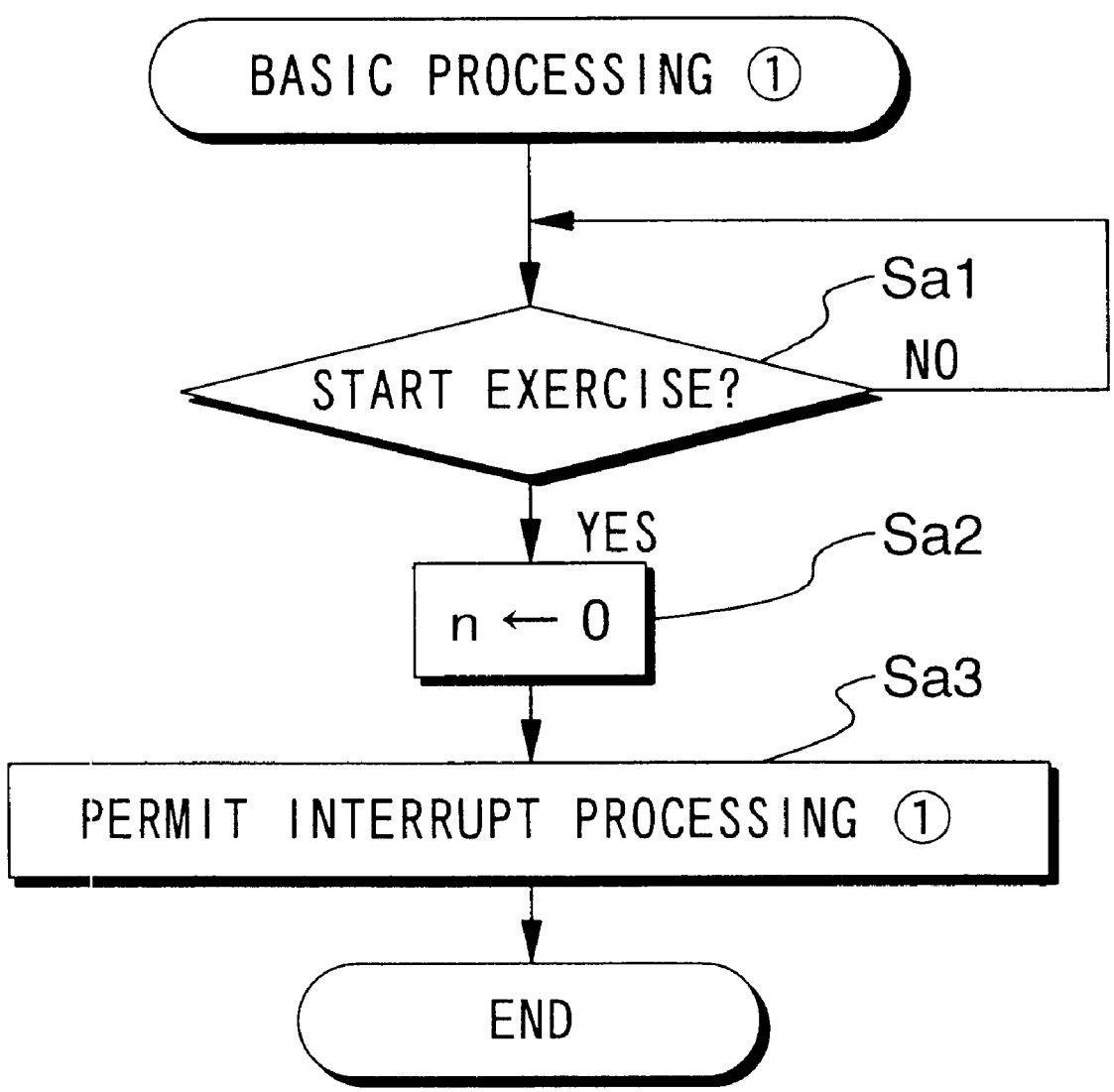
FIG. 48 is a flow chart showing basic processing (1) executed by the same exercise index measuring device in Chapter 2.
Figure 49:
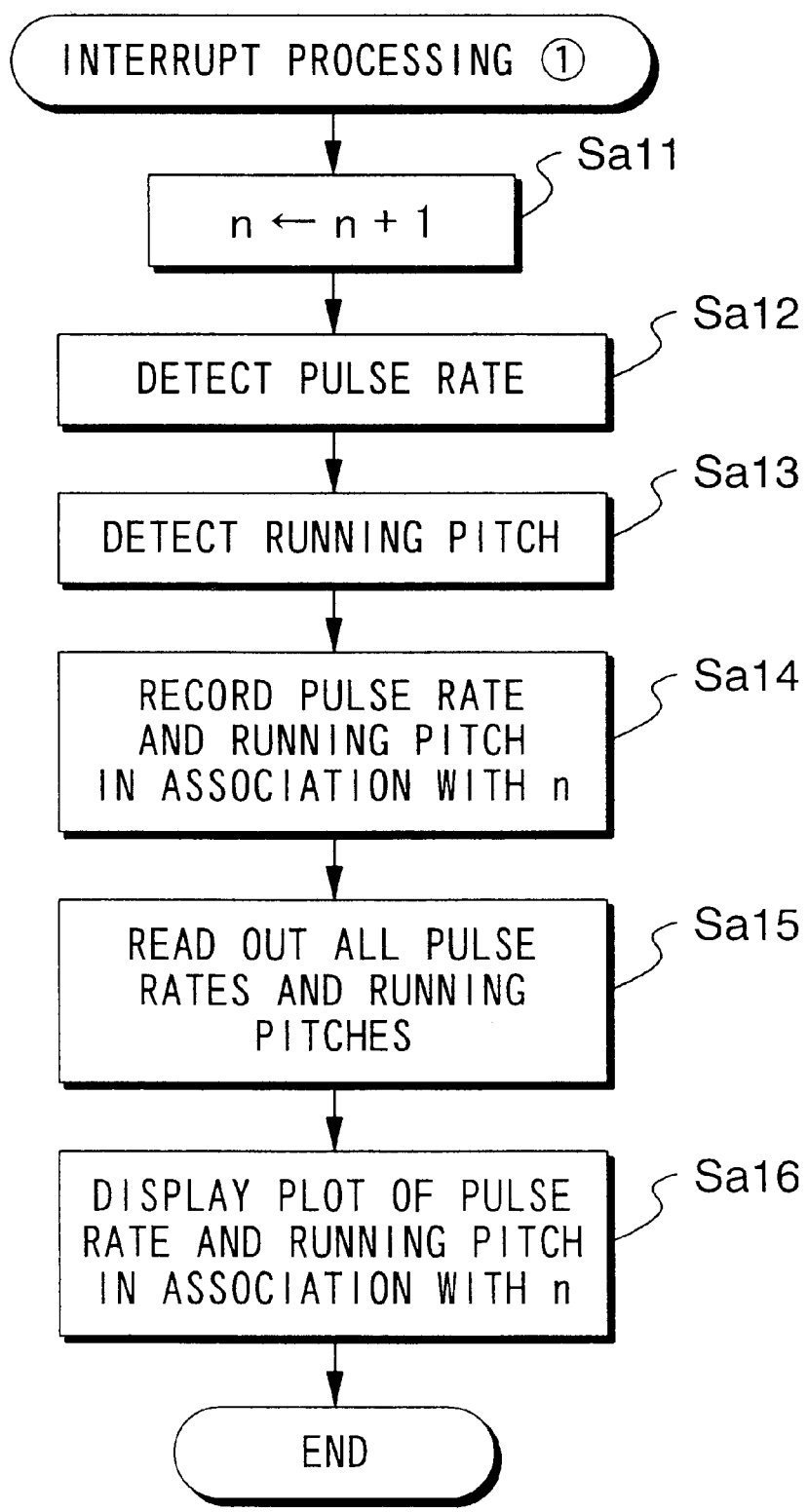
FIG. 49 is a flow chart showing interrupt processing (1) executed by the same exercise index measuring device in Chapter 2.

When the test subject operates button switch 111 to place the device in the mode for executing the first function, CPU 2201 in FIG. 43 (controller 2160 in FIG. 42) first executes the basic program shown in FIG. 48, and then regularly executes the interrupt processing shown in FIG. 49.

First, the details of this basic processing (1) will be explained in reference to FIG. 48. In step Sa1, CPU 2201 inputs the body motion signal detected by body motion detector 2111 via sensor interface 2204, subjects this to FFT processing, and determines whether or not the subject has actually begun running. If CPU 2201 determines that exercise has not begun, then the processing sequence again returns to step Sa1. Namely, the device is designed so that the processing sequence queues at step Sa1 until the subject begins running. When the subject begins to run, CPU 2201 clears the value in register n to zero in step Sa2. In step Sa3, CPU 2201 permits the execution of interrupt processing (1), and then terminates basic processing (1). Interrupt processing (1) referred to here is processing for regularly executing an interrupt signal from watch circuit 2205 at one minute intervals, for example.

Thus, in basic processing (1), the mode for executing the first function is set and permission is given for regular execution of interrupt processing (1) once the subject has actually begun to run.

The details of interrupt processing (1) will now be explained with reference to FIG. 49. CPU 2201 increments register n by "1" in step Sa11. Since register n was cleared to zero in step Sa2, its contents indicate the number of times that interrupt processing (1) was executed after the subject began to run. Since interrupt processing (1) is executed at constant intervals, register n directly indicates the time elapsed since the start of exercise.

In step Sa12, CPU 2202 reads out the pulse wave signal detected by pulse wave detector 2101 via sensor interface 2204, subjects it to FFT processing, and determines the subject's pulse rate, i.e., "beats/min". Next, in step Sa13, CPU 2201 reads out the body motion signal detected by body motion detector 111 via sensor interface 204, subjects it to FFT, and determines the subject's running pitch (times/min). When the subject is exercising, the spectrum accompanying the regularity of movement is detected. Thus, by characterizing the frequency of the spectrum, the exercise pitch (running pitch here) can be determined.

In step Sa14, CPU 2201 pairs the obtained pulse rate and running pitch, and stores them in RAM 2203 in association with the value of register n at the current point in time. Thus, each time interrupt processing (1) is executed, the detected pulse rate and running pitch accumulate and are stored in RAM 2203.

Figure 56:
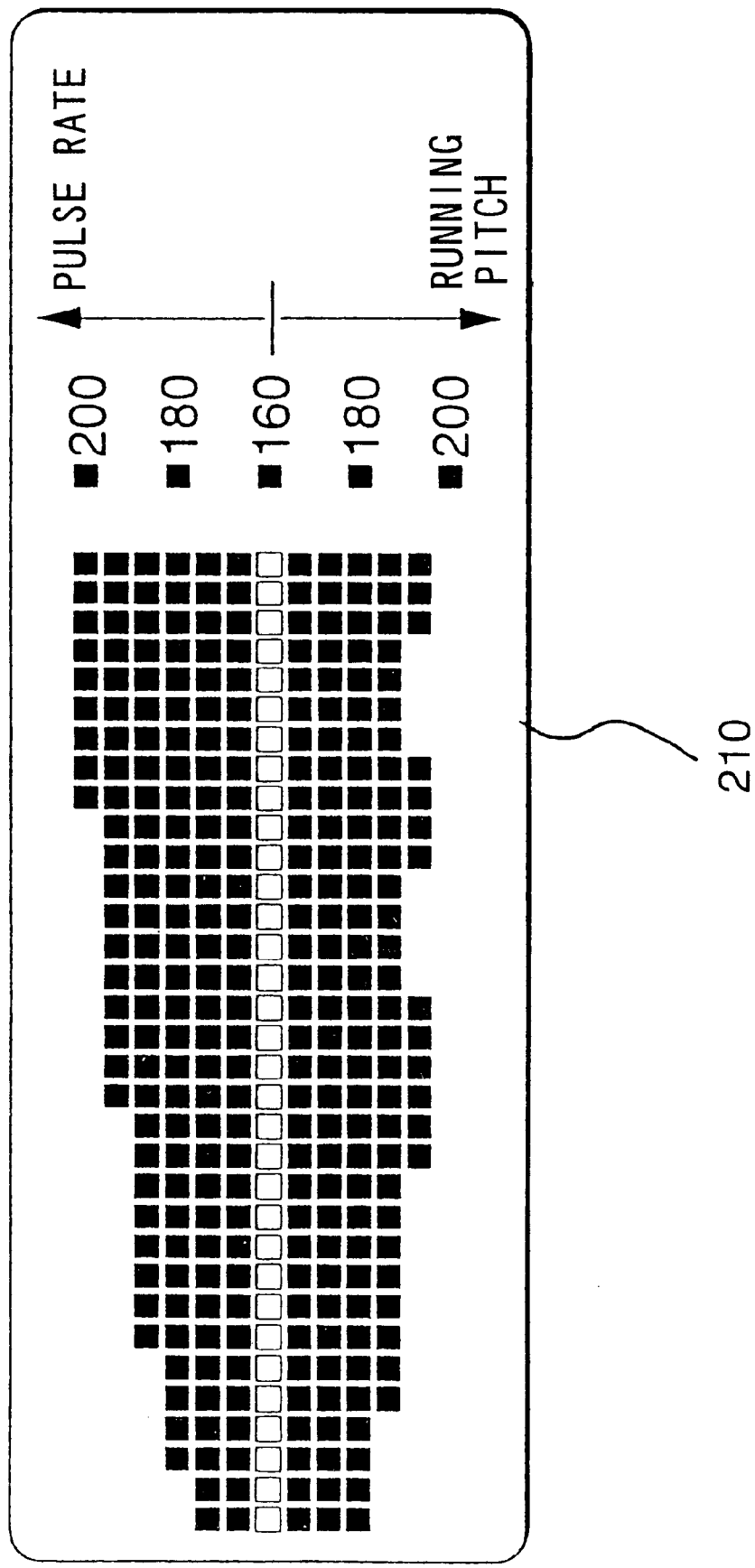
FIG. 56 is a diagram showing an example of the display shown on the display in the same exercise index measuring device in Chapter 2.

Next, in step Sa15, CPU 2201 reads out all the recorded pulse rates and running pitches from RAM 2203. In step Sa156, CPU 2201 directs display 2210 to execute a two-dimensional display by plotting the read out pulse rates and running pitches on the y-axis and their corresponding values in register n on the x-axis. An example of this display is shown in FIG. 56. As discussed above, since the value of register n expresses the time elapsed since the subject began running, provision of this type of display on display 2210 shows how the pulse rate and running pitch have changed since exercise began. As a result, the subject is able to know how his pulse and running pitch are changing. However, when the exercise index measuring device takes the form of a wristwatch as shown in FIG. 2, the display capacity of display 210 is of course limited. For this reason, it is preferable to send the read out information to an external device for analysis, as will be explained below. When the display processing in step Sa15 is executed, CPU 2201 terminates the current interrupt processing (1) in order to be ready for the next program execution.

By executing this type of basic processing (1) and interrupt processing (1), the first function, which is executed by means of the functional structure shown in FIG. 42, i.e., the function for displaying the pulse rate and running pitch stored in third recording member 121 in association with the time elapsed since exercise began, is executed equivalently by the internal structure shown in FIG. 43.

2-3-5-2: Second Function

Next, the operations when executing the second function (i.e., the function for displaying the targeted exercise intensity) will be explained.

Figure 50:
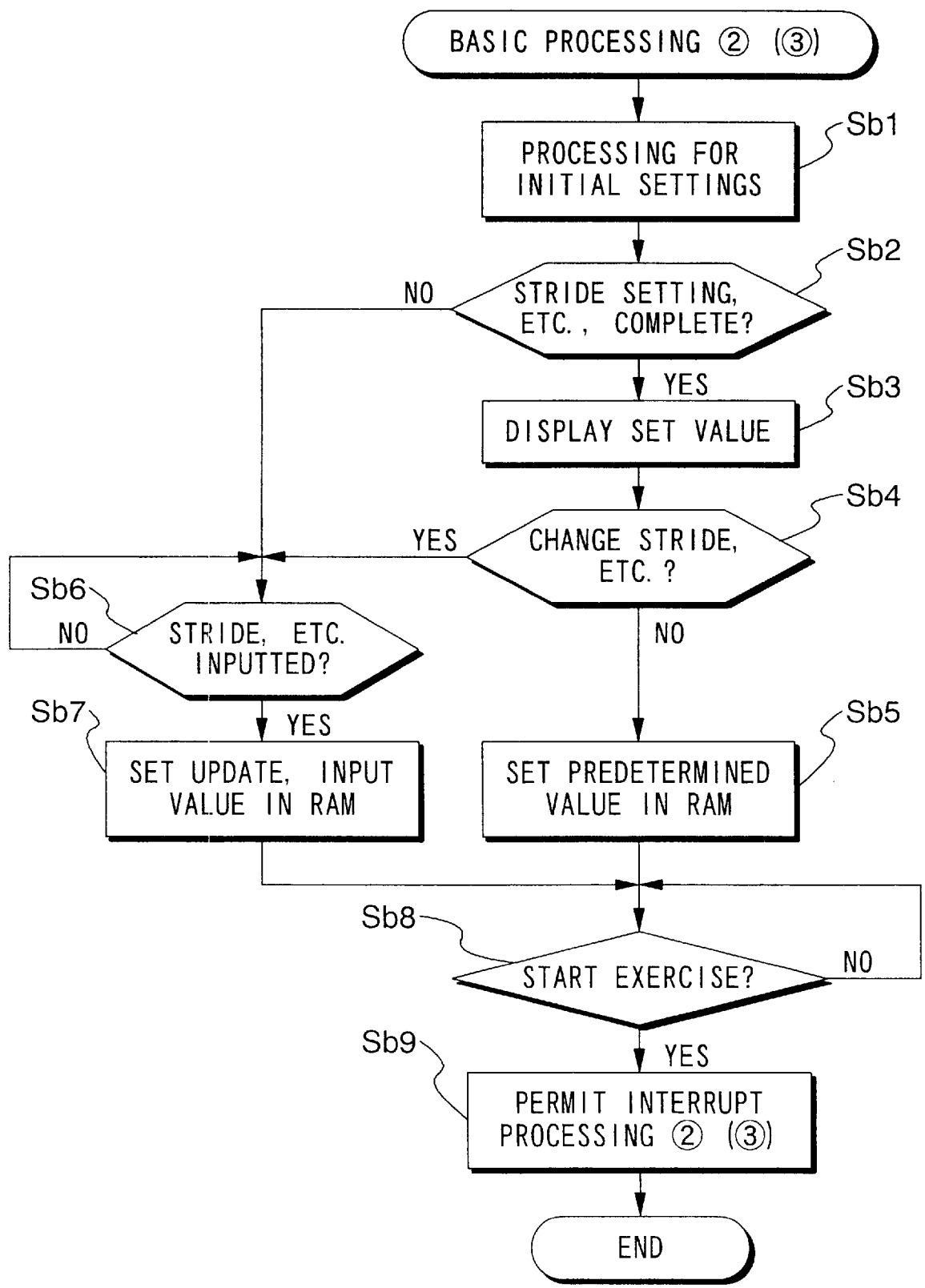
FIG. 50 is a flow chart showing basic processing (2) or (3) executed by the same exercise index measuring device in Chapter 2.
Figure 51:
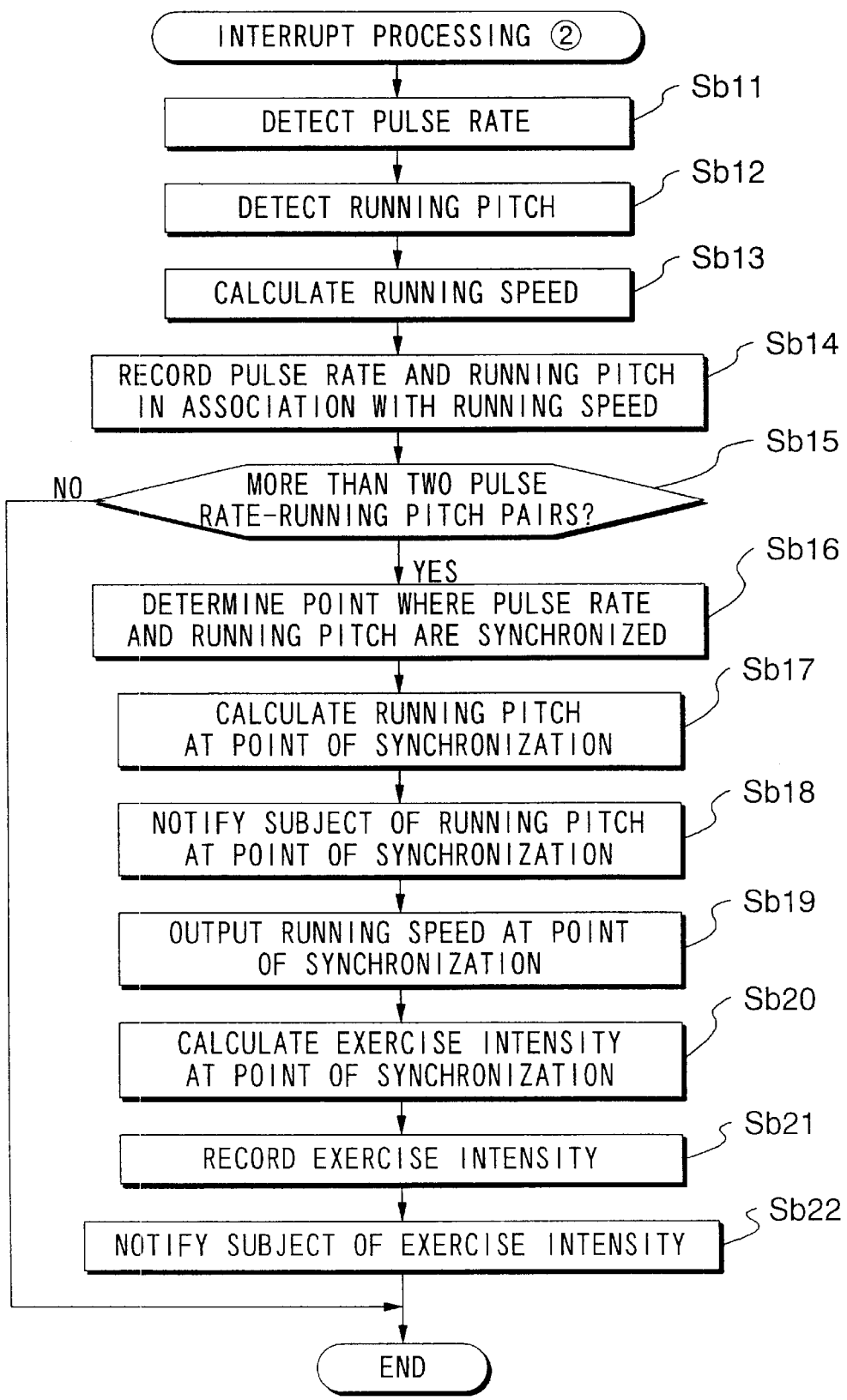
FIG. 51 is a flow chart showing interrupt processing (2) executed by the same exercise index measuring device in Chapter 2.

When the test subject operates button switch 111 to place the device in the mode for executing the second function, CPU 2201 in FIG. 43 first executes the basic program (2) shown in FIG. 50, and then. regularly executes interrupt processing (2) shown in FIG. 51.

First, the details of this basic processing (2) will be explained in reference to FIG. 50. This basic processing (2) sets the information on which display of the targeted exercise intensity is premised, and permits interrupt processing (2). More specifically, basic processing (2) is composed of the following steps Sb1~Sb9.

In step Sb1, CPU 2201 executes such initial processing as securing the necessary area in RAM 2203 and clearing this area, for example.

Next, in step Sb2, CPU 2201 determines whether or not information such as the amount of shift per repetitive motion, the subject's body weight, etc., is set in RAM 2203. Since the exercise in this embodiment is running, CPU 2201 determines whether or not the subject's stride and body weight information are set. In this embodiment, no information is set in RAM 2203 the first time the second function is executed. Accordingly, the determination in step Sb2 is carried out.

When the above information has been set, CPU 2201 reads out the set values from RAM 2203 and displays them on display 210 in step Sb3. In step Sb4, CPU 2201 provides a message prompting the subject to select whether or not to change these values.

When the subject indicates that the values should not be changed, CPU 2201 resets the above information as existing values in RAM 2203 in step Sb5.

In contrast, when the above information has not been set in RAM 2203, or when the subject indicates that the values should be changed, CPU 2201 determines whether or not the information has been input in step Sb6. If the information has not been input, the processing sequence again returns to step Sb6. In other words, the processing sequence queues in step Sb6 until the subject's stride and body weight have been input. Once this information is input and changed, then, in step Sb7, CPU 2201 sets these values in RAM 2203.

When indicating a desire to change information such as the stride, the subject operates button switch 111 to set the operational mode of device main body 110 to the input/change mode. With respect to the indication not to change the aforementioned information, an arrangement may be considered in which the subject does not operate button switch 111 for a fixed period of time. As a method for changing and inputting information such as stride, a method may be considered in which the subject sets the device to the input/change mode, uses button switch 514 to set stride or body weight as the subject to be input or changed, and then manipulates button switch 111 or 116 to raise or lower the targeted value by one.

When information such as the subject's stride or body weight have been set in RAM 2203, then, in step Sb8, CPU 2201 determines whether or not the subject is actually exercising in the same manner as in step Sa1 in basic processing (1). When CPU 2201 determines that the subject has not begun to exercise, the processing sequence returns to step Sb8. Namely, the processing sequence queues at step Sb8 until the subject begins to exercise. When the subject begins to exercise, CPU 2201 permits execution of interrupt processing (2) and terminates execution of basic processing (2) in step Sb9. Interrupt processing (2) is regularly executed, every 2 minutes for example, by an interrupt signal from watch circuit 205.

Thus, when basic processing (2) is executed, the information needed to calculate the exercise intensity is set, the device is set in the mode for executing the second function and the regular execution of interrupt processing (2) is permitted once the subject actually begins to exercise.

Next, the details of interrupt processing (2) will be explained in reference to FIG. 51.

CPU 2201 obtains the subject's pulse rate (beats/min) in step Sb11, and obtains the subject's running pitch (times/min) in step Sb12. This point is the same as that of steps Sa12,13 in interrupt processing (1). In step Sb13, CPU 2201 multiplies the subject's stride recorded in RAM 2203 with the running pitch detected in the immediately preceding step in order to calculate the subject's running speed.

In step Sb14, CPU 2201 stores the detected pulse rate and running pitch in RAM 2203 in association with the running speed.

The second function is for displaying as the targeted value the point at which the pulse rate and running pitch coincide. In this case, if the pulse rate and running pitch cannot be obtained at two or more points where the running speed differs, then it is not possible to determine the point at which they coincide.

For this reason, CPU 2201 stores at least two or more pulse rate-running pitch pairs in step Sb15, and then executes the processing in the following steps Sb16~Sb22 under the condition that these running speeds are not equivalent values.

In other words, if the result of determination in step Sb15 is "Yes", then, in step Sb16, CPU 2201 first reads out all of the pulse rate and running pitch values stored in RAM 2203. Second, CPU 2201 determines the regression line for the pulse rate corresponding to the running speed, and determines the regression line for the running pitch corresponding to running speed. Third, CPU 2201 determines the intersection of the regression line for the pulse rate with the regression line for running speed, and determines the point at which the pulse rate and running pitch are synchronized.

Taking into consideration measurement error, it is not absolutely essential to employ the point of intersection. Rather, when detecting the point of coincidence, the pulse rate and running pitch may be considered equivalent if the difference between them is in the range of ±10%.

Next, CPU 2201 determine s the running pitch corresponding to the obtained point of intersection (step Sb17), and controls alarm 2208 so as to generate as the exercise index an alarm sound corresponding to this running pitch (step Sb8). For example, an arrangement may be considered in which a beep alarm is sounded which is associated with the frequency of the running pitch. The design is not limited to a display in this case, but rather a variety of approaches may be considered for informing the subject, including using a synthetic voice, varying the intensity of the alarm sound, and the like.

CPU 2201 determines the running speed corresponding to the obtained point of intersection (step Sb19), and calculates the exercise intensity corresponding to the running speed (step Sb20). This calculation may be obtained by multiplying the subject's body weight recorded in RAM 2203 with the running speed, or may be obtained from the relationship between running speed and exercise intensity.

CPU 2201 associates the obtained exercise intensity with the date on which that exercise (running) was performed, stores this in RAM 2203 (step Sb21), and displays the obtained exercise intensity on display 2210 as the targeted exercise index (step Sb22).

The exercise intensity obtained in this way is the value at which the pulse rate and the running pitch are synchronized, and is the value which should serve as the index for performing exercise to increase overall body endurance. As in the case of step Sb20, when the exercise intensity is obtained as the physical intensity of the exercise performed by the subject, it is possible to obtain an absolute intensity during running. Accordingly, this is convenient for performing various comparisons. From the subject's perspective, however, the targeted exercise intensity can be easily understood directly by expressing the running pitch (or pulse rate) using alarm 2208 during exercise. In other words, the targeted exercise can be achieved if the subject performs exercise in accordance with indices expressed in terms of the senses. Accordingly, this arrangement is more convenient.

Therefore, interrupt processing (2) is designed to notify and display the physical exercise intensity and the running pitch as exercise indices as described above.

Note that the pulse rate may also be employed as the exercise index, or anyone of the pulse rate, running pitch or exercise intensity may be selected and displayed to inform the subject.

When informing the subject of both the pulse rate and the running pitch as exercise indices, there are two methods available for the subject to increase or decrease the intensity of the running exercise. In the first method, the pulse rate which is informed as the exercise index is designated as the priority target, with the subject himself controlling the running speed. In the second method, the pulse rate is controlled by the subject himself controlling running speed which was informed to him as the exercise index priority target.

Assuming the exercise is running, then running speed, which is the product of running pitch and stride, the product of running speed and pulse rate, the product of pitch and pulse rate, or the product of stride and pulse rate, may be employed as the exercise intensity, and a design which informs and displays these values as exercise indices is acceptable. Since an exercise index such as this serves as an indicator for carrying out efficient running, the subject may use these as the target values during running.

After completion of the processing in step Sb22, or when the results of the determination in step Sb15 is "No", CPU 2201 terminates the current interrupt processing (2) in order to be ready for the next program execution.

Note that interrupt processing (2) is executed at regular intervals, at which time the pulse rate and pitch being recorded in RAM 2203 are increasing. Accordingly, when the running speed is separated into at least two stages, then the exercise index is informed and displayed when the result of the determination in step Sb15 is "YES".

By executing this type of basic processing (2) and interrupt processing (2), the second function executed by means of a functional structure in which switch 2132 selects input terminal a in FIG. 42, i.e., the function for displaying the targeted exercise intensity, is executed equally by the internal structure shown in FIG. 43.

2-3-5-3: Third Function

Next, the operation when executing the third function (i.e., the function for displaying the intensity of the exercise performed by the subject) will be explained.

Figure 52:
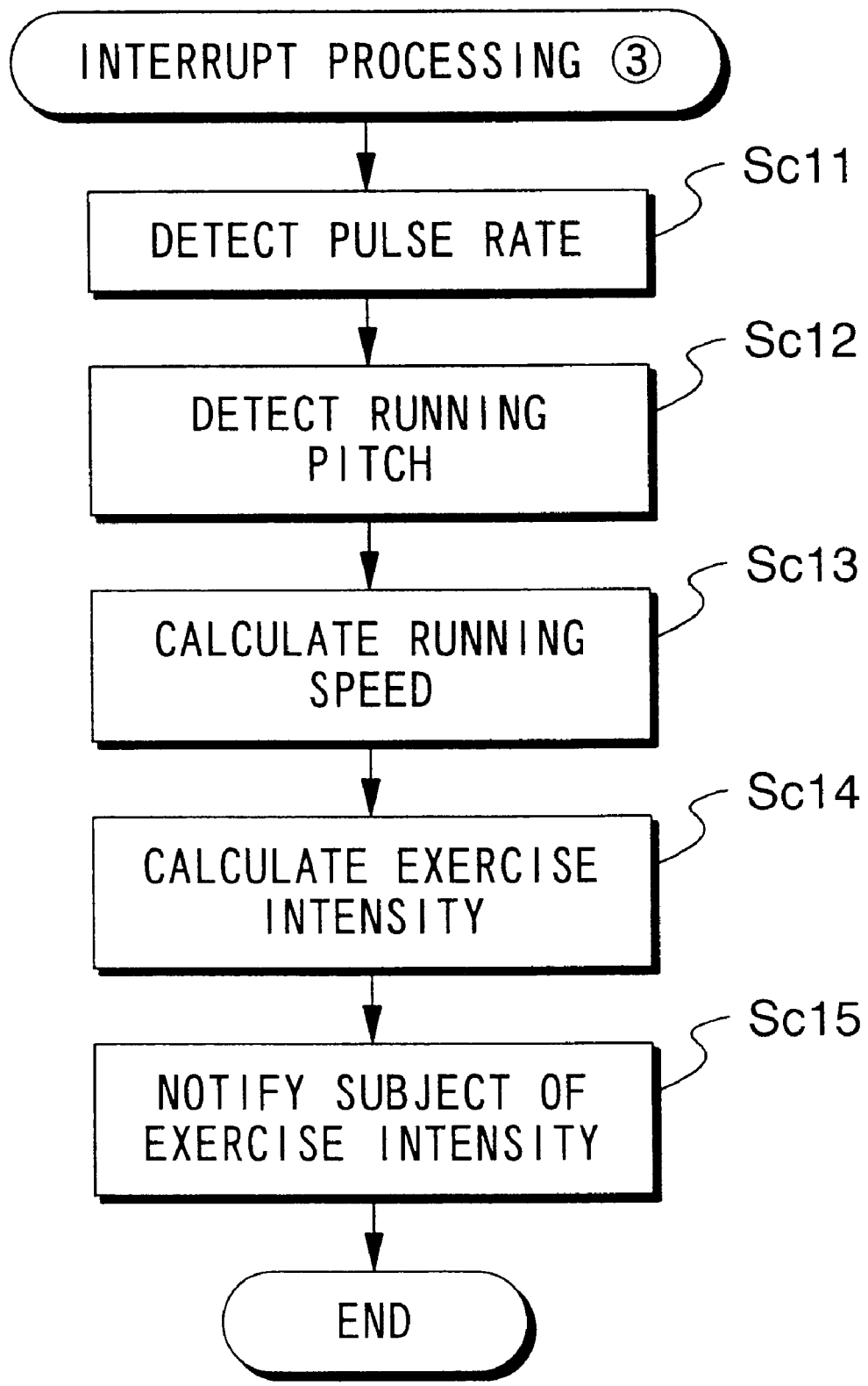
FIG. 52 is a flow chart showing interrupt processing (3). executed by the same exercise index measuring device in Chapter 2.

When the test subject operates button switch 111 to place the device in the mode for executing the third function, CPU 2201 in FIG. 43 first executes basic program (3), and then regularly executes interrupt processing (3) shown in FIG. 52. The details of basic processing (3) are the same as that of basic processing (2) shown in FIG. 50.

Namely, basic processing (3) is the processing for setting the information necessary for calculating the exercise intensity, setting the device in the mode for executing the third function, and permitting the regular execution of interrupt processing (3) once the subject begins to exercise.

Accordingly, an explanation of basic processing (3) will be omitted, and the processing details of interrupt processing (3) will be explained in reference to FIG. 52.

CPU 2201 obtains the subject's pulse rate (beats/min) in step Sc11, and obtains the subject's running pitch (times/min) in step Sc12. This point is the same as that of steps Sa12,13 in interrupt processing (1).

CPU 2201 then multiplies the subject's stride recorded in RAM 2203 with the running pitch detected in the immediately preceding step, in order to calculate the subject's running speed. In step Sc14, the exercise intensity corresponding to this running speed is determined. This calculation is the same as in step Sb2O above.

In step Sb21, CPU 2201 displays the obtained exercise intensity on display 210. The exercise intensity displayed in this way is determined at the timing for execution of interrupt processing (3) for the running exercise actually being performed by the subject. In other words, the exercise intensity expresses the intensity of the running actually being performed by the subject. The execution interval for interrupt processing (3) is the sampling interval for the exercise intensity.

By executing basic processing (3) and interrupt processing (3), the third function executed by a functional structure in which switch 132 selects input terminal b, i.e., the function expressing the targeted exercise intensity, is carried out equivalently by the internal structure shown in FIG. 43.

2-3-5-4: Fourth Function

Next the operation when executing the fourth function (i.e., the function for showing how much the intensity of the exercise performed by the subject differs from the targeted exercise intensity) will be explained.

Figure 53:
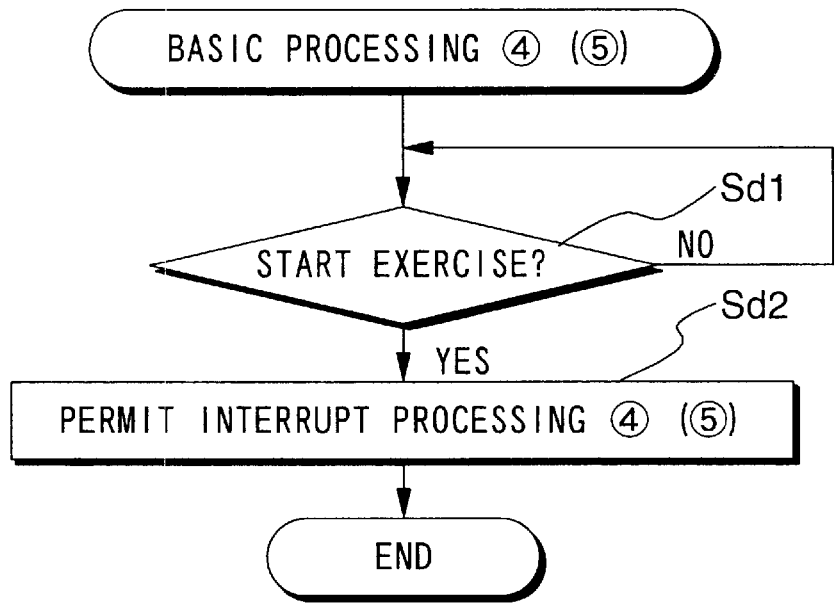
FIG. 53 is a flow chart showing basic processing (4) or (5) executed by the same exercise index measuring device in Chapter 2.
Figure 54:
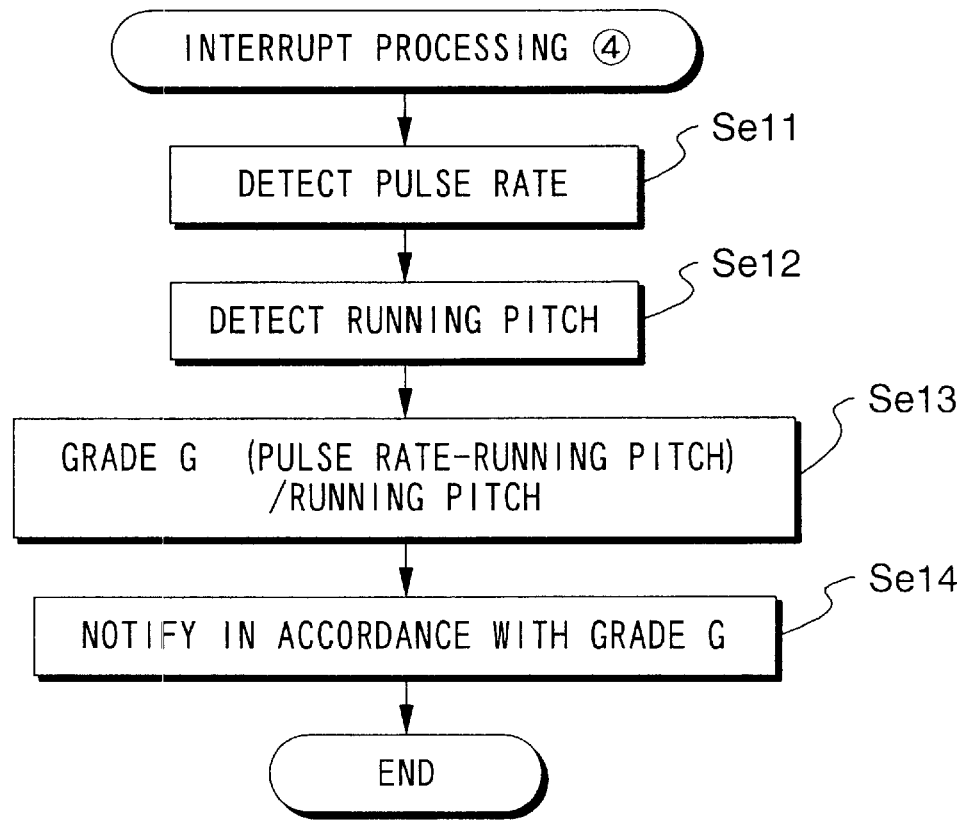
FIG. 54 is a flow chart showing interrupt processing (4) executed by the same exercise index measuring device in Chapter 2.

When the test subject operates button switch 111 to place the device in the mode for executing the fourth function, CPU 2201 in FIG. 43 first executes basic program (5) shown in FIG. 53, and then regularly executes interrupt processing (4) shown in FIG. 54. The details of basic processing (4) are the same as that of basic processing (1) shown in FIG. 48 with the exception of step Sa2.

Namely, basic processing (4) when executing the fourth function sets the device in the mode for executing this function, and permits the regular execution of interrupt processing (4) once the subject begins to exercise.

Next, the details of interrupt processing (4) will now be explained with reference to FIG. 54.

First, CPU 2201 determines the subject's pulse rate (beats/min) in step Sd11, and determines the subject's running pitch (times/min) in step Sd12. This point is the same as in steps Sa12,13 in interrupt processing (1). In step Sd13, CPU 2201 calculates the grade G from the obtained pulse and running pitch using the following equation $$\text{grade } G = (\text{pulse rate-running pitch})/\text{running pitch}$$

In step Sd14, CPU 2201 directs display 2210 to show a display in accordance with the value of grade G, and then terminates the current interrupt processing (4) in order to be ready for the next program execution.

The grade G obtained here expresses what proportion the difference between the pulse rate and the running pitch comprises of the running pitch. The closer this value is to zero, the more suitable is the intensity of the current exercise with respect to training to improve endurance. A negative value for grade G indicates that the current exercise intensity is low for accomplishing this training, while a positive value for grade G indicates that the current exercise intensity is high for accomplishing this training.

Accordingly, it is preferable that the content of display 2210 be such that the subject is able to directly know the symbol for grade G and the size of that value, as shown in FIG. 57 for example. As a result, the subject is able to know whether or not the current exercise intensity (running speed) is suitable by comparing it to the intensity for performing training to improve endurance. Moreover, if the current training intensity is not suitable, then the subject is also able to quantitatively know by how much he should increase or decrease the intensity of his exercise in order to achieve the aforementioned training.

Note that FIG. 57 shows an example of the display in which an upward directed arrow prompts the subject to increase the exercise intensity and a downward directed arrow prompts the subject to decrease the exercise intensity, with the number of arrows indicating the extent of that increase or decrease. The design is not limited to a display, however. Rather, notification may be performed using a variety of arrangements in which intensity is expressed, including a voice synthesizer or alarm.

By executing this type of basic processing (4) and interrupt processing (4), the fourth function, i.e., the function for informing and displaying how different the current exercise intensity is from the targeted exercise intensity, which is executed by the functional structure shown in FIG. 42, is equally and regularly executed by the internal structure shown in FIG. 43.

2-3-5-5: Fifth Function

Next, the operation when executing the fifth function (i.e., the function for providing an index so that the current exercise intensity approaches the targeted exercise intensity) will be explained.

The test subject operates button switch 111 to place the device in the mode for executing the fifth function. As a result, CPU 2201 in FIG. 43 first executes basic program (5), and then regularly executes interrupt processing (5) shown in FIG. 55. The details of basic processing (5) are the same as that of basic processing (4) shown in FIG. 53.

Namely, basic processing (5) permits regular execution of interrupt processing (5) when the mode for executing the fifth function is set and the subject has actually begun running.

Figure 55:
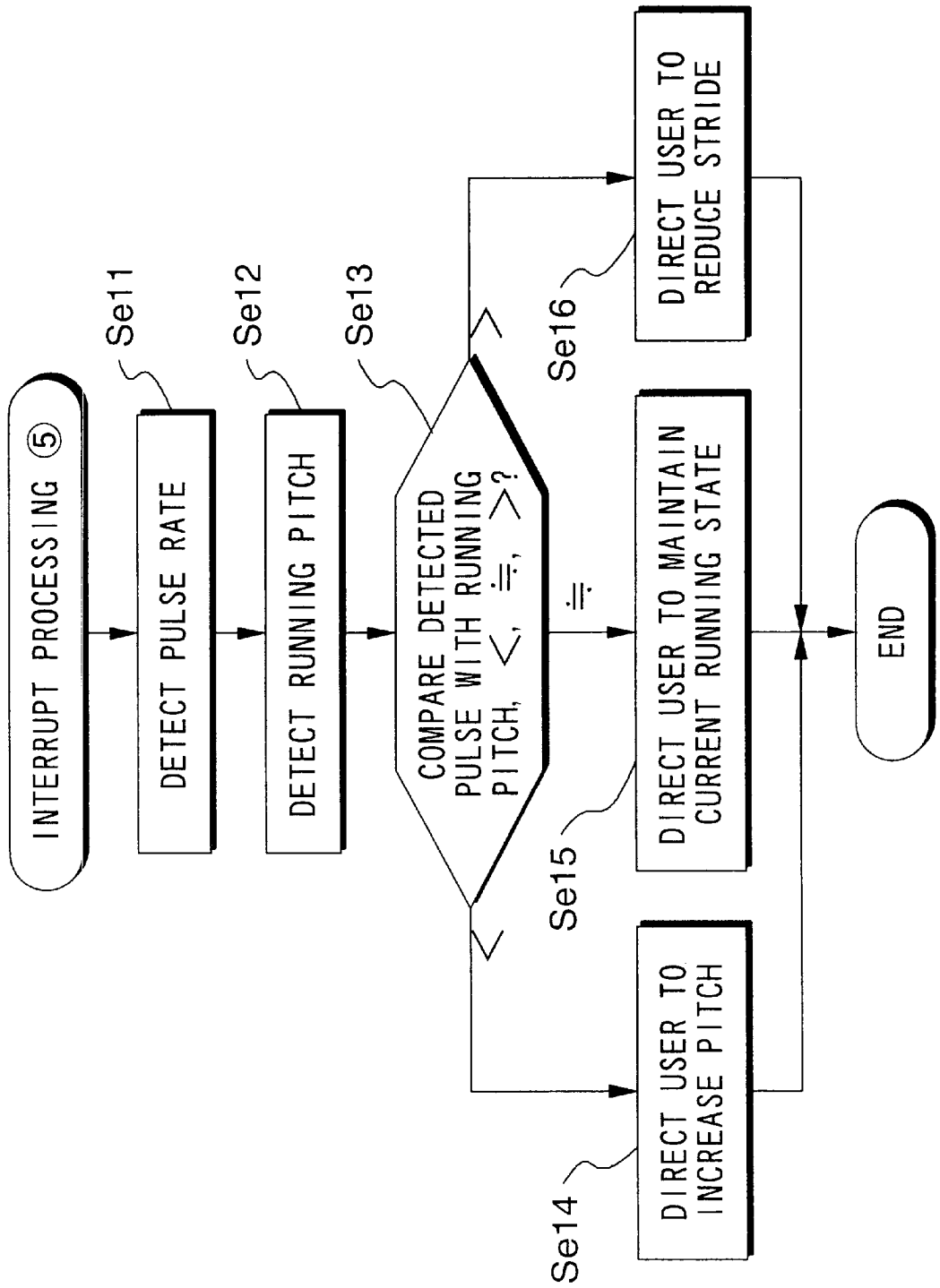
FIG. 55 is a flow chart showing interrupt processing (5). executed by the same exercise index measuring device in Chapter 2.

The details of interrupt processing (5) will now be explained with reference to FIG. 55.

First, CPU 2201 determines the subject's pulse rate (beats/min) in step Se11, and determines the subject's running pitch (times/min) in step Se12. This point is the same as in steps Sa12,13 in interrupt processing (1). In step Se13, CPU 2201 compares the obtained pulse rate and running pitch. When the pulse rate is smaller than the running pitch, then, in step Se14, CPU 2201 provides a display on display 210 for raising the pitch. If the pulse rate is approximately the same as the pitch, then, in step Se15, CPU 2201 provides a display on display 210 directing the subject to maintain the current running state. If the pulse rate is larger than the pitch, then, in step Se16, CPU 2201 provides a display on display 2210 directing the subject to reduce his stride. Thereafter, CPU 2201 terminates the current interrupt processing (5) in order to be ready for the next program execution.

As may be understood by referring to FIG. 44A, a pulse rate which is smaller than the running pitch means that the running speed is too low for performing training to increase endurance. In this case, it is necessary to provide a notice to the subject to prompt him to increase the running speed. Two approaches may be considered in this case, namely, a display for increasing the running pitch and a display for increasing the stride.

Conversely, as may also be understood by referring to FIG. 44A, a pulse rate which is larger than the running pitch means that the running speed is too high for performing training to increase endurance. In this case, it is necessary to provide a notice to the subject to prompt him to decrease the running speed. Two approaches may be considered in this case, namely, a display for decreasing the running pitch and a display for decreasing the stride.

One of the characteristics of running in general is that, if the stride is increased, then running speed increases. However, physical fatigue begins to occur, and the pulse rate tends to fall. In addition, when the running pitch is increased, the pulse rate tends to increase accompanying this.

In addition, as may be understood from the figure, the running pitch within the range in which running speed is high does not change that much as compared to the increase in the speed of running. This means that in the area where the running speed is low, an increase in the running speed is carried out primarily by increasing running pitch. Conversely, in the area where the running speed is high, an increase in the running speed is primarily carried out by increasing the stride. Moreover, the change in the pulse rate in the region where the running speed is low is considerable as compared to the increase in the running pitch.

Drawing on the above then, when the pulse rate is lower than the running pitch, this embodiment is designed to increase the subject's running speed without causing physical fatigue, by providing a directive to increase the running pitch. In contrast, when the pulse rate is larger than the running pitch, this embodiment is designed to decrease the subject's running speed while decreasing the pulse rate, by providing a directive to decrease the stride.

A pulse rate which is roughly equivalent to the running pitch indicates that the exercise intensity corresponding to the current running speed is appropriate as a training intensity for performing maintenance exercise. Accordingly, an indicator is provided directing the subject to maintain the current running state. Given measurement error, however, it is not absolutely essential that the pulse rate and running pitch be equal in this case. Rather, the two values may be considered equivalent if the difference between them is in the range of ±10%.

When the difference between the pulse rate and the running pitch is considerably large, a directive may be provided to the subject to change both values, without relying on a determination such as in this embodiment.

By executing this type of basic processing (5) and interrupt processing (5), the fifth function, i.e., the function for providing a directive to bring the current exercise intensity closer to the targeted exercise intensity, which is executed by the functional structure shown in FIG. 42, is equally and regularly executed by means of the internal structure shown in FIG. 43. Accordingly, it becomes an easy matter for the subject to achieve the targeted exercise intensity, i.e., an exercise intensity which is optimal for maintenance exercise, by performing running in accordance with the content of the directive provided by executing the fifth function.

2-3-5-6: Sixth Function

Next, the operation when executing the sixth function (i.e., the function for showing how the exercise intensity obtained via the second function is progressing as time elapses in months and days) will be explained.

When the test subject operates button switch 111 to place the device in the mode for executing the sixth function, CPU 2201 in FIG. 43 controls the system to first read out all the exercise intensities recorded in step Sb21, and second, provide a two-dimensional display by plotting the read out exercise intensity on the y-axis and the corresponding date on the x-axis.

The exercise intensity displayed here is the value at which the pulse rate and running pitch coincide when running is performed, and is the value which serves as the exercise index. This value will vary over days and months as training accumulates. Accordingly, by displaying the exercise intensity in correspondence with the day, the subject is able to know the efficacy of training over time.

Note that the preceding explanation described structures for separately carrying out each of the first through sixth functions. However, a design is also acceptable in which the first through sixth functions are all executed or are selectively executed when the subject begins running. In particular, since the processing details for the fourth and fifth functions are similar, it is preferable to carry out these functions simultaneously.

2-3-5-7: Communication Function

Next, the operation of the exercise index measuring device according to this embodiment when communicating with the external device shown in FIG. 47 in order to send and receive a variety of information will be explained.

In order to communicate with an external piece of equipment, the subject removes connector piece 80 from connector 70 of device main body 110, exposing LED 507 and photo transistor 508, and facing them toward communication window 606 of the external device.

The transmitting function for transmitting information to the external device and the receiving function for receiving information from the external device will be explained below separately.

2-3-5-7-1: Transmitting Function

When the subject operates button switch 111 to set the device in the mode for executing the transmitting function, CPU 2201 transmits information stored in step Sa14 when the first function was executed, i.e., pulse rate and pitch rate information associated with elapsed time since the subject started running, to device main body 600 via I/O interface 2209 and the optical interface of the external device. An IrDA (Infrared Data Association) method or the like may be used for this type of optical communication protocol.

By transmitting from device main body 110, it becomes possible for not only the subject, but also a third party such as a trainer or physician positioned at the external device, to objectively know how the subject's pulse rate and running pitch have changed since the subject began running. Moreover, this information can be stored and analyzed at the external device.

Note that the information relayed is not restricted, but may include the information recorded in step Sb21, for example. In this case, the fifth function described above is executed at the external device.

2-3-5-7-2: Receiving Function

Target values for running, such as running pitch for example, may be set at the external device along with elapsed time. The exercise index measuring device according to this embodiment receives the targeted value set in the external device, and employs this as the targeted value once the subject actually begins to run.

More specifically, with LED 507 and photo transistor 508 directed toward communication window 606 on the external device, the subject operates button switch 111 to set the device to the mode for executing the receiving function. CPU 2201 in FIG. 43 then transmits a signal to the external device requesting data, via I/O interface 2209 and the external device's optical interface. When main body 600 of the external device receives this signal, it transmits information which serves as the set target value via the external device's optical interface and I/O interface 2209.

When the information which serves as the target value is received by device main body 110, CPU 2201 temporarily stores the received information in RAM 2203. When the subject begins running, CPU 2201 reads out the target values corresponding to time elapsed since running began, and informs the subject of these. When the running pitch is employed as the target value in this case, it is also acceptable to employ grading as in the case of the fourth function, to indicate how different the actual running pitch during running is from the informed target value.

As a result, it is possible for the subject to perform running at the set running pitch, even when exercising over a long period of time. Thus, this can be employed in training or in pace setting during a competition.

By employing the exercise index measuring device according to the present embodiment, it is possible to execute the first through sixth functions and the communication function. In particular, by executing the second function, it is possible to comprehensively consider the subject's physical and psychological strength during exercise when determining the exercise intensity which should serve as an index for performing exercise to increase endurance. By executing the fourth function, it is possible to quantitatively obtain how different the current exercise intensity is from the exercise intensity required for increasing endurance. By executing the fifth function, it is possible to provide an index for bringing the current exercise intensity closer to the targeted exercise intensity.

When a design is provided in which the exercise index obtained in the second function is notified to the subject as the product of a physiological index and a physical index, such as the product of running speed and pulse rate, the product of running pitch and pulse rate, or the product of stride and pulse rate, then it is possible to evaluate a physical index and physiological index comprehensively. Specifically, even when the same course and the same time goals are employed, the physiological indices will vary according to the body's condition, so that a comprehensive evaluation is made with the physical indices. In other words, the physical index and the physiological index can be evaluated as one new index.

2-3-6: Other Embodiments

The preceding embodiment employed the case where the exercise index measuring device took the form of a wristwatch. However, the present invention is not limited thereto, but may also be designed as a pair of eyeglasses (see FIG. 34), necklace (see FIG. 35), card (see FIG. 36), or pedometer (see FIG. 37) as explained in Chapter 1.

2-3-7: Displaying and Informing Function

The preceding embodiments were designed to display the results of execution of the first through fifth functions on display 2210. However, the present invention is not limited thereto. Namely, the present invention is not limited to a display means which relies on a sense of sight. Instead, notification may be carried out through a variety of arrangements. Namely, notification in the present invention relies on one of the five senses. For example, a design is acceptable in which the targeted running pitch or pulse rate is informed using the sense of touch, by means of a vibration, for example. Similarly, a design is acceptable in which the results to be provided are informed using the sense of hearing, by means of a voice synthesizer for example.

2-4: Embodiment 2

The second embodiment of the present invention will now be explained.

Although there may be slight individual differences, in general, the stride during running becomes shorter as the running pitch increases.

However, in the first embodiment, even though the pitch fluctuated, the stride remained a constant value because the value set in RAM 2203 was used without modification. Namely, the aforementioned characteristic of running was not taken into consideration. Accordingly, the first embodiment has a disadvantage in that results obtained by calculations involving the stride may not be accurate.

Accordingly, in the second embodiment, a table showing the relationship between pitch and the correction coefficient for stride are determined in advance and stored. When calculations using stride are performed during running, the stride correction coefficient corresponding to the current pitch is read out from the table. The set stride is then corrected by multiplying it with the correction coefficient, thus eliminating the drawback associated with the first embodiment.

Figure 58:
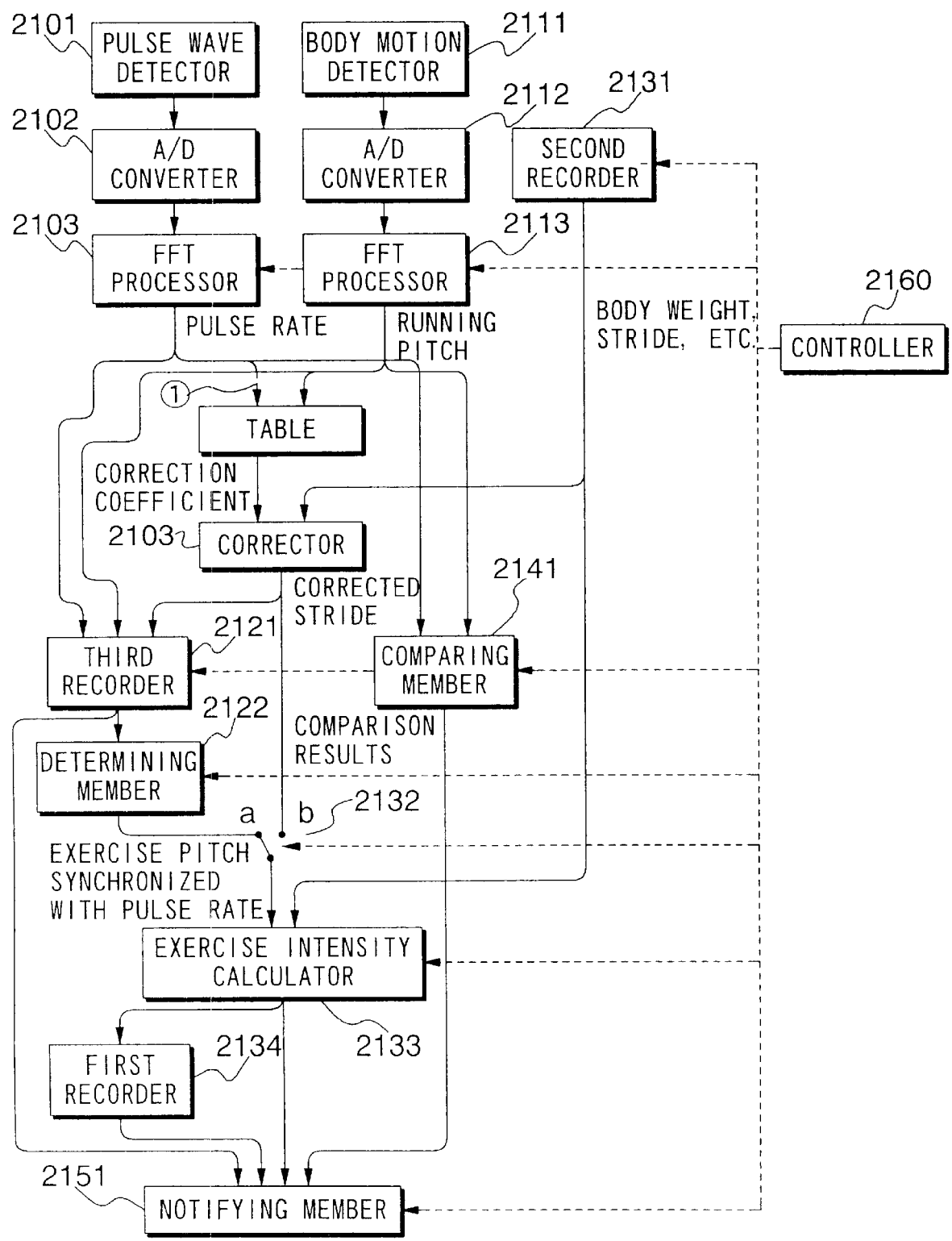
FIG. 58 is a block diagram showing the functional structure of an exercise index measuring device according to the second embodiment in Chapter 2.

Accordingly, the design of the exercise index measuring device according to the second embodiment is as shown in FIG. 58, wherein a table 2135 and a corrector 2136 have been added to the structure shown in FIG. 42. Table 2135 prestores the pitch and stride correction coefficient, and outputs the stride correction coefficient corresponding to the pitch determined by FFT processor 2113. Corrector 2136 multiplies the stride correction coefficient output by FFT processor 2113 with the stride stored in second recording member 131, so that the stride is corrected by matching it to the pitch.

Table 2135 corresponds to the RAM 2203 in FIG. 43, while the corrector 2136 corresponds to CPU 2201. Accordingly, there is essentially no addition of compositional components to the device shown in FIG. 43.

Figure 59:
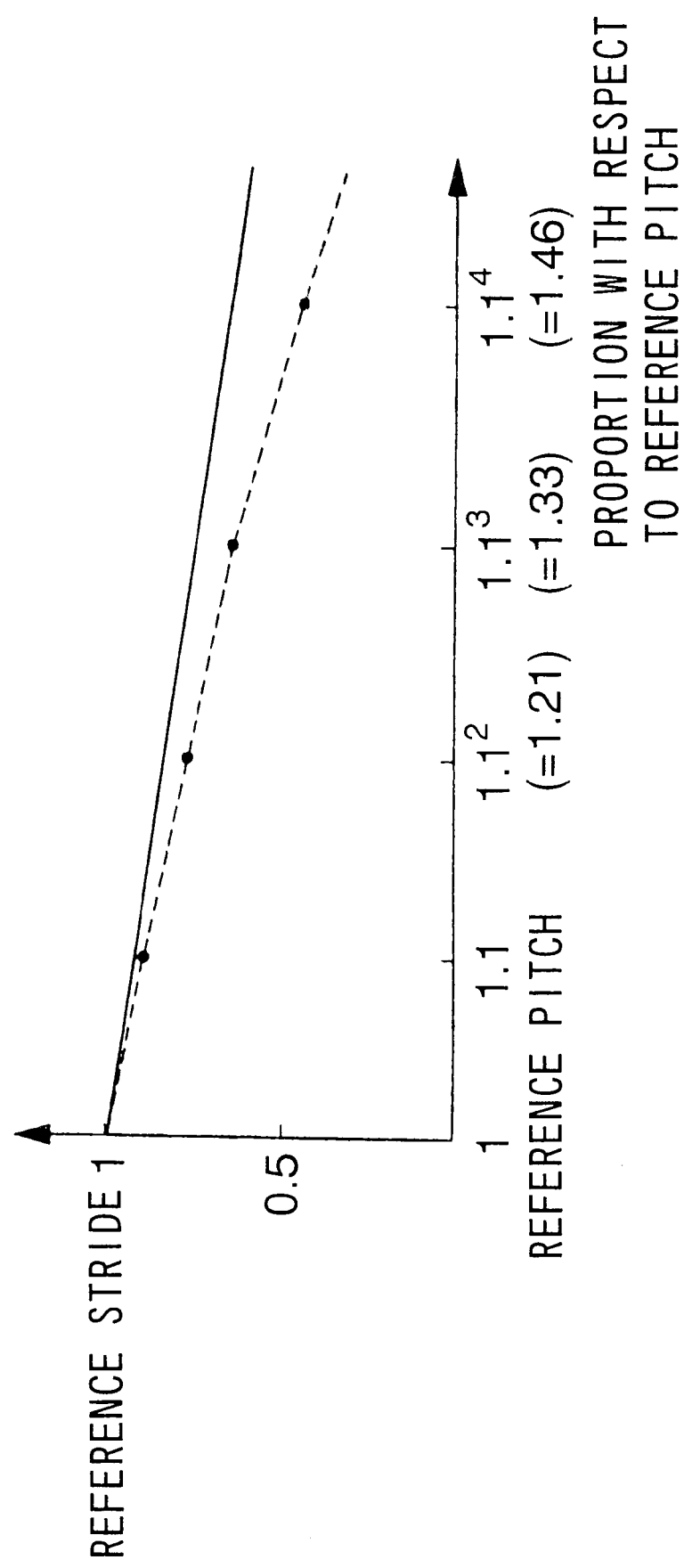
FIG. 59 is a diagram showing the content of the table in the second embodiment in Chapter 2.

When the characteristics of the stride correction coefficient and the pitch stored in table 2135 are studied, it is appears that the stride correction coefficient gradually becomes smaller than "1" as the pitch increases. This is shown by the solid line in FIG. 59. Note that in this figure, the reference pitch is the pitch when the stride (reference stride) is input during running.

The relationship between pitch and the stride correction coefficient will differ greatly between subjects. Thus, the characteristics indicated by the solid line in FIG. 59 must be edited to match the subject's own characteristics, as shown by the broken line in FIG. 59.

This editing function is carried out as follows.

First, the subject measures the stride after increasing the reference pitch in 10% stages, for example, and determines what its ratio is compared to the reference stride. Second, the subject inputs this ratio and the ratio with respect to the reference pitch to device main body 110 using button switches 111~114, for example.

When this happens, CPU 2201 carries out the following operation. Namely, CPU 2201 plots the input pitch ratio and stride ratio, and interpolates between these plots to obtain the characteristics shown by the broken line in FIG. 59, for example. This result is then rendered into the form of a table in a specific area in RAM 2203, and held there.

When the subject is running and calculations are performed using the stride which is recorded in RAM 2203, CPU 2201 first compares the detected pitch with the reference pitch to determine the ratio. Second, CPU 2201 determines the stride correction coefficient corresponding to this ratio by reading it out from the table. Third, CPU 2201 multiplies this coefficient with the reference stride read out from RAM 2203 to correct the stride corresponding to the running pitch. Finally, fourth, CPU 2201 employs the corrected stride in the calculation of exercise intensity.

As a result, the functional structure shown in FIG. 58 is executed equally by means of the internal structure shown in FIG. 43.

In the second embodiment, the stride is corrected even though the pitch is changing during running. Moreover, since this correction is carried out to fit the characteristics of the subject, it is possible to more accurately perform calculations that employ the stride.

When the subject is running, the corrected stride is linked with the current pulse rate and running pitch, and is stored in association with the time elapsed since running began. Namely, the first function in the first embodiment is for displaying the stride corrected in the second embodiment, in addition to the pulse rate and running pitch, since the subject began running. In the transmitting function, the corrected stride is also transmitted to the external device. It is also acceptable to set the stride in association with elapsed time in the external device as the target value for running. In the receiving function, this set stride information is received, and employed as a target value when the subject begins running.

When correcting the stride, in addition to the correction method using the table, a method may also be considered in which button switches 111,116 are depressed and the input stride is manually increased or decreased.

Note that stride, rather than the correction coefficient corresponding to running pitch, may be stored in table 2135.

2-4-1: Modifications of Embodiment 2

The second embodiment employed a design in which the stride was corrected according to the pitch during running. However, a situation may be considered in which the stride varies not only with the pitch during running, but also in accordance with the pulse.

A design is also acceptable employing a table similar to table 2135 in which the relationship between pulse rate and the stride correction coefficient is stored in advance.

When both pitch and pulse rate are taken into consideration when correcting the stride, then a design is also acceptable which employs both pitch and pulse rate as parameters when recording the stride correction coefficient, to generate a two-dimensional table. In this case, as shown by the broken line (1) in FIG. 58, the pulse rate obtained by FFT processor 2103 is supplied as a parameter for two dimensional table 2135.

2-5: Modifications for Chapter 2

The exercise performed by the subject in the first and second embodiments was running, however, the present invention is not limited thereto. For example, the exercise may be swimming. In this case, the same results may be obtained if the distance moved during one stroke, which corresponds to stride during running, is input, and the number of strokes per unit time is detected, corresponding to pitch. If the exercise is climbing a stand, then the same effects may be obtained by inputting the amount of rise with each step and detecting the number of steps climbed per unit time. In other words, the present invention provides a novel indicator in the form of an exercise index in which pulse rate and exercise pitch are synchronized for all regular exercise carried out at a constant rhythm, including actions typically performed during daily activities.

2-6: Effect of the Embodiments

As explained above, the exercise index measuring device according to Chapter 2 enables provision of a means for obtaining the exercise intensity which comprehensively considers the subject's physical and psychological strength during exercise, and which should be employed as the index when performing training to increase endurance.

Moreover, the exercise index measuring device according to Chapter 2 enables the subject to know how the results of training are varying over time.

The subject is also able to know the intensity of the exercise being conducted currently.

The subject can compare his current exercise intensity with the training intensity necessary for performing maintenance exercise, and determine whether or not the current intensity is appropriate. If the current intensity is not appropriate, then the subject is able to quantitatively know how much he should increase or decrease his current exercise intensity so that it will match the training intensity for performing maintenance exercise.

In addition, it becomes an easy matter for the subject to achieve a training intensity for performing maintenance exercise.

Because the stride is corrected in accordance with the running pitch or the pulse rate in the case of running, results obtained from calculations are made more accurate.

By sending and receiving information with an external device, the measured results can be analyzed at the external device, and the targeted value set more precisely.

3. Chapter 3

3-1: Summary

The method in Chapter 3 in which the blood lactic acid concentration is measured is one known method for objectively measuring the exercise intensity during running or weight training. This method of measurement employs the fact that lactic acid is a metabolite of fatigue, to determine that exercise intensity is large when the lactic acid concentration is high.

It is useful for individuals who are training during exercise to be able to know their exercise intensity, since this enables them to perform health management or more scientific training. However, in order to measure the lactic acid concentration, it is necessary to check its concentration by drawing blood. Accordingly, it is not possible to conduct measurements while continuing to exercise.

After studying indices which express the exercise intensity, the present inventors discovered that there is a close relationship between exercise intensity and the respiratory wave form. In this case, however, how to measure the respiratory wave form becomes a serious problem.

Methods for measuring a subject's respiratory waveform while at rest include a method in which a band is wrapped around the chest or stomach to measure the expansion and contraction state, and a method in which thermocouples are inserted into the nostrils and the fluctuation in the resistance value thereof is counted. However, wearing such an apparatus would be extremely inconvenient for a subject who is in training, or a subject who is trying to perform daily health monitoring.

An analysis of the frequency components of the variation in the R-R interval in the electrocardiogram of a subject at rest reveals that a component corresponding to the respiratory rate is present. Since the pulse wave is synchronized with the electrocardiogram, a component corresponding to the respiratory waveform is included in the variation frequency component of the pulse cycle (or pulse amplitude).

There is a device available for measuring the respiratory waveform based on the electrocardiogram or pulse wave by extracting this component. For example, Japanese Patent Application 62-22627 discloses a technique in which a continuous pulse interval is measured, the period of change in this pulse interval is measured, and the respiratory rate is calculated by taking the reciprocal of the period of change. Japanese Utility Model 4-51912 discloses a technique for detecting a first respiratory rate based on the variation in the envelope of peak values of the pulse waveform or the period of change in the R-R interval of the electrocardiogram, detecting a second respiratory rate by detecting the cyclic motion on the surface of the subject's stomach, and then recording and displaying the lower of the two respiratory rates. Japanese Utility Model 4-136207 discloses a technique for reducing noise or swell by estimating the respiratory rate based on the period of the variation in the amplitude of the pulse waveform, calculating an average value for the pulse waveform (the undulation in the low frequency component), and then using the data for which the trend in this average value is smallest. Further, Japanese Patent Application 6-142082 discloses a technique for multiplying the subject's pulse rate and systolic blood pressure which have been successively obtained and calculating the respiratory rate based on the pulse cycle of this multiplied value. Japanese Utility Model 6-22325 discloses a technique for determining the respiratory rate in the body based on the period of change in the curved line linking the peak values in the pulse wave.

However, if the subject is exercising, then an electromyogram waveform becomes superimposed on the electrocardiogram waveform, causing a body motion component to be superimposed on the pulse wave. These components are of a higher level than those corresponding to the respiratory waveform, causing the respiratory waveform to be calculated in error.

Accordingly, Chapter 3 provides an exercise intensity detecting device for extracting the respiratory component from the pulse waveform and easily detecting the exercise intensity based on the result of this extraction.

3-2: Outline of Theory

Figure 60A:
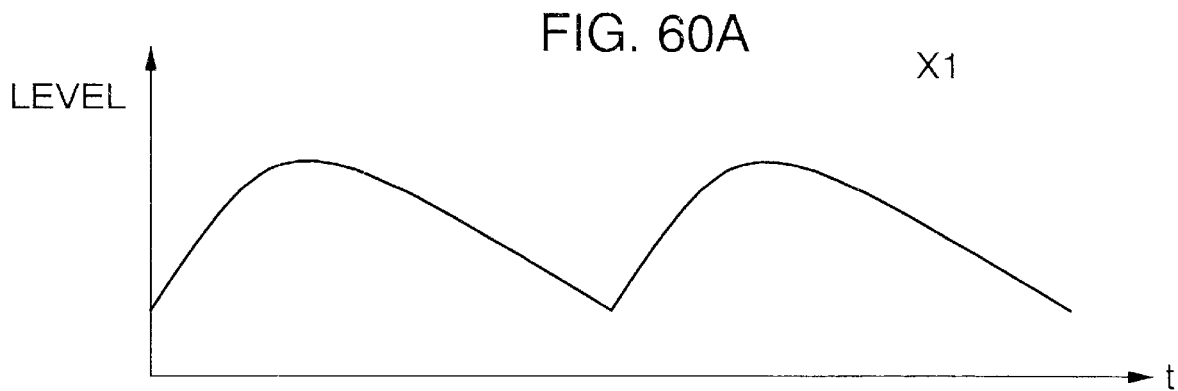
FIGS. 60A–60D are diagrams showing the relationship between exercise intensity and the respiratory waveform in Chapter 3.
Figure 60B:
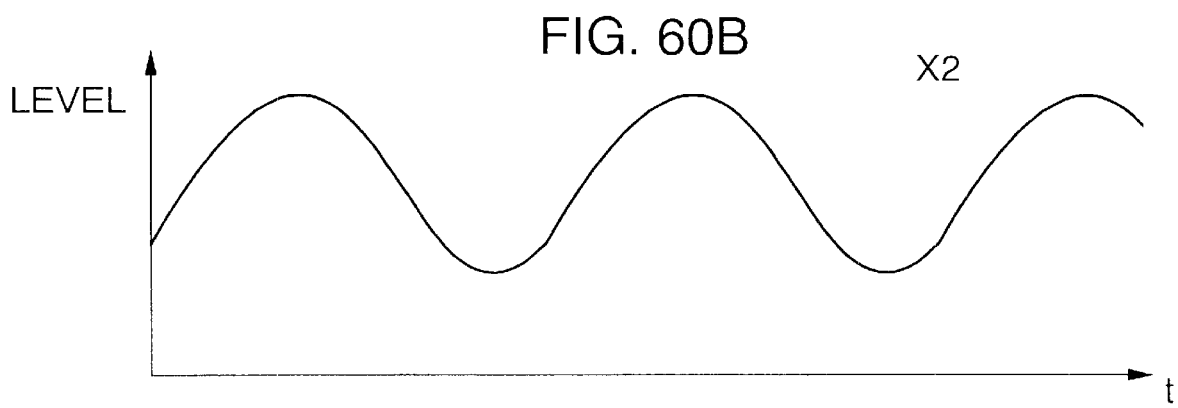
Figure 60C:
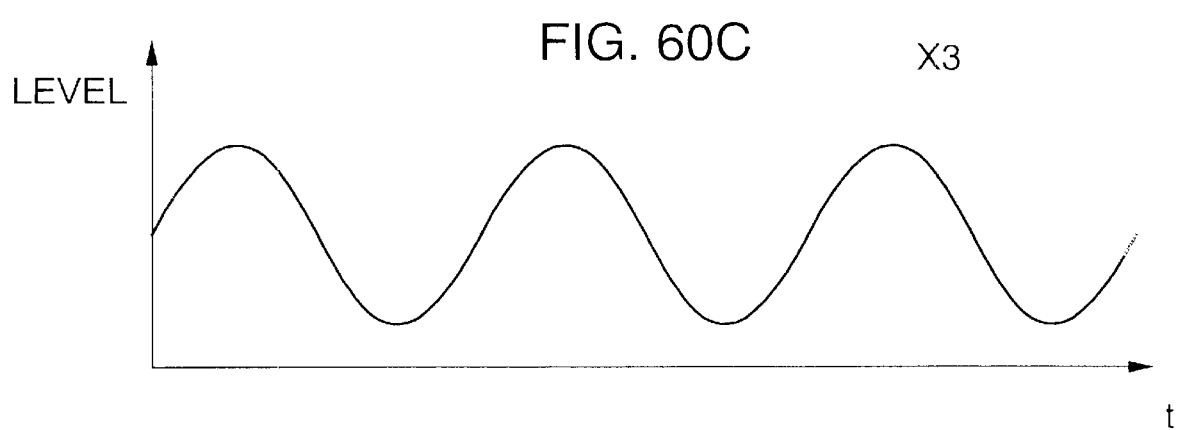
Figure 60D:
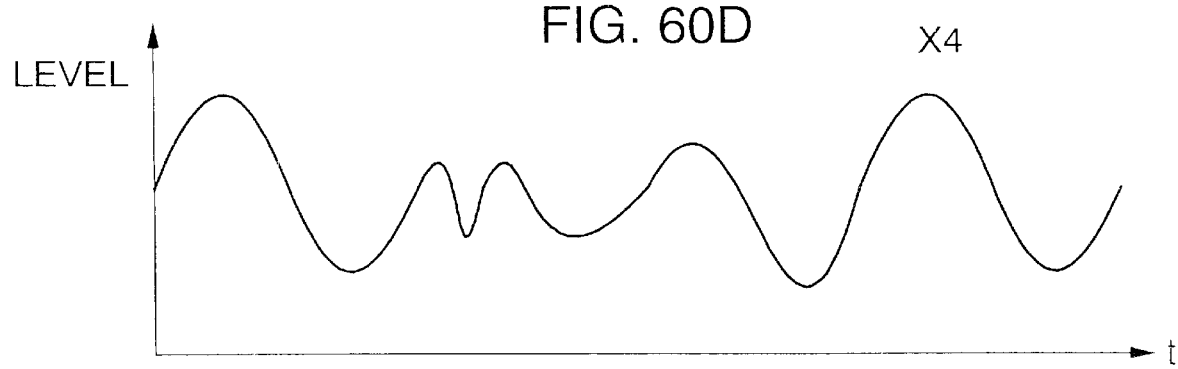

As the exercise intensity increases, the amount of oxygen consumed by skeletal muscle increases. As a result, the respiratory rate also increases. The relationship between exercise intensity and the respiratory waveform is shown in FIG. 60. Note that in this figure, the positive direction along the vertical axis indicates inhalation, while the negative direction indicates exhalation. FIG. 60A shows the respiratory waveform when at rest (exercise intensity X1), FIG. 60B shows the respiratory waveform at exercise intensity X2, FIG. 60C shows the respiratory waveform at exercise intensity X3, and FIG. 60D shows the respiratory waveform at exercise intensity X4. Exercise intensities X1~X4 are related as follows:

$$X1 < X2 < X3 < X4$$

From these figures it may be understood that the inhalation period is longer than the exhalation period when the subject is at rest. However, as the exercise intensity increases, the difference between the inhalation and exhalation periods becomes smaller, and the respiratory waveform gradually approaches a sinusoidal wave. As the exercise intensity become even greater, the respiratory waveform becomes greatly disturbed.

The respiratory wave's approach toward a sinusoidal wave in this way means that the higher harmonic components are decreasing with respect to the fundamental components. In particular, provided that the exercise intensity does not exceed a given limit, the respiratory waveform will change from a saw-toothed shaped wave to a sinusoidal wave. Thus, the third order higher harmonic wave components decrease as the exercise intensity increases.

Accordingly, by performing frequency analysis on the respiratory waveform, it is possible to obtain an index for exercise intensity.

Focusing on this point, the applicants detected the exercise intensity by extracting the respiratory components from the pulse waveform and performing frequency analysis thereon.

3-3: Functional Structure

Next, the function of the exercise intensity detecting device according to the present invention will now be explained. FIG. 61 is a function block diagram for the exercise intensity detecting device according to the present embodiment. In the figure, f31 is the pulse wave detecting means, which detects the pulse waveform at a detection site on the body. Pulse wave detecting means f31 corresponds to an optical pulse wave sensor or pressure sensor, for example. f32 is the body motion detecting means for detecting body motion waveforms which express the body's motion. An acceleration sensor may be employed for body motion detecting means f32, for example.

f33 is a body motion component removing means for generating the body motion components in the pulse waveform based on the body motion waveform, and then removing the body motion components from the pulse waveform to generate a pulse waveform from which body motion components have been removed. Specifically, a waveform from which body motion components have been removed is generated by performing the appropriate waveform processing on the body motion waveform and then subtracting this result from the pulse waveform, or by analyzing each frequency spectrum in the pulse waveform and the body motion waveform, and removing the frequency components which are equivalent to the frequency spectrum of the body motion waveform from the frequency spectrum of the pulse waveform.

f34 is a respiratory component extracting means for extracting the respiratory component based on the pulse waveform from which body motion components have been removed. Respiratory component extracting means f34 may be provided with a wavelet transformer for performing wavelet transformation on the pulse waveform from which body motion components have been removed and generating analyzed pulse wave data from which body motion components have been removed; and a respiratory waveform generator for generating analyzed respiratory waveform data by removing frequency components corresponding to pulse wave components from the analyzed pulse wave data from which body motion components have been removed, and generating as the respiratory component a respiratory waveform by performing inverse wavelet transformation on the analyzed respiratory waveform data. f35 is an exercise intensity generating means for calculating the exercise intensity based on the respiratory components extracted by the respiratory component extracting means. In this case, the exercise intensity can be calculated based on the ratio of the frequency components obtained by performing frequency analysis on the extracted respiratory component.

3-4: Embodiment 1
3-4-1: Structure of Embodiment 1

The structure of exercise intensity detecting device 3 according to the first embodiment in Chapter 3 will now be explained with reference to the figures.

3-4-1-1: External Structure of Embodiment1

The external structure of exercise intensity detecting device 3 is the same as the pulse wave diagnosing device explained in the first chapter (see FIG. 2). Namely, exercise intensity detecting device 3 is approximately formed of device main body 110 having a wristwatch structure, cable 120 connected to device main body 110, and pulse wave detection sensor unit 130 provided to the end of cable 120.

The circuit structure for pulse wave detection sensor unit 130 which functions as pulse wave detecting means f31 is the same as that of the pulse wave diagnosing device explained in Chapter 1 (see FIG. 3).

3-4-1-2: Electrical Structure of Embodiment 1

Figure 62:
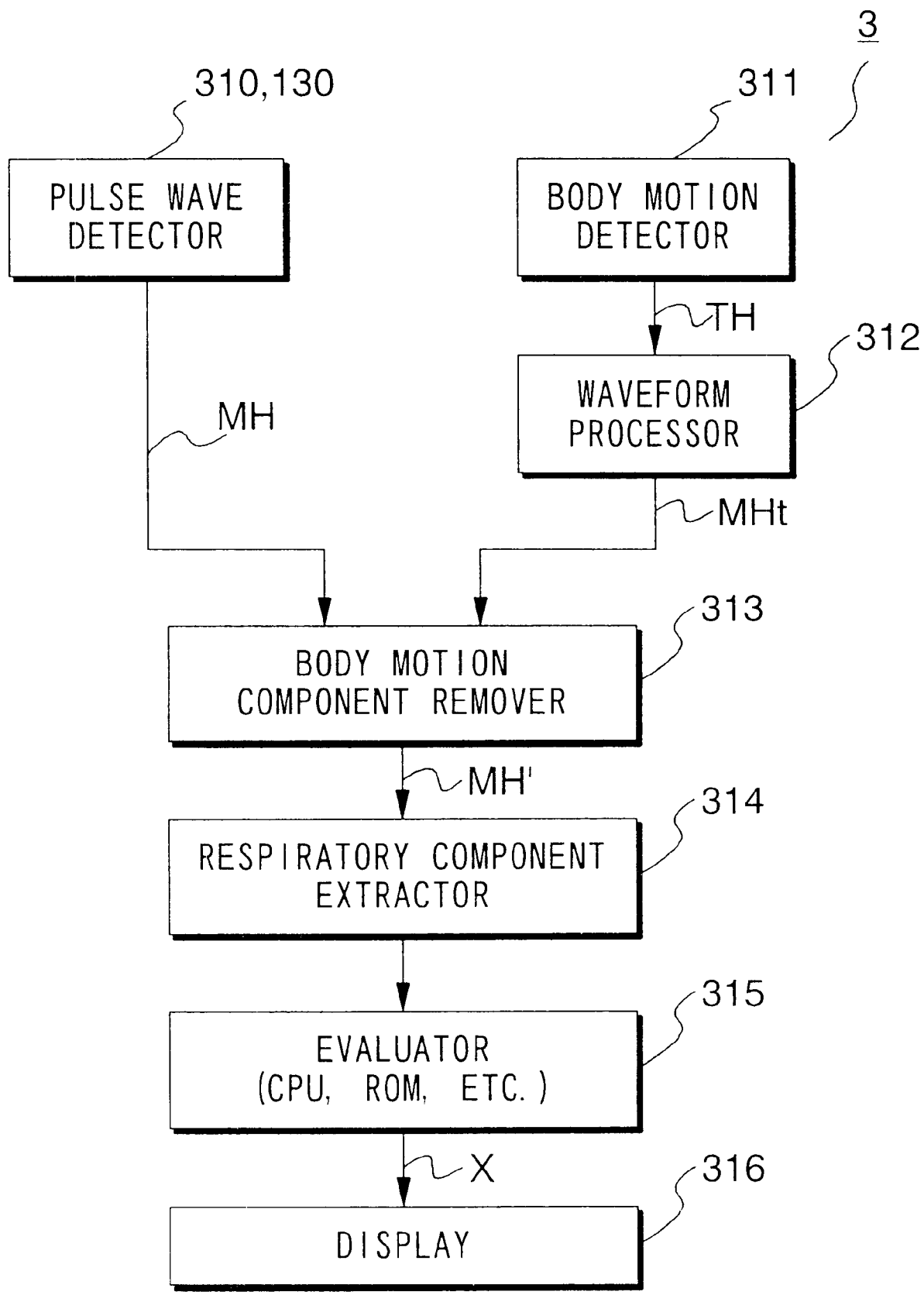
FIG. 62 is a block diagram showing the electrical structure of the exercise intensity detecting device according to the first embodiment in Chapter 3.

Next, the electrical structure of the first embodiment is shown in FIG. 62. In this figure, 310 is a pulse wave detector, corresponding to pulse wave detection sensor unit 130 explained above. Pulse wave detector 310 detects pulse waveform MH which expresses the size of the pulse. 311 is a body motion detector, composed of an acceleration sensor for example. Body motion detector 311 is provided inside watch case 200, and detects the body motion waveform TH expressing the body motion generated by the swinging movement of the arms, etc., during running.

312 is a waveform processor for performing a fixed waveform processing on body motion waveform TH. 313 is a body motion component remover. Waveform processing is performed to accurately remove the body motion components in body motion component remover 313. If a body motion component in pulse waveform MH is designated as MHt and the true pulse wave component (i.e., the pulse waveform from which body motion components have been removed) is designated as MH', then MH=MHt+MH'. Body motion waveform TH is detected as the acceleration speed of arm swinging for example. However, since blood flow is effected by the blood vessels and tissues, body motion component MHt blunts body motion waveform TH. Accordingly, waveform processor 312 is formed of a suitable low-pass filter. Note that the form and coefficient of the low-pass filter can be calculated from a value obtained by experiments. As a result, body motion component MHt can be obtained from body motion waveform TH. Body motion component remover 313 generates pulse waveform MH' from which body motion components have been removed by subtracting body motion component MHt from pulse waveform MH.

Next, 314 is a respiratory component extractor, formed from a CPU (central processing unit), A/D converter, and the like. In this example, pulse waveform MH' from which body motion components have been removed is converted from an analog to a digital signal by A/D converter, and taken up by the CPU as pulse wave data MH' from which body motion components have been removed. Respiratory component extractor 314 performs frequency analysis by carrying out FFT processing on pulse wave data MH' from which body motion components have been removed.

Figure 63:
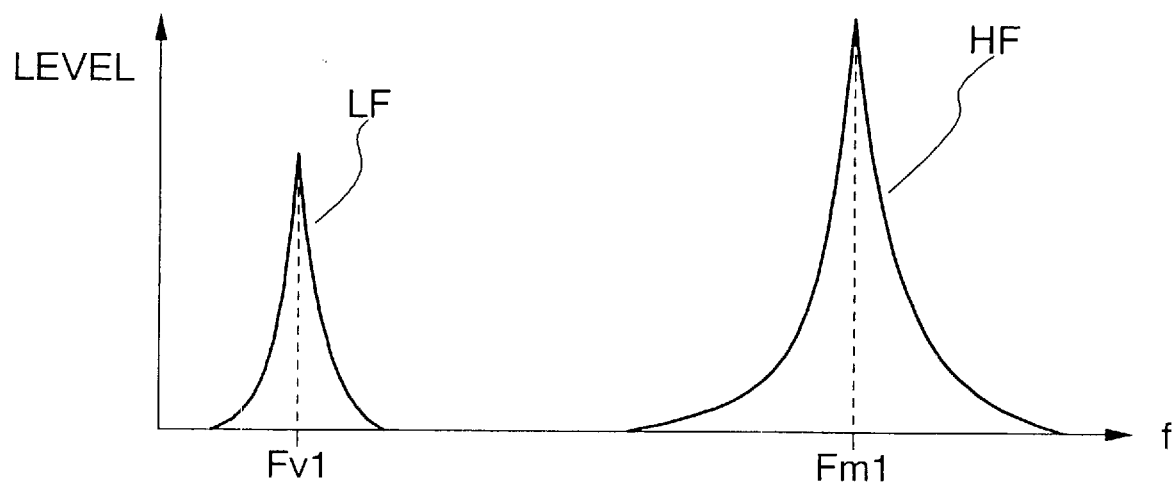
FIG. 63 is a diagram showing the results obtained when FFT processing is performed on pulse wave data MH' from which body motion components have been removed in Chapter 3.
Figure 64:
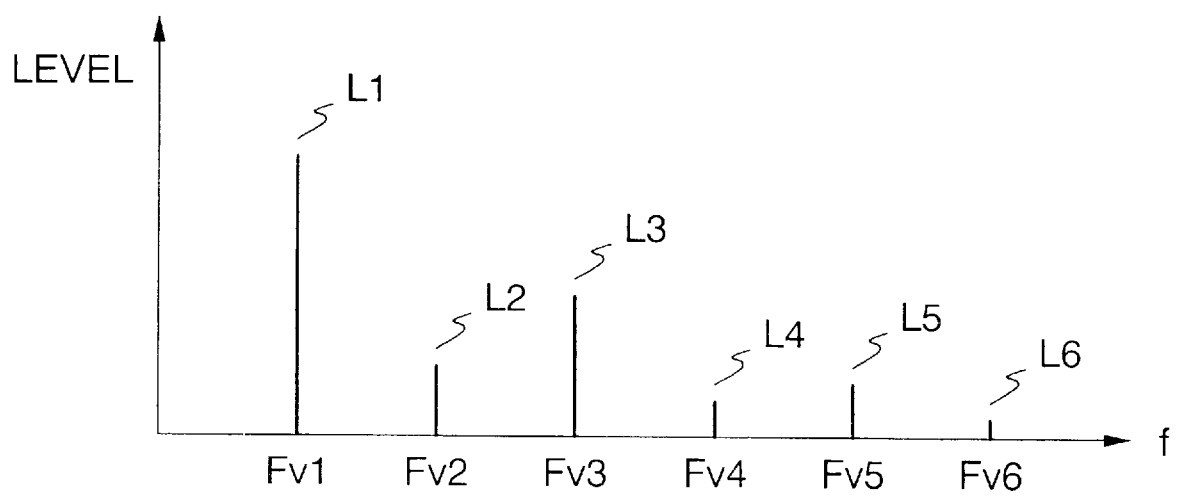
FIG. 64 is an enlarged view of low frequency region LF shown in FIG. 63.

FIG. 63 is a figure schematically showing a simplification of the results obtained when FFT processing is performed on pulse wave data MH' from which body motion components have been removed. In this figure, the maximum peak frequency in low frequency region LF is fundamental frequency Fv1 of the respiratory component, while the maximum peak frequency in high frequency region HF is fundamental frequency component Fm1 of the pulse wave. FIG. 64 shows an enlargement of low frequency region LF shown in FIG. 63. It may be understood from this figure that the respiratory components are formed of the fundamental frequency Fv1 and higher harmonic waves Fv2, Fv3, Fv4 . . . thereof. In this example, respiratory component extractor 314 specifies the maximum peak frequency by performing FFT processing on pulse waveform MH' from which body motion components have been removed. Since the fundamental component of the pulse wave is maximal, Fm1 is specified as the maximum peak frequency. The maximum peak frequency in the frequency region which is lower than Fm1 is then specified. Frequency components which are in a region which is lower than the pulse wave component correspond to the respiratory component. Accordingly, the frequency Fv1 of the fundamental wave of the respiratory component is specified. Respiratory component extractor 314 detects level L1 of Fv1, and levels L2, L3, L4 . . . of the higher harmonic wave frequencies Fv2, Fv3, Fv4 . . . thereof. Note that in this example, the higher harmonic wave frequencies are limited to a frequency below Fm1. This is because when the frequency is above Fm1, a pulse wave component is present so that, assuming that Fm1 is an integer multiple of Fv1, it is not possible to separate the respiratory component.

315 is an evaluator and is formed of a CPU, ROM or the like. The CPU calculates distortion factor K in the respiratory waveform based on L1, L2, L3, L4 . . . detected by respiratory component extractor 314. Specifically, the CPU calculates distortion factor K according to the following equation.

$$K=(L2^2+L3^2+L4^2 \ldots )^{1/2}/L1$$

However, as explained above, when the subject is at rest, the duration of inspiration is longer than the duration of exhalation. However, as exercise intensity X increases, the difference between the duration of inhalation and expiration becomes smaller, with the respiratory waveform gradually approaching a sinusoidal wave. Moreover, as exercise intensity X becomes larger, the respiratory waveform becomes considerably disturbed. In other words, provided that exercise intensity X does not exceed a given limit, then as exercise intensity X becomes larger, the ratio of the higher harmonic wave components with respect to the fundamental components decreases. When exercise intensity X exceeds a given limit, the ratio of the higher harmonic wave components with respect to the fundamental components increases suddenly. This means that there is a constant relationship between exercise intensity X and distortion factor K in the respiratory waveform, such that as exercise intensity X increases, distortion factor K decreases, with distortion factor K increasing suddenly when exercise intensity X exceeds a given limit. Accordingly, if the relationship between distortion factor K and exercise intensity X is determined in advance, then exercise intensity X can be obtained from distortion factor K.

Next, exercise intensity X is stored in ROM in association with distortion factor K. Accordingly, provided that distortion factor K can be accessed in ROM as an address, exercise intensity X can be calculated. In this sense, then, ROM functions as an exercise intensity table. Note that exercise intensity X may be graded in five stages or three stages. In this case, the exercise intensities X stored in ROM may be expressed in the form of a specific number of stages.

Figure 65:
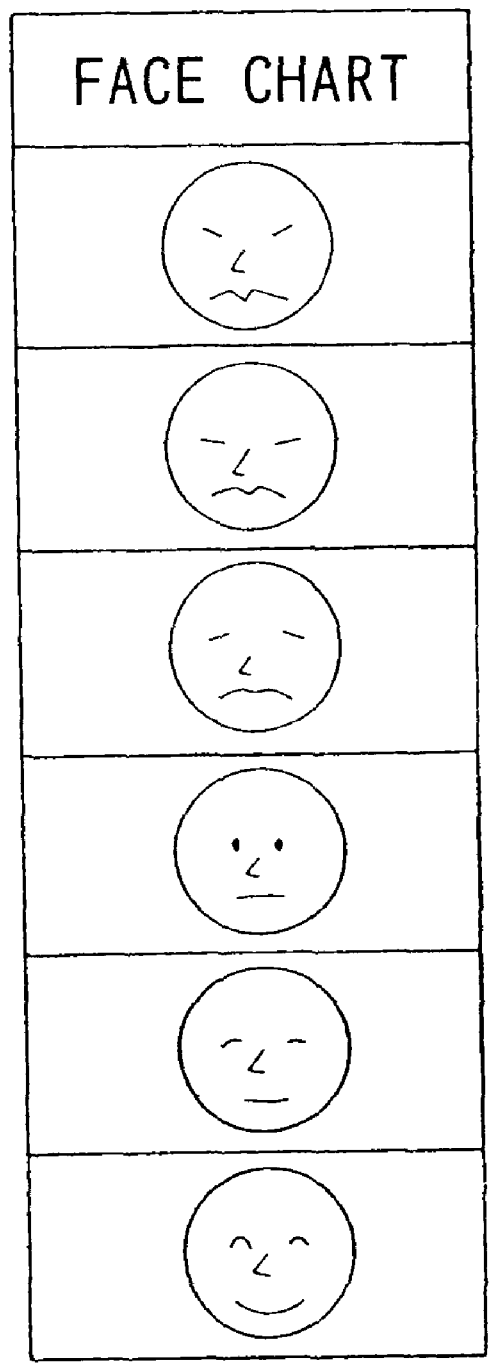
FIG. 65 is a face chart showing one aspect for the display in the first embodiment in Chapter 3.

Next, 316 is a display. The LCD 210 explained above corresponds to display 316. Display 316 may display exercise intensity X as a numerical number without modification, or may employ a bar graph or the like using a dot display region. Evaluator 316 may be designed to grade exercise intensity X, and display letters or symbols according to the stage. For example, if exercise intensities corresponding to walking, jogging, and short distance running are designated as X1, X2, and X3, while an exercise intensity that is too large and may impair health is designated as X4, display 316 may display messages stating "light exercise" at X1, "moderate exercise" at X2, "intense exercise" at X3, and "danger" at X4. In addition, it is also acceptable to display exercise intensity X in association with the face chart shown in FIG. 65.

3-4-2: Operation of Embodiment 1

Figure 66:
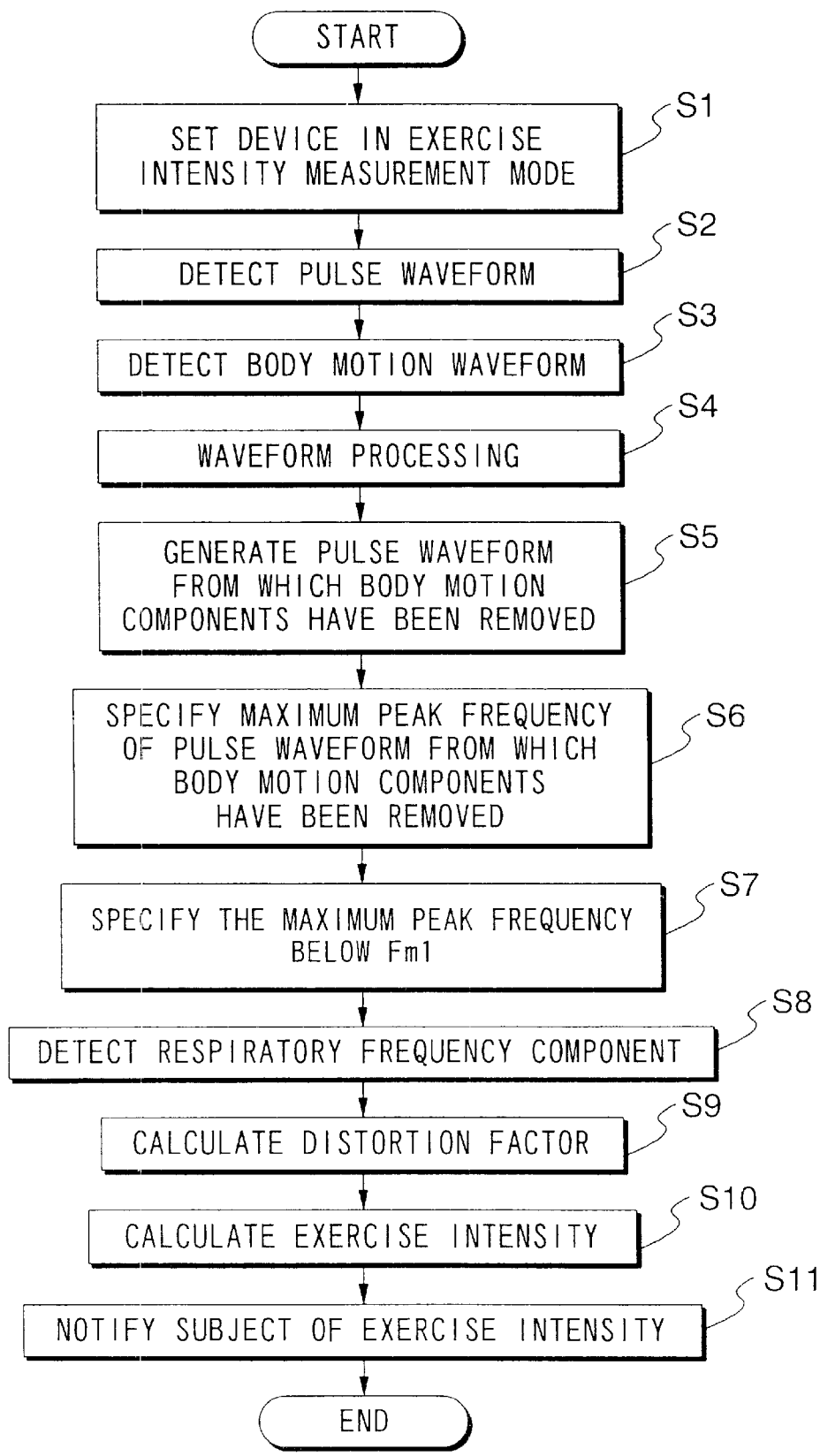
FIG. 66 is a flow chart showing the operation of an exercise intensity detecting device according to the first embodiment in Chapter 3.

The operation of the first embodiment will now be explained with reference to the figures. FIG. 66 is a flow chart showing the operation of the first embodiment. The example explained here will be one in which a subject who is not moving begins to run, with his running speed gradually increasing. First, the subject operates button switches 111–115 (see FIG. 3) to place the device in the exercise intensity measurement mode (step S1). Pulse waveform MH is then detected by pulse wave detector 310 (step S2).

Body motion detector 311 detects body motion waveform TH expressing the subject's body motion (step S3), and pulse wave processor 312 performs waveform processing on body motion waveform TH (step S4). This waveform processing is performed to transform body motion waveform TH into body motion component MHt in pulse waveform MH. Accordingly, body motion component remover 313 generates pulse waveform MH' from which body motion components have been removed by subtracting body motion component MHt from pulse waveform MH (step S5).

Respiratory component extractor 313 performs frequency analysis by carrying out FFT on pulse waveform MH' from which body motion components have been removed. Based on the results of this analysis, the maximum peak frequency is specified out of all the frequency components of pulse waveform MH' from which body motion components have been removed (step S6). In this case, fundamental frequency Fm1 of the pulse wave component is specified. Subsequently, respiratory component extractor 313 detects the fundamental frequency Fv1 of the respiratory component by specifying the maximum peak frequency below Fm1 (step S7). Next, respiratory component extractor 313 calculates the respiratory frequency components. Specifically, the frequencies Fv2, Fv3, Fv4 . . . of each of the higher harmonic waves are detected by using integer multiplies of fundamental frequency Fv1, and the levels L1, L2, L3, L4, . . . corresponding to fundamental frequency Fv1 and each higher harmonic wave frequency Fv2, Fv3, Fv4 . . . are determined.

Next, evaluator 315 calculates distortion factor K in the respiratory frequency components based on respiratory frequency components L1, L2, L3, L4 . . . (step S9). Since the relationship between distortion factor K and exercise intensity X is stored in advance in ROM, exercise intensity X is obtained by accessing ROM based on distortion factor K (step S10). Exercise intensity X is displayed on display 316, thereby informing the subject thereof.

In the first embodiment, body motion detector 311 and waveform processor 312 are employed to generate the body motion component MHt which is superimposed on pulse waveform MH, and this body motion component MHt is then removed. As a result, respiratory component extractor 314 can extract the respiratory component even during exercise. In addition, since exercise intensity X can be calculated based on distortion factor K in the respiratory component, it becomes possible for the subject to readily know his exercise intensity X without any additional burden placed on him.

3-5: Embodiment 2

3-5-1: Structure of Embodiment 2

The structure of exercise intensity detecting device 3 according to the second embodiment of the present invention will now be explained with reference to the figures. The external structure of exercise intensity detecting device 3 according to the second embodiment is the same as that of the first embodiment. With the exception of the internal structure of respiratory component extractor 314 and evaluator 315, the electrical structure of exercise intensity detecting device 3 according to the second embodiment is the same as that of exercise intensity detecting device 3 according to the first embodiment shown in FIG. 62. An explanation will now be made of respiratory component extractor 314 and evaluator 315.

Figure 67:
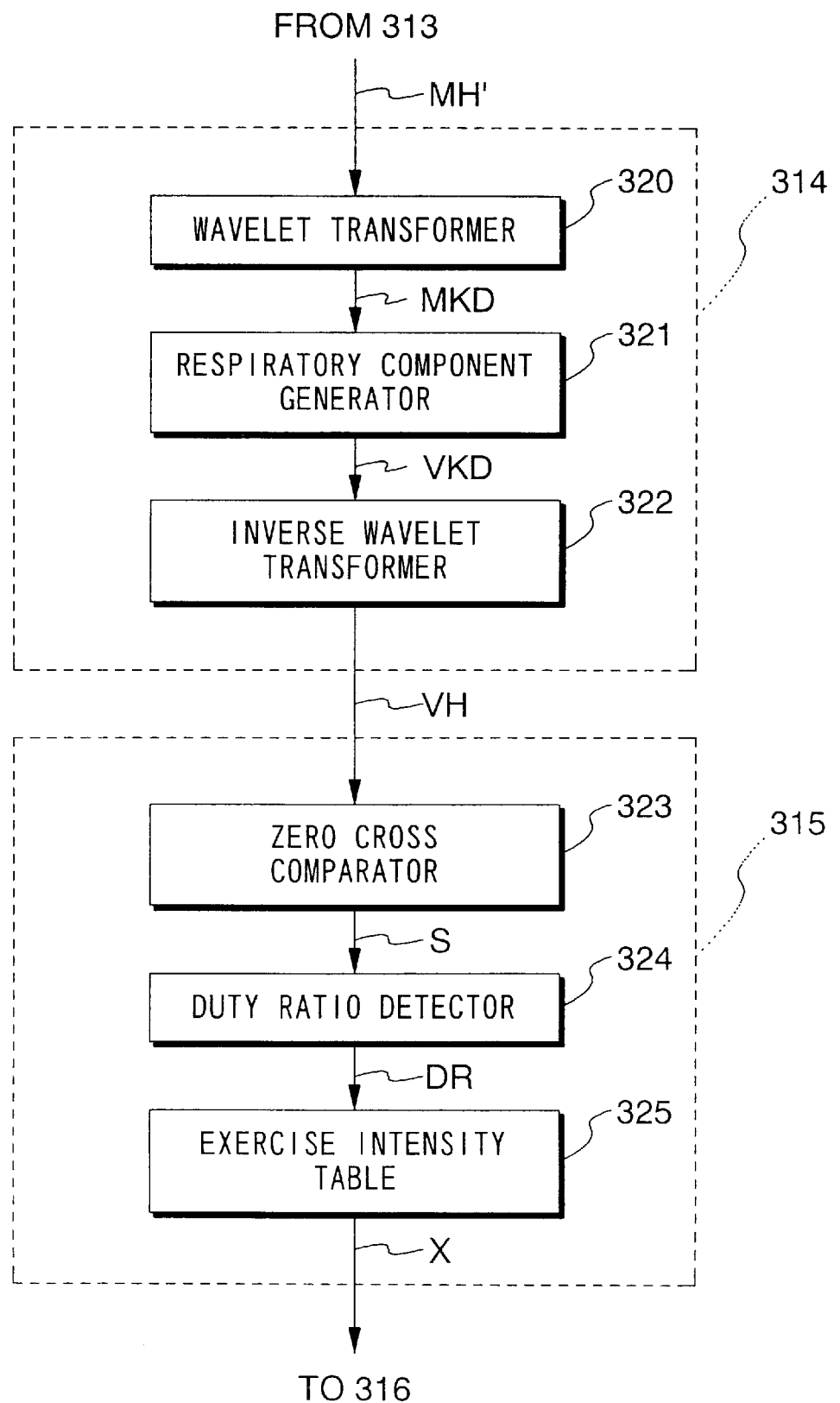
FIG. 67 is a block diagram showing the internal structure of the evaluator and the respiratory component extractor according to the second embodiment in Chapter 3.

FIG. 67 is a block diagram showing the internal structure of respiratory component extractor 314 and evaluator 315 according to the second embodiment. Respiratory component extractor 314 is formed of wavelet transformer 320, respiratory component generator 312 and inverse wavelet transformer 322.

3-5-1-1: Wavelet Transformer

Wavelet transformer 320 carries out conventional wavelet transformation on pulse waveform MH' from which body motion components have been removed which is output from body motion component remover 313, and generates analyzed pulse wave data MKD from which body motion components have been removed.

Wavelet transformation is defined by equation 1 explained in Chapter 1, with wavelet transformer 320 formed so as to be able to calculate equation 1. The main parts of wavelet transformer 320 are formed in the same way as base function developer W shown in FIG. 5. However, in this case, pulse wave data MH' from which body motion components have been removed, which is obtained by subjecting a pulse waveform MH' from which body motion components have been removed to A/D conversion, is supplied instead of pulse wave data MD.

In this example, analyzed pulse wave data MDK from which body motion components have been removed is segregated into the frequency regions 0 Hz~0.5 Hz, 0.5 Hz~1.0 Hz, 1.0 Hz~1.5 Hz, 1.5 Hz~2.0 Hz, 2.0 Hz~2.5 Hz, 2.5 Hz~3.0 Hz, 3.0 Hz~3.5 Hz, and 3.5 Hz~4.0 Hz, and output.

3-5-1-2: Respiratory Component Generator

At each frequency region, respiratory component generator 321 compares analyzed pulse wave data MKD from which body motion components have been removed, and specifies the region having the maximum energy component. Frequency components above this are removed to generate analyzed respiratory waveform data VKD. The reason why frequency regions above the region having the maximum energy component are removed is because fundamental frequency components of the pulse wave component are present in the frequency region having the maximum energy component.

Figures 70, 71:
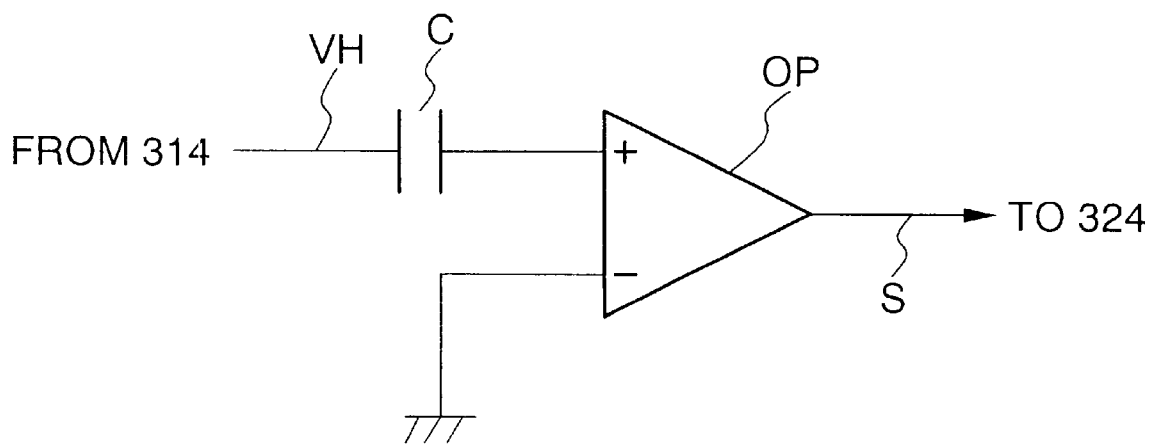
FIG. 70 is a diagram showing an example of the analyzed respiratory waveform data VKD according to the second embodiment in Chapter 3.
FIG. 71 is a circuit diagram of a zero cross comparator according to the second embodiment in Chapter 3.

If analyzed pulse wave data MKD from which body motion components have been removed is as shown in FIG. 68, the region indicated by the oblique lines in FIG. 69 is specified as the maximum energy component in each period t1~t8. In this case, the high frequency regions above the region indicated by the oblique lines are substituted by "0", and the data shown in FIG. 70 is generated as analyzed respiratory waveform data VKD.

3-5-1-3: Inverse Wavelet Transformer

Conversely, inverse wavelet transformer 322 has a correlative relationship with wavelet transformer 320. Inverse wavelet transformer 322 calculates equation 2 explained in Chapter 1, generates respiratory waveform data VD, performs A/D conversion on this waveform data, and outputs respiratory waveform VH.

Respiratory component extractor 314 extracts respiratory waveform VH based on pulse wave data MH' from which body motion components have been removed. Next, evaluator 315 is formed of zero cross comparator 323, duty ratio detector 324 and exercise intensity table 325.

3-5-1-4: Zero Cross Comparator

Zero cross comparator 323 is formed of a condenser C and OP amp OP as shown in FIG. 71. The value of condenser C is set so that respiratory waveform VH can be sufficiently transmitted. OP amp OP generates rectangular wave S by comparing respiratory waveform VH with the zero level. Respiratory waveform VH is supplied to OP amp OP via condenser C. Accordingly, waveform shaping is performed on rectangular wave S using the average value level of respiratory waveform VH as a threshold value.

As discussed above, as exercise intensity X increases, the difference between the duration of inspiration and the duration of exhalation decreases. Accordingly, as exercise intensity X increases, the duty ratio of rectangular wave S approaches 50%.

3-5-1-5: Duty Ratio Detector

Figure 72:
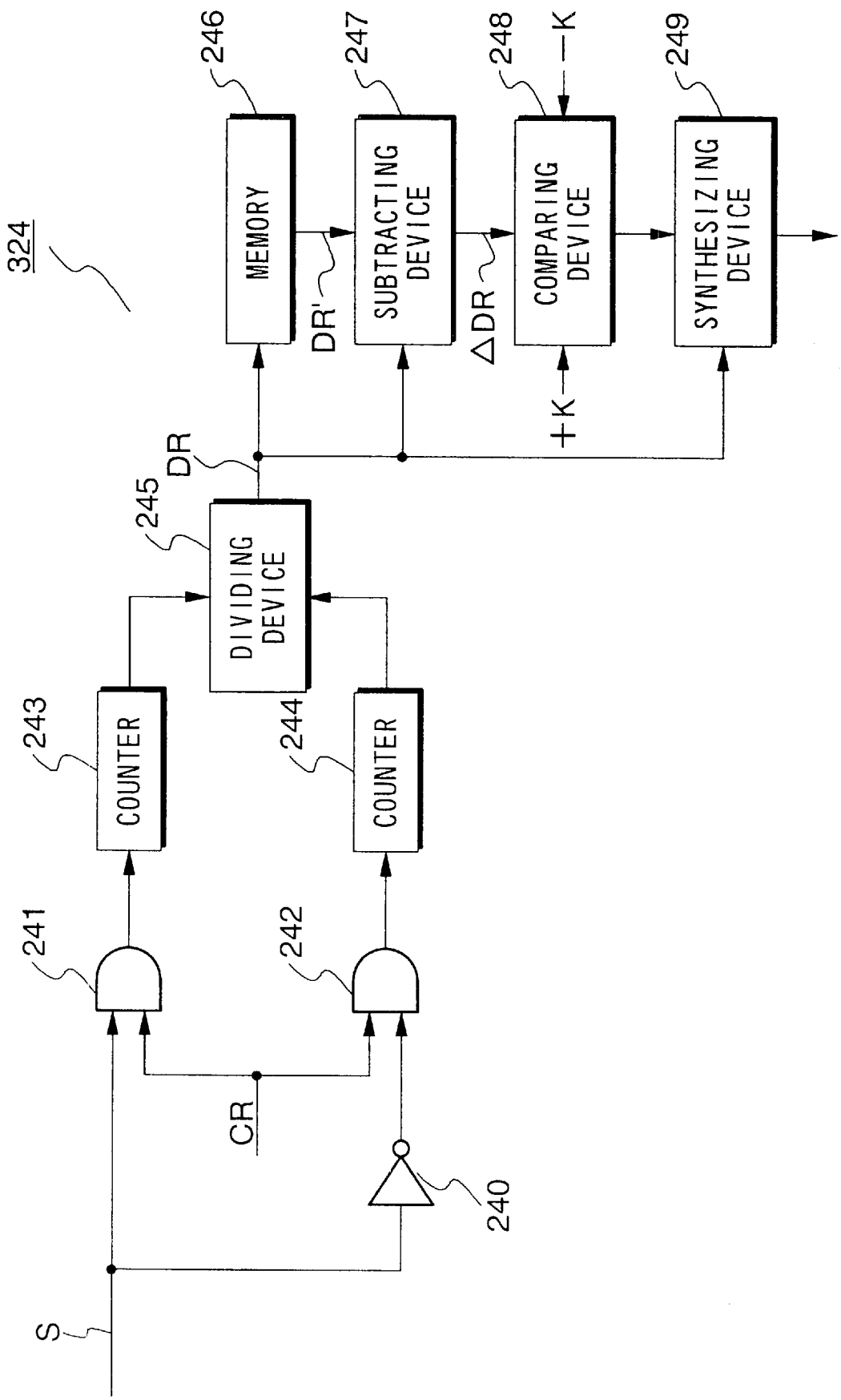
FIG. 72 is a circuit diagram for the duty ratio detector according to the second embodiment in Chapter 3.
Figure 73A:
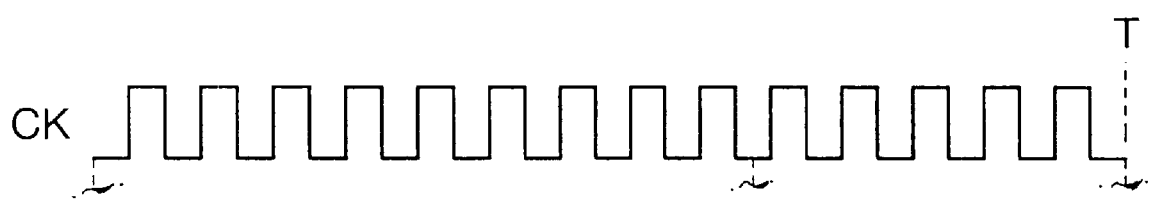
FIGS. 73A–73D are timing charts for the duty ratio detector according to the second embodiment in Chapter 3.
Figure 73B:
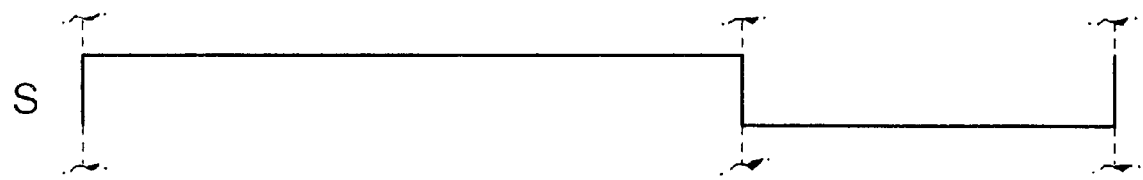
Figure 73C:
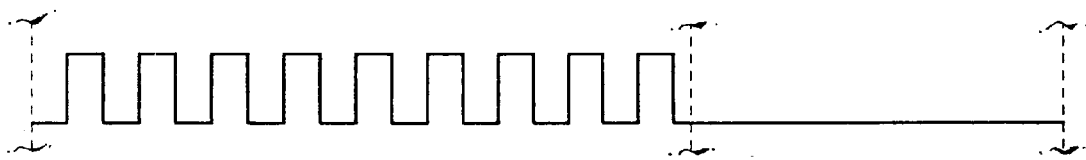
Figure 73D:

Next, the circuit diagram for duty ratio detector 324 and the timing chart therefor are shown in FIG. 72 and FIG. 73 respectively. Clock signal CK (see FIG. 73A) is supplied to one of the inputs of gates 241, 242. Rectangular wave S (see FIG. 73B) is supplied to the other input of gate 241. A rectangular wave S which has been inverted by inverter 240 is supplied to the other input of gate 242. Gates 241,242 are controlled by clock signal CK. The output signal of gate 241 permits passage of clock signal CK only during periods when rectangular wave S is at a high level as shown in FIG. 73C. On the other hand, the output signal of gate 242 permits passage of clock signal CK only during periods when rectangular wave S is at a low level as shown in FIG. 73D.

The output signals from gates 241,242 are supplied to counters 243,244. The counter value C1 of counter 243 indicates the high level interval for rectangular wave S and the counter value C2 of counter 244 indicates the low level interval for rectangular wave S.

Divider 245 calculates C1/C2, and outputs this result as the duty ratio. This division calculation is performed at time T shown in FIG. 73, with counters 243,244 immediately reset thereafter.

The division result DR in this example is equal to high level interval C1/low level interval C2. Thus, as exercise intensity X becomes larger, the calculated result DR approaches "1". However, when exercise intensity X increases considerably, exceeding a given limit, the respiratory waveform becomes greatly disturbed. Thus, in the case of an exercise intensity X of this type, the division result DR changes violently. Conversely, in the region of an ordinary exercise intensity X, the duty ratio of the respiratory waveform does not change suddenly. The structure explained below is for specifying the limit value Xmax for exercise intensity X by detecting the continuity of the calculated result DR, i.e., by detecting the continuity of the duty ratio.

Division result DR is supplied to and stored in memory 246. The memory contents are renewed each time the next calculated result DR is output. Subtracting member 247 subtracts the immediately preceding calculated result DR' from the current calculated result DR, and comparing member 248 determines whether or not the subtracted result ΔDR is present within limits which have been determined in advance. Specifically, comparing member 248 determines whether or not the following equation is satisfied.

$$+K > \Delta DR > -K$$

+K, −K are set so that it is possible to determine whether or not the continuity of the duty ratio of the respiratory waveform has been interrupted once exercise intensity X exceeds a limit value Xmax.

When the above equation is satisfied, a determination is made that the current exercise is of a regular intensity, and the signal output from comparing member 248 becomes high level. Conversely, when the above equation is not satisfied, a determination is made that exercise intensity X has exceeded limit value Xmax, and the signal output from comparing member 248 becomes low level.

Synthesizer 249 outputs calculated result DR when the output signal from comparing member 248 is at a high level, and outputs a value for which a calculated result DR cannot be obtained, "0" for example, when the output signal from comparing member 248 is at a low level.

3-5-1-6: Exercise Intensity Table

Next, exercise intensity table 325 (see FIG. 67) is formed of ROM or the like. Exercise intensities X are stored in exercise intensity table 325 in association with calculated results DR. Accordingly, exercise intensity X can be obtained by accessing exercise intensity table 325 and referencing calculated results DR. When a value such as "0" for which a calculated result DR cannot be obtained has been input, limit value Xmax is output.

As a result, the respiratory waveform is extracted from the pulse waveform, and exercise intensity X can be obtained from the duty ratio thereof.

3-5-2: Operation of Embodiment 2

Next, the operation of the second embodiment will be explained with reference to the figures. FIG. 74 is a flow chart showing the exercise intensity detecting device 3 according to the second embodiment. In this figure, the processing in steps S1 through S5, which is the same as the operations of the first embodiment shown in FIG. 66, removes the body motion waveform from the pulse waveform and generates pulse waveform MH' from which body motion components have been removed.

Wavelet transformer 320 performs wavelet transformation on pulse wave data MH' from which body motion components have been removed, to generate analyzed pulse wave data MKD from which body motion components have been removed. This analyzed pulse wave data MKD from which body motion components have been removed contains a pulse wave component and a respiratory component. The pulse wave component is present at a higher frequency region than the respiratory component and has higher energy as compared to the energy of the respiratory component. Respiratory component generator 321 substitutes a "0" for the regions above the maximum energy frequency region of analyzed pulse wave data MKD from which body motion components have been removed, and the generates respiratory waveform data VKD (step S21).

Conversely, when inverse wavelet transformer 322 performs inverse wavelet transformation on respiratory waveform data VKD and generates respiratory waveform VH, zero cross comparator 323 compares respiratory waveform VH with the level of the average value therefor and generates rectangular wave S. Duty ratio detector 324 detects the duty ratio of rectangular wave S (step S23).

Exercise intensity table 325 determines exercise intensity X by referencing the data output by duty ratio detector 324 (step S24), and display 316 displays exercise intensity X (step S25). As a result, the subject is informed of exercise intensity X.

In the second embodiment, the body motion component MHt which is superimposed on pulse waveform MH is generated by body motion detector 311 and waveform processor 312, and removed. As a result, respiratory component extractor 314 is able to extract the respiratory waveform using wavelet transformation, even when the subject is exercising. By calculating exercise intensity X based on the duty ratio of the respiratory waveform, it becomes possible for the exercise intensity X to be readily known by the subject without imposing any additional burden on him.

3-6: Embodiment 3

3-6-1: Structure of the Third Embodiment

The structure of exercise intensity detecting device 3 according to the third embodiment of the present invention will now be explained with reference to the figures. The external structure of exercise intensity detecting device 3 according to the third embodiment is the same as that of the first embodiment. With the exception that removal of body motion components is performed after FFT processing, the electrical structure of exercise intensity detecting device 3 according to the third embodiment is the same as that of exercise intensity detecting device 3 according to the first embodiment shown in FIG. 62.

Figure 75:
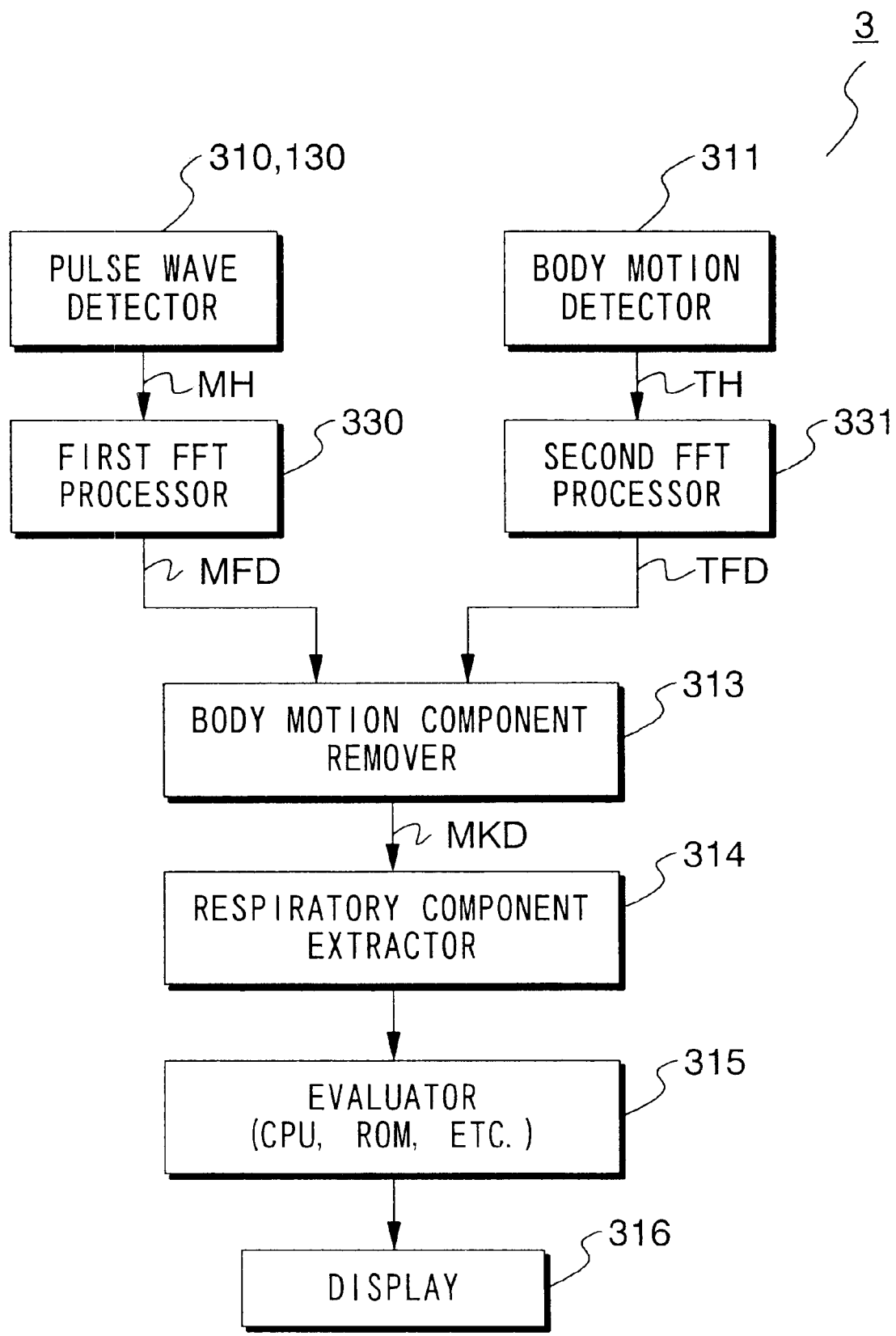
FIG. 75 is a block diagram showing the electrical structure of an exercise intensity detecting device according to the third embodiment in Chapter 3.

FIG. 75 is a block diagram showing the structure of exercise intensity detecting device 3 according to the third embodiment. In this figure, the numerals 30 and 31 indicate first and second FFT processors respectively, which are formed of a CPU and the like. First FFT processor 330 performs FFT processing on pulse waveform MH to generate analyzed pulse wave data MFD. Second FFT processor 331 performs FFT processing on body motion waveform TH and generates analyzed body motion data TFD.

Body motion component remover 313 removes the spectrum frequency components corresponding to each of the spectrum frequencies in analyzed body motion data TFD from among the spectrum frequency components of analyzed pulse wave data MFD, and generates analyzed pulse wave data MKD from which body motion components have been removed. In this analyzed pulse wave data MKD from which body motion components have been removed, the maximum peak frequency in the low frequency region is fundamental frequency Fv1 of the respiratory component, while the maximum peak frequency in the high frequency region is fundamental frequency Fm1 for the pulse wave.

Respiratory component extractor 314, evaluator 315, and display 316 are identical to the first embodiment, so that an explanation thereof will be omitted here.

3-6-2: Operation of Third Embodiment

Figure 76:
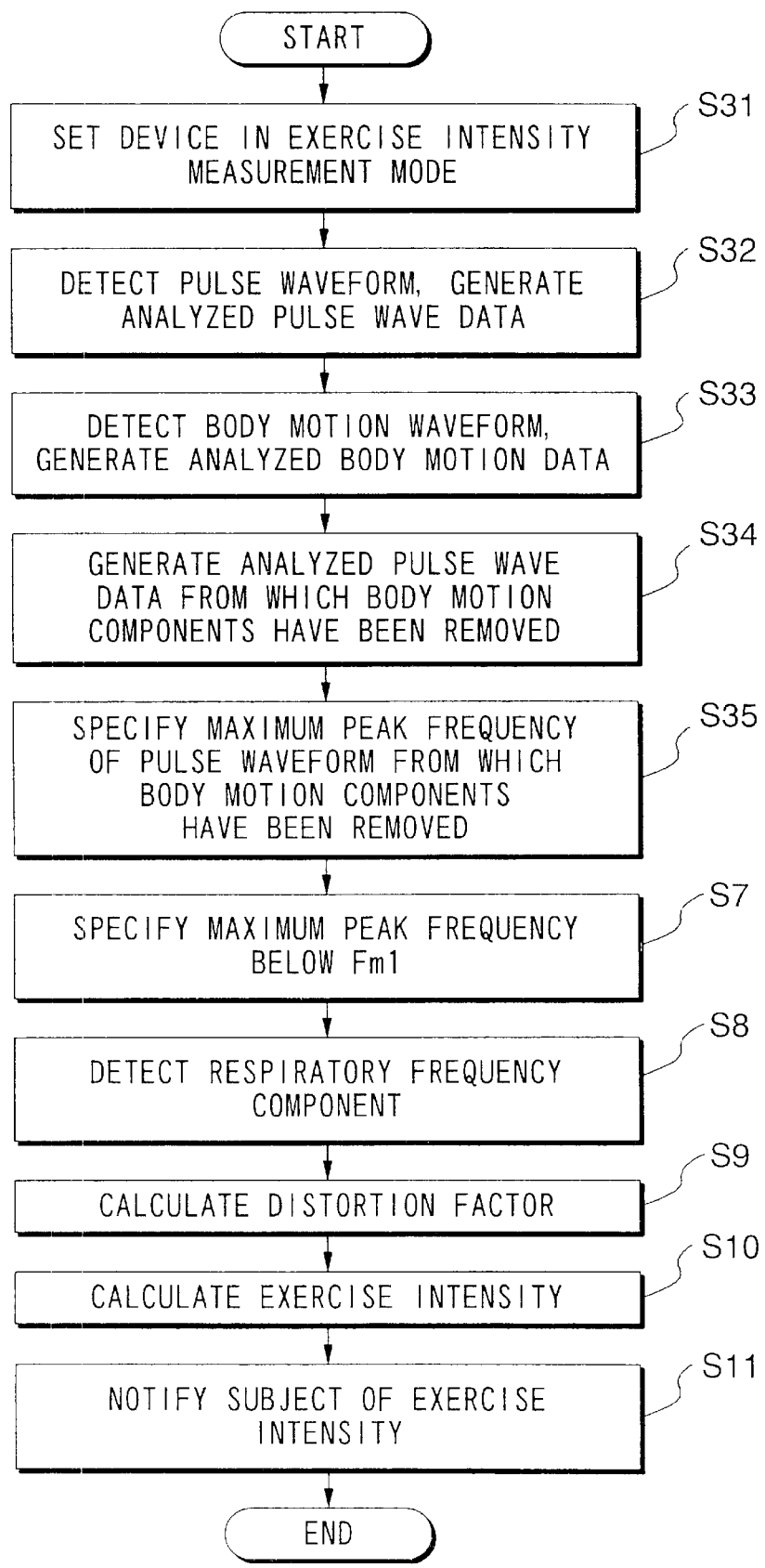
FIG. 76 is a flow chart showing the operation of the exercise intensity detecting device according to the third embodiment in Chapter 3.

Next, the operation of exercise intensity detecting device 3 according to the third embodiment will be explained with reference to the figures. FIG. 76 is a flow chart showing the operation of exercise intensity detecting device 3 according to the third embodiment.

First, when the main body of the device is set in the exercise intensity measurement mode (step S1), pulse wave detector 310 detects pulse waveform MH. First FFT processor 330 performs FFT processing on pulse waveform MH, and generates analyzed pulse wave data MFD (step S32). When body motion detector 311 detects body motion waveform TH expressing the subject's body motion, second FFT processor 331 performs FFT processing on body motion waveform TH, and generates analyzed body motion data TFD.

Figure 77A:
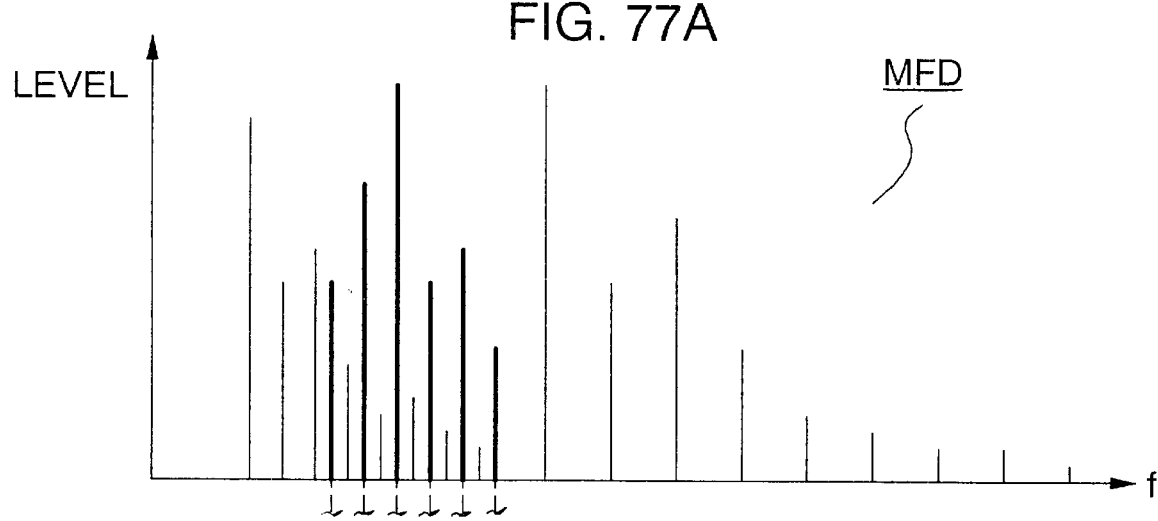
FIGS. 77A–77C are diagrams showing one example of the relationship between analyzed pulse wave data MFD, analyzed body motion data TFD, and analyzed pulse wave data MKD from which body motion components have been removed, according to the third embodiment in Chapter 3.
Figure 77B:
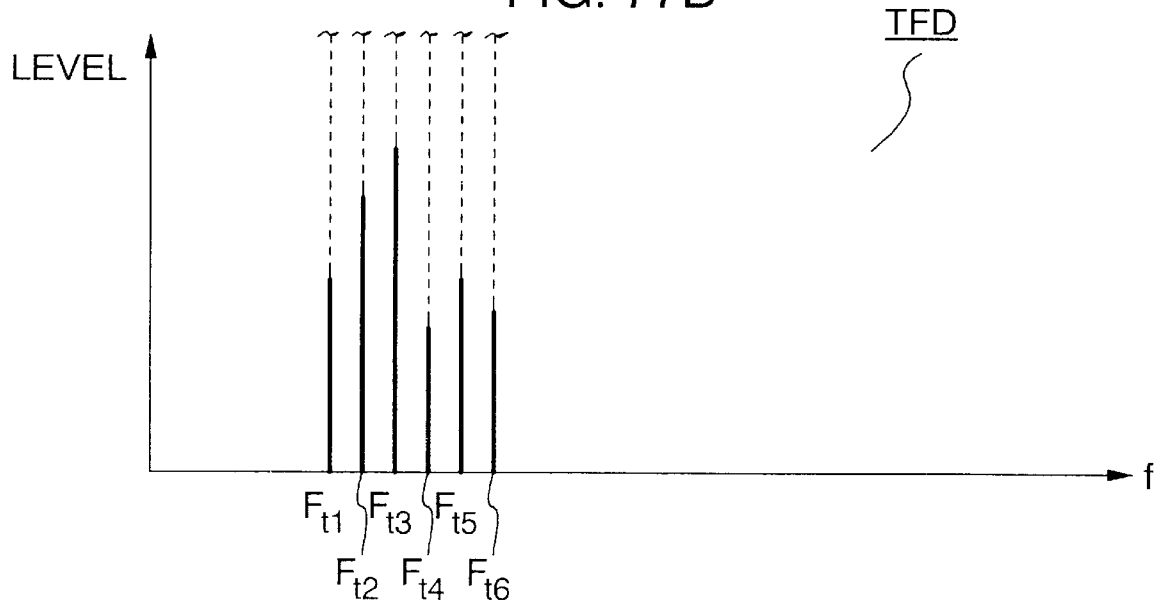
Figure 77C:
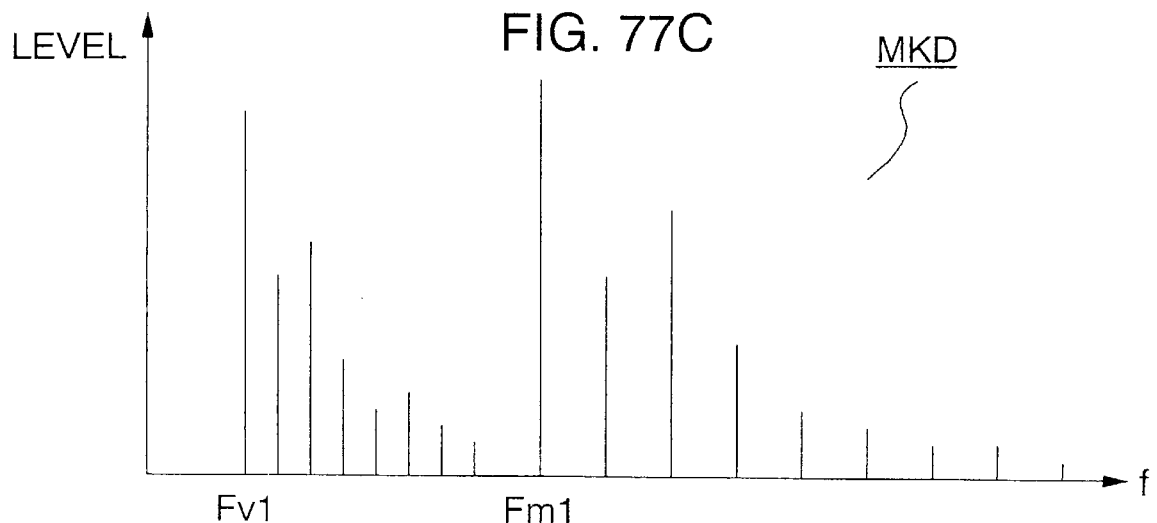

Body motion component remover 313 removes the body motion components from analyzed pulse wave data MFD, and generates analyzed pulse wave data MKD from which body motion components have been removed. FIG. 77 shows one example of the relationship between analyzed pulse wave data MFD, analyzed body motion data TFD and analyzed pulse wave data MKD from which body motion components have been removed. The operation to remove body motion components will be explained using this figure. First, FIG. 77A shows the details of analyzed pulse wave data MFD, while FIG. 77B shows the details of analyzed body motion data TFD. In this example, body motion component remover 313 specifies each of the spectrum frequencies Ft1~Ft6 shown in FIG. 77B based on analyzed body motion data TFD. Body motion component remover 313 then removes the spectrum frequency components corresponding to spectrum frequencies Ft1~Ft6 from among all the spectrum frequency components of analyzed pulse wave data MFD, and generates the analyzed pulse wave data MFD from which body motion components have been removed which is shown in FIG. 77C.

Body motion waveform TH may be detected as the acceleration of arm swinging for example. However, since blood flow is influenced by the blood vessels and tissues, analyzed body motion data TFD and the body motion component of analyzed pulse wave data MFD are not equivalent. Specifically, as shown in FIGS. 77B and 77A, the spectrum frequency components corresponding to spectrum frequencies Ft1~Ft6 differ between analyzed pulse wave data MFD and analyzed body motion data TFD. Accordingly, in this example, analyzed body motion data TFD is not subtracted from analyzed pulse wave data MFD, but rather the spectrum frequency components corresponding to spectrum frequencies Ft1~Ft6 are removed. As a result, it is possible to generate pulse wave analysis data MKD from which body motion components have been sufficiently removed.

Next, respiratory component extractor 313 specifies the maximum peak frequency out of all the spectrum frequency components based on analyzed pulse wave data MKD from which body motion components have been removed (step S35). In this case, fundamental frequency Fm1 of the pulse wave component is specified. Next, the processing in steps S7~S11 explained using FIG. 66 in the first embodiment are executed, and exercise intensity X is displayed on display 316.

Thus, in the third embodiment, FFT processing is performed on pulse waveform MH and body motion waveform TH to remove the body motion components. Accordingly, the waveform processor 312 discussed in the first embodiment can be omitted. As a result, respiratory component extractor 314 is able to extract the respiratory component even during exercise. Moreover, since exercise intensity X is calculated by evaluator 315 based on distortion factor K in the respiratory component, the subject is able to readily know the exercise intensity without any additional burden being applied on him.

3-7: Embodiment 4

In the first through third embodiments, body motion components were removed by detecting the body motion waveform using body motion detector 310 and then removing the body motion components from the frequency components of pulse waveform MH based on the detected body motion waveform. In the fourth embodiment, however, body motion components are removed without using a body motion detector 310.

3-7-1: Overall Structure of Embodiment 4

Figure 78:
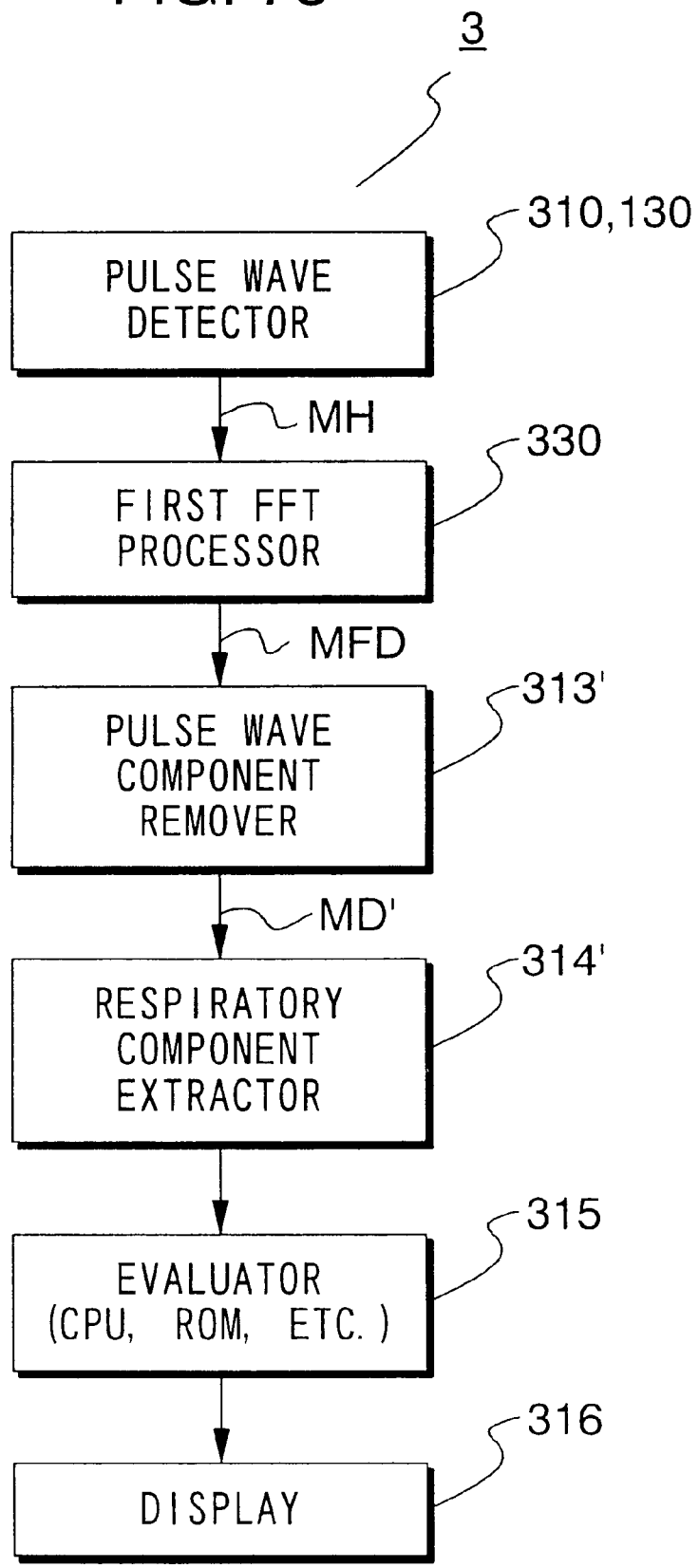
FIG. 78 is a block diagram showing the electrical structure of an exercise intensity detecting device according to a fourth embodiment in Chapter 3.

The structure of exercise intensity detecting device 3 according to the fourth embodiment will be explained with reference to the figures. The external structure of exercise intensity detecting device 3 according to fourth embodiment is the same as that of the first embodiment. The electrical structure of exercise intensity detecting device 3 according to the fourth embodiment is shown in FIG. 78. The same numerical symbols have been applied to structures which are the same as those shown in FIG. 75.

The structure of the exercise intensity detecting device 3 of this embodiment differs from that of the exercise intensity detecting device 3 of the third embodiment shown in FIG. 75 in that body motion detector 311 and second FFT processor 331 are not provided, pulse wave component remover 314 is provided in place of body motion component remover 313, and a respiratory component extractor 313' having an altered internal structure as compared to respiratory component extractor 313 is provided. These points of difference will be explained below.

3-7-1-1: Pulse Wave Component Remover

Pulse wave component remover 313' is formed of a low-pass filter and removes pulse wave components from analyzed pulse wave data MFD, to generate analyzed data MD' from which the pulse wave components have been removed. The cut-off frequency of the low-pass filter is selected to be slightly lower than the fundamental frequency of the pulse wave components in this case. This is because the frequencies of the fundamental waves of the body motion component and the respiratory component are lower than the fundamental frequency of the pulse wave component. Specifically, a cut-off frequency is set which is slightly lower than the fundamental frequency of the pulse wave component measured when the subject is at rest.

Figure 79:
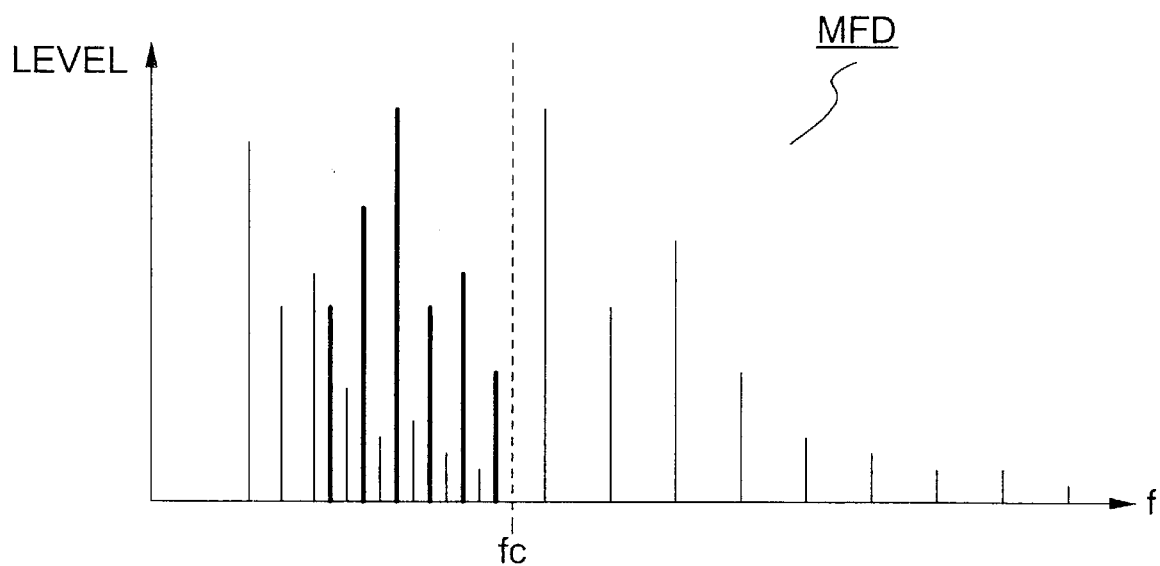
FIG. 79 is a diagram showing an example of the relationship between cut off frequency fc and analyzed pulse wave data MFD according to a fourth embodiment in Chapter 3.
Figure 80:
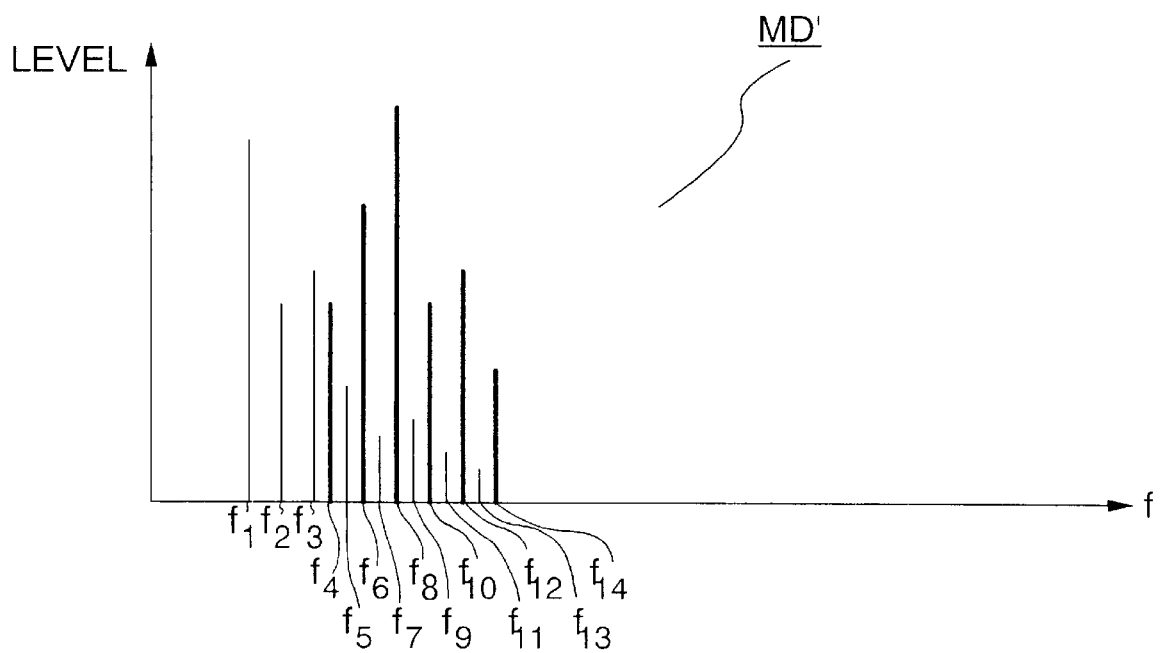
FIG. 80 is a diagram showing an example of analyzed data MD' from which the pulse wave component has been removed according to the fourth embodiment in Chapter 3.

For example, if the cut-off frequency fc of the low-pass filter and the analyzed pulse wave data MFD are related as shown in FIG. 79, then analyzed data MD' from which the pulse wave components have been removed becomes as shown in FIG. 80.

3-7-1-2: Respiratory Component Extractor

Figure 81:
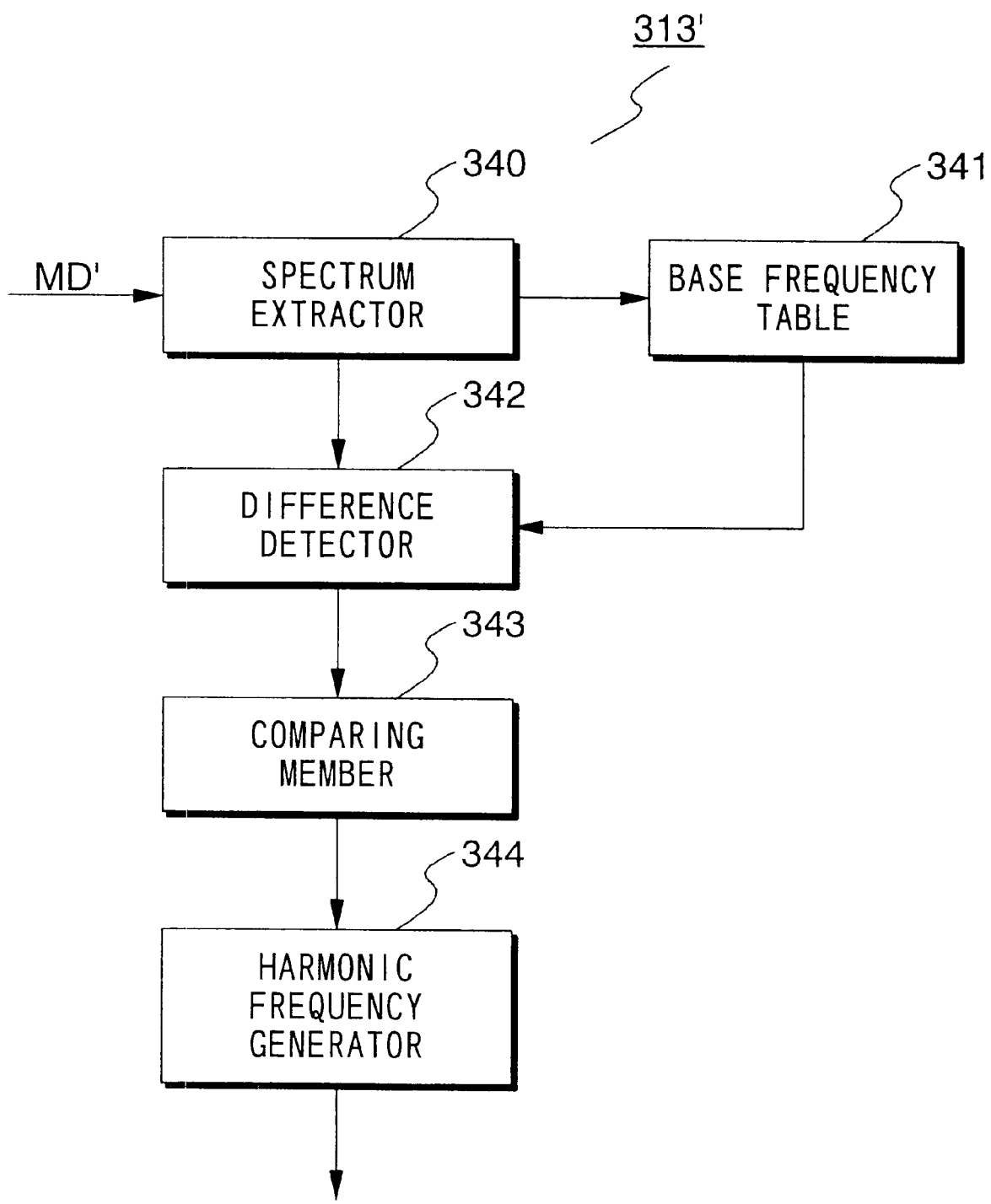
FIG. 81 is a block diagram showing in detail the structure of respiratory component extractor 13' according to the fourth embodiment in Chapter 3.

Respiratory component extractor 313' extracts the respiratory components from analyzed data MD' from which the pulse wave components have been removed, and is formed of a CPU and the like. FIG. 81 is a block diagram of the detailed functional structure of respiratory component extractor 313'.

In this figure, spectrum extractor 340 extracts two spectrum frequencies as one pair from each spectrum frequency in analyzed data MD' from which the pulse wave components have been removed. The lower spectrum frequency is output to fundamental frequency table 341 and the higher spectrum frequency is output to difference detector 342.

For example, if the analyzed data MD' from which the pulse wave components have been removed is as shown in FIG. 80, then optional spectrum frequencies are extracted as one pair from among the spectrum frequencies f1~f14. In this case, the number of pairs of extracted spectrum frequencies is just 91 ($=_{14}C_2$). If the pair of spectrum frequencies is f1 and f3, then f1 is output to fundamental frequency table 341 and f3 is output to difference detector 342.

Fundamental frequency table 341 is composed of ROM or the like, and stores in advance fundamental frequency Ft1 of the body motion component in association with fundamental frequency fm1 of the respiratory component. The content of this fundamental frequency table 341 is formed of actual measured values.

Figure 82:
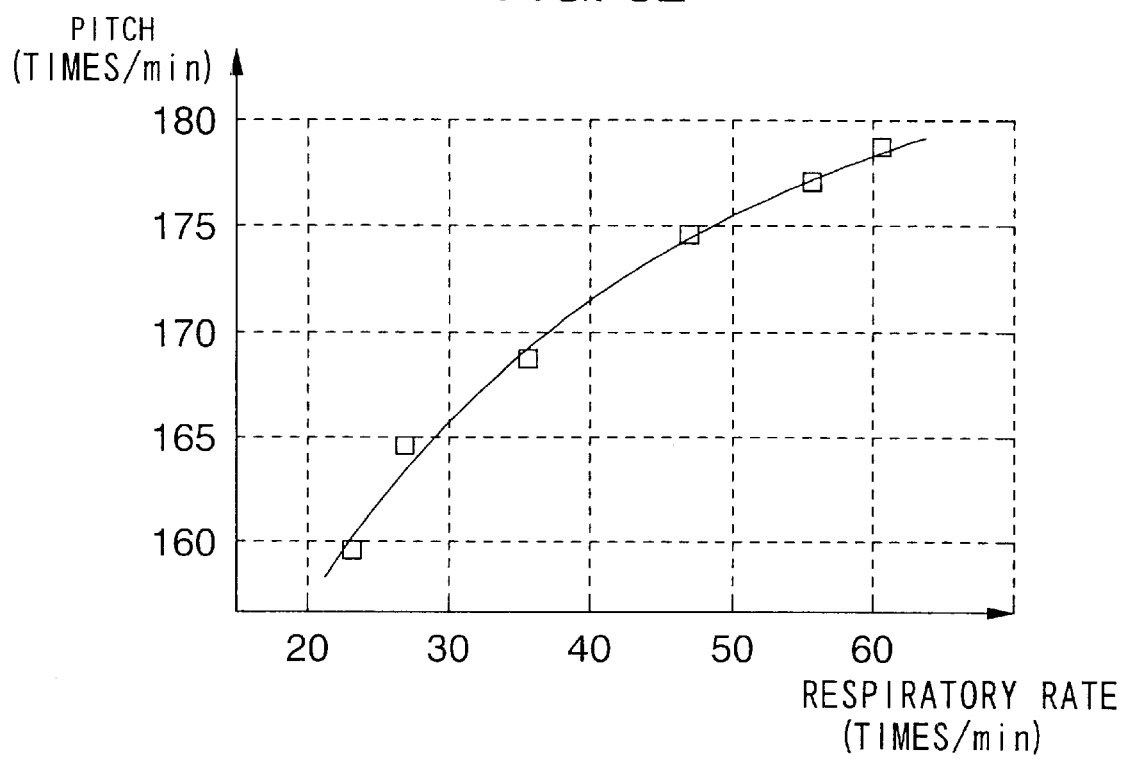
FIG. 82 is a diagram showing the results obtained when the relationship between running pitch and respiratory rate is measured in the fourth embodiment in Chapter 3.

In order to set the data for fundamental frequency table 341, the present inventors varied the running speed of test subjects in a stage-like manner, and measured the relationship between respiratory rate and running pitch. FIG. 82 shows the results of these measurements. Running pitch is the number of steps per unit time. In this example, pulse wave detector 310 (pulse wave detection sensor unit 130) is attached to the base of the finger as shown in FIG. 3. Accordingly, the body motion components present in pulse waveform MH detected in this way will be effected by the swinging motion of the arms. Although the relationship between running pitch and arm swinging varies depending on whether the arms are swung vigorously or smoothly, in general the arms swing one time per two pitches. The period of one arm swing corresponds to the period of the body motion waveform. Accordingly, if running pitch (times/min) is designated as P and the respiratory rate (breaths/min) is designated as V, then the fundamental frequency Ft1 of the body motion component and the fundamental frequency Fv1 of the respiratory component are given by the following equation using running pitch P and respiratory rate V.

$$Ft1=P/(60\cdot 2),\ Fv1=V/60$$

Figure 83:
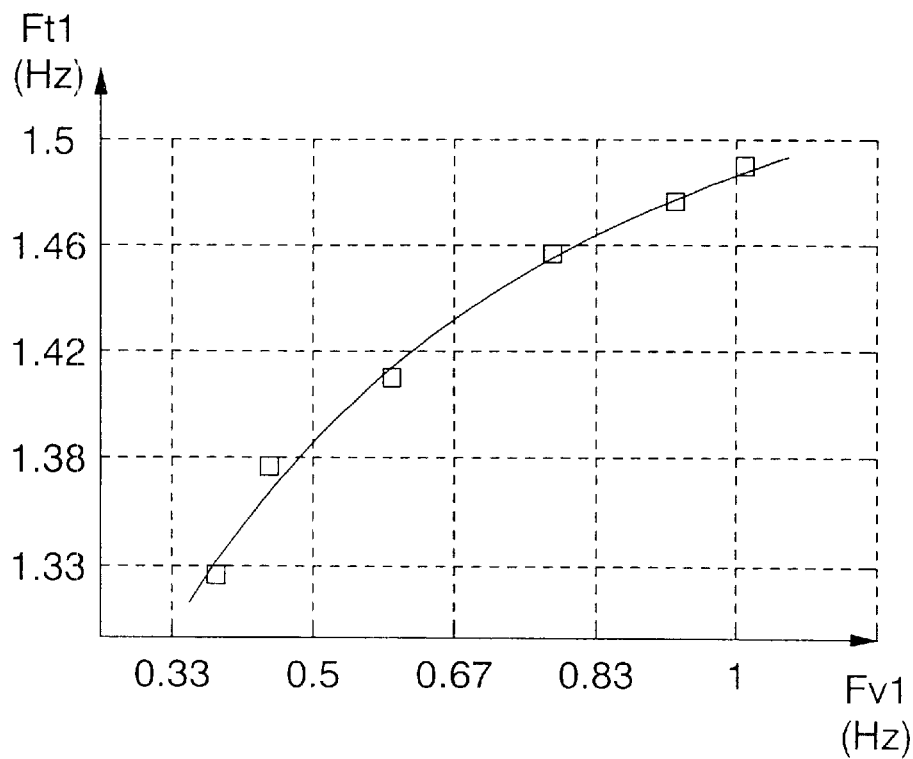
FIG. 83 is a graph showing the relationship between fundamental frequency Fv1 of the respiratory component and the fundamental frequency Ft1 of the body motion component in the fourth embodiment in Chapter 3.

By converting into the graph shown in FIG. 82 using the above equation, the relationship between the fundamental frequency Ft1 of the body motion component and the fundamental frequency Fv1 of the respiratory component can be obtained. This is shown in FIG. 83. The content of fundamental frequency table 41 is shown in FIG. 83, for example.

Next, difference detector 342 detects the difference between the other spectrum frequencies output from spectrum extractor 340 and the frequency output from fundamental frequency table 41. Assuming that the pair of spectrum frequencies extracted by spectrum extractor 340 is fundamental frequency Ft1 of the body motion component and fundamental frequency Fv1 of the respiratory component, then Fv1 is supplied to fundamental frequency table 41 and Ft1 is output. Accordingly, the output of difference detector 342 become "0". On the other hand, if the pair of spectrum frequencies extracted by spectrum extractor 340 is Fv1 and F (where Fv1<F), then the output from difference detector 342 is "|F−Ft1|". Accordingly, the pair of spectrum frequencies at which the output of difference detector 342 is smallest becomes Ft1,Fv1.

Next, comparing member 343 compares the output of difference detector 342 for each pair of spectrum frequencies output from spectrum extractor 340, specifies the pair for which the output difference is smallest, and outputs the lower spectrum frequency forming the pair. In this case, the specified pair is Ft1,Fv1, which are related such that Ft1>Fv1. Accordingly, fundamental frequency Fv1 of the respiratory component is output from comparing member 343.

Next, higher harmonic wave frequency generator 344 multiplies fundamental frequency Fv1 of the respiratory component by an integer to generate Fv2, Fv3, Fv4 . . . , and outputs levels L1, L2, L3, L4 . . . corresponding to these, as the respiratory components.

In this way, the generated respiratory component is supplied to evaluator 315 explained in the first embodiment, exercise intensity X is generated based on distortion factor K, and then displayed on display 316.

This embodiment focuses on the relationship between fundamental frequency Ft1 of the body motion component and fundamental frequency Fv1 of the respiratory component, removing the body motion components and the respiratory components at respiratory component extractor 314'. Thus, exercise intensity X can be obtained based on the respiratory component, even if a body motion detector 311 and second FFT processor 331 are not employed. As a result, it is possible to make the device smaller and lighter, enabling the provision of an exercise intensity detecting device 3 which is easier for the subject to use.

3-8: Modifications for Chapter 3

The present invention is not limited to the embodiments described above, but rather, the following modifications are possible.

3-8-1: Filtering Based on Pulse Rate

Figure 84:
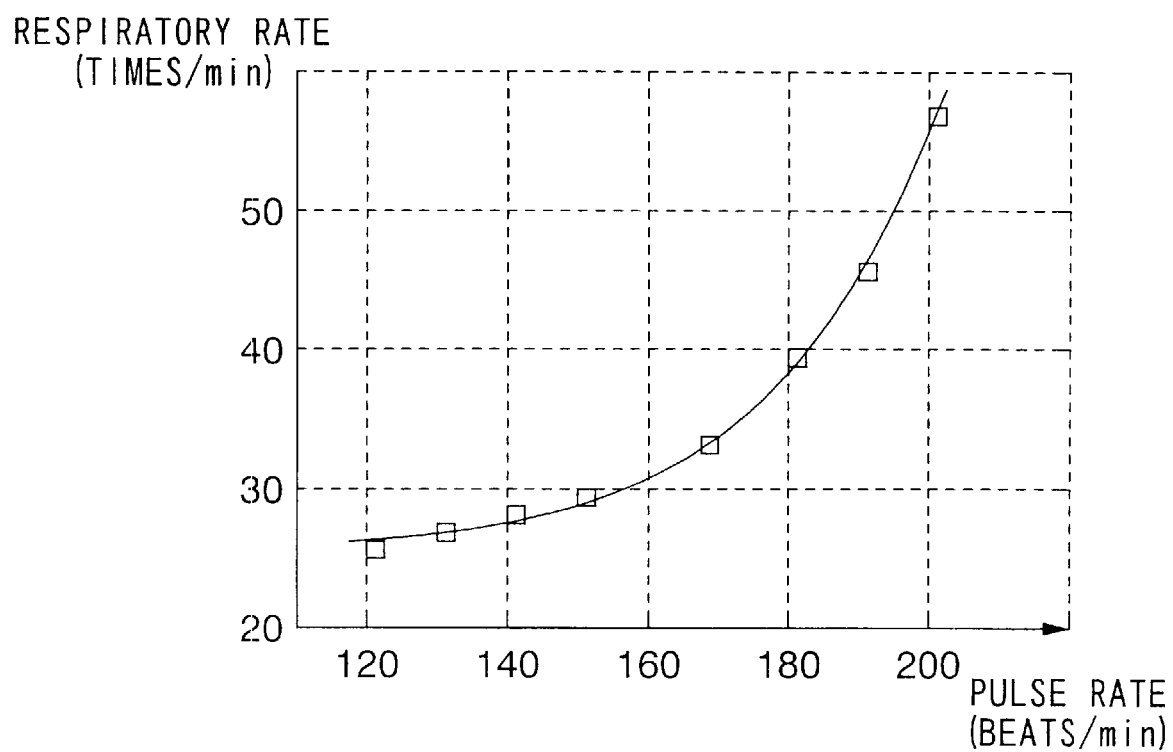
FIG. 84 is a diagram showing the relationship between pulse rate and respiratory rate in Chapter 3.

As exercise intensity X increases, the oxygen consumed by skeletal muscle also increases, causing the respiratory and pulse rates to increase. There is a constant relationship between the respiratory and pulse rates. FIG. 84 shows one example of the pulse and respiratory rates while running. Respiratory component extractor 314 in the first through fourth embodiments may perform filtering in association with the pulse rate.

Specifically, a table is provided in which the relationship between pulse rate and respiratory rate has been stored in advance, and the respiratory rate (60/Fv1) estimated from the pulse rate (60/fm1) using this table is obtained. A band pass filter in which the estimated fundamental frequency of the respiratory component is designated as the central frequency is employed to extract fundamental frequency Fv1 of the respiratory component. It is acceptable in this case that filtering be carried out digitally.

As a result, a more accurate respiratory component can be extracted.

3-8-2: Calculation of Exercise Intensity X Focusing on Third Order Higher Harmonic Wave Component Fv3

It was considered in the first embodiment that the characteristics of the respiratory waveform were best expressed in the third order higher harmonic wave component Fv3. Accordingly, it is acceptable to obtain exercise intensity X by focusing on the third order higher harmonic wave component Fv3 of fundamental frequency Fv1. In this case, respiratory component extractor 314 extracts fundamental frequency Fv1 and its third order higher harmonic wave Fv3. Evaluator 315 calculates L3/L1 from levels L1, L3 corresponding to fundamental frequency Fv1 and third order higher harmonic wave Fv3. Exercise intensity X can then be determined by referencing the exercise intensity table in which the relationship between L3/L1 and exercise intensity X were stored in advance. As a result, it is not necessary to calculate distortion factor K. Thus, calculation processing becomes simple and, as a result, a faster processing speed can be realized and the load on the CPU reduced.

3-8-3: Frequency Analysis Method in First Embodiment

Frequency analysis was performed in the first embodiment using FFT, however the present invention is not limited thereto. Rather, any method may be employed provided it carries out frequency analysis. For example, wavelet transformation may be employed. While frequency analysis can be conducted in a short time in wavelet transformation, the frequency analysis tends to become rough as the amount of time allotted therefor is reduced. Accordingly, the frequency region can be made finer if the unit (time resolution) for the analysis duration can be lengthened to some extent.

3-8-4: Example of Filter Bank Use

Wavelet transformer 320 carried out base function development to realize wavelet transformation in the second embodiment. However, the present invention is not limited thereto. Rather wavelet transformation can be realized using a filter bank. An arrangement such as shown in FIG. 30 explained in Chapter 1 may be employed for the filter bank. High-pass filter 1A and low-pass filter 1B may be formed of transversal filters which include a delay element (D flip-flop) internally. The human pulse rate is in the range of 40–200 beats/min. The fundamental frequency of pulse waveform MH varies over time according to the physiological state. If the region divided in synchronization with the fundamental frequency can be varied, then dynamic information tracking the physiological state can be obtained. Accordingly, the band to be divided can be varied by setting the clock supplied to the transversal filter to pulse waveform MH.

It is also acceptable to use a filter bank to form inverse wavelet transformer 22. In this case, the arrangement shown in FIG. 31 explained in Chapter 1 may be employed for the filter bank. High-pass filter 2A and low-pass filter 2B may be formed of a transversal filter including a delay element (D flip-flop) internally.

3-8-5: Modification of Notifying Means

The preceding embodiments employed display 316 as one example of a notifying means, however, various modifications are of course possible, as explained in section 1-8-6, entitled "Other examples of notifying means", in Chapter 1.

3-8-6: Modification of Arrangement for Use

In the preceding embodiments, the exercise intensity detecting device took the form of a wristwatch structure, however, the present invention is not limited thereto. For example, the device may also be in the form of a pair of eyeglasses (see FIG. 34), necklace (see FIG. 35), card (see FIG. 36) or pedometer (see FIG. 37), as described in Chapter 1.

3-8-7: Modification of Pulse Wave Detecting Means

In the preceding embodiments, pulse wave detection sensor unit 130 was used as one example of pulse wave detecting means f1. However, the present invention is not limited thereto. Rather, any means is acceptable as long as it can detect the pulse.

For example, the pulse wave may be detected using a pressure sensor or transmitted light method as explained in Chapter 1 under section 1-8-7-1, entitled "Detection method".

Chapter 4

4-1: Summary

The heart is a muscular organ comprised primarily of cardiac muscle, which contracts at a regular rhythm to expel blood into the aorta. The heart is divided into atria, positioned at the top portion thereof, and ventricles, positioned at the lower portion thereof. The atria and ventricles are divided into left and right sides by atrial and ventricular septa. The atria and ventricles repeatedly contract and expand with a regular rhythm, with there being a slight delay between atrial and ventricular contraction. Namely, when the atria are contracting, the ventricles are expanding, so that atrial blood pushes open the atrioventricular valve and blood rushes into the ventricle. The aortic value is closed at this time, preventing the blood in the aorta from flowing into the ventricle.

Conversely, when the atria are expanding and blood from the pulmonary vein is being pulled in, the ventricles are contracting, sending ventricular blood into the aorta. At this point, the atrioventricular valve is pushed up from the ventricular side. The atrioventricular valve does not become inverted, however, due to the extension of tendonous threads which are formed extending from the ventricular wall to the valve. When the ventricles contract, the aortic valve is pushed against the aortic wall, allowing the blood to pass. At this point, the aorta expands and a portion of the blood expelled from the ventricle accumulates.

Next, as the ventricles are expanding, the aorta is gradually contracting, propelling the accumulated blood toward the periphery. Accordingly, even when blood from the ventricles is not being expelled, blood is always flowing through the aorta.

The heart sends blood to the aorta in this way, with the volume of blood sent with each contraction referred to as the stroke-volume-per-beat SV. The unit for stroke volume is liters. The product of stroke-volume-per-beat SV and heart rate HR (beats/min) is referred to as cardiac output CO. The cardiac output CO indicates the amount of blood which is expelled from the heart each minute and has as its unit liters/min.

In the case of a heart ailment, cardiac muscle function deteriorates, so that it is no longer possible to expel a large volume of blood. As a result, stroke-volume-per-beat SV and cardiac output CO drop. On the other hand, in the case of an individual who is in training, such as a sports athlete, stroke-volume-per-beat SV and cardiac output CO increase as the exercise intensity increases. Thus, stroke-volume-per-beat SV and cardiac output CO reflect the quality of cardiac function. Accordingly, these values are frequently used as indicators when evaluating cardiac function.

One of the inventors, Dr. Kazuo Uebaba, measured heart rate HR and stroke-volume-per-beat SV values when heart patients and healthy patients were sitting upright, reclining and standing upright. FIG. 85 shows the results of these measurements.

As shown in this figure, the heart rate HR of a healthy patient corresponds to the load applied by each position, with the highest value reached when the subject was standing upright when the applied load is greatest. Since heart rate HR varies in response to the blood flow which is to be ejected from the heart, heart rate HR may be considered an index for the contractile force required of the cardiac muscle at that point in time.

The heart rate HR of a heart patient, however, is not dependent on the subject's position, but is approximately constant. This phenomenon is also seen in patients, such as the elderly, in which cardiac function has deteriorated considerably, and who must rely on a pacemaker to set the heartbeat. In cases such as this, where it is not possible to control the heart rate so that it is proportional to the blood volume to be expelled by the heart, the heart rate is insufficient for the contractile force demanded of the cardiac muscle.

In contrast, the stroke-volume-per-beat SV and cardiac output CO of heart patients have the same characteristics of variation as demonstrated by the heart rate of healthy patients. Accordingly, stroke-volume-per-beat SV and cardiac output CO are extremely useful as indices for evaluating cardiac function not only in healthy patients, but also in individuals such as heart transplant patients who are unable to control their heart rate HR.

When measuring the cardiac output CO, it is necessary to first measure stroke-volume-per-beat SV. As one method of direct measurement, the internal pressure of the heart is measured using a cardiac catheter, and stroke-volume-per-beat SV is calculated from this measured result.

Figure 86:
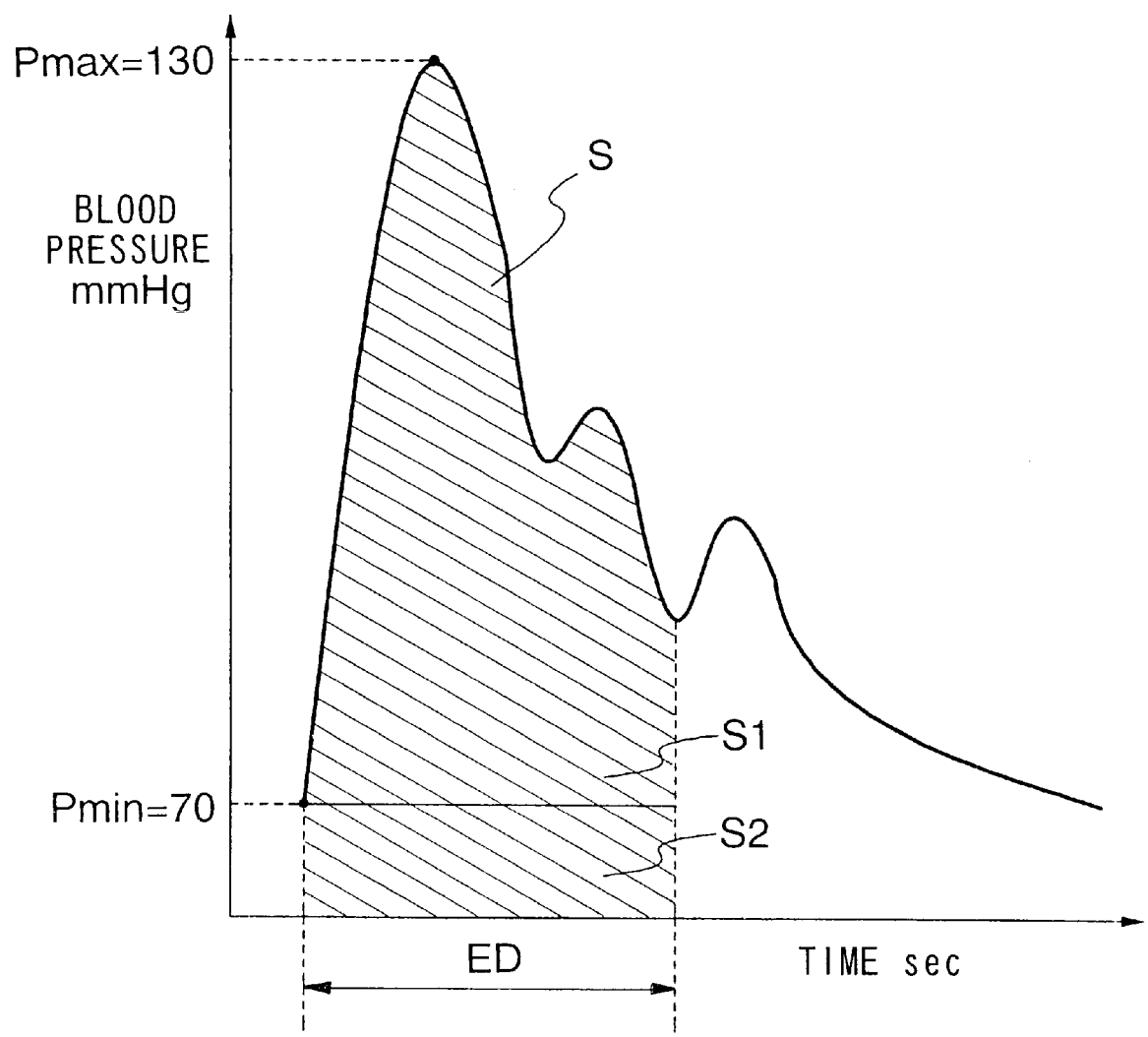
FIG. 86 is a diagram for explaining the contraction period area method in Chapter 4.

In another method, the contraction period area method, arterial pressure is measured by attaching a cuff to the upper arm, and stroke-volume-per-beat SV is calculated from this pulse waveform. FIG. 86 shows a typical pulse waveform. For this pulse waveform, the pulsation of blood caused by the heart's contraction and expansion is measured at the periphery. Accordingly, the movement of the heart is reflected in the shape of this waveform. The symbol ED indicated in the figure refers to the ejection duration, and corresponds to the duration during which blood flows out from the heart during one beat. In the contraction period area method, area S is calculated by integrating ejection duration ED and the blood pressure value for the pulse waveform corresponding to this duration. The calculated result is then multiplied by coefficient Ksv to calculate stroke-volume-per-beat SV. Cardiac output CO is calculated by the following equation.

$$CO = S * K_{sv} * HR$$

The stroke-volume-per-beat SV and cardiac output CO are employed as indices for evaluating cardiac function as described above. If the subject is able to know stroke-volume-per-beat SV and cardiac output CO during an exercise such as running, then he is able to carry out scientific training. Moreover, in the case of patients with a heart ailment, cardiac function may deteriorate during daily activities leading to a critical state. Since stroke-volume-per-beat SV and cardiac output CO fall during this type of situation, knowing the stroke-volume-per-beat SV and cardiac output CO during physical labor aids the patient in managing his health.

However, the method for measuring the internal pressure of the heart using a cardiac catheter assumes that the subject is in a state of repose, so that it is not possible to continuously measure stroke-volume-per-beat SV and cardiac output CO during exercise or daily activities.

Moreover, when employing a cuff, it becomes necessary to cover a large portion of the arm, increasing the burden on the subject. Moreover, when the subject moves his arms during exercise or daily activities, blood flow is effected by that body motion, so that body motion components become superimposed on the pulse waveform. As a result, it is not possible to continuously measure the stroke-volume-per-beat SV or cardiac output CO during exercise or daily activities.

Therefore, in Chapter 4, an explanation will be made in regard to a cardiac output detecting device and a stroke-volume-per-beat detecting device for continuously detecting the cardiac output CO and stroke volume per beat SV respectively while the subject is exercising or performing daily activities. In addition, a cardiac function diagnosing device for evaluating cardiac function based on cardiac output CO and stroke-volume-per-beat SV will also be explained.

4-2: Cardiac Output Detecting Device and Cardiac Function Diagnosing Device

A cardiac output detecting device and a cardiac function diagnosing device employing this cardiac output detecting device will now be explained with reference to the figures.

4-2-1: Functional Structure

Figure 87:
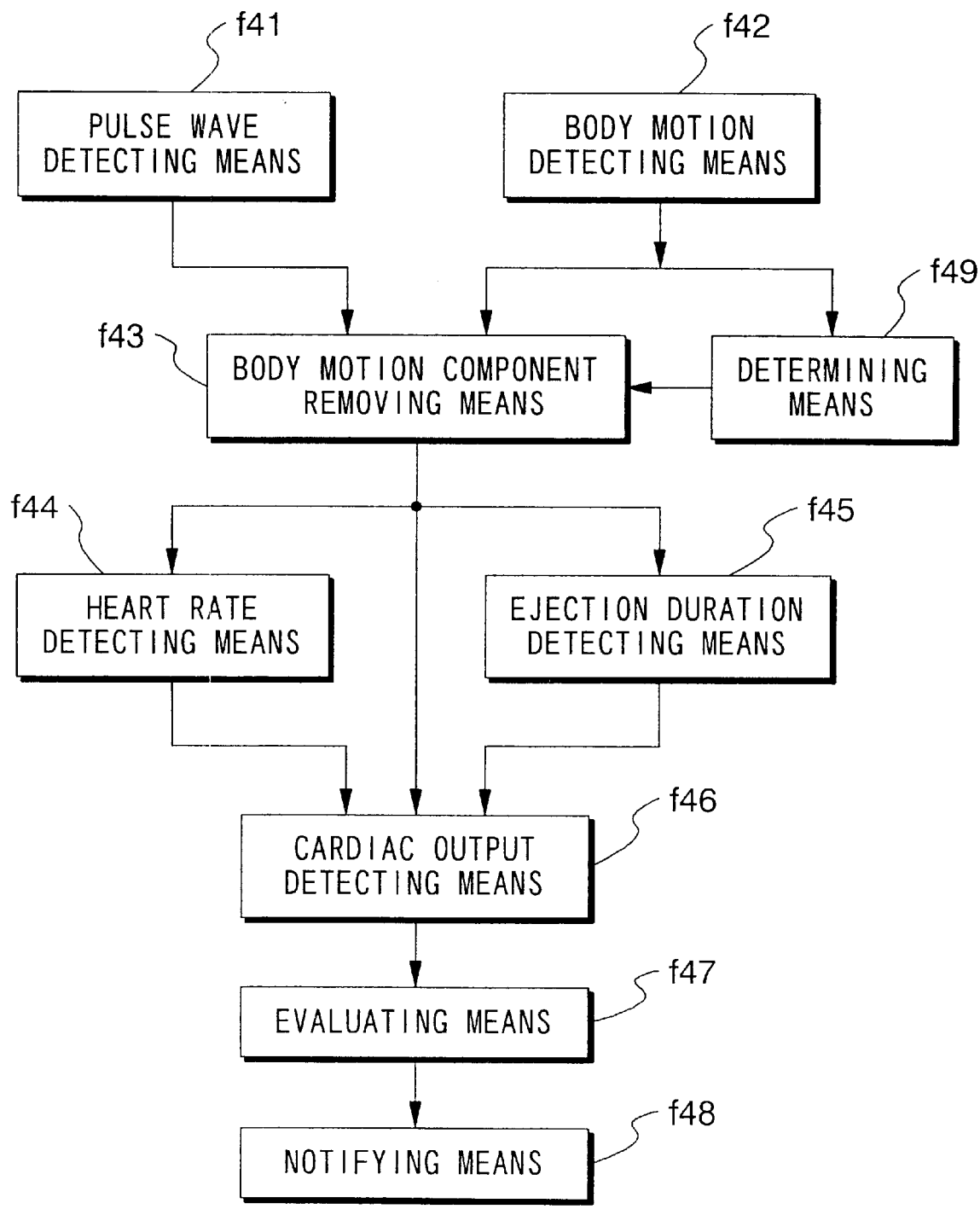
FIG. 87 is a function block diagram showing the functional structure of cardiac function diagnosing device employing the cardiac output detecting device in Chapter 4.

The function of a cardiac function diagnosing device using a cardiac output detecting device will be explained with reference to the figures. FIG. 87 is a function block diagram of a cardiac function diagnosing device employing a cardiac output detecting device. In this figure, f41 is a pulse wave detecting means for detecting the pulse waveform. The pulse waveform is obtained by detecting the blood flow at the periphery, such as at the fingertip or base of the finger, using an optical sensor. f42 is a body motion detecting means for detecting body motion and outputting a body motion waveform. In this way, motion of the body is detected.

f43 is a body motion component removing means for generating the body motion components in the pulse waveform based on the body motion waveform, removing the body motion components from the pulse waveform and generating a pulse waveform from which body motion components have been removed. As a result, it is possible to generate a pulse waveform which is not effected by body motion, even when the subject is exercising.

Next, f44 is a heart rate detecting means for detecting the heart rate based on the pulse waveform from which body motion components have been removed. f45 is an ejection duration detecting means for detecting the ejection duration of the heart based on the pulse waveform from which body motion components have been removed. The ejection duration is the duration of time required for the heart to expel blood into the aorta during one contraction. This ejection duration will now be explained in detail.

Figure 88:
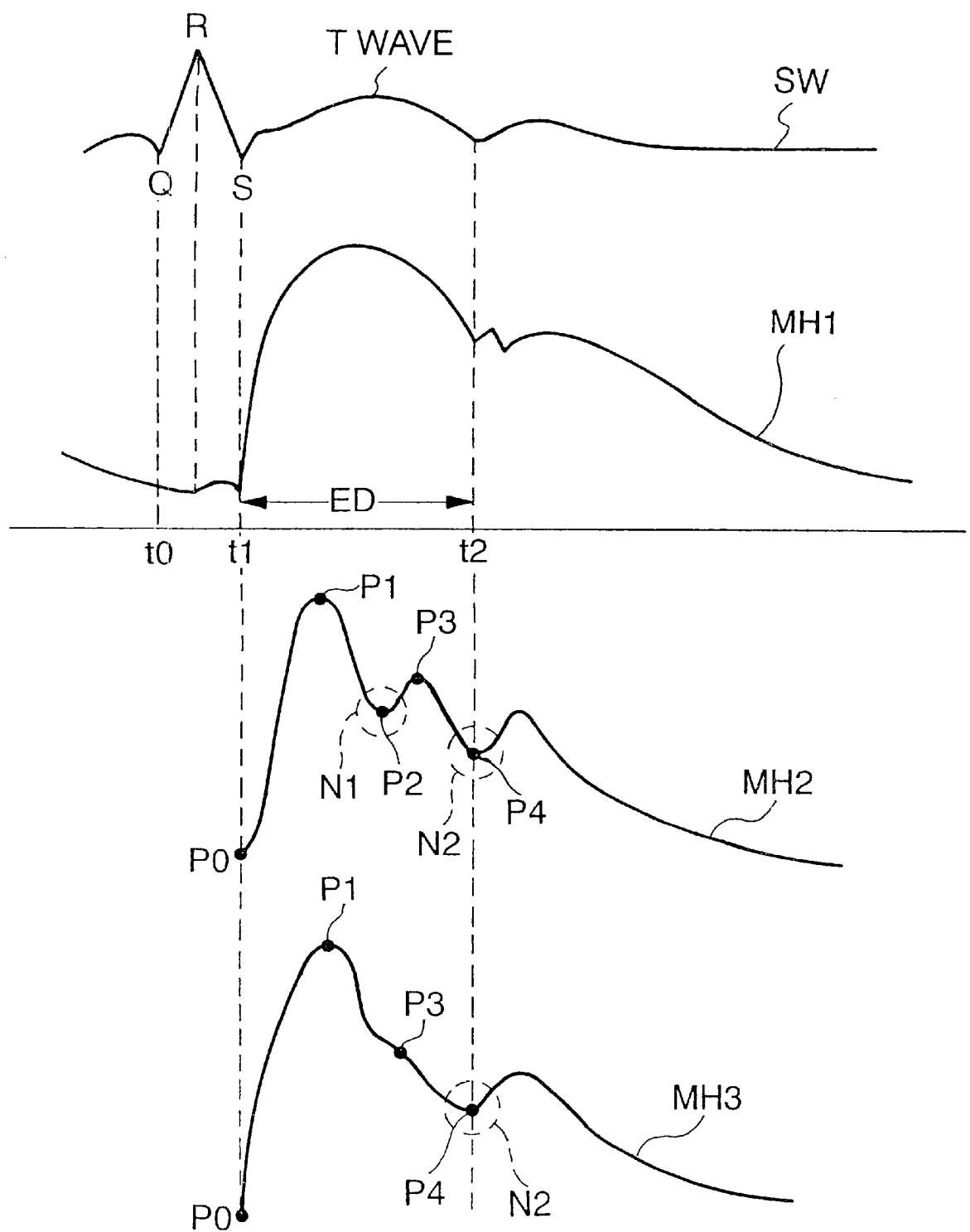
FIG. 88 shows the relationship between the electrocardiowaveform, aortic pressure waveform, and the pulse waveform at the periphery in Chapter 4.

FIG. 88 shows the relationship between the electrocardiogram, aortic pressure waveform, and the pulse waveform at the periphery. In this figure, SW is the electrocardio waveform, MH1 is the aortic pressure waveform immediately after the blood has been ejected from the heart, and MH2 is the general pulse waveform at the periphery (radius artery). In this figure, the time delay accompanying the flow of blood is ignored. Strictly speaking, the ejection duration ED is the time interval between the opening of the aortic valve at t1 and the closing of the aortic valve at t2 in the aortic pressure waveform MH1. At rest, the ejection duration is 280 ms. The closing of the aortic valve occurs due to the contraction of the ventricles. Accordingly, this time duration is approximately equivalent to the contraction time of the ventricles (i.e., systolic time). Notch N2 in pulse waveform MH at the periphery is referred to as the dicrotic notch N2, and is caused by closure of the aortic valve. The time interval from minimum peak P1 to peak P4 in pulse waveform MH2 corresponds to ejection duration ED.

There are known to be individual differences in the pulse waveform, as well as variation within the same individual due to changes in body condition, etc. For this reason, notch N1 may be absent in a pulse waveform MH2 measured at the periphery due to superimposition of peaks P1 and P3 as shown in MH3. In this case as well, ejection duration ED is the time duration from minimum peak P0 to peak P4.

The duration from minimum peak P0 to peak P2 of notch N in pulse waveform MH2 is known as the estimated systolic time. Accordingly to one theory, this time duration is considered to be the ejection duration ED. In any case, it is safe to view this duration as a value representing the duration of contraction of the heart.

Accordingly, the ejection duration ED employed in this specification includes not only the ejection duration in the strictest sense, but also the systolic time and estimated systolic time of ventricular contraction. This will be the view employed in the following explanation. Specifically, ejection duration ED can be obtained as the duration from the minimum peak to negative peaks P2,P4 which are the first and second peaks to appear following maximum peak P1.

f46 is a cardiac output detecting means for detecting cardiac output CO. For example, cardiac output CO is detected by calculating the stroke-volume-per-beat SV based on the pulse waveform from which body motion components have been removed during the ejection duration, and then multiplying the stroke-volume-per-beat SV and the cardiac rate.

f47 is an evaluating means for evaluating the state of cardiac function based on cardiac output. Namely, the evaluation of cardiac function is performed based on the blood volume which is ejected from the heart each minute. f48 is a notifying means for informing the subject of the results of this evaluation. As a result, the subject or a third party such as a physician is able to know the patient's cardiac function.

f49 is a determining means for determining whether or not body motion is present based on changes in the level of the body motion waveform. When body motion is not present, f49 halts the operation of body motion component removing means f3. As a result, it is possible to reduce the calculations accompanying the processing to remove body motion components.

4-2-2: Embodiment 1

The first through seventh embodiments relate to a cardiac function diagnosing device employing a cardiac output detecting device. The eighth through fourteenth embodiments relate to a cardiac function diagnosing device employing a stroke-volume-per-beat detecting device.

4-2-2-1: Structure of Embodiment 1

The structure of a cardiac function diagnosing device employing the cardiac output detecting device according to the first embodiment of the present invention will now be explained with reference to the accompanying figures.

4-2-2-1-1: External Structure of Embodiment 1

The external structure of cardiac function diagnosing device 42 in this example is the same as that of pulse wave diagnosing device1 explained in Chapter 1 (see FIG. 2). Namely, roughly speaking, cardiac function diagnosing device 42 is formed of a device main body 110 in the form of a wrist watch, a cable 120 which connects to device main body 110, and pulse wave detection sensor unit 130 which is provided to one end of cable 120.

The circuit structure of pulse wave detection sensor unit 130 which functions as pulse wave detecting means f41 is the same as that of pulse wave diagnosing device 1 in Chapter 1 (see FIG. 3).

4-2-2-1-2: Electrical Structure of Embodiment 1

Figure 89:
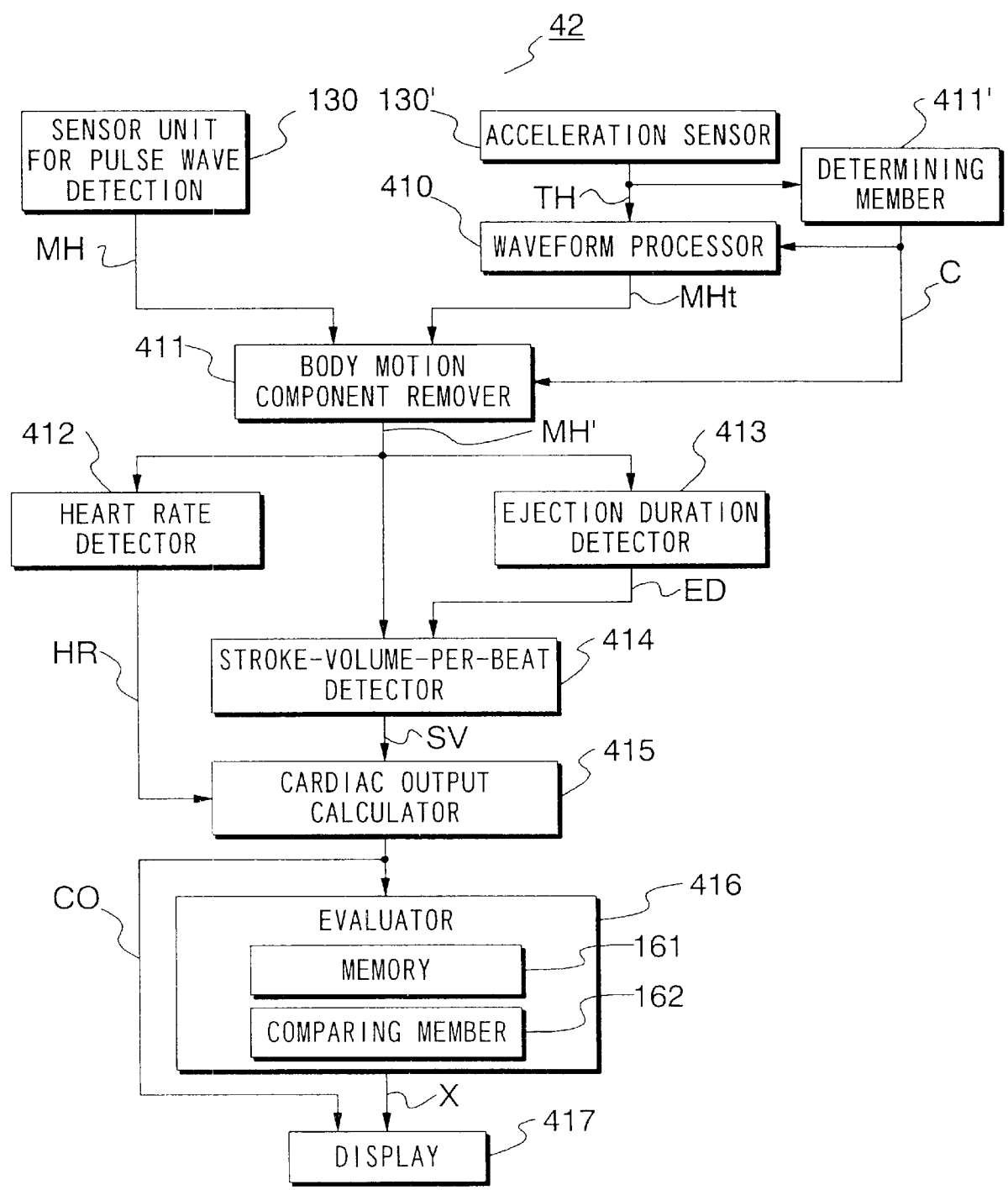
FIG. 89 is a block diagram showing the electrical structure of the cardiac function diagnosing device according to the first embodiment in Chapter 4.

The electrical structure of a cardiac function diagnosing device will be explained with reference to FIG. 89. FIG. 89 is a block diagram showing the electrical structure of a cardiac function diagnosing device.

Cardiac function diagnosing device 42 is formed of the following parts. Pulse wave detection sensor unit 130 detects pulse waveform MH and outputs it to body motion component remover 411. Acceleration sensor 130' generates body motion waveform TH by detecting body motion in the form of acceleration. Waveform processor 410 performs waveform processing on body motion waveform TH in order to accurately remove the body motion component at body motion component remover 411.

If the body motion components in pulse waveform MH are expressed as MHt, and the true pulse wave component (i.e., the pulse waveform from which body motion components have been removed) is expressed as MH', then MH=MHt+MH'. Body motion waveform TH is detected as the acceleration in the swinging motion of the arms. However, since blood flow is effected by the blood vessels and tissues, body motion component MHt is blunted by body motion waveform TH. For this reason, waveform processor 410 is formed using a low-pass filter. The form and constants for the low-pass filter are determined from actually measured data.

Next, body motion component remover 411 subtracts the output waveform MHt of waveform processor 410 from pulse waveform MH, and generates pulse waveform MH' from which body motion components have been removed. Pulse waveform MH' is converted to a digital signal via an A/D converter (not shown), and supplied to heart rate detector 412 and ejection duration detector 413.

If body motion component remover 411 is operated to remove body motion components even when body motion is not present, then the SN ratio of the signal output from body motion component remover 411 deteriorates due to noise from acceleration sensor 130'. Moreover, electrical power is consumed by the operation to remove body motion components. For this reason, in this embodiment, a determining member 411' is provided. Determining member 411' determines whether or not body motion is present based on body motion waveform TH, and generates a control signal C. Specifically, determining member 411' carries out the determination by comparing a threshold value and body motion waveform TH. This threshold value is determined in advance after taking into consideration the noise level of acceleration sensor 130', so that a determination can be made of whether or not body motion is present. When control signal C indicates that body motion is absent, then the operation of waveform processor 410 and body motion component remover 411 is halted. In this case, pulse waveform MH is directly output from body motion component remover 411. As a result, the SN ratio of the signal output from body motion component remover 411 can be improved, and the power consumed by the device reduced.

Next, heart rate detector 412 and ejection duration detector 413 detect the heart rate HR and ejection duration ED based on pulse waveform MH' from which body motion components have been removed. In this embodiment, heart rate HR and ejection duration ED are obtained by analyzing the amplitude level of pulse waveform MH' from which body motion components have been removed.

Heart rate detector 412 and ejection duration detector 413 extract the waveform parameters for specifying the shape of pulse waveform MH' from which body motion components have been removed. The waveform parameters here are the same as those explained with reference to FIG. 25 in Chapter 1. In order to calculate the waveform parameters, pulse rate detector 412 and ejection duration detector 413 extract so-call "speak information" related to maximum and minimum points. Note that peak information as used here is the same as that explained in Chapter 1 with reference to FIGS. 27 and 28.

Heart rate detector 412 and ejection duration detector 413 are composed of the computer system shown in FIG. 26 and explained in Chapter 1. However, pulse waveform MH' from which body motion components have been removed is input instead of pulse waveform TMH from which body motion components have been removed. The peak information shown in FIG. 28 is stored in peak information memory 205.

Next, the operation of heart rate detector 412 and ejection duration detector 413 under the control of microcomputer 181 will be explained. Note that (a) collection of the waveforms and their peak information, (b) processing to divide the pulse waveform, and (c) extraction of the waveform parameters, which were explained in Chapter 1, are equivalent in this example. Accordingly, an explanation thereof will be omitted here.

(d) Calculation of Heart Rate Based on Waveform Parameters

Time $t_6$ (see FIG. 25) which is calculated as a waveform parameter is the time duration of one beat. Microcomputer 181 calculates $60/t_6$ based on this time duration $t_6$, to obtain heart rate HR.

(e) Calculation of Ejection Duration Based on Waveform Parameters

Microcomputer 181 accesses its internal buffer memory, and specifies minimum peak Pmin and maximum peak Pmax in one beat based on the waveform parameters. For example, in the case of the waveform shown in FIG. 6, P0 is specified as minimum peak Pmin and P1 is specified as maximum peak Pmax.

The first or second appearing negative peak (notches) following maximum peak Pmax is specified. Assuming in this example that the negative peak which appears second after maximum peak Pmax is specified, then, in the case of the waveforms shown in FIG. 6, P4 is specified as a negative peak. The duration from minimum peak Pmin to negative peak P4 is calculated as the ejection duration ED. For example, in the waveform shown in FIG. 25, time duration $t_4$ is output as ejection duration ED.

In this way, heart rate HR and ejection duration ED are calculated.

Based on pulse waveform MH' from which body motion components have been removed and the ejection duration ED, stroke-volume-per-beat detector 414 shown in FIG. 89 specifies pulse waveform MH' from which body motion components have been removed during ejection duration ED, and calculates the area S under the waveform. Specifically, a pulse waveform MH' from which body motion components have been removed is integrated and area S is calculated by sequentially adding the pulse waveform MH' from which body motion components have been removed during each sampling in ejection duration ED. By multiplying area S by coefficient $K_{sv}$, the stroke-volume-per-beat SV can be calculated. In other words, stroke-volume-per-beat SV is calculated from the following equation.

$$SV = K_{sv} * S$$

Cardiac output calculator 415 calculates cardiac output CO by multiplying heart rate HR and stroke-volume-per-beat SV. In other words, cardiac output CO is calculated from the following equation.

$$CO = K_{sv} * S * HR$$

Note that when calculating cardiac output CO, it is also acceptable to calculate cardiac output CO by sequentially adding stroke-volume-per-beat SV values over a minute time period.

Evaluator 416 is formed of memory 161 and comparing device 162. Evaluator 416 evaluates cardiac function and generates evaluation index X. Threshold values employed in grading cardiac output CO are stored in memory 161. The threshold values are set in response to the grade number. In this example, R1 and R2 are set as threshold values. Threshold values R1,R2 may be set in advance, or may be set by a physician or trainer.

Comparing device 162 compares cardiac output CO and threshold values R1,R2, and generates evaluation index X. In this example, evaluation indices X1, X2, and X3 are generated at CO<R1, R1≦CO<R2, and R2≦CO, respectively. The significance of evaluation indices X1~X3 will vary depending on how cardiac function diagnosing device 42 is employed. For example, when employed in exercise training, evaluation indices X1~X3 serve as a measure for maintaining a suitable exercise intensity. However, when monitoring a heart patient's cardiac function during rehabilitation, evaluation indices X1~X3 serve as measurements of the degree of recovery.

Display 417 is formed of LCD 210 and the like shown in FIG. 2, and is for displaying cardiac output CO, evaluation index X or a message associated with evaluation index X. This display may be in the form of a face chart, letters, symbols or the like. In this way, the subject is informed of the results of the evaluation of cardiac function.

For example, when employing cardiac function diagnosing device 42 during running, the subject can be informed so as to maintain a suitable cardiac output CO by means of the setting of threshold values R1,R2 by the trainer. In this case, messages such as "increase pace" in the case of evaluation index X1, "maintain pace" in the case of evaluation index X2, and "decrease pace" in the case of evaluation index X3, can be displayed on display 417.

4-2-3: Embodiment 2

A cardiac function diagnosing device according to the second embodiment will now be explained.

4-2-3-1: External Structure of Embodiment 2

1. Structure of Embodiment 2

Figure 90:
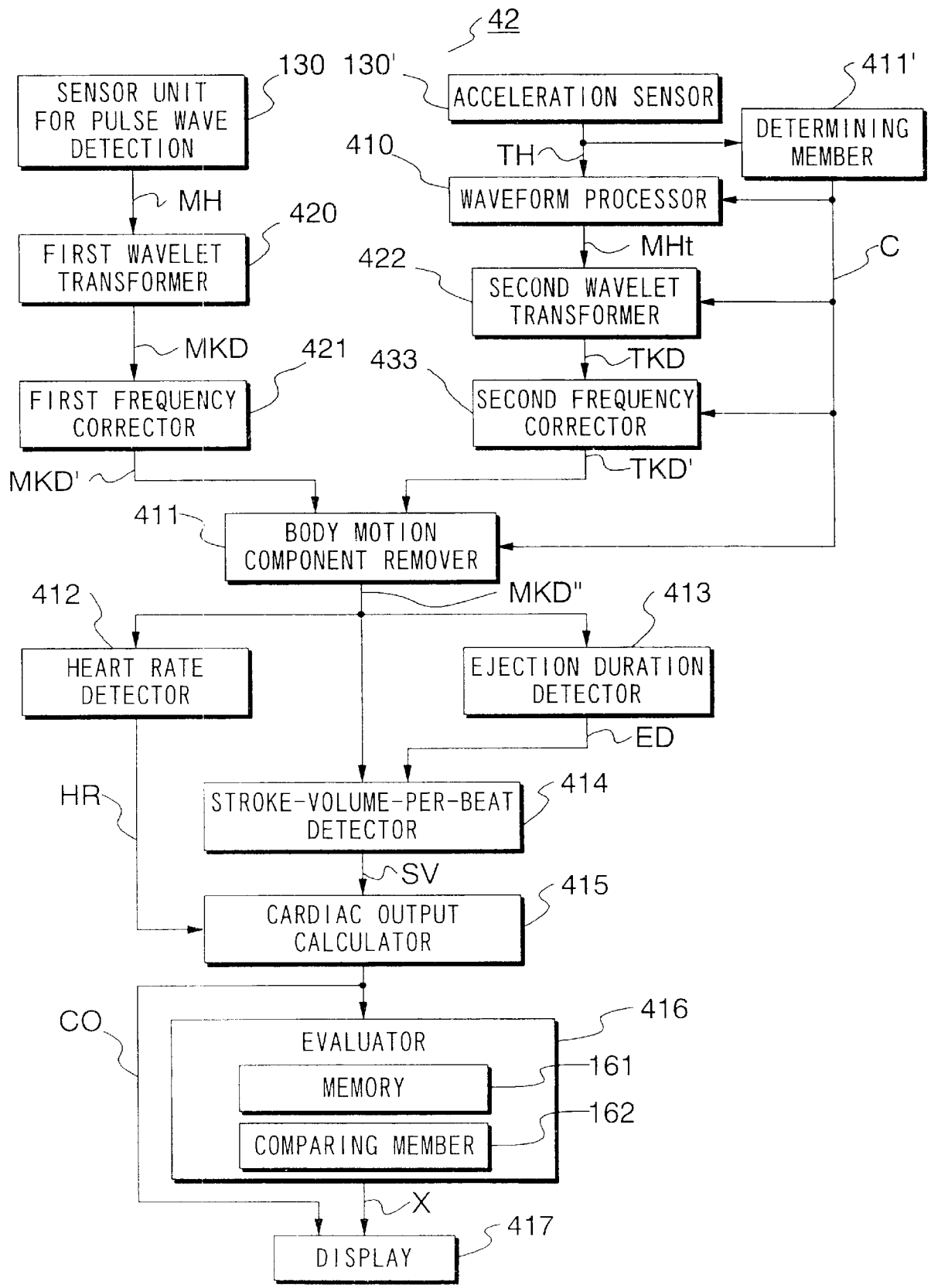
FIG. 90 is a block diagram showing the electrical structure of the cardiac function diagnosing device according to the second embodiment in Chapter 4.

FIG. 90 is a block diagram of a cardiac function diagnosing device 42 according to the second embodiment. As in the first embodiment, in the second embodiment, the body motion component MHt is detected using acceleration sensor 130' and waveform processor 410. However, this embodiment differs from the first embodiment in that body motion component removal and heart rate and ejection duration detection are carried out using wavelet transformation. The external structure of the second embodiment is the same as that of the first embodiment shown in FIG. 2.

4-2-3-1-1: First and Second Wavelet Transformers, and First and Second Frequency Correctors In FIG. 90, a first wavelet transformer 420 performs conventional wavelet transformation on pulse waveform MH output from pulse wave detection sensor unit 130, to generate analyzed pulse wave data MKD. Second wavelet transformer 422 performs conventional wavelet transformation on body motion waveform MHt output from acceleration sensor 130', to generate analyzed body motion data TKD. In this case, first and second wavelet transformers 420 and 422 are formed so as to be able to calculate equation 1 explained in Chapter 1. The principle parts of first and second wavelet transformers 420 and 422 are formed in the same way as base function developer W shown in FIG. 5. In this example, wavelet transformation is performed at each heartbeat unit, to generate analyzed pulse wave data MDK. In this example, analyzed pulse wave data MDK is output after being divided into the frequency regions 0 Hz~0.5 Hz, 0.5 Hz~1.0 Hz, 1.0 Hz~1.5 Hz, 1.5 Hz~2.0 Hz, 2.0 Hz~2.5 Hz, 2.5 Hz~3.0 Hz, 3.0 Hz~3.5 Hz, and 3.5 Hz~4.0 Hz, and output.

Next, first frequency corrector 421 performs frequency correction on analyzed pulse wave data MKD. The preceding equation 1 contains a term "$1/a^{1/2}$" corresponding to frequency. When comparing data over different frequency regions, it is necessary to correct for the influence of this term. First frequency corrector 421 is provided for this purpose. Namely, first frequency corrector 421 multiplies wavelet data WD by the coefficient $a^{1/2}$, to generate corrected pulse wave data MKD'. As a result, correction can be performed to that the power density at each frequency becomes constant. Second frequency corrector 423 performs frequency correction in the same way as first frequency corrector 421, to generate corrected body motion data TKD' from analyzed body motion data TKD.

Figure 91:
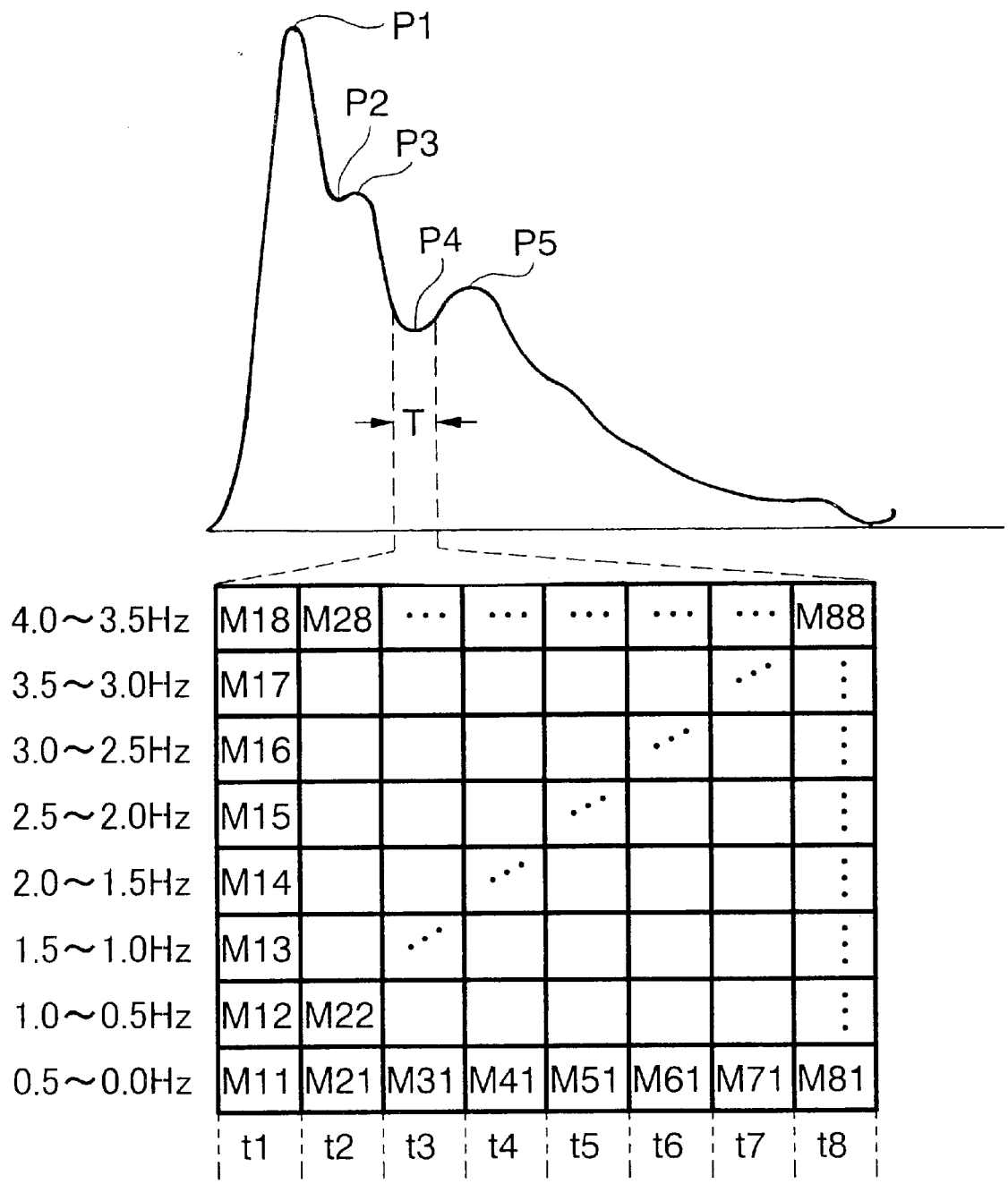
FIG. 91 shows analyzed pulse wave data for the duration of a portion of the pulse waveform according to the second embodiment in Chapter 4.

FIG. 91 shows analyzed pulse wave data MKD for the time interval of a portion of pulse waveform MH. Note that in this example, the time scale is more finely divided as compared to that shown in FIG. 8 explained in Chapter 1.

In FIG. 91, time interval T is near peak P4. Time interval T is divided into 8 parts, and analyzed pulse wave data MKD is obtained over these time intervals. When performing wavelet transformation, there is a trade-off relationship between the frequency and time resolutions. Accordingly, if frequency resolution is sacrificed, then it becomes possible to obtain analyzed pulse wave data over even smaller time intervals.

Generated analyzed pulse wave data MKD and analyzed body motion data TKD are subjected to frequency correction by first and second frequency correctors 421,423 in this way, and are output as corrected pulse wave data MKD' and corrected body motion data TKD'.

4-2-3-1-2: Body Motion Component Remover

Body motion component remover 411 subtracts corrected body motion data TKD' from corrected pulse wave data MKD', to generate pulse wave data MKD" from which body motion components have been removed. This point will be explained more concretely. Note that the following discussion will employ an example in which the user lifts a cup with his hand, and then returns it to its original position. Here, pulse waveform MH shown in FIG. 16A is detected using pulse wave detection sensor unit 130, and body motion waveform MHt shown in FIG. 16B is detected using waveform processor 410.

Body motion waveform MHt begins to increase from time T1, and reaches a positive peak at time T2. Thereafter, body motion waveform MHt gradually falls, passing through level 0 at time T2, reaching a negative peak at time T3, and returning to level 0 at time T4. Since body motion waveform TH is detected by acceleration sensor 21, time T3 corresponds to the clock time at which the cup is maximally lifted by the user, time T1 corresponds to the clock time at which the subject starts to lift the cup, and time T4 corresponds to the clock time at which the lifting operation is terminated. Accordingly, the time period from time T1 to T4 is the time period during which body motion is present. Note that FIG. 16C shows pulse waveform MH' in the case where body motion is assumed to be absent. In this example, the fundamental frequency of pulse waveform MH is 1.3 Hz.

FIG. 17 shows corrected pulse wave data MKD' in the interval Tc (see FIG. 16) and FIG. 18 shows corrected body motion data TKD' in the interval Tc. It may be understood from these figures that frequency components of a relatively large level are present in the 0.0 Hz~0.1 Hz frequency region in body motion waveform TH. When corrected pulse wave data MKD' and corrected body motion data TKD' are supplied to body motion component remover 411, body motion component remover 411 subtracts corrected body motion data TKD' from corrected pulse wave data MKD', to generate the pulse wave data MKD" from which body motion components have been removed shown in FIG. 19. As a result, even if body motion is present, its effect is canceled.

4-2-3-1-3: Determining Member

Determining member 411' compares body motion waveform TH with a predetermined threshold value, and generates a control signal C for expressing the presence or absence of body motion. This control signal C is supplied to waveform processor 410, second wavelet transformer 422 and second frequency corrector 423. As a result, the operation of waveform processor 410, second wavelet transformer 422 and second frequency corrector 423 are suspended when body motion is not present, thereby reducing the processing time for calculations, decreasing the amount of power consumed, and improving the SN ratio.

4-2-3-1-4: Heart Rate Detector

Heart rate detector 412 calculates the heart rate based on pulse wave data MKD" from which body motion components have been removed. Heart rate detector 412 specifies maximum peak Pmax in one beat based on pulse wave data MKD" from which body motion components have been removed. High frequency components increase at maximum peak Pmax of pulse waveform MH'. Accordingly, a threshold value corresponding to the high frequency components is decided in advance, pulse wave data MKD" from which body motion components have been removed is compared with the threshold value, and maximum peak Pmax is specified. Time duration T between maximum peak Pmax and the next maximum peak Pmax is determined, and the heart rate HR is calculated from 60/T.

4-2-3-1-5: Ejection Duration Detector

Ejection duration detector 413 may be formed in the same way as embodiment 1. In this example, minimum peak Pmin is specified based on pulse wave data MKD" from which body motion components have been removed, and negative peak P4 (notch) hich the second peak to appear after maximum peak Pmax is specified. Here, the frequency component corresponding to minimum peak Pmin and the frequency component corresponding to peak P4 are recorded in advance as threshold values. Minimum peak Pmin and peak P4 are specified by comparing these threshold values with pulse wave data MKD" from which body motion components have been removed, and the time interval between minimum peak Pmin and peak P4 is calculated as ejection duration ED.

4-2-3-1-6: Stroke-volume-per-beat Calculator

In each of the frequency regions, stroke-volume-per-beat calculator 414 adds pulse wave data MKD" from which body motion components have been removed in ejection duration ED, determines the energy quantity E in this time interval, and calculates contraction period area S based on energy quantity E.

The pulse waveform from minimum peak Pmin to peak P4 takes the form of a relatively steep mountain-shaped waveform. Accordingly, the frequency components included in this waveform are almost entirely in the high frequency region. Thus, pulse wave data MKD" from which body motion components in the low frequency region (0~1 Hz, for example) have been removed may be viewed to be a noise component. Accordingly, rather than adding pulse data MKD" from which body motion components have been removed from all the frequency regions in ejection duration ED, it is acceptable to determine energy E by summing pulse wave data MKD" from only a portion of the frequency regions.

Figure 92:
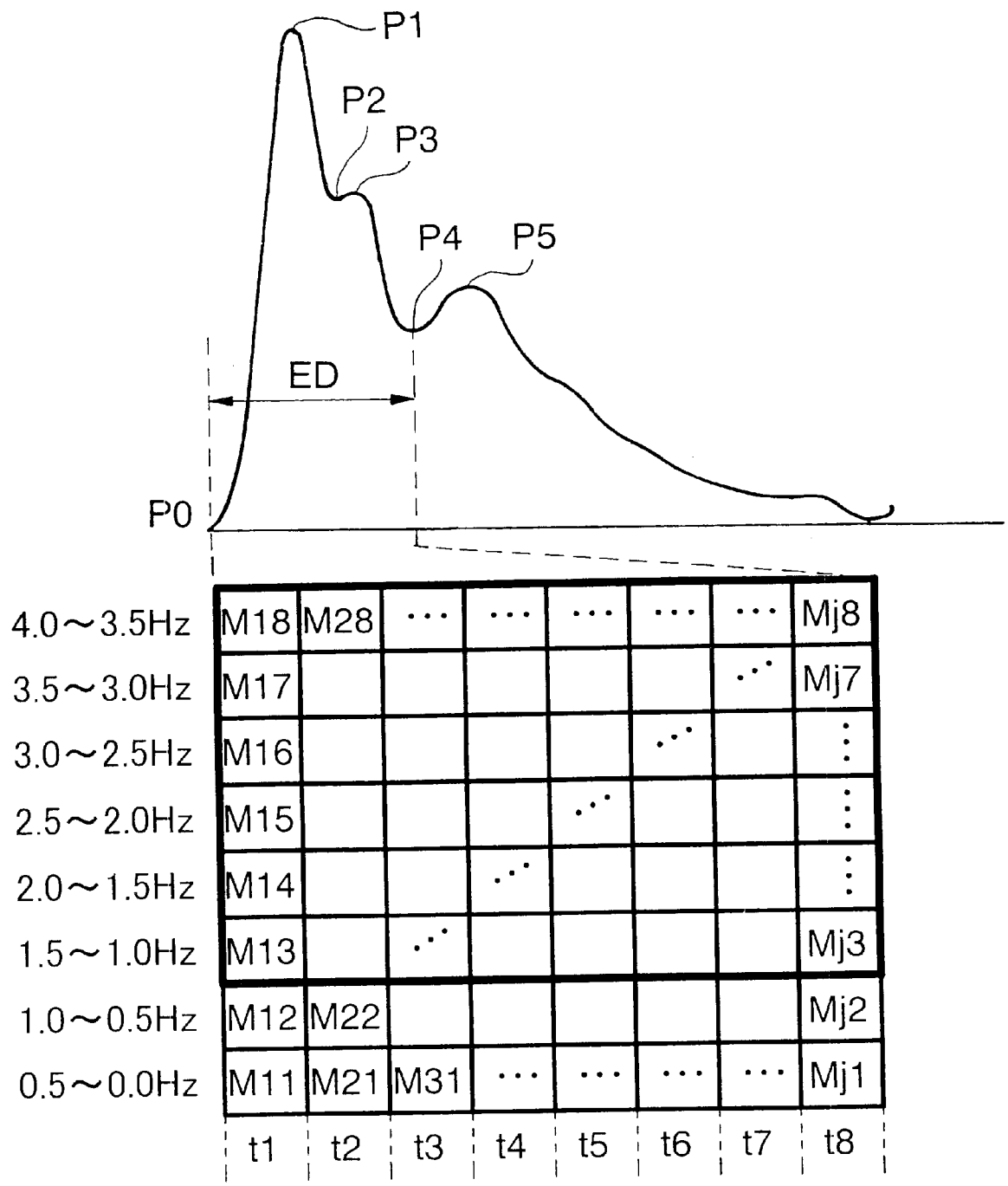
FIG. 92 is a diagram for explaining the operation of the stroke-volume-per-beat calculator in the second embodiment in Chapter 4.

For example, as shown in FIG. 92, there are numerous noise components in the 0~1 Hz frequency region in the pulse wave data MKD" from which body motion components have been removed. Accordingly, pulse wave data MKD" from which body motion components have been removed which is in the 1~4 Hz frequency region may be summed. If the pulse wave data MKD" from which body motion components have been removed in each of the frequency regions is expressed as Mnm, then the total energy E may be obtained from the following equation.

$$E = \sum_{n=3}^{8} \sum_{m=1}^{j} Mnm$$

Stroke volume per beat is calculated from the following equation.

$$SV = K_{sv} * S = K_{sv} * K_e * E$$

Where, $K_e$ is the coefficient for converting between energy E and area S.

In the second embodiment, contraction period area S is calculated using wavelet transformation. Thus, the stroke-volume-per-beat SV can be obtained while removing the noise components in the pulse waveform, so that an accurate cardiac output CO can be calculated.

4-2-4: Embodiment 3

The second embodiment employed first and second wavelet transformers 420,422 and first and second frequency correctors 421,423 to perform frequency analysis using wavelet transformation. In contrast, the third embodiment differs from the second embodiment in the omission of second wavelet transformer 422 and second frequency corrector 423.

Figure 93:
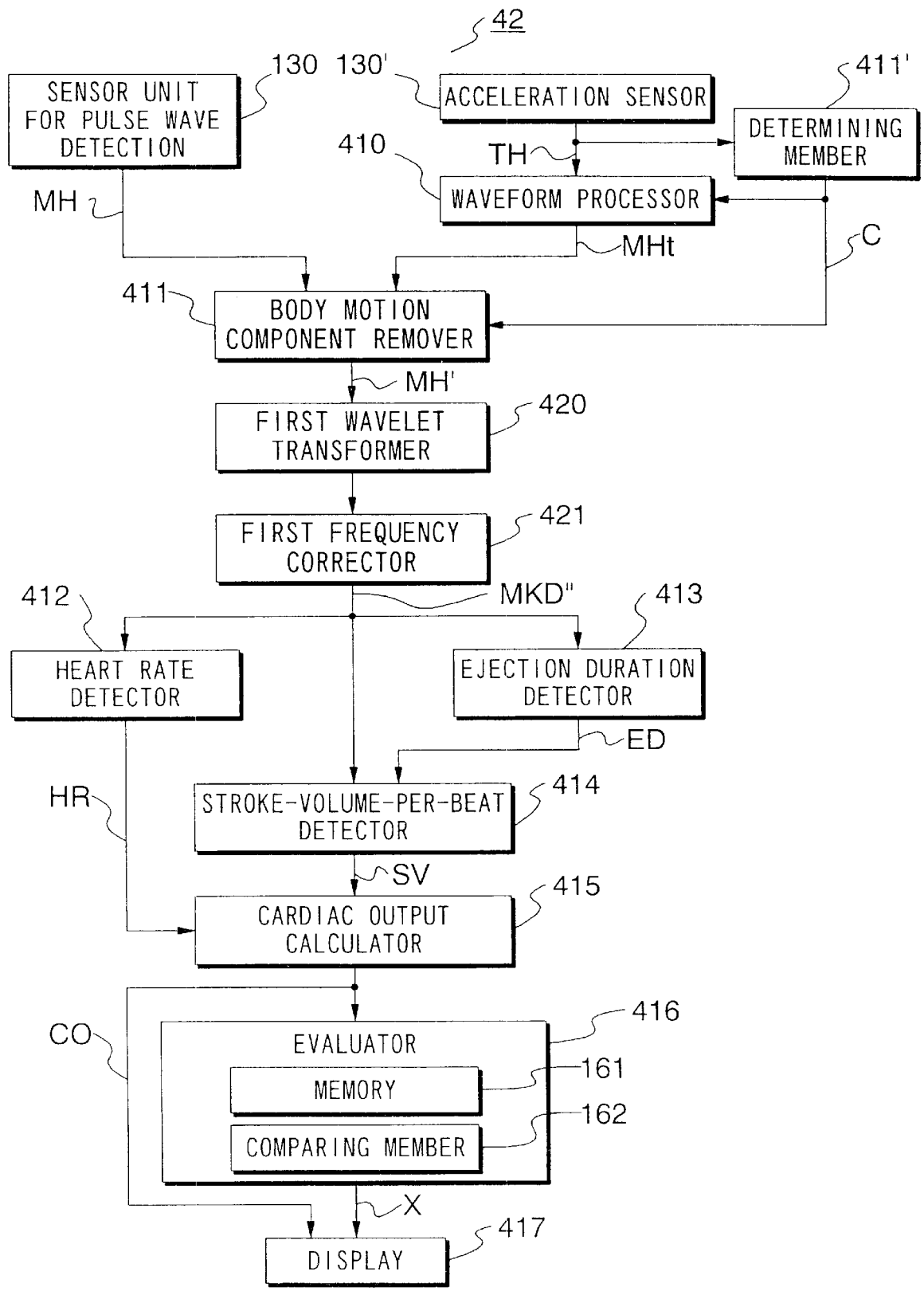
FIG. 93 is a block diagram of a cardiac function diagnosing device according to the third embodiment in Chapter 4.

FIG. 93 is a block diagram of a cardiac function diagnosing device 42 according to the third embodiment. In this figure, pulse waveform MH' from which body motion components have been removed by body motion component remover 411 is generated, and first wavelet transformer 420 performs wavelet transformation on this pulse waveform MH' from which body motion components have been removed. First frequency corrector 421 performs frequency correction on the output from first wavelet transformer 416, to generate pulse wave data MKD" from which body motion components have been removed.

The output from first frequency corrector 421 is equivalent to the output from body motion component remover 411 shown in FIG. 90. In other words, since wavelet transformation is linear, the processing sequence may be switched. Thus, performing wavelet transformation following body motion component removal using an analog signal (third embodiment) is equivalent to performing body motion component removal based on wavelet-transformed corrected pulse wave data MKD' and corrected body motion data TKD' (embodiment 2).

Note that determining member 411' is the same as in the first embodiment, while heart rate detector 412, ejection duration detector 413, stroke-volume-per-beat calculator 414, cardiac output calculator 415, evaluator 416 and display 417 are the same as in the second embodiment. Accordingly, an explanation of these components will be omitted here.

The third embodiment permits calculation of cardiac output CO even though second wavelet transformer 422 and second frequency corrector 423 are omitted. As a result, it becomes possible to diagnose the state of cardiac function by means of a simpler structure.

4-2-5: Embodiment 4

In the first through third embodiments, body motion waveform TH was detected by acceleration sensor 130, and compared to pulse waveform MH. The body motion components included in the frequency components of pulse waveform MH were then canceled, and heart rate HR and ejection duration ED were calculated. A diagnosis of the cardiac function state was then made based on these values. However, the structure of the device became complex due to the requirement for acceleration sensor 130, waveform processor 410 and the like. The fourth embodiment was conceived in consideration of this point, and therefore provides a cardiac function diagnosing device 42 which employs a simple structure and is capable of accurately diagnosing the state of cardiac function even when body motion is present.

Figure 94:
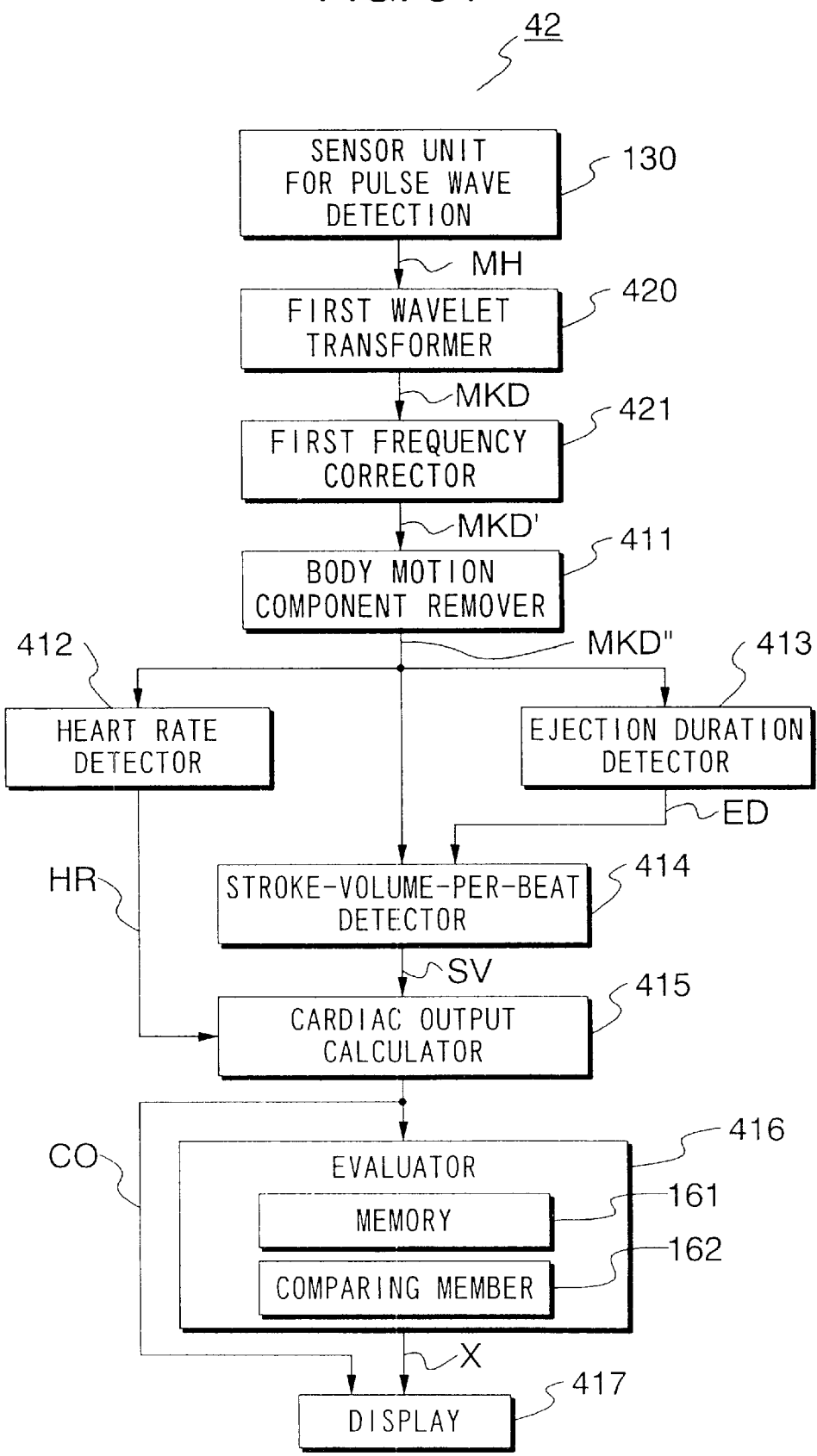
FIG. 94 is a block diagram of a cardiac function diagnosing device according to the fourth embodiment in Chapter 4.

FIG. 94 is a block diagram of cardiac function diagnosing device 42 according to the fourth embodiment. This cardiac function diagnosing device 42 is equivalent to the cardiac function diagnosing device 42 according to the second embodiment shown in FIG. 90, with the exception of the internal structure of body motion component remover 411 and the omission of acceleration sensor 130, waveform processor 410, second wavelet transformer 422 and second frequency corrector 423. These points of difference will be explained below.

Body motion component remover 411 separates and removes body motion components from corrected pulse wave data MKD', and generates pulse wave data TBD from which body motion components have been removed. Body motion component remover 411 exploits the properties of body motion explained below.

Namely, body motion is generated as a result of the vertical movement of the arms or the swinging motion of the arms during running. During the course of daily activities, there is almost no instantaneous movement of the body. For this reason, during daily activities, the frequency components in body motion waveform TH are not that high, but typically are in the range of 0 Hz~1 Hz. In this case, the fundamental frequency of pulse waveform MH is often in the range of 1 Hz~2 Hz. Accordingly, during daily activities, the frequency components in body motion waveform TH are in a frequency region which is lower than the fundamental frequency of pulse waveform MH.

During sports such as jogging, however, the swinging motion of the arms and the like exerts an influence, causing the frequency components of body motion waveform TH to become somewhat higher. At the same time, heart rate increases in accordance with the amount of exercise, so that the fundamental frequency of pulse waveform MH also becomes higher. Accordingly, even during sports, the frequency components of body motion waveform TH are typically in a frequency range which is lower than the fundamental frequency of pulse waveform MH.

Body motion component remover 411 takes advantage of this point to separate the body motion components, and is designed to ignore frequency regions which are lower than the fundamental component of pulse waveform MH. In this case, if body motion components are present in a frequency region which is higher than the fundamental component of pulse waveform MH, then the accuracy of detection of cardiac function falls. However, since it is more likely that body motion components will be in a frequency region which is lower than the fundamental component of pulse waveform MH, it is possible to carry out a highly accurate detection of cardiac function.

Figures 95, 96:
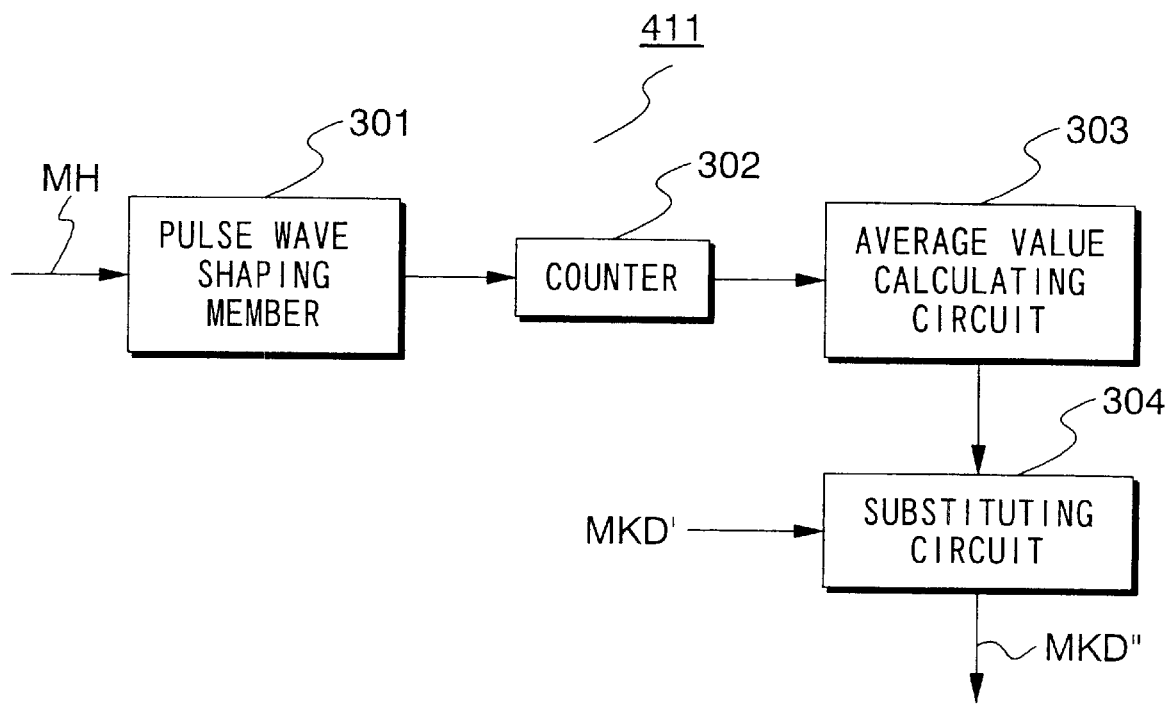
FIG. 95 is a block diagram showing the details of body motion component remover 411 in the fourth embodiment in Chapter 4.
FIG. 96 is a diagram showing one example of pulse wave data MKD" from which body motion components have been removed in the fourth embodiment in Chapter 4.

FIG. 95 is a detailed block diagram of body motion component remover 411. Waveform shaping member 4301 performs waveform shaping on pulse waveform MH, and generates a reset pulse synchronized with pulse waveform MH. Counter 302 counts clock pulses, which are not shown in the figures, and is designed so that the counter value is reset according to the reset pulse. Average value calculating circuit 303 calculates the average of the counter values from counter 302. In this case, the average value calculated by average value calculating circuit 303 corresponds to the average period of pulse waveform MH. Accordingly, the fundamental frequency of pulse waveform MH can be detected by referencing the average value.

Based on the aforementioned average value, substituting circuit 304 specifies the frequency region which includes the fundamental frequency of pulse waveform MH. For example, when the average value is 0.71 sec, then the fundamental frequency becomes 1.4 Hz. Thus, the frequency region specified is 1 Hz~1.5 Hz. Substituting circuit 304 then substitutes corrected pulse wave data MKD' with "0" in the frequency regions below the specified frequency region, and generates pulse wave data TBD from which body motion components have been removed. As a result, components in frequency regions below the fundamental frequency of pulse waveform MH are ignored. While pulse wave components as well as body motion components are substituted by "0" in this case, the effect on the pulse waveform is negligible since the characteristic portion of pulse waveform MH is present in a frequency region which is higher than the fundamental frequency.

For example, if pulse waveform MH (fundamental frequency 1.3 Hz) shown in FIG. 16A is detected by pulse wave detection sensor unit 130, then the corrected pulse wave data MKD' for time interval Tc becomes as shown in FIG. 17. In this case, the frequency region specified by substituting circuit 194 is 1.0 Hz~1.5 Hz, so that the frequency regions subject to replacement are Ma12~Ma82, corresponding to 0.5 Hz~1.0 Hz, and Ma11~Ma81, corresponding to 0 Hz~0.5 Hz. Accordingly, data Ma12~Ma82 and Ma11~M81 of corrected pulse wave data MKD' are substituted by "0", and the pulse wave data MKD" from which body motion components have been removed shown in FIG. 96 is generated.

Heart rate detector 412 and ejection duration detector 413 shown in FIG. 94. detect heart rate HR and ejection duration ED respectively, based on the thus-generated pulse wave data MKD" from which body motion components have been removed.

In the fourth embodiment, body motion components are removed by taking advantage of the properties of body motion, namely, that there is a high probability that the body motion components are present in a frequency region which is lower than the fundamental frequency components of pulse waveform MH. Thus, components such as acceleration sensor 130 and waveform processor 410 which are required in the first through third embodiments can be eliminated here, and an accurate diagnosis of the cardiac function state can be made even if body motion is present.

4-2-6: Embodiment 5

The fifth embodiment relates to a modification of stroke-volume-per-beat measurer 414 explained in the first embodiment. Other structural components are equivalent to the first embodiment. The stroke-volume-per-beat measurer 414 according to the fifth embodiment may have the following aspects.

4-2-6-1: First Aspect

In the first aspect, the blood pressure values of peaks P1~P4 of pulse waveform MH' from which body motion components have been removed in ejection duration ED, and stroke-volume-per-beat SV from the time these peaks were generated, are calculated. For example, if pulse waveform MH' from which body motion components have been removed is as shown in FIG. 25 and the interval from P0 to P4 is designated as ejection duration ED, then stroke-volume-per-beat SV is calculated from the following equation.

$$SV=Ksv*S=Ksv*f1(t_1, t_2, t_3, t_4, y_1, y_2, y_3, y_4)=Ksv*\{t_1*y_1+(t_2-t_1)*(y_1+y_2)+(t_3-t_2)(y_2+y_3)+(t_4-t_3)(y_3+y_4)\}/2$$

In this example, stroke-volume-per-beat SV is calculated based on contraction period area S which is calculated using linear approximation. Accordingly, the amount of calculations can be reduced as compared to the method for calculating area S by adding the pulse waveform MH' from which body motion components have been removed for all samples in ejection duration ED.

4-2-6-2: Second Aspect

In the second aspect, stroke-volume-per-beat SV is determined from ejection duration ED and heart rate HR. Contraction period area S in the contraction period area method is calculated from ejection duration ED and heart rate HR.

Individual differences, as well as differences within the same individual, are present in pulse waveform MH. However, it is possible to specify the approximate shape of the pulse waveform MH for a given heart rate HR by measuring numerous actual data. When pulse waveform MH is specified, area S which corresponds to ejection duration ED can be obtained.

Figure 97:
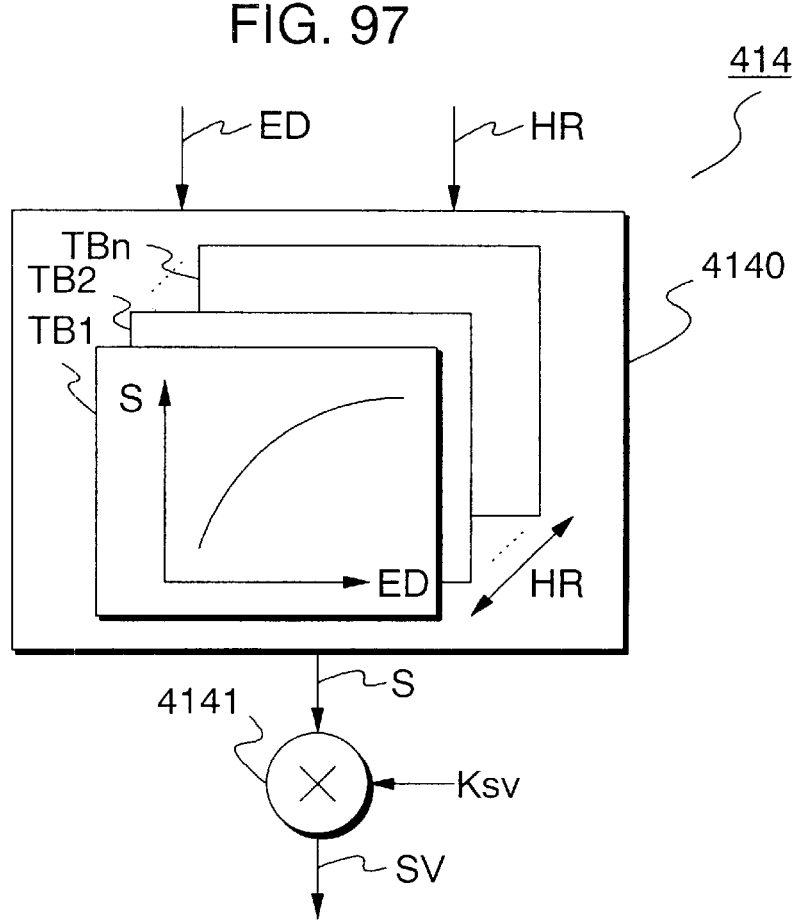
FIG. 97 is a block diagram showing the stroke-volume-per-beat calculator according to the fifth embodiment in Chapter 4.

FIG. 97 is a block diagram of stroke-volume-per-beat detector 414 according to the second aspect of the fifth embodiment. 4140 is a stroke-volume-per-beat table, in which contraction period areas S are stored in association with ejection durations ED and heart rates HR for the heart. Stroke-volume-per-beat table 4140 is formed of a plurality of tables TB1, TB2, . . . TBn provided for each heart rate HR. Contraction period area S which corresponds to ejection duration ED is stored in each of tables TB1, TB2 . . . TBn. The content of these tables is generated by numerous actual measured data. 4141 is a multiplier provided at a step subsequent to stroke-volume-per-beat table 140, for calculating stroke-volume-per-beat SV by multiplying coefficient Ksv and contraction period area S.

When ejection duration ED and heart rate HR are supplied to stroke-volume-per-beat table 140 in the above-described structure, stroke-volume-per-beat detector 414 specifies one table TB corresponding to heart rate HR. When contraction period area S which corresponds to ejection duration ED is read out from table TB thereafter, multiplier 4141 calculates stroke-volume-per-beat SV.

Since stroke-volume-per-beat SV can be calculated from ejection duration ED and heart rate HR in this way in this second aspect of the fifth embodiment, it becomes possible to obtain stroke-volume-per-beat SV by means of a simple structure within a short period of time.

Note that multiplier 4141 may be omitted if stroke-volume-per-beat SV associated with ejection duration ED is stored in tables TB1, TB2, . . . TBn. In this case, S*Ksv may be stored in tables TB1, TB2, . . . TBn in place of contraction period area S.

Figure 98:
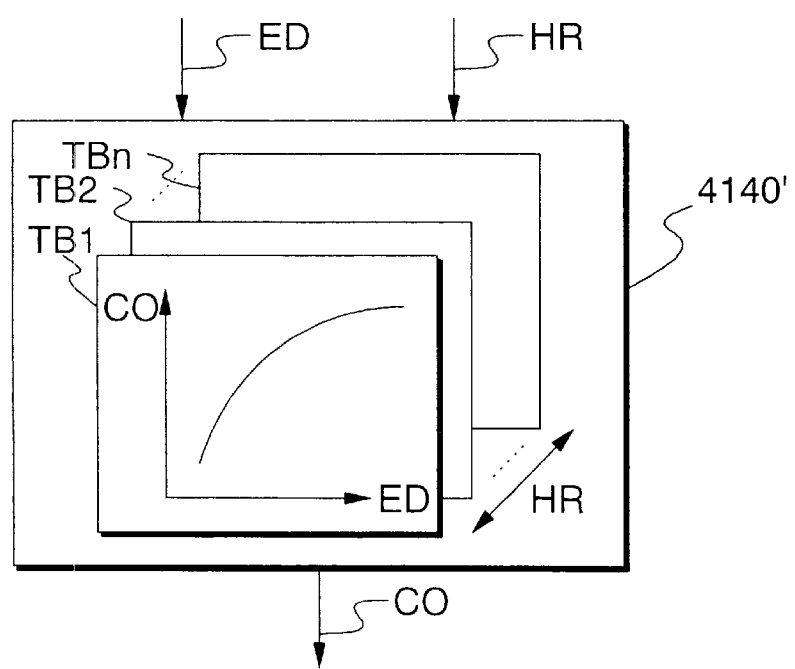
FIG. 98 is a block diagram showing the cardiac output table according to the fifth embodiment in Chapter 4.

If cardiac output CO in association with ejection duration ED is stored in tables TB1, TB2, . . . TBn, then cardiac output CO can be calculated directly from ejection duration ED and heart rate HR. FIG. 98 shows cardiac output table 4140'. In this case, S*Ksv*HR may be stored in tables TB1, TB2, . . . TBn in place of contraction period area S.

4-2-7: Embodiment 6

Cardiac function diagnosing device 42 according to the first through fifth embodiments employs a contraction period area method, in which area S of the pulse waveform during ejection duration ED is multiplied by a given coefficient Ksv to calculate stroke-volume-per-beat SV. Strictly speaking, coefficient Ksv differs between test subjects. For this reason, in order to calculate an accurate stroke-volume-per-beat SV, it is desirable to correct the stroke-volume-per-beat SV obtained by the contraction period area method.

Accordingly, in the sixth embodiment, a stroke-volume-per-beat corrector 424 for correcting stroke-volume-per-beat SV is provided in between cardiac output calculator 415 and stroke-volume-per-beat calculator 414 of the first through fifth embodiments shown in FIGS. 88, 90, 93, and 94.

Figure 99:
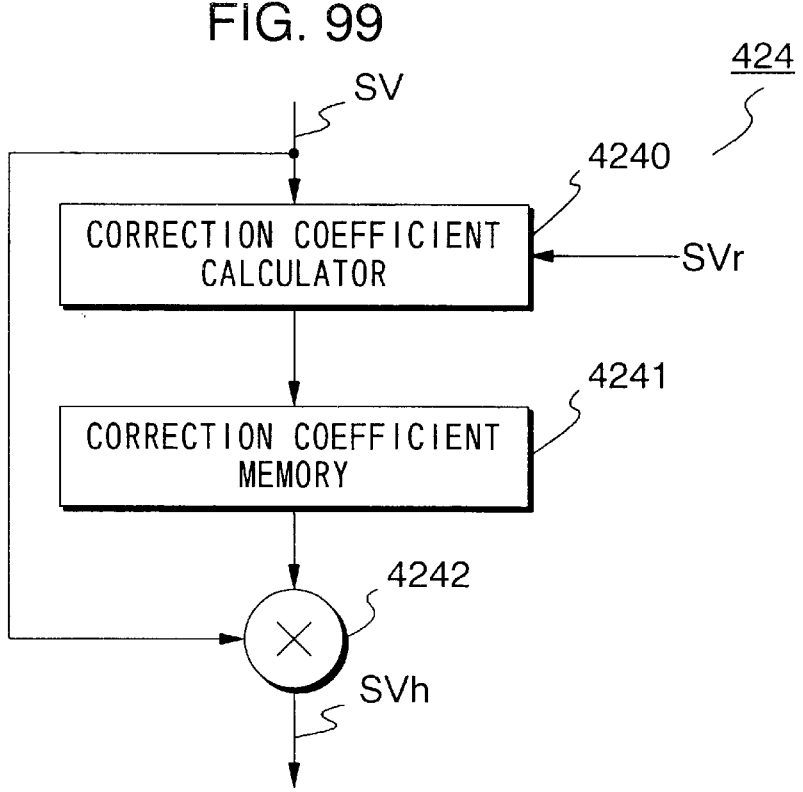
FIG. 99 is a block diagram showing stroke-volume-per-beat corrector 424 according to the sixth embodiment in Chapter 4.

FIG. 99 is a block diagram of stroke-volume-per-beat corrector 424 according to this embodiment. As shown in this figure, stroke-volume-per-beat corrector 424 is formed of correction coefficient calculator 4240 for calculating correction coefficient KH, correction coefficient memory 4241 for storing correction coefficient KH, and multiplier 4242.

Reference stroke-volume-per-beat SVr, which is precisely measured using a thermodye dilution method or the like and supplied from an external piece of equipment, and stroke-volume-per-beat SV, which is calculated by stroke-volume-per-beat calculator 414, are supplied to correction coefficient calculator 4240. Correction coefficient calculator 4240 is formed of a dividing device. When the test subject manipulates operational buttons to set the device in the correction mode, correction coefficient calculator 4240 calculates SVr/SV as the correction coefficient KH. The calculated correction coefficient KH is stored in correction coefficient memory 4241, and is employed by being read out therefrom during the regular measurement mode. Multiplier 4242 then generates a corrected stroke-volume-per-beat SVh by multiplying stroke-volume-per-beat SV and correction coefficient KH.

In this embodiment, correction coefficient KH is calculated in the correction mode, and a corrected stroke-volume-per-beat SVh is calculated using correction coefficient KH during the regular measurement mode. As a result, it is possible to more accurately determine cardiac output CO.

Cardiac function diagnosing device 42 in this embodiment may be optimally employed in the management of a patient's health during hospitalization or rehabilitation. More specifically, an accurate reference stroke-volume-per-beat SVr is measured for a post-operative heart patient using the thermodye dilution method, while stroke-volume-per-beat SV is measured using a portable cardiac function diagnosing device 42. The correction coefficient KH calculated from these measured results is stored, and the precise cardiac output co is determined using this correction coefficient KH when the device is in the mode for performing regular measurements. As a result, a diagnosis of cardiac function can be obtained based on an accurate cardiac output CO as the patient undergoes rehabilitation to return to health.

4--2-8: Embodiment 7

The seventh embodiment varies the threshold values which serve as references for evaluation index X in accordance with the surface area of the body. With the exception of the structure of evaluator 416, the design of the seventh embodiment is equivalent to that of the first through sixth embodiments. Accordingly, evaluator 416, the point of difference between these embodiments, will be explained below.

Figure 100:
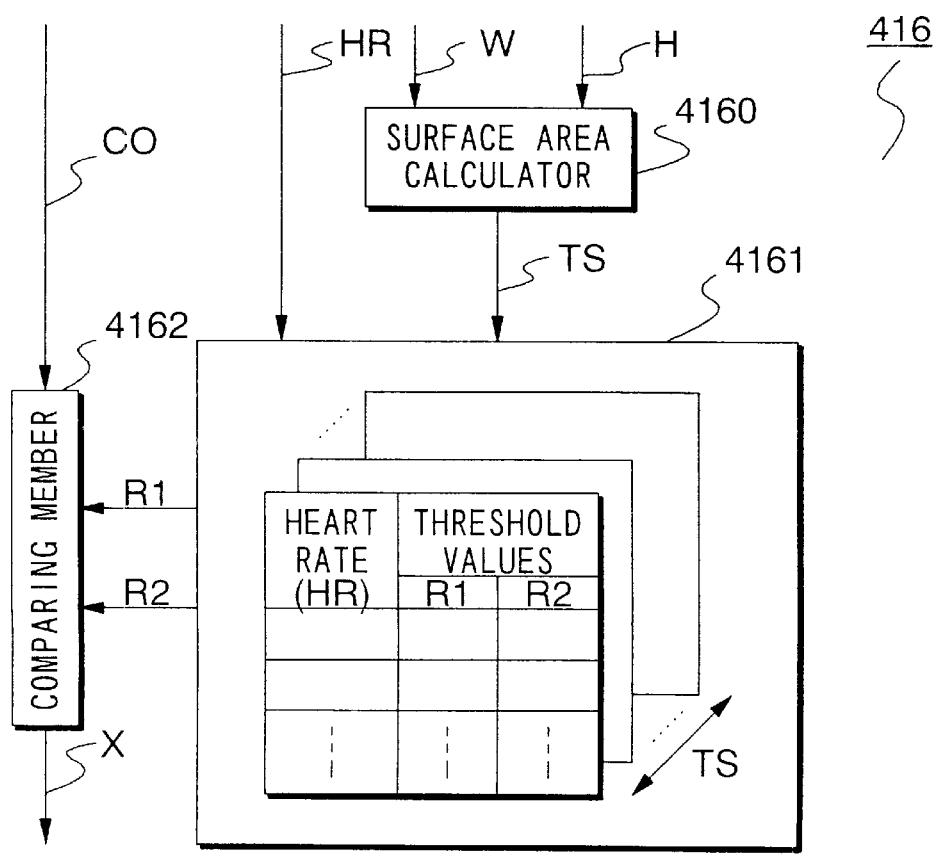
FIG. 100 is a block diagram of evaluator 416 according to the seventh embodiment in Chapter 4.

FIG. 100 is a block diagram of evaluator 416 according to the seventh embodiment. 416 is a body surface area calculator into which body weight W (kg) and height H (cm) are input. Body surface area TS is then calculated based on these values. In this example, body surface area TS is calculated using a conventional formula known as the DuBois equation shown below.

$$TS = W^{0.425} \times H^{0.725} \times 71.84$$

4161 is a threshold table for storing threshold values R1,R2 in association with body surface area TS and heart rate HR. Threshold values R1,R2 are for generating evaluation index X. Threshold value table 4161 is formed of a plurality of tables TB1', TB2', . . . TBn. Threshold values R1,R2 are stored in association with heart rate HR in each table. When body surface area TS is supplied, one of the tables is selected in accordance with the supplied body surface area TS. Accordingly, by referencing threshold value table 4161, threshold values R1,R2 in accordance with the body surface area TS and heart rate HR are obtained.

Next, 162 indicates a comparing member for comparing threshold values R1,R2 and cardiac output CO, and then generating an evaluation index X.

Threshold values R1,R2 were varied in accordance with body surface area TS in the preceding discussion. The reason for this is as follows. In general, a person having a large body surface area TS has a large body and a high cardiac output. Conversely, a person having a small body surface area TS tends to have a smaller body and a lower cardiac output. For this reason, it is difficult to evaluate individual cardiac function if the cardiac output CO of both individuals is evaluated using the same threshold values R1,R2. By employing an evaluation index X which depends on body surface area TS, however, an evaluation can be made of cardiac function in accordance with individual body types.

The reason for varying threshold values R1,R2 in accordance with heart rate HR is as follows. Namely, when running or otherwise exercising, skeletal muscle consumes a large amount of oxygen, with heart rate HR and cardiac output CO increasing. Stated another way, heart rate HR and cardiac output CO vary in response to the intensity of exercise. Accordingly, by employing an evaluation index X that depends on the heart rate HR, it is possible to continuously evaluate cardiac function even when the intensity of exercise by the test subject varies.

Accordingly, by employing cardiac function diagnosing device 42 according to this embodiment, threshold values R1,R2 can be automatically varied in accordance with the subject's body size and dynamically changing heart rate HR. As a result, it becomes possible to continuously evaluate cardiac function during daily activities.

Figure 101:
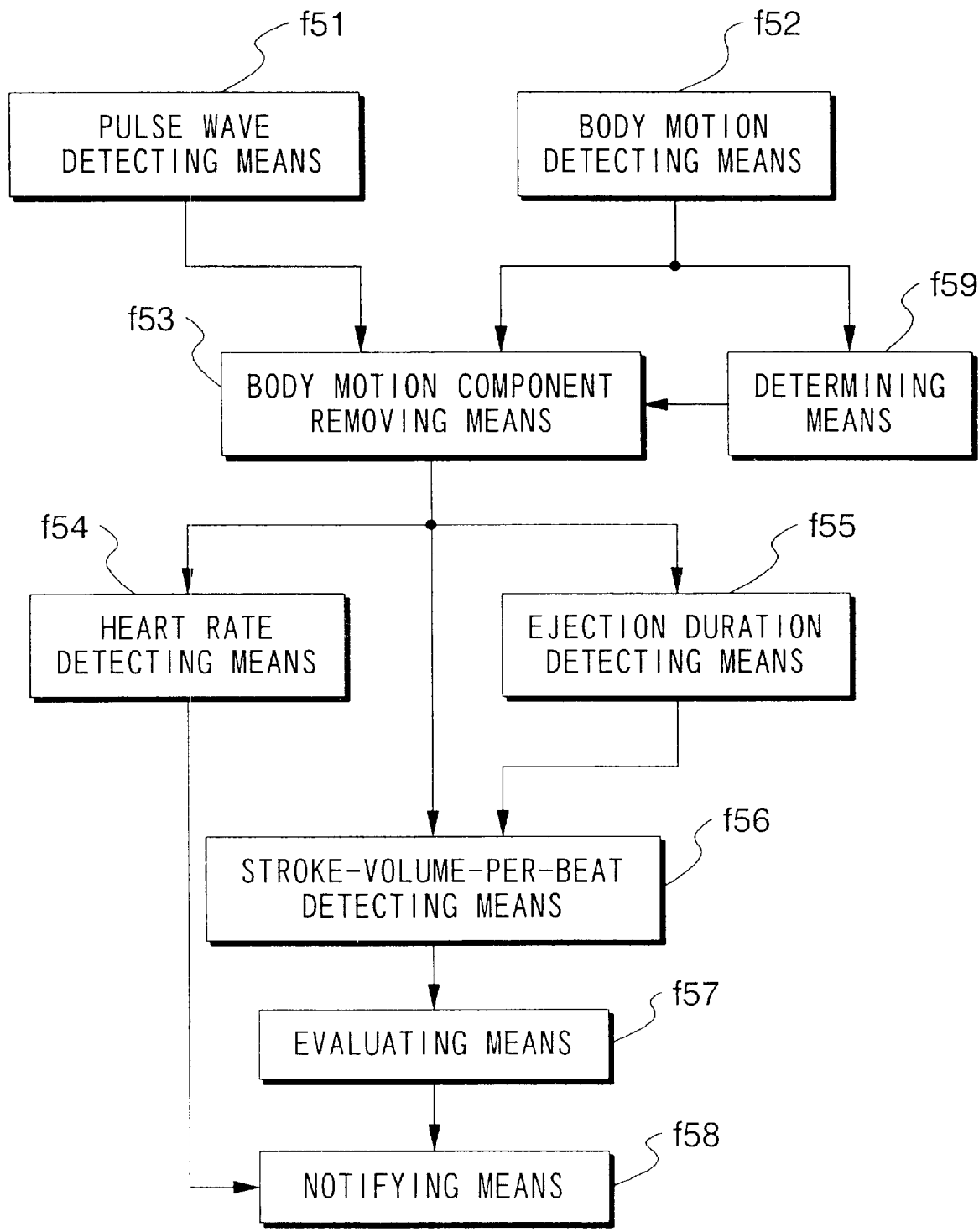
FIG. 101 is a function block diagram showing the functional structure of a cardiac diagnosing device employing a stroke-volume-per-beat detecting device in Chapter 4.

4-3: Stroke-volume-per-beat Detecting Device and Cardiac Function Diagnosing Device 4-3-1: Functional Structure The function of a cardiac function diagnosing device employing a stroke-volume-per-beat detecting device will now be explained with reference to the figures. FIG. 101 is a function block diagram of a cardiac function diagnosing device employing a stroke-volume-per-beat detecting device. In this figure, f51 is a pulse wave detecting means for detecting the pulse waveform. The pulse waveform can be obtained by using an optical sensor to detect the flow of blood at a peripheral site such as the fingertip or base of the finger. f52 is a body motion detecting means for detecting body motion and outputting the body motion waveform. In this way, body motion is detected.

f53 is a body motion component removing means for generating the body motion components in the pulse waveform based on the body motion waveform, removing the body motion components from the pulse waveform, and then generating a pulse waveform from which body motion components have been removed. As a result, it is possible to generate a pulse waveform which is not effected by body motion, even if the subject is exercising.

f54 is a determining means for determining whether or not body motion is present based on changes in the level of the body motion waveform. When body motion is not present, determining means f54 terminates the operation of body motion component removing means f3. As a result, the calculations to remove body motion components can be reduced.

f55 is an ejection duration detecting means for detecting the ejection duration of the heart based on the pulse waveform from which body motion components have been removed. The ejection duration is the interval during which the heart contracts once, sending blood into the aorta. Note that ejection duration ED includes not only the ejection duration in the strictest sense, but also the systolic time and estimated systolic time of ventricular contraction.

f56 is a stroke-volume-per-beat detecting means for calculating stroke-volume-per-beat SV based on the pulse waveform from which body motion components have been removed during the ejection duration.

Next, f57 is an evaluating means for evaluating the state of cardiac function based on the stroke volume per beat. Namely, the evaluation of cardiac function is performed based on the blood volume which is ejected by each contraction of the heart. f58 is a notifying means for informing the subject of the results of this evaluation. As a result, the subject or a third party such as a physician can be made aware of the patient's cardiac function.

4-3-2: Embodiment 8

The structure of a cardiac function diagnosing device 43 employing a stroke-volume-per-beat detecting device will now be explained with reference to the figures. Note that the external structure of the cardiac function diagnosing device 43 in this example is equivalent to that of pulse wave diagnosing device1 in Chapter 1 as explained in Section 4-2.

Figure 102:
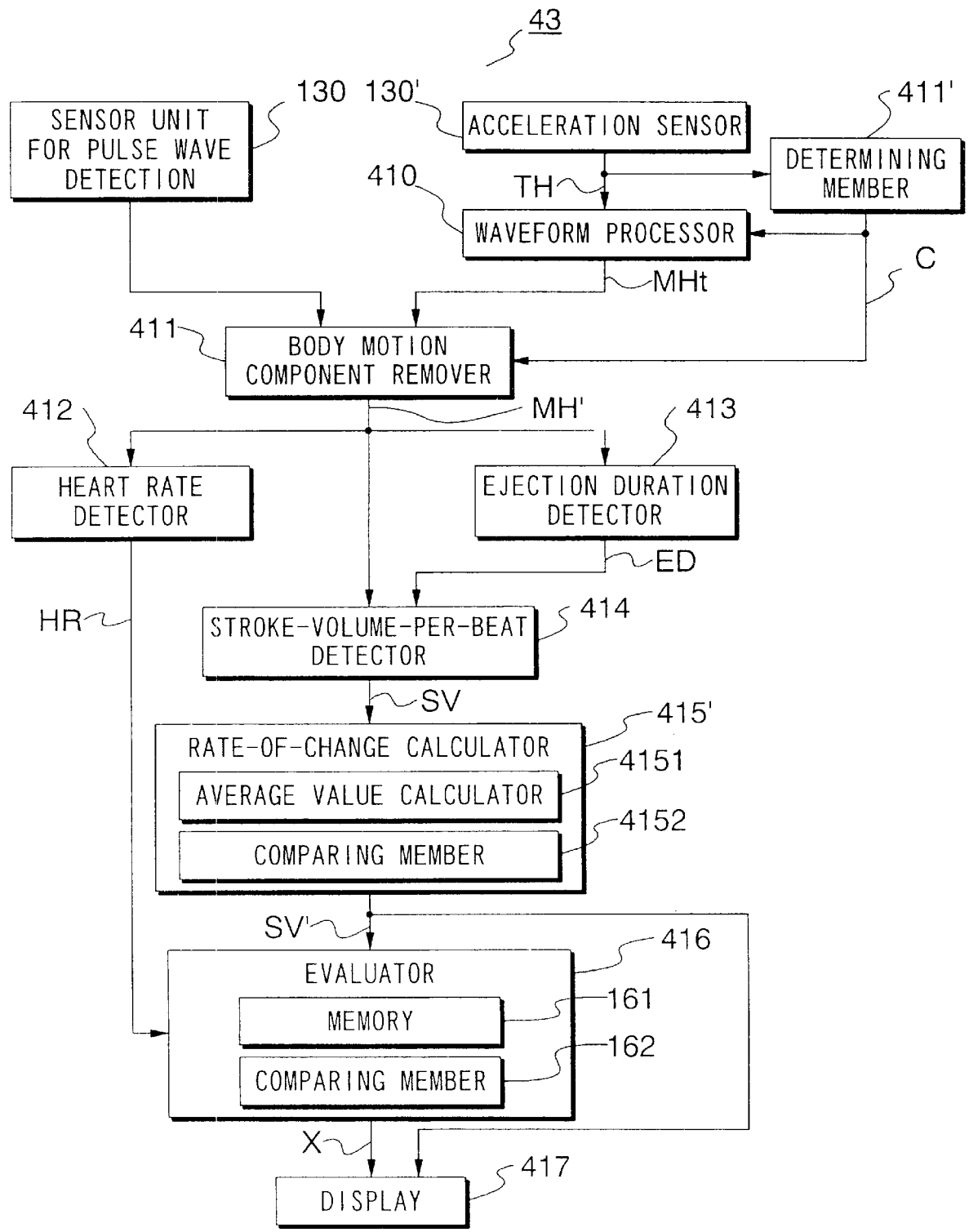
FIG. 102 is a block diagram showing the electrical structure of a cardiac function diagnosing device according to the seventh embodiment in Chapter 4.

FIG. 102 is a block diagram showing the electrical structure of cardiac function diagnosing device 43. The cardiac function diagnosing device 43 shown in this figure differs from the cardiac function diagnosing device 42 shown in FIG. 89 in that a rate-of-change calculator 415' is provided in place of cardiac output calculator 415.

Rate-of-change calculator 415' is formed of an average value calculator 4151 and comparing member 4152, and calculates the rate-of-change SV' in stroke-volume-per-beat SV. Average value calculator 4151 calculates the average value SVa of stroke-volume-per-beat SV. For example, if the nth detected stroke volume per beat is indicated as SVn, then the average value SVa at the timing for detecting stroke-volume-per-beat SVn may be the average value for all values detected since measurements began. Alternatively, it is also acceptable for SVa to be a moving average obtained from the following equation.

$$SVa=(SVn-m+1+SVn-m+2+\ldots+SVn-1+SVn)/m$$

For example, if m=60, then the average for approximately one minute intervals can be calculated.

Next, comparing member 4152 calculates SV/SVa, and calculates the stroke-volume-per-beat rate-of-change SV'. The respiratory rate per heartbeat is usually 4 times or less. In addition, stroke-volume-per-beat SV is known to vary in synchronization with respiration. Accordingly, in order to cancel the variation due to respiration, the stroke-volume-per-beat SV may be added k times and averaged, and the stroke-volume-per-beat rate-of-change SV' may be calculated from this average value and SVa. In this case, k may be selected so that m>k≧4.

Next, evaluator 416 is formed of memory 161 and comparing device 162. Evaluator 416 evaluates cardiac function and generates evaluation index X based on rate-of-change SV'. Threshold values employed in grading rate-of-change S SV' are stored in memory in association with heart rate HR. In this way, the threshold values in accordance with the heart rate HR at the time of detection can be read out from memory. Threshold values can be set in accordance to the grade number. In this example, R1 and R2 are set as threshold values. Threshold values R1,R2 may be stored in advance at the time of shipment of the product, or may be suitably set by a physician or trainer when training is initiated.

Comparing device 162 compares the stroke-volume-per-beat rate-of-change SV1 and threshold values R1,R2, and generates evaluation index X. In this example, evaluation indices X1, X2, and X3 are generated at SV<R1, R1≦SV<R2, and R2≦SV, respectively. The significance of evaluation indices X1~X3 will vary depending on how cardiac function diagnosing device 43 is employed. For example, when employed in exercise training, evaluation indices X1~X3 serve as a measure for maintaining a suitable exercise intensity. However, when monitoring a heart patient's cardiac function during rehabilitation, evaluation indices X1~X3 serve as measurements of the degree of recovery.

Display 417 is formed of LCD 210 and the like explained above, and is for displaying stroke-volume-per-beat SV, evaluation index X or a message associated with evaluation index X. This display may be in the form of a face chart, letters, symbols or the like, enabling the subject to know the results of the evaluation of cardiac function.

For example, when employing cardiac function diagnosing device 43 during running, the subject can be informed so as to maintain a suitable stroke-volume-per-beat SV as a result of the setting of threshold values R1,R2 by the trainer. In this case, messages such as "increase pace" in the case of evaluation index X1, "maintain pace" in the case of evaluation index X2, and "decrease pace" in the case of evaluation index X3, can be displayed in characters on display 417.

As an aside, autogenic training methods, referred to as focused self-relaxation methods, are known to be helpful in health improvement and health recovery by eliminating tension. The objective is to relax the subject's psychological state. However, in the process of attempting to relax, the subject's attention may become overly focused on this objective, leading conversely to a state of tension.

In situations such as this, the subject is better able to effectively perform training if he is aware of his own psychological state. In this case, stroke-volume-per-beat rate-of-change SV' can serve as an indicator of the degree of relaxation. Namely, if the stroke-volume-per-beat rate-of-change SV' becomes smaller, then the psychological state is nearing a more stable and relaxed state.

Threshold values R1,R2 may be set so that a determination can be made of the degree of relaxation. For example, in the case of a physician-directed autogenic training method, the physician sets threshold values R1,R2 to inform him of the subject's psychological state. In this case, messages may be provided such as "very relaxed" in the case of evaluation index X1, "maintain state" in the case of evaluation index X2, and "release tension, imagine relaxing sensation" in the case of evaluation index X3.

4-3-3: Embodiment 9

Figure 103:
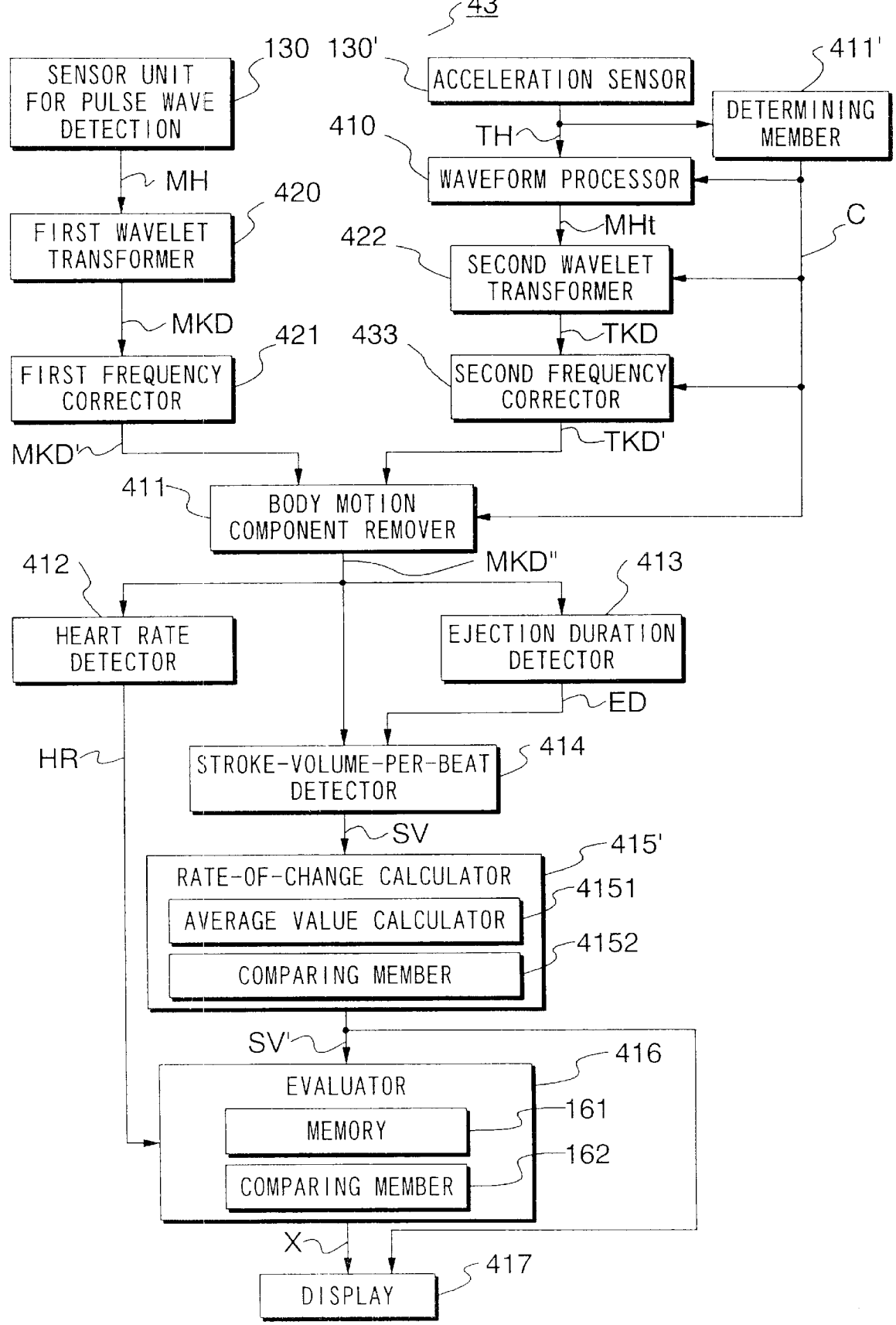
FIG. 103 is a block diagram showing the electrical structure of a cardiac function diagnosing device according to the ninth embodiment in Chapter 4.

Cardiac function diagnosing device 43 according to the ninth embodiment will now be explained. FIG. 103 is a block diagram of cardiac function diagnosing device 43 according to the ninth embodiment. As in the eighth embodiment, the device according to the ninth embodiment detects body motion component MHt using acceleration sensor 130' and waveform processor 140. However, the ninth embodiment differs from the eighth embodiment in that the removal of body motion and the detection of heart rate and ejection duration are carried out using wavelet transformation. Namely, the device according to the ninth embodiment corresponds to that of the second embodiment explained with reference to FIG. 90. Structural components which are equivalent as those in FIG. 90 have been assigned the same numerical symbol.

In this example, body motion component remover 411 subtracts corrected body motion data TKD' obtained based on body motion waveform TH from corrected pulse wave data MKD' obtained based on pulse waveform MH, and generates pulse wave data MKD" from which body motion components have been removed. Calculation of stroke-volume-per-beat SV and the like is performed based on pulse wave data MKD" from which body motion components have been removed.

Thus, as in the eighth embodiment, contraction period area S is calculated using wavelet transformation while the effect of body motion is removed. By calculating stroke-volume-per-beat SV in this way, an accurate value therefor can be obtained. As a result, an accurate evaluation of cardiac function can be provided.

4-3-4: Embodiment 10

In the ninth embodiment, frequency analysis was performed using wavelet transformation. The ninth embodiment employed a first wavelet transformer 420, first frequency corrector 421, second wavelet transformer 422, and second frequency corrector 423 for this reason. In contrast, the tenth embodiment differs from the ninth embodiment in the omission of second wavelet transformer 422 and second frequency corrector 423. Namely, the tenth embodiment corresponds to the third embodiment (see FIG. 93) described above.

Figure 104:
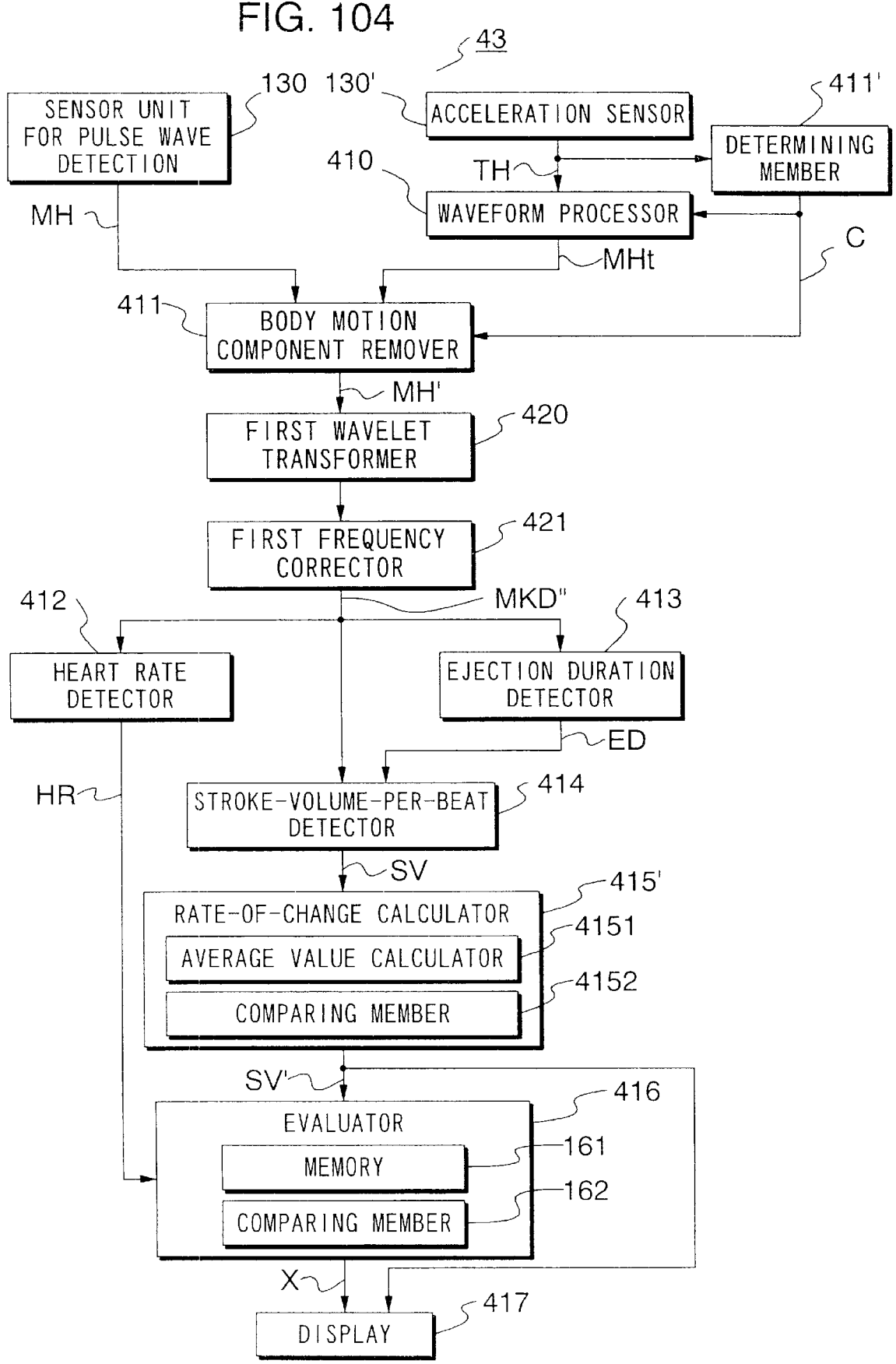
FIG. 104 is a block diagram of a cardiac function diagnosing device according to the tenth embodiment in Chapter 4.

FIG. 104 is a block diagram of a cardiac function diagnosing device 43 according to the tenth embodiment. In this figure, when pulse waveform MH' from which body motion components have been removed is generated by body motion component remover 411, first wavelet transformer 420 performs wavelet transformation on this pulse waveform MH'. First frequency corrector 421 performs frequency correction on the output from first wavelet transformer 416 and generates pulse wave data MKD" from which body motion components have been removed.

Thus, as in the case of the third embodiment, even though second wavelet transformer 422 and second frequency corrector 423 are omitted in the tenth embodiment, stroke-volume-per-beat SV and stroke-volume-per-beat rate-of-change SV' can be calculated. Thus, it is possible to diagnose the state of cardiac function by means of a simpler structure.

4-3-5: Embodiment 11

In the eighth through tenth embodiments, body motion waveform TH is detected by acceleration sensor 130. Pulse waveform MH and body motion waveform TH are compared, and the body motion components included in the frequency components of pulse waveform MH are canceled. Heart rate HR and ejection duration ED are then calculated, and a diagnosis of the state of cardiac function is made based on these values. However, since acceleration sensor 130 and waveform processor 410 are necessary, the structure becomes more complicated. The eleventh embodiment was conceived in view of this problem, and has as its objective the provision of a cardiac function diagnosing device capable of diagnosing the state of cardiac function by means of a simple structure accurately, even when body motion is present. In other words, the eleventh embodiment corresponds to the above-described fourth embodiment.

Figure 105:
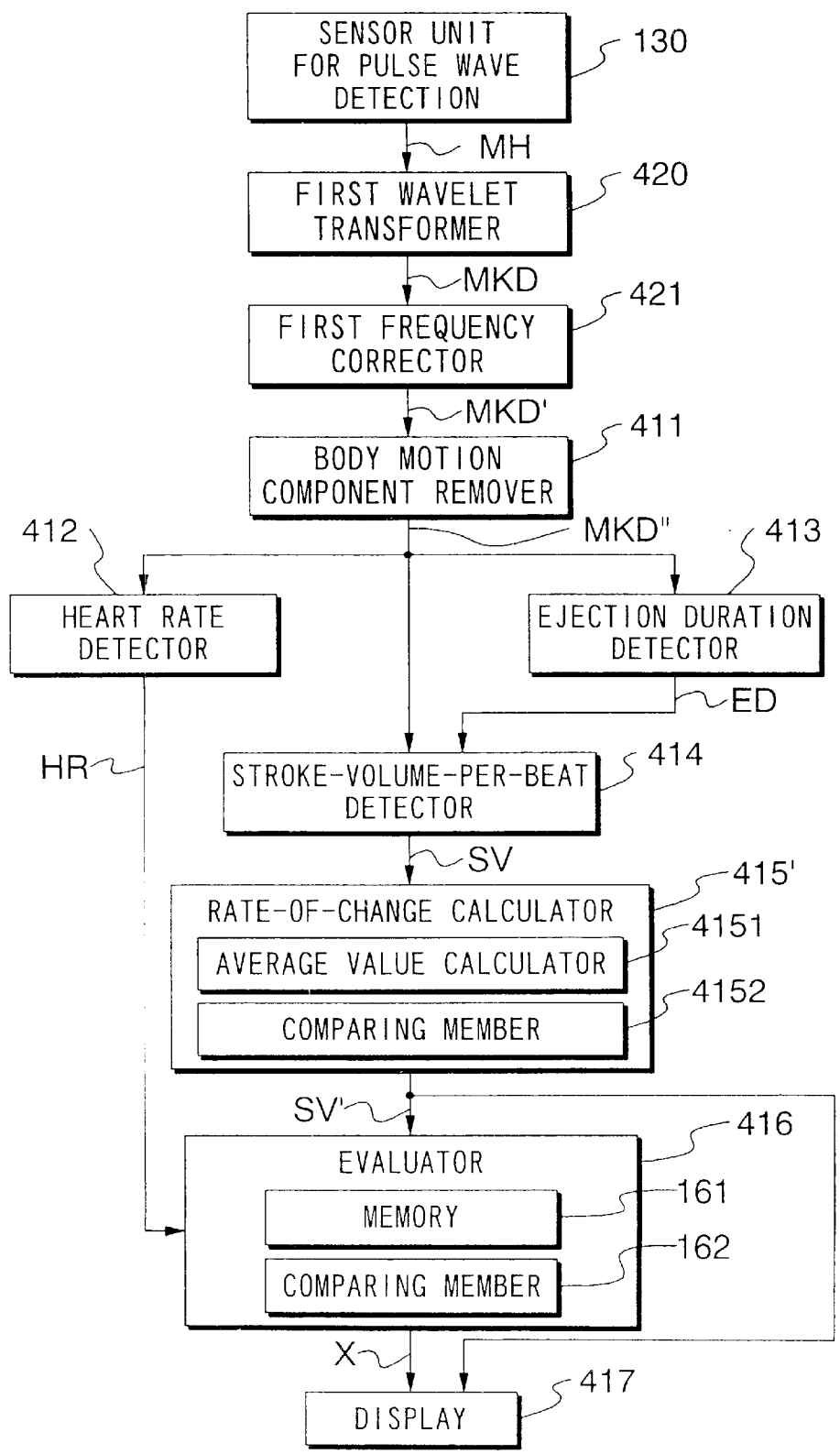
FIG. 105 is a block diagram of a cardiac function diagnosing device according to the eleventh embodiment in Chapter 4.
Figure 106A:
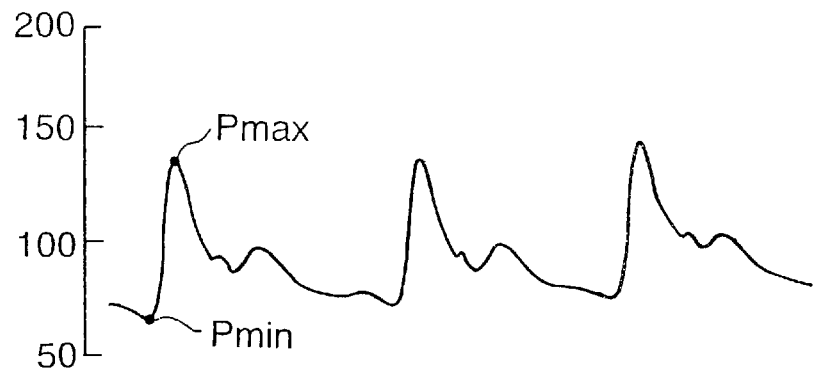
FIGS. 106A–106D are diagrams showing the shape of the pulse waveform in response to exercise intensity in Chapter 4.
Figure 106B:
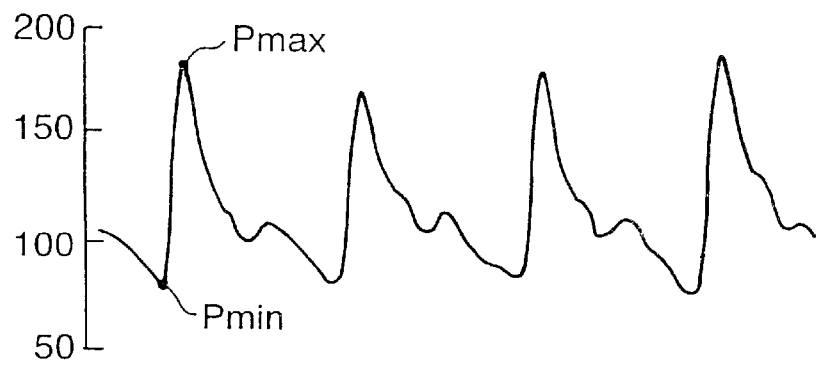
Figure 106C:
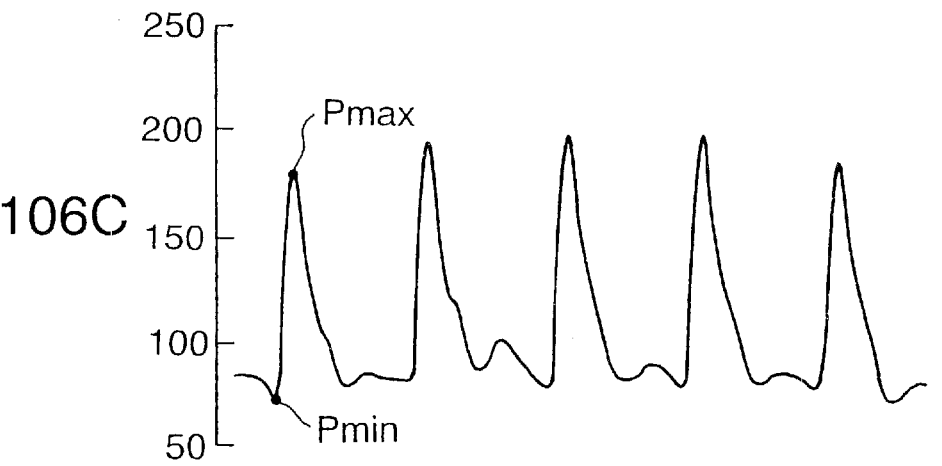
Figure 106D:
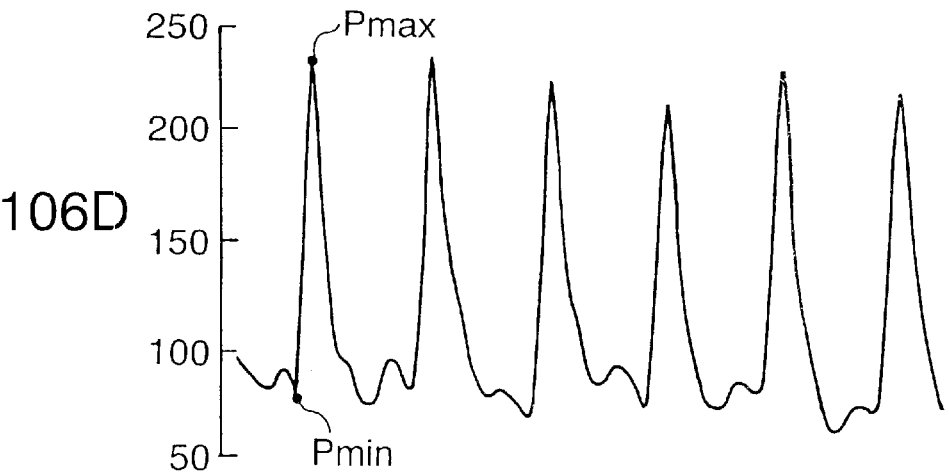

FIG. 105 is a block diagram of cardiac function diagnosing device 43 according to the eleventh embodiment. This cardiac function diagnosing device 43 is equivalent to cardiac function diagnosing device 43 according to the ninth embodiment shown in FIG. 103, with the exception of the internal structure of body motion component remover 411 and the omission of acceleration sensor 130', determining member 411', waveform processor 410, second wavelet transformer 422, and second frequency corrector 423.

Body motion component remover 411 in this example is formed in the same manner as body motion component remover 411 according to the fourth embodiment. In other words, body motion component remover 411 according to the eleventh embodiment utilizes the fact that the frequency components of body motion waveform TH are in a lower frequency region than the fundamental frequency of pulse waveform MH, in order to remove body motion components from corrected pulse wave data MKD' and generate pulse wave data MKD" from which body motion components have been removed.

Accordingly, the acceleration sensor 130 and waveform processor 410 which were required in the eighth through tenth embodiments can be omitted, while an accurate diagnosis of the state of cardiac function can be performed even when body motion is present.

4-3-6: Embodiment 12

The twelfth embodiment relates to a modification of stroke-volume-per-beat calculator 414 explained in the eighth embodiment. All other structural components are the same as in the eighth embodiment. Stroke-volume-per-beat calculator 414 according to the twelfth embodiment has the following aspects.

4-3-6-1: First Aspect

In the first aspect of the twelfth embodiment, the blood pressure values of peaks P1~P4 of pulse waveform MH' from which body motion components have been removed in ejection duration ED, and stroke-volume-per-beat SV from the time these were generated, are calculated. For example, if pulse waveform MH' from which body motion components have been removed is as shown in FIG. 6 and the interval from P0 to P4 is designated as ejection duration ED, then stroke-volume-per-beat SV is calculated from the following equation.

$$SV = Ksv*S = Ksv*f1(t_1, t_2, t_3, t_4, y_1, y_2, y_3, y_4) = Ksv*\{t_1*y_1 + (t_2-t_1)*(y_1+y_2) + (t_3-t_2)(y_2+y_3) + (t_4-t_3)(y_3+y_4)\}/2$$

In this example, contraction period area S is calculated using linear approximation, and stroke-volume-per-beat SV is calculated based on this calculated value.

Accordingly, the amount of calculations can be reduced as compared to the method for calculating area S by adding the pulse waveform MH' from which body motion components have been removed for all samples in ejection duration ED. The first aspect of the twelfth embodiment is equivalent to the first aspect of the fifth embodiment with respect to this point (see section 4-2-6-1).

4-3-6-2: Second Aspect

In the second aspect of the twelfth embodiment, stroke-volume-per-beat SV is calculated based on systolic pressure Pmax, diastolic pressure Pmin, and ejection duration ED.

First, the relationship between pulse waveform MH and ejection duration ED, on which this second aspect of the twelfth embodiment is premised, will be explained. A variety of medical research has been carried out with respect to this subject. Regarding the relationship between the radius artery waveform and the intensity of exercise performed by a cardiac patient, the graphs shown in FIGS. 106A–106D are disclosed in Disparities Between Aortic and Peripheral Pulse Pressures Induced by Upright Exercise and Vasomotor Changes in Man, Circulation, VOL. XXVII, June 1968. In this figure, as the exercise intensity increases, the pulse waveform of the radius artery changes in sequence, 106A→106B→106C→106D. It may be understood from this figure that as the exercise intensity increases, systolic pressure Pmax gradually increases and ejection duration ED becomes shorter. Conversely, diastolic pressure Pmin does not change to as great an extent when exercise intensity is increasing. In other words, the shape of the pulse waveform changes dynamically, with stroke-volume-per-beat SV varying in accompaniment with these changes.

Figure 107A:
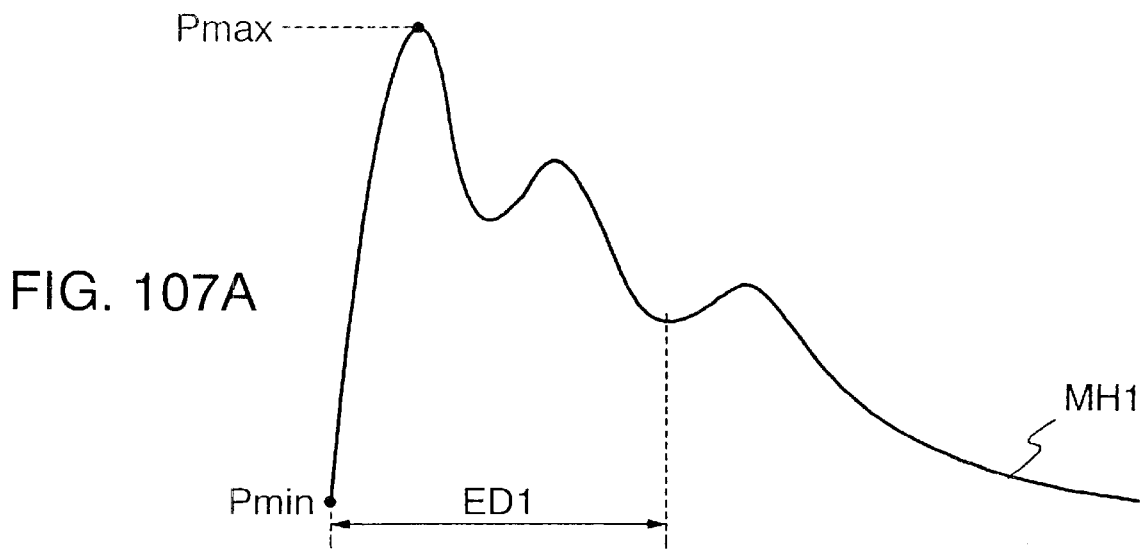
FIGS. 107A–107C are diagrams modeling the shape of the pulse waveform in accordance with exercise intensity in Chapter 4.
Figure 107B:
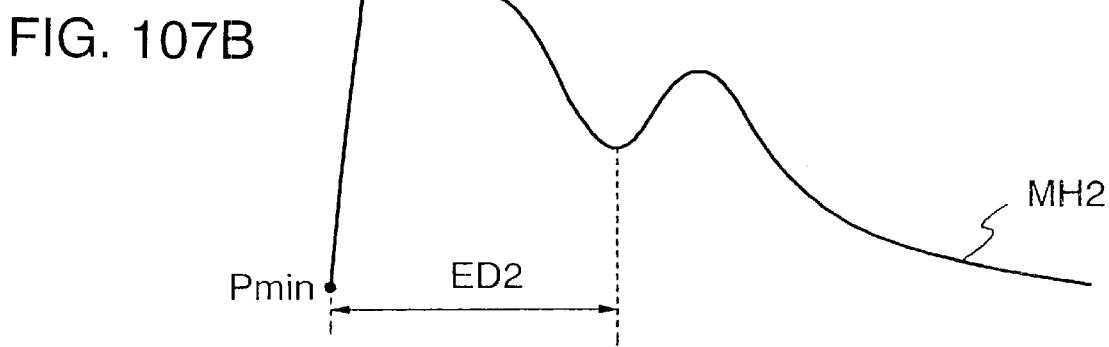
Figure 107C:
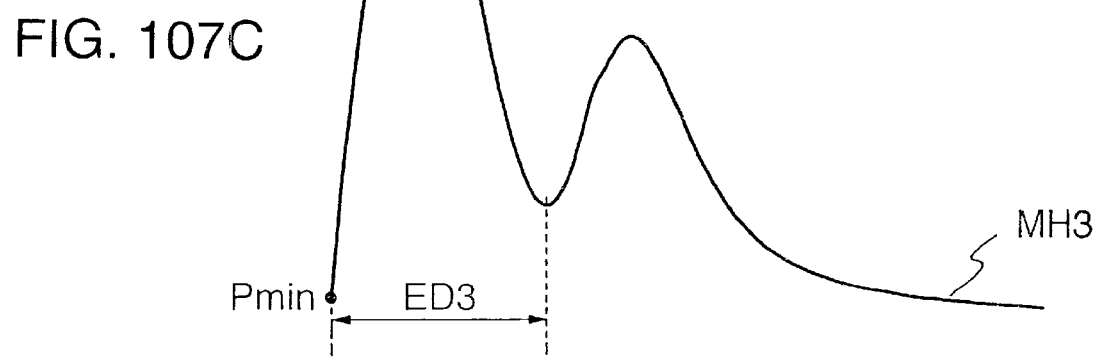

The shape of the pulse waveform of the radius artery shown in FIGS. 106A–106D is schematically shown in FIGS. 107A–107C. FIG. 107A is a typical example of pulse waveform MH of an individual at rest. The waveform shape is that for a so-called "Ping mai" pulse, characterized in that the tidal wave is clearly apparent. This tidal wave is generated according to the correlation between the elastic expansion of the aorta as blood is sent out from the heart and the reflected wave at the periphery.

When a person with a Ping mai exercises, the shape of the pulse waveform changes as shown from FIG. 107A→FIG. 107B→FIG. 107C. Namely, the clarity of the tidal wave is gradually lost as exercise intensity increases, until the shape becomes a so-called "Hua mai". Stating this another way, the shape of the pulse waveform changes in accordance with the change in exercise intensity, accompanied by a change in contraction period area S.

From FIGS. 107A–107C, it may be understood that when the shape of the waveform changes accompanying an increase in exercise intensity, ejection duration ED decreases from ED1→ED2→ED3. This is because the interval of time from when the aortic valve opens to when it closes becomes gradually shorter as exercise intensity increases. The main wave and the peripheral reflected waves become closer, and the tidal wave disappears. Accordingly, ejection duration ED is closely related to contraction and relaxation of the heart, and can serve as an index for specifying the shape of the pulse waveform.

Ejection duration ED serves as a reference for specifying the shape of the pulse waveform, while the difference between systolic pressure Pmax and diastolic pressure Pmin serves as an index expressing the size of pulse waveforms MH1~MH3 shown in FIGS. 107A–107D. As shown in FIG. 36, contraction period area S can be expressed as the sum of area S1 corresponding to the alternating flow component (hereinafter, referred to as "alternating flow area") and area S2 corresponding to the direct flow component (hereinafter, referred to as "direct flow area"). In this case, direct flow area S2 is Pmin×ED, while alternating flow area S1 is defined according to Pmax–Pmin and ED.

Thus, in the second aspect of the twelfth embodiment, contraction period area S is calculated based on systolic pressure Pmax, diastolic pressure Pmin and ejection duration ED. Stroke-volume-per-beat SV is determined from the result of this calculation.

Figure 108:
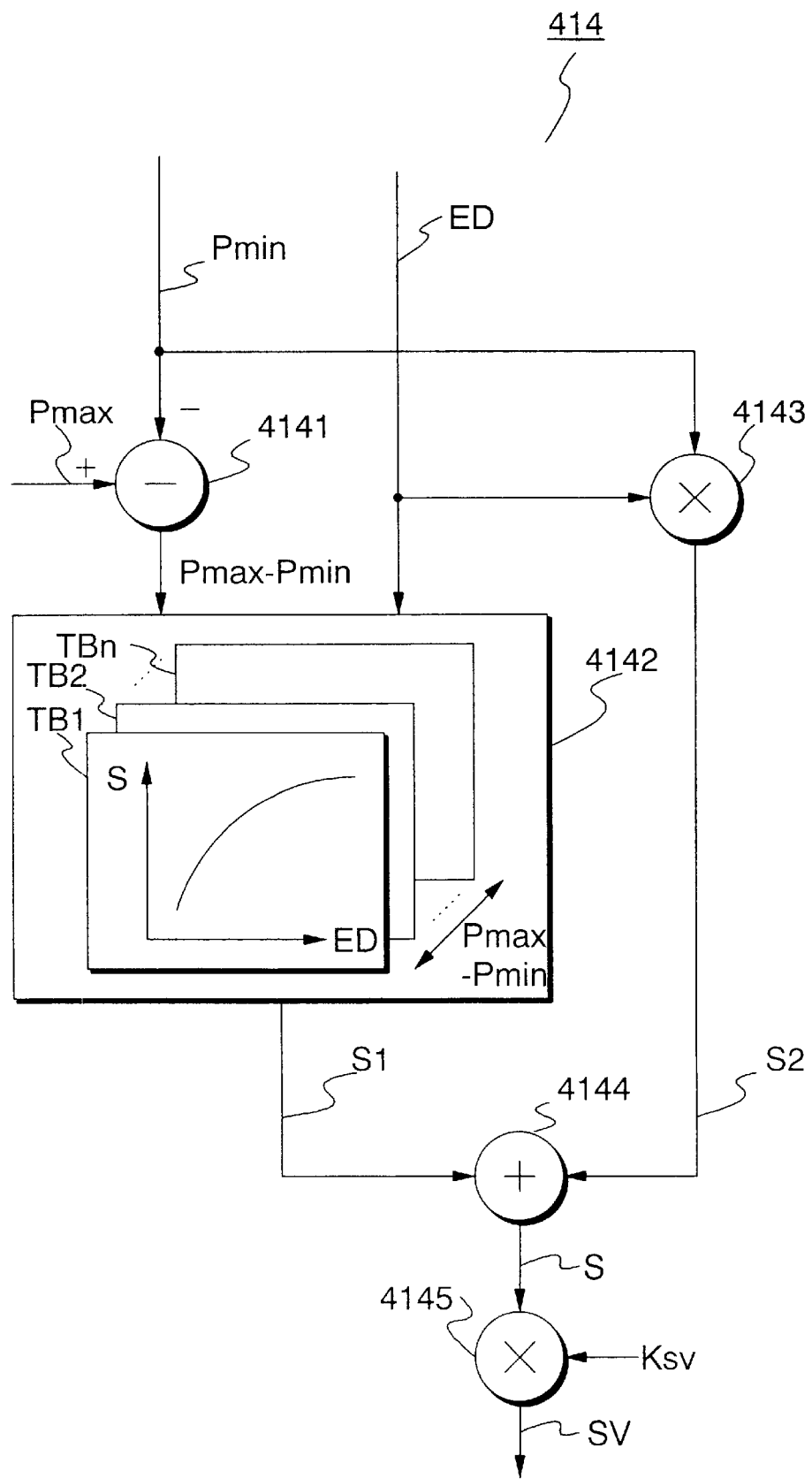
FIG. 108 is a block diagram showing the structure of a stroke-volume-per-beat calculator according to a second aspect for the twelfth embodiment in Chapter 4.

FIG. 108 is a block diagram of stroke-volume-per-beat detector 414 according to this second aspect. 4141 is a subtracting member for subtracting diastolic pressure Pmin from systolic pressure Pmax. In this case, systolic pressure Pmax is the blood pressure data for peak P1 in the pulse waveform from which body motion components have been removed, while diastolic pressure Pmin is blood pressure data for peak P0 of the pulse waveform from which body motion components have been removed. 4142 is a contraction period area table, in which alternating flow areas S1 are stored in association with the ejection duration ED and Pmax–Pmin. This contraction period area table 4142 is formed of a plurality of tables TB1, TB2, . . . Tsn provided in accordance with Pmax–Pmin. Alternating flow area S1 (see FIG. 86) associated with ejection duration ED is stored in tables TB1, TB2 . . . TBn. The content of these tables is generated based on numerous actual measured data.

4143 is a multiplier provided for outputting direct flow area S2 (see FIG. 86) by multiplying ejection duration ED and diastolic pressure Pmin. 4144 is an adder for generating contraction period area S by adding alternating flow area S1 and direct flow area S2. 4145 is a multiplier for calculating stroke-volume-per-beat SV by multiplying coefficient Ksv and contraction period area S.

In the preceding design, when ejection duration ED and Pmax–Pmin are supplied to contraction period area table 4141, one table TB is specified corresponding to Pmax–Pmin. When alternating flow area S1 which corresponds to ejection duration ED is subsequently read out, the sum of alternating flow area S1 and direct flow area S2 is calculated at adding device 4144, and stroke-volume-per-beat Sv in accordance with this calculated result is generated.

Thus, in the second aspect of the twelfth embodiment, stroke-volume-per-beat SV is obtained based on systolic pressure Pmax, diastolic pressure Pmin, and ejection duration ED. Accordingly, a simple structure can be employed to calculate stroke-volume-per-beat SV within a short period of time.

Note that a plurality of tables TB1, TB2, . . . TBn were provided in accordance with the value of Pmax–Pmin in the preceding discussion. However, it is also acceptable to provide one representative table, and then correct the alternating flow area S1 obtained therefrom using Pmax–Pmin, and make this the output of contraction period area table 142.

4-3-6-3: Third Aspect

Figure 109:
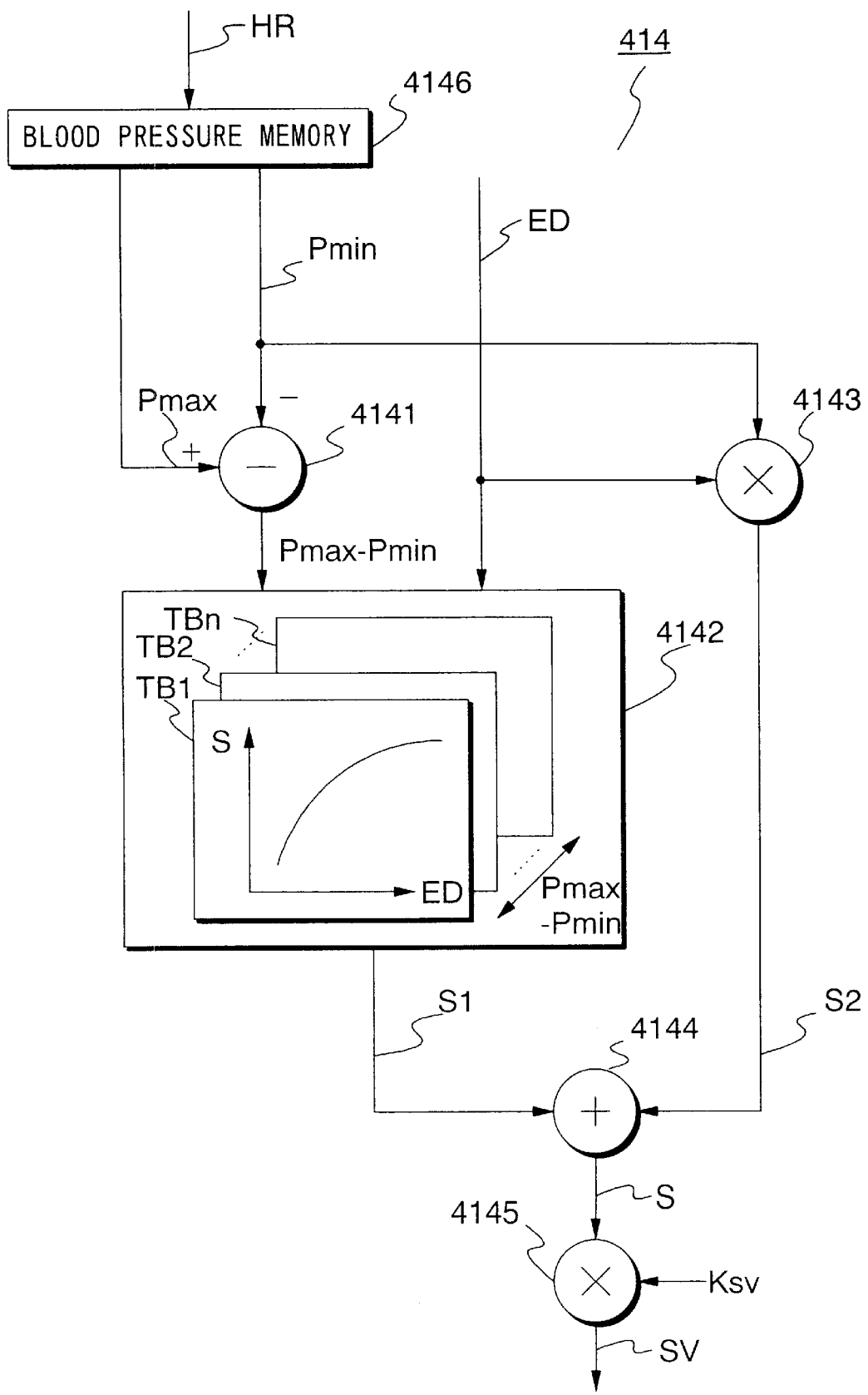
FIG. 109 is a block diagram showing the structure of a stroke-volume-per-beat calculator according to a third aspect for the twelfth embodiment in Chapter 4.

Stroke-volume-per-beat detector 414 according to the third aspect of the twelfth embodiment will now be explained. FIG. 109 is a block diagram of stroke-volume-per-beat detector 414 according to this third aspect. Excluding the provision of blood pressure memory 146, this device is equivalent to stroke-volume-per-beat detector 414 according to the second aspect shown in FIG. 108. Systolic pressure Pmax and diastolic pressure Pmin in accordance with heart rate HR are stored in advance in blood pressure memory 4146. When storing data in blood pressure memory 4146, cardiac function diagnosing device 43 is set in a preparation mode, and the subject performs suitable exercise to vary the heart rate HR. The subject's heart rate HR varies in accordance with exercise, with systolic pressure Pmax and diastolic pressure Pmin varying in response to the changes in heart rate HR. Blood pressure memory4146 stores systolic pressure Pmax and diastolic pressure Pmin obtained at this time in association with heart rate HR.

Conversely, when the measured heart rate HR is supplied to blood pressure memory146 in the mode for measuring stroke-volume-per-beat SV, systolic pressure Pmax and diastolic pressure Pmin are output.

Accordingly, in this example, systolic pressure Pmax and diastolic pressure Pmin can be determined by supplying heart rate HR to stroke-volume-per-beat detector 414. Then, stroke-volume-per-beat SV can be calculated based on these values and ejection duration ED in the same manner as the second aspect.

4-3-6-4: Fourth Aspect

In the preceding third aspect of the twelfth embodiment, heart rate HR and ejection duration ED were designated as the inputs for stroke-volume-per-beat detector 414 by associating heart rate HR and systolic pressure Pmax and diastolic pressure Pmin. This means that stroke-volume-per-beat SV can be expressed as a function in which heart rate HR and ejection duration ED are variables. The fourth aspect of the twelfth embodiment was conceived in view of this point, and has as its objective the calculation of stroke-volume-per-beat SV using a simpler structure.

Stroke-volume-per-beat detector 414 according to this fourth aspect is equivalent to that shown in FIG. 97. When ejection duration ED and heart rate HR are supplied to stroke-volume-per-beat table 4147 in this case, stroke-volume-per-beat detector 414 specifies one table TB corresponding to heart rate HR. When contraction period area S which corresponds to ejection duration ED is read out from table TB thereafter, multiplier 4141 calculates stroke-volume-per-beat SV.

Since stroke-volume-per-beat SV can be calculated from just ejection duration ED and heart rate HR in this way in the fourth aspect, it becomes possible to obtain stroke-volume-per-beat Sv by means of a simple structure within a short period of time. Note that multiplier 4141 may be omitted if stroke-volume-per-beat SV associated with ejection duration ED is stored in tables TB1, TB2, . . . TBn. In this case, S*Ksv may be stored in tables TB1, TB2, . . . TBn in place of contraction period area S.

4-3-7: Embodiment 13

The cardiac function diagnosing device 43 in the eighth through twelfth embodiments employs the contraction period area method, multiplying a given coefficient Ksv and area S of the pulse waveform in ejection duration ED to calculate stroke-volume-per-beat SV. Coefficient Ksv will differ depending on the test subject. For this reason, in order to calculate an accurate stroke-volume-per-beat SV, it is desirable to correct stroke-volume-per-beat Sv obtained using the contraction period area method.

Accordingly, in the thirteenth embodiment, stroke-volume-per-beat corrector 424 explained in the sixth embodiment is provided in between rate-of-change calculator 415' and stroke-volume-per-beat calculator 414 according to the eighth through twelfth embodiments shown in FIGS. 102,103, 104, and 105. Stroke-volume-per-beat corrector 424 carries out correction of stroke-volume-per-beat SV (see FIG. 99).

Namely, stroke-volume-per-beat corrector 424 generates a corrected stroke-volume-per-beat SVh in the same manner as in the sixth embodiment.

Thus, in this embodiment, a correction coefficient KH is calculated in the correction mode, with this correction coefficient KH employed in the regular measurement mode to calculate a corrected stroke-volume-per-beat SVh. As a result, a more accurate evaluation of cardiac function can be made.

4-3-8: Embodiment 14

In the fourteenth embodiment, the threshold values which serves as a reference for evaluation index X are varied in accordance to the surface area of the body. With the exception of the structure of evaluator 416, the structure of the fourteenth embodiment is equivalent to that of the eighth through thirteenth embodiments. In other words, the fourteenth embodiment corresponds to the seventh embodiment.

Figure 110:
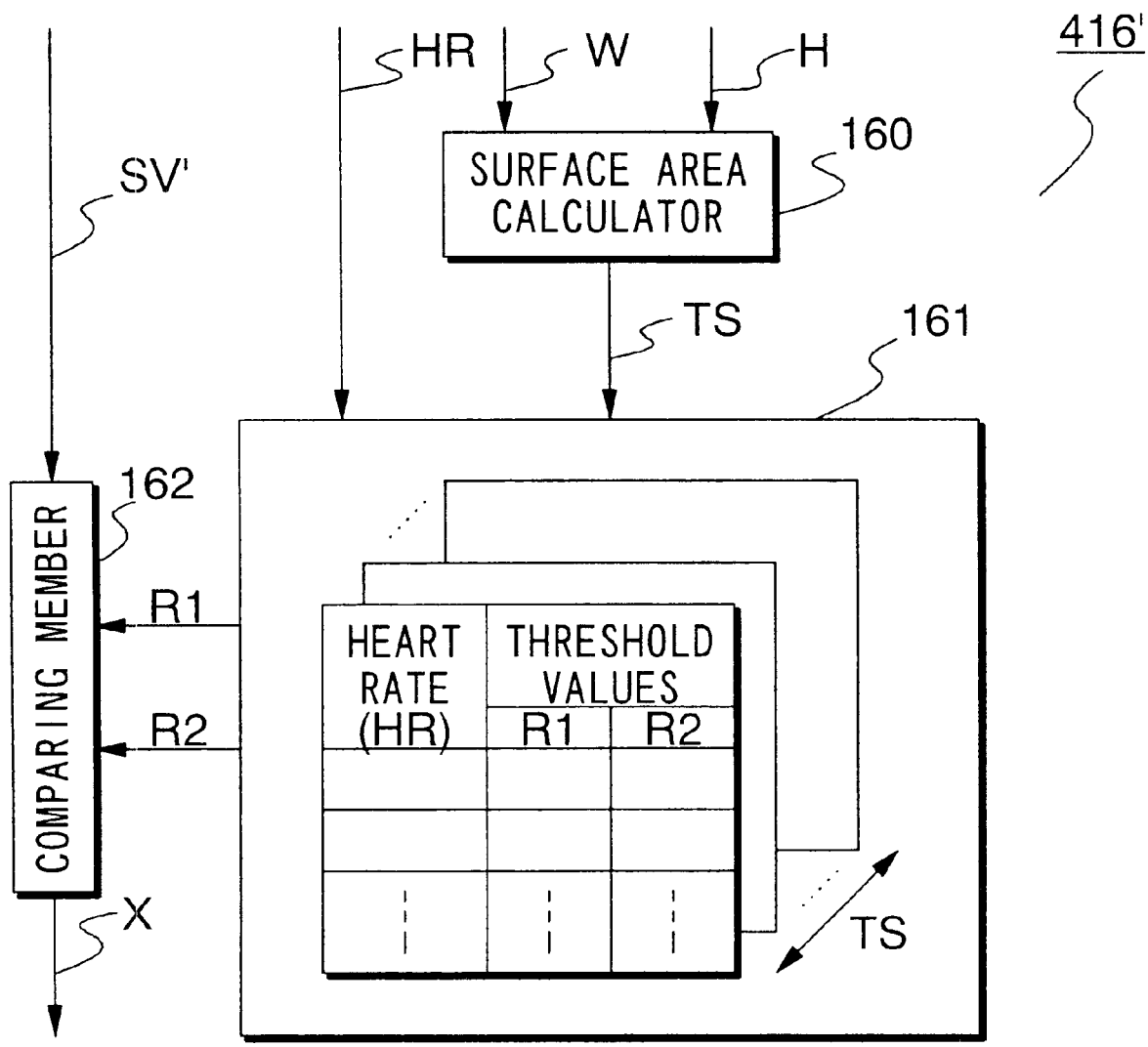
FIG. 110 is a block diagram of evaluator 16 in the fourteenth embodiment in Chapter 4.

FIG. 110 is a block diagram of evaluator 416' according to the fourteenth embodiment. Evaluator 416' differs from evaluator 416 according to the seventh embodiment shown in FIG. 100 in that stroke-volume-per-beat rate-of-change SV' is input into comparing member 162 rather than cardiac output CO.

In this evaluator 416', body surface area calculator 4160 calculates body surface area TS based on body weight W (kg) and height H (cm). When body surface area TS is supplied to threshold table 161, one of the tables is selected in response to the supplied body surface area TS from among the various tables. Threshold values R1,R2 are stored in association with heart rate HR in the selected table. On the other hand, because the heart rate HR during measurements is input to threshold table 161, it is possible to obtain threshold values R1,R2 in accordance with the heart rate HR at the time of measurement. Next, comparing member 4162 compares threshold values R1,R2 and stroke-volume-per-beat rate-of-change SV', and generates an evaluation index X.

Accordingly, by employing cardiac function diagnosing device 43 according to this embodiment, threshold values R1,R2 can be automatically varied in accordance with the subject's body size and dynamically changing heart rate HR. As a result, it becomes possible to continuously evaluate cardiac function during daily activities.

4-4: Example Modifications

The present invention is of course not limited to the preceding embodiments. For example, the following modifications are also possible.

4-4-1: Omission of Frequency Corrector

In the preceding second through forth embodiments, and in the ninth through eleventh embodiments, first frequency corrector 421 or second frequency corrector 423 were employed to compare energy in different frequency regions. The corrected result was then compared to a threshold value to determine maximum peak Pmax, etc. It is also acceptable in this case that the threshold value itself be selected to incorporate frequency correction, thus permitting elimination of the frequency corrector.

4-4-2: Application of Filter Bank

The preceding second through forth embodiments, and ninth through eleventh embodiments, employed wavelet transformation. It is also acceptable to perform wavelet transformation using a filter bank. For example, the filter bank shown in FIG. 30 and explained in Chapter 1 may be used.

4-4-3: Modification of Body Motion Component Remover 411

Body motion component remover 411 in the first and eighth embodiments may perform the wavelet transformation explained in the fourth embodiment. In this case, the waveform may be resynthesized by performing the inverse wavelet transformation expressed by Equation 2 in Chapter 1 on a wavelet from which body motion components have been removed. Heart rate HR and ejection duration ED may then be calculated based on the resynthesized pulse waveform. The inverse wavelet may be formed using an inverse filter bank. In this case, the inverse wavelet transformer may be formed of the filter bank show in FIG. 31.

4-4-4: Modification of Notifying Means

In the preceding embodiments, display 417 was explained as one example of a notifying means. However, modifications thereof as explained in Chapter 1, Section 1-8-6, entitled "Other examples of notifying means" are of course acceptable.

4-4-5: Modification of Arrangements for Use

In the preceding embodiments, the cardiac function diagnosing device took the form of a wristwatch structure, however, the present invention is not limited thereto. For example, the device may also be in the form of a pair of eyeglasses (see FIG. 34), necklace (see FIG. 35), card (see FIG. 36) or pedometer (see FIG. 37), as described in Chapter 1.

4-4-6: Modification of Pulse Wave Detecting Means

In the preceding embodiments, pulse wave detection sensor unit 130 was cited as one example of pulse wave detecting means f1. However, the present invention is not limited thereto. Rather, any means is acceptable as long as it can detect the pulse.

For example, the pulse wave may be detected using a pressure sensor or transmitted light method as explained in Chapter 1 under section 1-8-7-1, entitled "Detection method".

4-4-7: Method for Calculating Heart Rate HR

Heart rate HR may be determined using FFT in the first and eighth embodiments explained above. In this case, heart rate HR is calculated by measuring the fundamental frequency f, and then calculating f·60.

4-4-8: Application of Individual Data Base

It is also acceptable in the preceding embodiments to provide an individual data base for storing cardiac output CO and stroke-volume-per-beat SV in association with heart rates HR. In this case, if cardiac output CO and stroke-volume-per-beat SV are automatically stored in an individual data base, with historical values for cardiac output CO and stroke-volume-per-beat SV displayed on display 417 by manipulating an operational button, then the subject can be made aware of trends in these values over time. For example, when running or performing other such training, the subject is able to know the effect of this training. In addition, in the case of rehabilitation for a cardiac patient, it becomes possible to understand the degree to which the patient's cardiac function has recovered by examining this trend.

4-4-9: Omission of Acceleration Sensor 130' and Body Motion Component Remover 411

In the case of the device for calculating cardiac output CO and stroke-volume-per-beat SV when the subject is at rest, acceleration sensor 130' (body motion detecting means) for detecting body motion waveforms and body motion component remover 411 for generating pulse waveform MH' from which body motion components has been removed by removing the body motion components from pulse waveform MH may be omitted in the preceding embodiments since body motion is not present. When employing stroke-volume-per-beat calculator 414 disclosed in the fifth embodiment in this case, the calculation steps can be reduced. Thus, it is possible to shorten the processing time and reduce the amount of power consumed.

4-4-10: Other Examples for Calculating Correction Coefficient TH

In the sixth and thirteenth embodiments, correction coefficient KH was calculated based on a precisely measured reference stroke-volume-per-beat SVr and the stroke-volume-per-beat SV calculated by stroke-volume-per-beat calculator 414. Correction coefficient KH was then stored in correction coefficient memory 241. However, it is also acceptable to store correction coefficient TH in correction coefficient memory 241 in association with heart rate HR. In this case, by reading out correction coefficient TH in accordance with heart rate HR during the regular measurement mode, a more accurate cardiac output CO can be calculated.

In addition, rather than calculating correction coefficient KH for stroke-volume-per-beat SV, correction coefficient KH may be calculated for cardiac output CO in accordance with heart rate HR. In this case, a reference cardiac output CO' precisely measured at an external device, and cardiac output CO calculated by cardiac output calculator 415, may be supplied to correction coefficient calculator 4240. Correction coefficient KH generated by correction coefficient calculator 4240 may then be stored in correction coefficient memory 4241 in association with heart rate HR. During the regular measurement mode, multiplier 4242 multiplies cardiac output CO by the correction coefficient KH read out from correction coefficient memory 4241 based on the current heart rate HR, thereby providing a corrected cardiac output CO.

What is claimed:

1. A pulse wave diagnosing device comprising:
   pulse wave detecting means for detecting a pulse waveform at a detection site on a body;
   pulse wave period detecting means for detecting a period of said pulse waveform; and
   wavelet transforming means for performing wavelet transformation on said pulse waveform in synchronization with said detected period, and generating analyzed pulse wave data.

2. A pulse wave diagnosing device according to claim 1 comprising:
   pulse type data generating means for performing calculations on said analyzed pulse wave data, and generating pulse type data indicating a type of said pulse waveform.

3. A pulse wave diagnosing device comprising:
   pulse wave detecting means for detecting a pulse waveform at a detection site on a body;
   pulse wave period detecting means for detecting a period of said pulse waveform;
   first wavelet transforming means for performing wavelet transformation on said pulse waveform in synchronization with said detected period, and generating analyzed pulse wave data;
   body motion detecting means for detecting body motion, and outputting a body motion waveform;
   second wavelet transforming means for performing wavelet transformation on said body motion waveform in synchronization with said detected period, and generating analyzed body motion data;
   mask means for subtracting said analyzed body motion data from said analyzed pulse wave data, and generating corrected pulse wave data from which body motion components have been removed; and
   pulse type data generating means for performing calculations on said corrected pulse wave data, and generating pulse type data indicating a type of said pulse waveform.

4. A pulse wave diagnosing device comprising:
   pulse wave detecting means for detecting a pulse waveform at a detection site on a body;
   first wavelet transforming means for performing wavelet transformation on said pulse waveform, and generating analyzed pulse wave data;
   body motion detecting means for detecting body motion, and outputting a body motion waveform;
   second wavelet transforming means for performing wavelet transformation on said body motion waveform, and generating analyzed body motion data;
   mask means for subtracting said analyzed body motion data from said analyzed pulse wave data, and generating corrected pulse wave data from which body motion components have been removed;
   inverse wavelet transforming means for performing inverse wavelet transformation on said corrected pulse wave data, and generating pulse wave data from which body motion components have been removed; and pulse type data generating means for generating pulse type data indicating a type of pulse waveform based on peak information in said pulse wave data.

5. A pulse wave diagnosing device comprising:

pulse wave detecting means for detecting a pulse waveform at a detection site on a body;

body motion detecting means for detecting body motion, and outputting a body motion waveform;

state detecting means for detecting a state of physiological exercise based on said body motion waveform;

first wavelet transforming means for performing wavelet transformation on said pulse waveform in a plurality of frequency band which is determined on the basis of said state of physiological exercise, and generating analyzed pulse wave data;

second wavelet transforming means for performing wavelet transformation on said body motion waveform, and generating analyzed body motion data;

mask means for subtracting said analyzed body motion data from said analyzed pulse wave data, and generating corrected pulse wave data from which body motion components have been removed; and pulse type data generating means for generating pulse type data indicating a type of pulse waveform based on said corrected pulse wave data.

6. A pulse wave diagnosing device comprising:

pulse wave detecting means for detecting a pulse waveform at a detection site on a body;

first wavelet transforming means for performing wavelet transformation on said pulse waveform in a plurality of frequency band having different frequency bandwidths, and generating analyzed pulse wave data;

first frequency correcting means for normalizing said analyzed pulse wave data based on each of said frequency bandwidths, and generating corrected pulse wave data;

body motion detecting means for detecting motion of said body, and outputting a body motion waveform;

second wavelet transforming means for performing wavelet transformation on said body motion waveform in each of said frequency bands, and generating analyzed body motion data;

second frequency correcting means for normalizing said analyzed body motion data based on each of said frequency bandwidths, and generating corrected body motion data;

mask means for subtracting said corrected body motion data from said corrected pulse wave data, and generating corrected pulse wave data from which body motion components have been removed; and pulse type data generating means for performing calculations on said corrected pulse wave data, and generating pulse type data indicating a type of said pulse waveform.

7. A pulse wave diagnosing device comprising:

pulse wave detecting means for detecting a pulse waveform at a detection site on a body;

first wavelet transforming means for performing wavelet transformation on said pulse waveform in a plurality of frequency band having different frequency bandwidths, and generating analyzed pulse wave data;

body motion detecting means for detecting motion of said body, and outputting a body motion waveform;

second wavelet transforming means for performing wavelet transformation on said body motion waveform in each of said frequency bands, and generating analyzed body motion data;

mask means for subtracting said analyzed body motion data from said analyzed pulse wave data, and generating pulse wave data from which body motion components have been removed;

frequency correcting means for normalizing said pulse wave data based on each of said frequency bandwidths, and generating corrected pulse wave data; and pulse type data generating means for performing calculations on said corrected pulse wave data, and generating pulse type data indicating a type of said pulse waveform.

8. A pulse wave diagnosing device according to claim 6 or 7, comprising:

pulse wave period detecting means for detecting a period of said pulse waveform; and wherein said first and second wavelet transforming means perform wavelet transformation in synchronization with said detected period.

9. A pulse wave diagnosing device according to claims 6 and 7, comprising:

state detecting means for detecting a state of physiological exercise based on said body motion waveform; and controlling means for determining said each of said frequency bands on the basis of said state of physiological exercise.

10. A pulse wave diagnosing device according to claim 9, wherein:

said controlling means comprise a recording means for recording in advance relationships between said state of physiological exercise and parameters to determine said frequency bands, reading out means for reading out said parameters based on said state of physiological exercise, and determining means for determining said frequency bands based on said parameters.

11. A pulse wave diagnosing device comprising:

pulse wave detecting means for detecting a pulse waveform at a detection site on a body;

wavelet transforming means for performing wavelet transformation on said pulse waveform in a plurality of frequency band having different frequency bandwidths, and generating analyzed pulse wave data;

frequency correcting means for normalizing said analyzed pulse wave data based on each of said frequency bandwidths, and generating corrected pulse wave data; and pulse type data generating means for performing calculations on said corrected pulse wave data, and generating pulse type data indicating a type of said pulse waveform.

12. A pulse wave diagnosing device comprising:

pulse wave detecting means for detecting a pulse waveform at a detection site on a body;

wavelet transforming means for performing wavelet transformation on said pulse waveform in a plurality of frequency band having different frequency bandwidths, and generating analyzed pulse wave data;

body motion component removing means for removing a frequency component corresponding to body motion from said analyzed pulse wave data, and generating analyzed pulse wave data;

frequency correcting means for normalizing said analyzed pulse wave data based on each of said frequency bandwidths, and generating corrected pulse wave data; and pulse type data generating means for performing calculations on said corrected pulse wave data, and generating pulse type data indicating a type of said pulse waveform.

13. A pulse wave diagnosing device according to claim 12, wherein said pulse type data generating means comprises:

inverse wavelet transforming means for performing inverse wavelet transformation on said corrected pulse wave data, and generating pulse wave data; and data generating means for generating pulse type data based on peak information in said pulse wave data.

14. A pulse wave diagnosing device according to claim 11 or 12, comprising:

pulse wave period detecting means for detecting a period of said pulse waveform; and wherein said wavelet transforming means perform wavelet transformation in synchronization with said detected period.

15. A pulse wave diagnosing device according to claims 1, 3–7, 11, or 12, comprising notifying means for informing an individual of said pulse type data generated by said pulse type data generating means.

16. A pulse wave diagnosing device according to claims 1, 3–7, 11, or 12, wherein said pulse wave detecting means comprises a pressure sensor for employing pressure to detect an arterial pulse in said body.

17. A pulse wave diagnosing device according to claims 1, 3–7, 11, or 12, wherein said pulse wave detecting means detect as said pulse waveform a received light signal in which reflected light obtained when said detection site on said body is irradiated with light of wavelength between 300 and 700 nm is received.

18. A pulse wave diagnosing device according to claims 1, 3–7, 11, or 12, wherein said pulse wave detecting means detect as said pulse waveform a received light signal in which transmitted light obtained when said detection site on said body is irradiated with light of wavelength between 600 and 1000 nm is received.

* * * * *